(12) United States Patent
Barry et al.

(10) Patent No.: US 9,605,079 B2
(45) Date of Patent: Mar. 28, 2017

(54) PROTEINS THAT BIND PI16 AND USES THEREOF

(75) Inventors: Simon Barry, Longwood (AU);
Doreen Krumbiegel, Edwardstown (AU); Nicola Ga-Ling Eastaff-Leung, Blackwood (AU); Ian Cameron Nicholson, Highbury (AU); Heddy Zola, Evandale (AU)

(73) Assignee: MEDVET SCIENCE PTY LTD., Underdale, South Australia (AU)

( * ) Notice: Subject to any disclaimer, the term of this patent is extended or adjusted under 35 U.S.C. 154(b) by 1088 days.

(21) Appl. No.: 13/640,356

(22) PCT Filed: Apr. 18, 2011

(86) PCT No.: PCT/AU2011/000498
§ 371 (c)(1),
(2), (4) Date: Mar. 26, 2013

(87) PCT Pub. No.: WO2011/127543
PCT Pub. Date: Oct. 20, 2011

(65) Prior Publication Data
US 2013/0171153 A1 Jul. 4, 2013

Related U.S. Application Data

(60) Provisional application No. 61/325,093, filed on Apr. 16, 2010, provisional application No. 61/426,019, filed on Dec. 22, 2010.

(51) Int. Cl.
*C07K 16/38* (2006.01)
*G01N 33/569* (2006.01)
*C07K 16/28* (2006.01)
*C12N 5/0783* (2010.01)
*A61K 39/00* (2006.01)

(52) U.S. Cl.
CPC .............. *C07K 16/38* (2013.01); *C07K 16/28* (2013.01); *C12N 5/0637* (2013.01); *G01N 33/56972* (2013.01); *A61K 2039/505* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 2006/0029984 A1* | 2/2006 | Reeves ................ C07K 14/47 435/7.2 |
| 2011/0059471 A1 | 3/2011 | Yamashiro et al. |
| 2012/0064100 A1* | 3/2012 | Barry ............... G01N 33/56972 424/184.1 |

FOREIGN PATENT DOCUMENTS

| EP | 2 264 071 A1 | 12/2010 |
| WO | 9829448 | 7/1998 |
| WO | 03093474 | 11/2003 |
| WO | 2006133560 | 12/2006 |
| WO | 2007/014420 A1 | 2/2007 |
| WO | 2007100684 | 9/2007 |
| WO | 2007/140472 A2 | 12/2007 |
| WO | 2008110356 | 9/2008 |
| WO | 2009143624 | 12/2009 |
| WO | 2010/105298 A1 | 9/2010 |

OTHER PUBLICATIONS

Rudikoff et al (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
International Search Report, PCT Application No. PCT/AU2011/000498, mailed Jul. 15, 2011.
Bresatz, et al., "Isolation, Propagation and Characterization of Cord Blood Derived CD4+CD25+ Regulatory T Cells", Journal of Immunological Methods, 2007, vol. 327, Nos. 1-2, pp. 53-62.
Liu et al., "CD4+CD25+ Regulatory T Cells in Health and Disease", Clinical and Experimental Pharmacology and Physiology, 2006, vol. 33, pp. 519-524.
Goodman, et al., "IL-6 Signaling in Psoriasis Prevents Immune Suppression by Regulatory T Cells", Journal of Immunology, 2009, vol. 183, pp. 3170-3176.
European Patent Application No. 11 76 8290, Supplemental European Search Report issued on Mar. 20, 2014.
Jonathan R. Reeves, et al., "Identification, purification and characterization of a novel human blood protein with binding affinity for prostate secretory protein of 94 amino acids", The Biochemical Journal, Jan. 1, 2005 (Jan. 1, 2005), pp. 105-114. Biochemical Society, Great Britain.
Ian C. Nicholson et al., "PI16 is expressed by a subset of human memory Treg with enhanced migration to CCL17 and CCL20", Cellular Immunology, vol. 275, No. 1-2, Jan. 1, 2012 (Jan. 1, 2012), pp. 12-18. Elsevier Inc.
Endocrine Reviews, 2008, vol. 29, No. 7, p. 865-897. The Endocrine Society. USA.
Presta, et al., Engineering of therapeutic antibodies to minimize immunogenicity and optimize function, Advanced Drug Delivery Reviews, 58, 2006, 640-656.
English translation of Decision of Rejection dated Mar. 28, 2016 in corresponding Japanese application JP 2013-504067, 11 pages.

* cited by examiner

Primary Examiner — Sharon Wen
(74) Attorney, Agent, or Firm — Kilpatrick Townsend & Stockton LLP

(57) ABSTRACT

The present disclosure provides an isolated protein comprising at least one antibody variable region that is capable of binding to peptidase inhibitor 16 (PI16), wherein the protein is also capable of competitively inhibiting binding of an antibody produced by a hybridoma designated CRCBT-02-001 deposited with the ATCC under Accession Number PTA-10685 to PI16. The present invention also provides use of the protein, e.g., in diagnosis, therapy or to isolate cells, preferably Treg cells.

11 Claims, 56 Drawing Sheets

```
Mus_musculus_PI16        MHGSCSPWVMLPPP----LLLLLLLIATGPTTALTEDEKQTMVDLHNQYR
Rattus_norvegicus_PI16   MHSSCSPWVMLPQLPLLLLLLLLLLTATGPATALTEDEKQTMVELHNHYR
Homo_sapiens_PI16        MHGSCSFLMLLLPL------LLLLVATTGPVGALTDEEKRLMVELHNLYR
Pan_troglodytes_PI16     MHGSCSFLMLLLPL------LLLLVATTGPVGALTDEEKRLMVELHNLYR
                         **.***   ::*        ****  :***. ***::**: **:*** **

Mus_musculus_PI16        AQVSPPASDMLQMRWDDELAAFAKAYAQKCVWGHNKERGRRGENLFAITD
Rattus_norvegicus_PI16   AQVSPPASDMLQMRWDDELAAFAKAYAQKCVWGHNKERGRRGENLFAITD
Homo_sapiens_PI16        AQVSPTASDMLHMRWDEELAAFAKAYARQCVWGHNKERGRRGENLFAITD
Pan_troglodytes_PI16     AQVSPPASDMLHMRWDEELAAFAKAYARQCVWGHNKERGRRGENLFAITD
                         *****.*****:****:***********::********************

Mus_musculus_PI16        EGMDVPLAVGNWHEEHEYYNFSTATCDPNQMCGHYTQVVWSKTERIGCGS
Rattus_norvegicus_PI16   EGMDVPLAVGNWHEEHEYYNLSTATCDPGQMCGHYTQVVWSKTERIGCGS
Homo_sapiens_PI16        EGMDVPLAMEEWHHEREHYNLSAATCSPGQMCGHYTQVVWAKTERIGCGS
Pan_troglodytes_PI16     EGMDVPLAMEEWHHEREHYNLSAATCSPGQMCGHYTQVVWAKTERIGCGS
                         ********: :**.*:*:**:*.***.*.*************:*******

Mus_musculus_PI16        HFCETLQGVEEANIHLLVCNYEPPGNVKGRKPYQEGTPCSQCPLGYSCEN
Rattus_norvegicus_PI16   HFCETLQGVEEANIHLLVCNYEPPGNVKGRKPYQEGTPCSQCPLGYSCVN
Homo_sapiens_PI16        HFCEKLQGVEETNIELLVCNYEPPGNVKGKRPYQEGTPCSQCPSGYHCKN
Pan_troglodytes_PI16     HFCEKLQGVEETNIELLVCNYEPPGNVKGKRPYQEGTPCSQCPSGYHCKN
                         ****.*******:**.***************.:************ ** * *

Mus_musculus_PI16        SLCEPMRNPEKAQDSPPRVTEVPSTRATEAPSSRETGTPSLATSETLHFS
Rattus_norvegicus_PI16   SLCEPERKPEKAQDSPPRVTEVP--------GSRETGIPSLATSESLHFS
Homo_sapiens_PI16        SLCEPIGSPEDAQDLPYLVTEAPSFRATEASDSRKMGTPSSLATG-IPAF
Pan_troglodytes_PI16     SLCEPIGSSEDAQDLPYLVTEAPSFRATEASDSRKMGTPSSLATG-IPAF
                         *****   ..*.*** * ***.*        .**: * **   ::   :

Mus_musculus_PI16        -VTKVSDSLATESSPAVETKAPSSLATEGPSSMATEAQAFVT-EVPLVSA
Rattus_norvegicus_PI16   SVTKVSDSLATEPSPAVETKAPSSLATEGPSSMATEAQSFLT-EVPSVSA
Homo_sapiens_PI16        LVTEVSGSLATKALPAVETQAPTSLATKDPPSMATEAPPCVTTEVPSILA
Pan_troglodytes_PI16     LVTEVSGSLATKALPAVETQAPTSLATKDPPSMATEAPPCVTTEVPSILA
                          **:**.****:. *****:**.****:.* ******  . :* *** : *

Mus_musculus_PI16        RHMQPSVDEGPVNFLTSTHIPVPKSMDEEAS-KSSATSVSPKKSLYPKMS
Rattus_norvegicus_PI16   THIQPSLDEGPVNFLTSTHIPVPKSTDKEASSKSRAASVSPEKSLYPKMS
Homo_sapiens_PI16        AHSLPSLDEEPVTFPKSTHVPIPKSADKVTD-KTKVPSRSPENSLDPKMS
Pan_troglodytes_PI16     AHSLPSLDEEPVTFPKSTHVPIPKSADKVTD-KTKVPSRSPENSLDPKMS
                          *  **:** **.* .***:*:*** *: :. *: ...* **::** ****

Mus_musculus_PI16        LTESGESVPQIQEEAEPKDELSEPEAILPEAEAAPTEAEVELREPEAESP
Rattus_norvegicus_PI16   PTETGESPPQIQEEAEPKAELPEREDELPEAEVELPEAEAELP-------
Homo_sapiens_PI16        LTGARELLPHAQEEAEAEAELPP---------------------------
Pan_troglodytes_PI16     LTGARELLPHAQEEAEAEAELPP---------------------------
                          * : *   *: *****.: *

Mus_musculus_PI16        KAESPEAEAESPLSSEALVPVLPAQERGG-QKASLEHSGHPASPSLPTFP
Rattus_norvegicus_PI16   -----EAKAELPVSSEALVPVLPAQERGG-PKASLEHSSYPVPTYLPNFP
Homo_sapiens_PI16        -------------SSEVLASVFPAQDKPGELQATLDHTGHTSSKSLPNFP
Pan_troglodytes_PI16     -------------SSEVLASVFPAQDKPGELQATLDHTGHTSSKSLPNFP
                                      ***.*...*:***:: *   :*:*:*:..  .  **.**

Mus_musculus_PI16        --SASGNATGGRTLALQSSWTGAENPEKADWDL---KNSAHVWGPFLGLL
Rattus_norvegicus_PI16   --SASGNATGGRTLALQSSRTGAEDPEKASWDS---KNSAPVWGPFPGLL
Homo_sapiens_PI16        NTSATANATGGRALALQSSLPGAEGPDKPSVVSGLNSGPGHVWGPLLGLL
Pan_troglodytes_PI16     NTSATANATGGRALALKSSLPGAEGPDKPSVVSGLNSGPGHVWGPLLGLL
                           **:.******:****:***.* ****.*:*..          ****: ***

Mus_musculus_PI16        LPSLLLLAGMV
Rattus_norvegicus_PI16   LPLLLLAGIF-
Homo_sapiens_PI16        LLPPLVLAGIF
Pan_troglodytes_PI16     LLPPLVLAGIF
                          *    *: . :
```

Figure 1

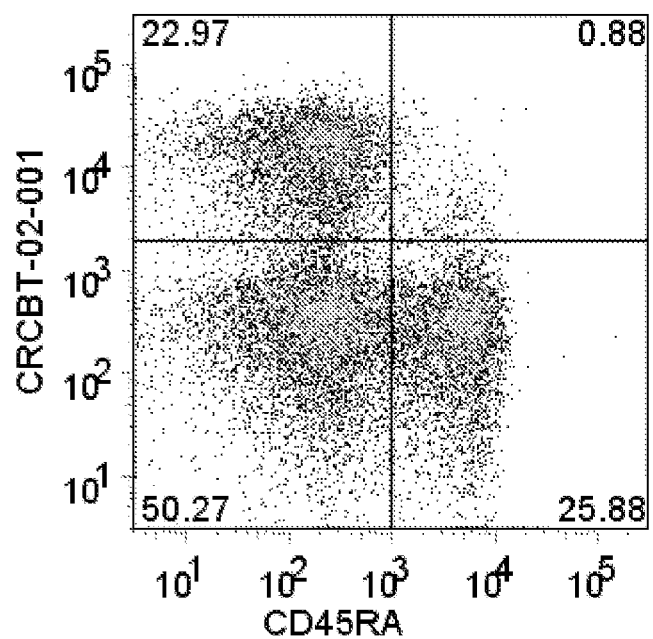
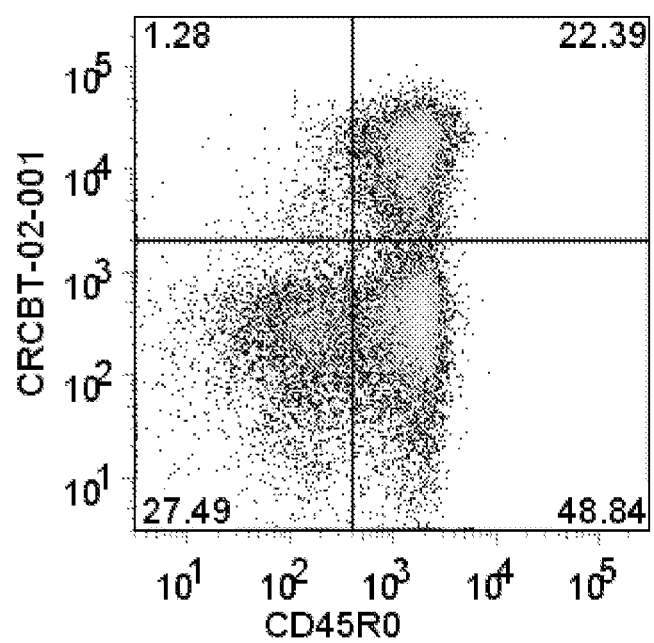
Figure 16

Heavy chain variable region of CRCBT-02-001 (CDRs highlighted in bold)

FGGGLVQPGGSMKLSCVASGFTFSYYWMNWVRQSPEQGLEWIAEIRLQSNDYPTHYAESVKGRFTISRD
DSKNSVYLQMNNLRPEDTGIYYCA----CRYADYFDHWGQGTTLTVSSAKTTPPSVY (SEQ ID NO: 9)

Light chain variable region of CRCBT-02-001 (CDRs highlighted in bold)

VMTQSPAILSVYPGEKVTMTCRASL-SVSYMHWCQQKPGSSPKSWIYATSNLASGVPARFSGSGSGTSY
SLTISRVEAEDAATYYCQQWSSNPFTFGSGTKLEIKRADAAPTV (SEQ ID NO: 10)

Figure 21

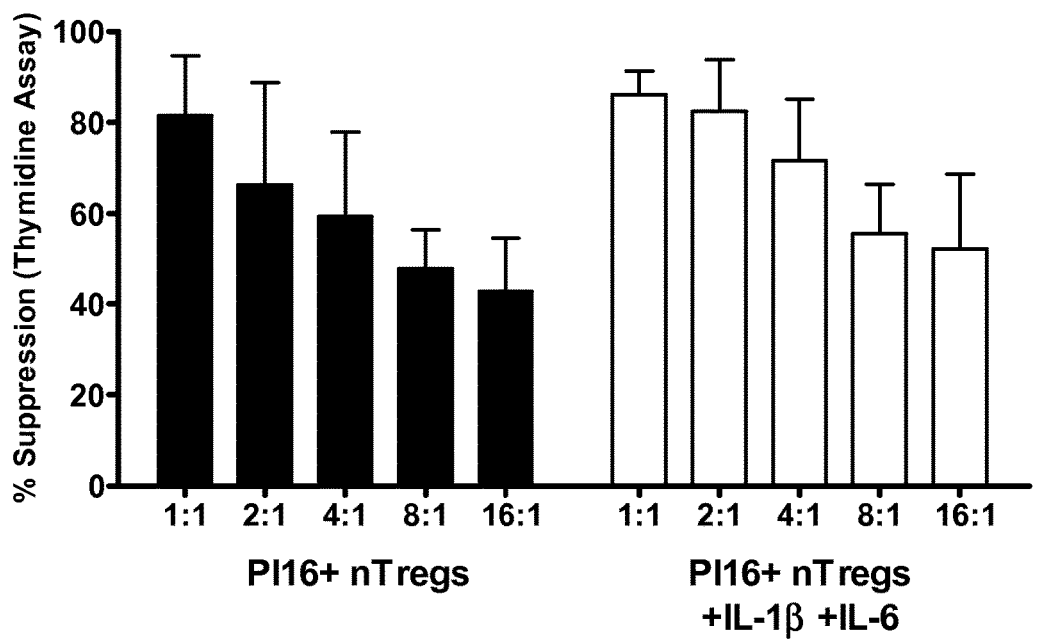
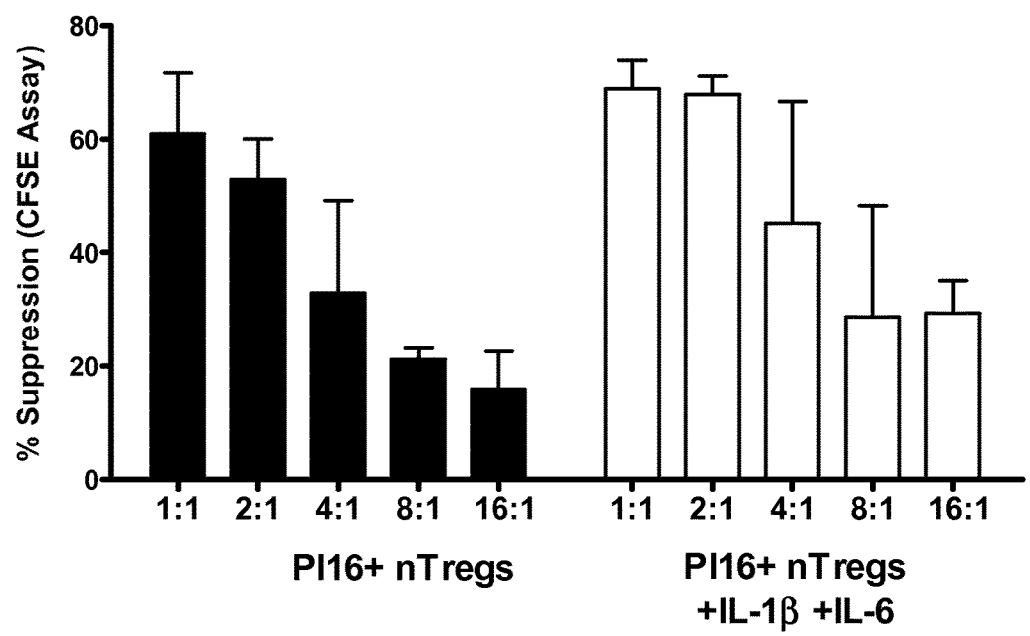
Figure 29A

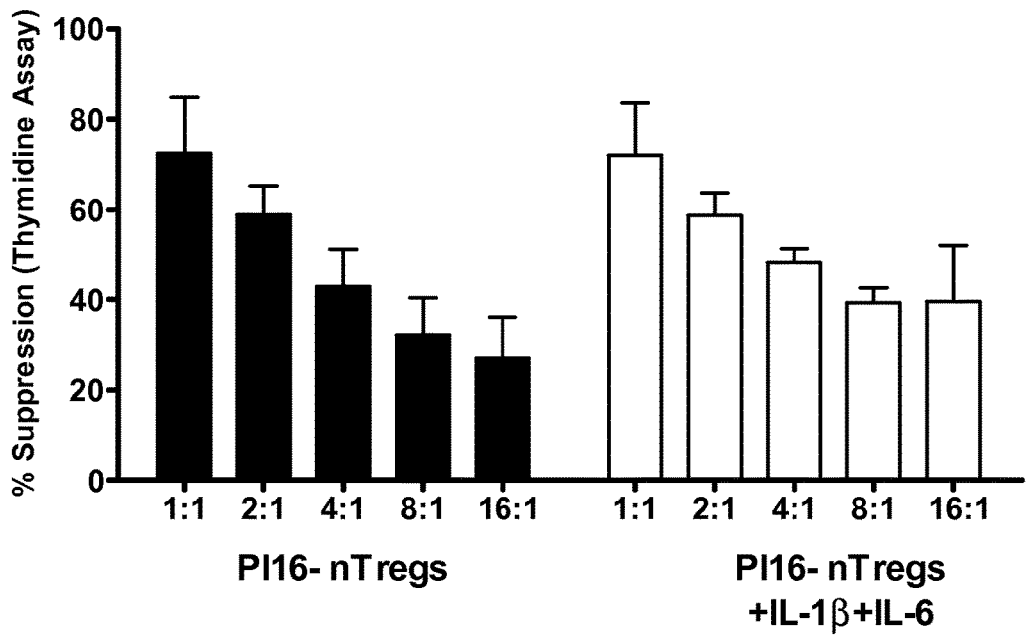
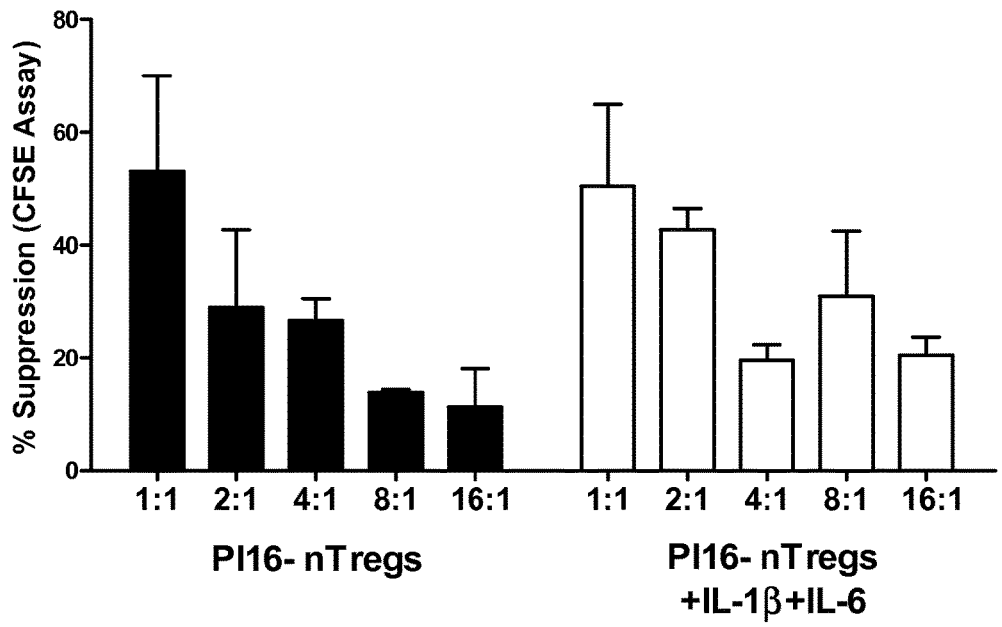
Figure 29B

PROTEINS THAT BIND PI16 AND USES THEREOF

INCORPORATION BY REFERENCE

This application is a national stage application of PCT/AU2011/000498 which claims priority to U.S. Provisional Application No. 61/325,093 filed on 16 Apr. 2010 entitled "Proteins that binds PI16 and uses therefor" and to US Provisional Application Ser. No. 61/426,019 filed on 22 Dec. 2010 entitled "Proteins that binds PI16 and uses therefore 2". The entire contents of all of these applications are hereby incorporated by reference.

FIELD

The present invention relates to proteins that bind to PI16 and uses thereof. The present disclosure also relates to methods of diagnosing/prognosing/treating/preventing conditions associated with regulatory T (Treg) cells.

BACKGROUND

Regulatory T (Treg) cells are characterized by expression of both CD4 and CD25 and the forkhead/winged transcription factor FoxP3. First characterized in mice, in which they constitute about 6-10% of lymph node and splenic $CD4^+$ T cell populations, $CD4^+CD25^+$ cells represent about 5-10% of human $CD4^+$ T cells (Wing and Sakaguchi, 2010). As discussed in more detail below, Treg cells have the ability to suppress the activity of $CD4^+$ T cells and $CD8^+$ T cells.

Treg cells can be divided into several subsets (Bluestone et al., 2000). One subset of Treg cells develops in the thymus (also known as natural Treg (nTreg) cells), and these thymic-derived Treg cells function by a cytokine-independent mechanism, which involves cell to cell contact (Shevach, 2002). These cells are essential for the induction and maintenance of self-tolerance and for the prevention of autoimmunity (Shevach 2000; Salomon et al, 2000; Sakaguchi et al, 2001). These regulatory cells prevent the activation and proliferation of autoreactive T cells that have escaped thymic deletion or recognize extrathymic antigens, and, as a consequence are critical for homeostasis and immune regulation, as well as for protecting the host against the development of autoimmunity (Suri-Payer et al, 1996; Asano 1996; Willerford et al, 1995; Salomon et al, 2000).

Treg cells can also be generated by the activation of mature, peripheral $CD4^+$ T cells (these cells are known as induced Treg (iTreg) cells). These cells can be generated ex vivo, e.g., by exposure to growth factors, and in vivo, e.g., in the gastrointestinal tract. Studies have indicated that peripherally derived Treg cells mediate their inhibitory activities by producing immunosuppressive cytokines, such as transforming growth factor-beta (TGF-β) and IL-10 (Kingsley 2002; Nakamura 2001). After antigen-specific activation, these Treg cells can non-specifically suppress proliferation of either $CD4^+$ or $CD8^+$ T cells (Baecher-Allan, 2001). Studies have shown that $CD4^+CD25^+$ cells are able to inhibit anti-CD3 stimulation of T cells when co-cultured with autologous antigen presenting cells (APC) (e.g., Stephens, 2001; Taams, 2001).

While both nTreg cells and iTreg cells have regulatory activity, a recent study indicates that iTreg cells lose this activity in vivo in a study of graft-versus-host disease (GVHD; Koenecke et al., 2009). In contrast nTreg cells maintain their regulatory activity and prevented development of GVHD. Thus, it is desirable to be able to identify/isolate populations of nTreg cells.

The immunomodulatory activity of Treg cells can be contact dependent, or the Treg cells may kill $CD4^+$ and $CD8^+$ T cells in a perforin- or granzyme-dependent manner or by the secretion of immunosuppressive cytokines, e.g., IL-10 and/or TGF-β (as reviewed in Dejaco et al., 2005).

Treg Cells and Autoimmunity/Tolerance

Depletion of Treg cells from various mouse strains has been shown to lead to a variety of autoimmune diseases that are tissue specific, including thyroiditis, oophoritis, gastritis or inflammatory bowel disease (Asano, 1996; Sufi-Payer, 1998; and McHugh, 2002). Furthermore, human patients having a mutation in the FoxP3 gene fail to produce Treg cells and develop autoimmune polyendocrinopathy (especially type I diabetes and hypothyroidism) and enteropathy (summarized as immunodysregulation, polyendocrinopathy, enteropathy X-linked (IPEX) syndrome). A polymorphism in the FoxP3 is associated with autoimmune diabetes (Bassuny et al, 2003). Moreover, mice deficient in FoxP3 develop an IPEX like syndrome (see, Dejaco et al., 2005).

The level of Treg cells in the circulation is reduced in subjects suffering from a variety of disorders as shown in Table 1. Moreover, lower levels of these cells are associated with higher disease activity and/or poorer prognosis.

TABLE 1

Autoimmune diseases associated with reduced levels of circulating $CD4^+CD25^+$ cells.

| Disease | | Level of CD4+ CD25+ cells (control) and significance | Reference |
|---|---|---|---|
| Juvenile arthritis | idiopathic | 1.2 (1.6) *** | De Kleer (2004) |
| Juvenile arthritis | idiopathic | 0.4 (1.2) *** | Cao et al., (2004). |
| Rheumatoid arthritis | | 0.7 (1.2)* | Cao et al., supra. |
| Rheumatoid arthritis | | 1.2 (3.7)* | Liu et al., (2004). |
| Psoriatic arthritis | | 0.6 (1.2)* | Cao et al., supra. |
| HCV cryoglobulinemia | mixed | 2.6 (7.9)** | Boyer et al., (2004) |
| Autoimmune disease | liver | 2.5 (6.8)*** | Longhi et al., (2004). |
| Systemic erythematodes (SLE) | lupus | 1.8 (3.7)* | Cao et al., supra. |
| SLE | | 0.9 (2.6)* | Crispin et al., (2003). |

*, p <0.05;
**, p < 0.01,
***, p < 0.001.

Increased levels of $CD4^+CD25^+$ T cells are observed at sites of inflammation, e.g., in subjects suffering from juvenile idiopathic arthritis, rheumatoid arthritis, sponyloarthritis and infections (as reviewed in Dejaco et al., 2005). These cells are considered to modulate local immune responses, e.g., to prevent collateral tissue damage.

Adoptive transfer of $CD4^+CD25^+$ T cells prevents the development of these diseases and, in some models can cure the disease after initiation (Mottet et al., 2003). Suri-Payer et al., (1998) also found that $CD4^+CD25^+$ T cells could prevent autoimmunity induced by autoantigen-specific T cell clones. Transfer of $CD4^+CD25^-$ T cells into nude mice also leads to development of autoimmune disease, which can be prevented by co-transfer of $CD4^+CD25^+$ T cells (Sakaguchi et al., 1995).

Tang et al., (2004) demonstrated that Treg cells are also useful for the treatment of autoimmune diabetes. The authors isolated Treg cells from non-obese diabetic (NOD) mice and expanded TCR transgenic cells specific for an autoantigen. Adoptive transfer of these cells to NOD mice reversed diabetes in newly transgenic mice.

Studies by Trenado (2002) also demonstrated that infusion of ex vivo activated and expanded CD4$^+$CD25$^+$ T cells significantly inhibit rapidly-lethal graft-versus-host disease (GVHD) in mice. Treg cells have also been shown to suppress allograft rejection in rodents with long term surviving cardiac (Van Maurik, 2002) or pancreatic islet (Gregori, 2001) allografts.

Based on the foregoing, it will be apparent to the skilled artisan that Treg cells are attractive for treatment or prevention of autoimmune disease or for inducing tolerance in a subject or that the detection of circulating levels of Treg cells is useful for the diagnosis or prognosis of those disorders. However, difficulties have arisen in translating the results of animal models to the human situation as a result of insufficient markers that permit isolation of Treg cells. To date, the only marker that clearly distinguishes Treg cells from other T cells is FoxP3. FoxP3 is an intracellular protein and, as a consequence, is not useful as a marker for isolating viable Treg cells. Accordingly, there is a need in the art for new markers, preferably cell surface markers of Treg cells that permit detection and/or isolation of those cells, e.g., for diagnostic and/or therapeutic and/or prophylactic purposes.

Treg Cells and Inducing an Immune Response

Treg cells also exist in markedly higher proportions within tumor-infiltrating lymphocytes, peripheral blood lymphocytes, and/or regional lymph node lymphocytes of patients with cancer. The frequency of cells is related to tumor progression and inversely correlated with the efficacy of treatment. Accordingly, the ability of Treg cells to suppress immune responses appears to suppress the ability of the immune system to kill tumor cells.

Wang et al., (2004) isolated a CD4$^+$CD25$^+$ tumor-infiltrating lymphocyte (TIL) from a human melanoma patient. This TIL recognized a tumor/self-antigen, LAGE-1. CD4$^+$ CD25$^+$ TILs have also been isolated from ascites of patients with ovarian cancer, and these cells were shown to be capable of suppressing T cell activity (Curiel et al., 2004).

Depleting populations of Treg has also been demonstrated to improve significantly the clearance of injected tumor cells. For example, Jones et al., 2002, depletion of CD25 expressing T cells using monoclonal antibody therapy facilitated long-term CD4+ T cell-mediated immunity against melanoma cells. The authors demonstrated that following anti-CD25 treatment, mice developed an immune response against a self-antigen (tyrosinase) that accompanies inhibition of tumor growth in mice.

Goforth et al., (2008) also demonstrated that poly lactic-co-glycolic acid (PLGA) polymer particles loaded with antigenic tumor lysate and immune stimulatory CpG oligonucleotides efficiently activated antigen-presenting cells and were incorporated into lysosomal compartments of macrophages and dendritic cells. Vaccination with the immune stimulatory antigen loaded particles (ISAPs) resulted in remarkable T cell proliferation, but only modestly suppressed tumor growth of established melanoma. When CD25' cells were suppressed with anti-CD25 antibody, ISAP vaccination induced complete antigen-specific immunity in a prophylactic model. These findings suggest that it may be necessary or desirable to suppress Treg cell activity prior to and/or during vaccination, particularly against self-antigens.

It will be apparent from the foregoing discussion that depletion of Treg cells provides an attractive means for improving an immune response, e.g., against a self antigen or a non-self antigen. However, as discussed above, insufficient markers that permit removal of Treg cells has hampered therapeutic strategies targeting these cells. For example, while the cell surface marker CD25 is highly expressed on Treg cells and has been traditionally used to isolate or target these cells, this protein is also expressed on other T cell populations (e.g., activated T cells) in addition to activated B cells, some thymocytes, myeloid precursors, and oligodendrocytes (see, for example, Robb et al., 1981; and Zola et al., 1989). Accordingly, there is a need in the art for new markers, preferably cell surface markers of Treg cells that permit detection and isolation of Treg cells, or removal or destruction of Treg cells, e.g., for diagnostic, prognostic, therapeutic and/or prophylactic purposes.

SUMMARY

In work leading up to the present invention, the inventors sought to identify new cell surface markers of Treg cells. The inventors identified the peptidase inhibitor 16 (PI16) protein as upregulated in Treg cells compared to other T cell types, e.g., Thelper cells. The inventors also showed that expression of PI16 is correlated with the Treg cell transcription factor FoxP3. Based on these data, the inventors concluded that PI16 is a biomarker of Treg cells. The inventors then produced proteins capable of binding to PI16. For example, the present inventors produced a series of monoclonal antibodies, one of which was shown to bind to cell surface PI16 and be capable of isolating a population of cells expressing cell surface markers of Treg cells. The hybridoma secreting this monoclonal antibody is designated CRCBT-02-001. This monoclonal antibody, and proteins that competitively inhibit binding of this monoclonal antibody are useful for a variety of applications, including identifying or isolating cells, e.g., Treg cells, preferably nTreg cells, such as memory nTreg cells or resting memory nTreg cells, diagnosing or prognosing PI16-related conditions (e.g., Treg cell associated conditions) and treating PI16 and/or Treg cell-associated conditions.

Accordingly, the present invention provides an isolated protein comprising at least one antibody (e.g., monoclonal antibody) variable region that is capable of binding to peptidase inhibitor 16 (PI16), wherein the protein is also capable of competitively inhibiting binding of an antibody produced by a hybridoma designated CRCBT-02-001 deposited with the ATCC under Accession Number PTA-10685 to PI16.

In one example, the protein binds to an epitope that overlaps with the epitope bound by the antibody produced by a hybridoma designated CRCBT-02-001. Alternatively, the protein binds to the same epitope as the antibody produced by a hybridoma designated CRCBT-02-001.

In one example, the protein binds to a membrane bound form of PI16, e.g., comprising the 21 C-terminal amino acids in SEQ ID NO: 1.

In one example, the protein specifically binds to an epitope comprising a sequence set forth in SEQ ID NO: 32 or 38.

In one example, the protein specifically binds to an epitope contained within a sequence selected from the group consisting of SEQ ID NOs: 33-37, 39 and mixtures thereof.

In one example, the protein specifically binds to a peptide consisting of the sequence selected from the group consisting of SEQ ID NOs: 32-39 and mixtures thereof.

In on example, the protein binds to a conformational epitope in PI16. For example, the conformational epitope is dependent of disulphide bond formation within PI16. For example, the conformational epitope bound by the protein is not present in a PI16 protein lacking disulphide bonds, e.g., PI16 in reduced form.

In one example, the protein does not substantially bind to PI16 in reduced form. For example, the protein does not detectably bind to PI16 in reduced form.

In one example, the protein binds to glycosylated or de-glycosylated PI16. For example, the protein binds to N-glycosylated or non-N-glycosylated PI16.

In one example, the protein binds to PI16 with an affinity (KD) of at least about 5 nM, such as, at least about 4 nM, for example, at least about 3 nM.

In one example, the protein binds to PI16 with an affinity (KD) of at least about 1.25 nM. In one example, the KD is assessed by immobilizing the extracellular region of PI16 fused to a Fc and assessing binding of the protein (e.g., a Fab) to the immobilized protein using surface plasmon resonance.

In one example, the protein binds to PI16 with an affinity (KD) of at least about 2.56 nM. In one example, the KD is assessed by immobilizing the protein and assessing binding of extracellular region of PI16 fused to a Fc to the immobilized protein using surface plasmon resonance.

In one example, the protein has an affinity (KD) of between 1 nM and 3 nM, such as between about 1.1 nM and 2.7 nM, such as between about 1.2 nM and 2.6 nM, such as, between about 1.25 nM and 2.56 nM.

In one example, the protein has a Ka of at least about $2 \times 10^5$, such as about $2.4 \times 10^5$, for example, about $2.6 \times 10^5$, such as, $2.8 \times 10^5$, for example at least about $2.97 \times 10^5$. In one example, the Ka is assessed by immobilizing the extracellular region of PI16 fused to a Fc and assessing binding of the protein (e.g., a Fab) to the immobilized protein using surface plasmon resonance.

In one example, the protein has a Ka of at least about $5 \times 10^4$, such as at least about $5.2 \times 10^4$, for example, at least about $5.3 \times 10^4$, such as at least about $5.5 \times 10^4$, for example, at least about $5.7 \times 10^4$, for example, at least about $5.82 \times 10^4$. In one example, the Ka is assessed by immobilizing the protein and assessing binding of extracellular region of PI16 fused to a Fc to the immobilized protein using surface plasmon resonance.

In one example, the protein has a Kd of at least about $4.5 \times 10^{-4}$, such as, at least about $4.2 \times 10^{-4}$, for example, at least about $4.0 \times 10^{-4}$, for example, at least about $3.8 \times 10^{-4}$, for example, at least about $3.72 \times 10^{-4}$. In one example, the Kd is assessed by immobilizing the extracellular region of PI16 fused to a Fc and assessing binding of the protein (e.g., a Fab) to the immobilized protein using surface plasmon resonance.

In one example, the protein has a Kd of at least about $2.5 \times 10^{-4}$, such as, at least about $2.2 \times 10^{-4}$, for example, at least about $2.0 \times 10^{-4}$, for example, at least about $1.8 \times 10^{-4}$, for example, at least about $1.49 \times 10^{-4}$. In one example, the Kd is assessed by immobilizing the protein and assessing binding of extracellular region of PI16 fused to a Fc to the immobilized protein using surface plasmon resonance.

In one example, the protein does not detectably bind mouse PI16.

In one example, the protein binds human PI16.

In one example, the variable region in the protein of the invention is an antibody heavy chain variable region ($V_H$) or an antibody light chain variable region ($V_L$).

Alternatively, the protein comprises at least two of the variable regions, wherein one of the variable regions is an antibody heavy chain variable region ($V_H$) and another of the variable region is an antibody light chain variable region ($V_L$). For example, the protein comprises a Fv in which the $V_L$ binds to the $V_H$ to form an antigen binding site. The $V_L$ and the $V_H$ which form the antigen binding site can be in a single polypeptide chain (e.g., in a scFv) or in different polypeptide chains (e.g., in an antibody or a diabody).

Preferably, the protein is an antibody, such as a monoclonal antibody. In one example, the protein is an antibody comprising an antibody heavy chain variable region ($V_H$) or an antibody light chain variable region ($V_L$) as discussed herein according to any example.

In one example of the invention, the variable region(s) is(are) human variable region(s). For example, an antibody of the invention may be a human antibody.

In another example, the variable region is a non-human variable region, or wherein the variable region comprises three complementarity determining regions of a non-human variable region. For example, the protein may be a chimeric protein or antibody, a de-immunized protein or antibody or a humanized protein or antibody.

In one example, the non-human variable region is from the antibody produced by a hybridoma designated CRCBT-02-001 deposited with the ATCC under Accession Number PTA-10685.

In one example, the protein comprises a heavy chain variable region comprising CDRs of a heavy chain variable region comprising a sequence set forth in SEQ ID NO: 8 and comprising CDRs of a light chain variable region comprising a sequence set forth in SEQ ID NO: 10. CDRs may be defined according to any known method, e.g., as described herein. In one example, the CDRs comprise the sequences shown in FIG. 21.

In one example, the protein comprises a heavy chain variable region comprising a sequence at least about 80% or 85% or 90% or 91% or 92% or 93% or 94% or 95% or 96% or 97% or 98% or 99% identical to the sequence set forth in SEQ ID NO: 8 and comprising a light chain variable region comprising a sequence at least about 80% or 85% or 90% or 91% or 92% or 93% or 94% or 95% or 96% or 97% or 98% or 99% identical to the sequence set forth in SEQ ID NO: 10.

In one example, the protein comprises a heavy chain variable region comprising a sequence set forth in SEQ ID NO: 8 and comprising a light chain variable region comprising a sequence set forth in SEQ ID NO: 10.

In the case of any difference between the sequence of the heavy chain variable region set forth in SEQ ID NO: 8 and/or the light chain variable region set forth in SEQ ID NO: 10 and the sequence(s) of that(those) region(s) in the antibody produced by a hybridoma designated CRCBT-02-001 deposited with the ATCC under Accession Number PTA-10685, the sequence of the antibody produced by CRCBT-02-001 will take precedence.

The present invention also provides an isolated protein, which is an antibody produced by a hybridoma designated CRCBT-02-001 deposited with the ATCC under Accession Number PTA-10685.

In one example, the protein of the invention inhibits or prevents Treg cell function.

In another example, the protein of the invention activates or enhances Treg cell function.

In some examples of the invention, the protein has a compound conjugated thereto. Exemplary compounds are selected from the group consisting of a radioisotope, a detectable label, a therapeutic compound, a colloid, a toxin, a nucleic acid, a peptide, a protein, a compound that increases the half life of the protein in a subject and mixtures of two or more thereof.

The present invention additionally provides a composition comprising the protein of the invention and a pharmaceutically acceptable carrier.

The present invention also provides a solid support or semi-solid support having immobilized thereon the protein of the invention.

The present invention additionally provides an isolated nucleic acid encoding a protein of the invention. An exemplary nucleic acid encoding a $V_H$ of an antibody produced by a hybridoma designated CRCBT-02-001 deposited with the ATCC under Accession Number PTA-10685 comprises a sequence set forth in SEQ ID NO: 8. An exemplary nucleic acid encoding a $V_L$ of an antibody produced by a hybridoma designated CRCBT-02-001 deposited with the ATCC under Accession Number PTA-10685 comprises a sequence set forth in SEQ ID NO: 10. In one example, the nucleic acid is operably linked to a promoter in an expression construct.

The present invention additionally provides an isolated cell expressing the protein of the invention. For example, the cell comprises the nucleic acid of the invention and/or the expression construct of the invention.

Alternatively, the cell is a hybridoma, for example, the hybridoma designated CRCBT-02-001 deposited with the ATCC deposited with the ATCC under Accession Number PTA-10685.

The present invention additionally provides a method for producing a protein of the invention, the method comprising expressing in a cell or cell free expression system the nucleic acid of the invention and/or the expression construct of the invention. In one example, the method comprises culturing the hybridoma designated CRCBT-02-001 deposited with the ATCC deposited with the ATCC under Accession Number PTA-10685 such that the protein is expressed. In some forms, the method additionally comprises isolating the protein.

The present invention additionally provides a method for detecting PI16 or a PI16 expressing cell in a sample, the method comprising contacting the sample with the protein of any one of the invention or the composition or the solid or semi-solid support of the invention such that the protein binds to PI16 in the sample, if present, and detecting the bound protein.

In one example, the method comprises:
(i) contacting a sample with the protein of the invention such that the protein binds to PI16 in the sample, if present;
(ii) contacting the sample with another protein that binds to a different epitope in PI16 than the protein of the invention such that the other protein binds to PI16 in the sample, if present,
and detecting one or other or both of the bound proteins.

In one example, the protein of the invention or the other protein is immobilized on a solid or semi-solid support.

In one example, the method additionally comprises determining if the PI16 expressing cell expresses CD4 and/or CD25 and/or CD127. In one example, the cell is a Treg cell. Preferably, the cell is a nTreg cell.

In another example, the cell expresses CD45RO and/or CD27 and/or CD95 and/or CCR6HLADR and/or CCR4 and/or CLA and/or expresses a low level of CD45RA and/or CD146 and/or CXCR5 and/or CD69. For example, the cell is a memory T cell, preferably a memory Treg cell (e.g., a cell expressing CD4, CD25, CD27, CD45RO, CD95, HLADR, CCR4 and CCR6 and expressing low levels of CD127 (or is CD127$^-$), CD45RA (or is CD45RA$^-$), CD146 (or is CD146$^-$), CD69 (or is CD69$^-$) and CXCR5 (or is CXCR5$^-$)). In another example, the cell is a memory T cell, preferably a memory Treg cell (e.g., a cell expressing CD4 and/or CD25 and/or low levels of CD127 and/or CD45RA).

In one preferred form of the invention, the cell is a memory nTreg cell, preferably a resting or non-activated memory nTreg cell.

In one example, the method additionally comprises detecting a cell expressing CLA. Expression of CLA indicates that the cell is capable of migrating to the skin or selectively migrates to the skin, e.g., for treating an inflammatory skin condition (such as, psoriasis).

In one example, the method additionally comprises detecting the level of methylation at Treg-specific demethylated region, wherein a reduced level or no detected methylation indicates that the cell is a Treg cell. Methods for determining the level of methylation of a nucleic acid will be apparent to the skilled person (e.g., bisulphate treatment followed by methylation-specific PCR or restriction endonuclease digestion and/or sequencing) and/or described herein.

The present invention also provides a method for distinguishing a natural regulatory T (nTreg) cell from an induced Treg (iTreg) cell, the method comprising contacting a sample comprising Treg cells with the protein of the invention or the composition of the invention or the solid support or semi-solid support of the invention such that the protein binds to Treg cells expressing PI16 in the sample and detecting a Treg cell expressing PI16, wherein the Treg cell expressing PI16 is a nTreg cell.

In one example, the method additionally comprises detecting a PI16 expressing cell that expresses CD4 and/or CD25 and/or expresses low levels of CD127.

In one example, the method additionally comprises detecting a PI16 expressing cell that expresses CD45RO and/or CD45RA and/or CD27 and/or CD95 and/or CCR6 and/or CCR4 and/or CD146 and/or CXCR5 and/or CD39 and/or CD73 and/or CD69 and/or HLADR and/or CCR5 and/or CXCR3 and/or CXCR4 and/or CLA.

In one example, the method additionally comprises detecting a cell expressing CD4, CD25, CD27, CD45RO, CD95, HLADR, CLA, CCR4 and CCR6 and expressing low levels of CD45RA, CD146, CD69 and CXCR5.

In one example, the method additionally comprises detecting an increased level of one or more proteins selected from the group consisting of LRRC32, CD33, TIGIT, IL1R1, ITGAM, NPAL2, CD88, IFNGR2 and PERP.

In one example, the method additionally comprises detecting a decreased level of one or more proteins selected from the group consisting of CD274, LASS6, ACVR2, CD200R1, CD82, CYBRD1, CYSLTR1, GPR174, NKG7, CD9, LRRN3, NRP2, GPR183, IER3, TMEM200A, LPCAT2 and ITGA1.

The present invention additionally provides a method for isolating a cell, the method comprising detecting the cell by performing the method of the invention and isolating the detected cell or distinguishing a nTreg cell by performing the method of the invention and isolating the distinguished nTreg cell.

The present invention additionally provides a method for producing a population of cells enriched for cells expressing PI16, the method comprising contacting a population of cells comprising PI16 expressing cells with the protein of the invention or the composition or the solid or semi-solid support of the invention such that the protein binds to a PI16 expressing cell in the sample and selecting cells to which the protein is bound. In one example, the enriched cells are Treg cells, e.g., cells that are CD4$^+$CD25$^+$CD127$^-$. In some forms, the method additionally comprises culturing the isolated cells.

The method of isolating the cells can additionally comprise formulating the cells with a pharmaceutically acceptable carrier to thereby produce a pharmaceutical composition.

The present invention also provides a cell isolated by a method described herein according to any example or a population of cells produced by a method as described herein according to any example.

In one example, the cell or population of cells is a natural regulatory T (Treg) cell or the population is enriched for nTreg cells.

In one example, the nTreg cells have a greater capacity to suppress an immune response following exposure to inflammatory cytokines than a Treg cell that does not express PI16.

In one example, the nTreg cells have a greater capacity to suppress an immune response at a site of inflammation in a subject.

In one example, the nTreg cells have a greater capacity to suppress an immune response than an induced Treg (iTreg) cell following exposure to inflammatory cytokines, e.g., IL-1 beta and IL-6.

The present disclosure also provides a population of cells enriched for regulatory T (Treg) cells expressing PI16 and one or more proteins selected from the group consisting of CLA, HLADR and CCR4.

In one example, the cells express CCR4 and/or CCR6.

In one example, the cells additionally express CD4 and CD25 and, optionally low or undetectable levels of CD127.

In one example, the cells additionally express CD27 and/or CD95 and/or CCR6.

In one example, the cells express low levels of CD45RA (or is CD45RA$^-$), CD146 (or is CD146$^-$) and CXCR5 (or is CXCR5$^-$))

In one example, the cells are capable of migrating to a site of inflammation in a subject. In one example, the cells preferentially migrate to a site of inflammation. In one example, the cells preferentially migrate to a site of $T_H17$-mediated inflammation.

In one example, the cells are capable of migrating to skin (e.g., at a site of inflammation in skin) in a subject. In one example, the cells preferentially migrate to skin (e.g., at a site of inflammation in skin). In one example, the cells preferentially migrate to a site of $T_H17$-mediated skin inflammation.

The present disclosure also provides a population of cells enriched for regulatory T (Treg) cells reactive with an antibody produced by a hybridoma designated CRCBT-02-001 deposited with the ATCC under Accession Number PTA-10685.

The present invention also provides a method for diagnosing and/or prognosing a condition in a subject, the method comprising performing the method of the invention to detect PI16 or a PI16 expressing cell in a sample from a subject, wherein detection of PI16 or a PI16 expressing cell or failure to detect PI16 or a PI16 expressing cell is diagnostic or prognostic of the condition.

In one example, the method comprises
(i) determining or estimating the amount of PI16 or PI16 expressing cells in the sample or a portion thereof;
(ii) comparing the amount of PI16 or PI16 expressing cells in a sample from a normal and/or healthy subject;
wherein an increased or decreased amount of PI16 or PI16 expressing cells at (i) compared to the amount of PI16 or PI16 expressing cells in the sample from a normal and/or healthy subject indicates that the subject suffers from the condition.

In another example, the present invention provides a method for monitoring the efficacy of treatment of a condition the method comprising:
(i) determining or estimating the amount of PI16 or PI16 expressing cells in the sample or a portion thereof by performing a method of the invention;
(ii) comparing the amount of PI16 or PI16 expressing cells in a sample from a control subject,
wherein:
(a) the control sample is from a normal or healthy subject and a similar amount of PI16 or PI16 expressing cells at (i) compared to the amount of PI16 or PI16 expressing cells in the control sample indicates that the subject is responding to treatment for the condition;
(b) the control sample is from a normal or healthy subject and an increased or decreased amount of PI16 or PI16 expressing cells at (i) compared to the amount of PI16 or PI16 expressing cells in the control sample indicates that the subject is not responding to treatment for the condition;
(c) the control sample is from the subject at an earlier point in time (e.g., prior to commencing treatment) and a similar amount of PI16 or PI16 expressing cells at (i) compared to the amount of PI16 or PI16 expressing cells in the control sample indicates that the subject is not responding to treatment for the condition; or
(d) the control sample is from the subject at an earlier point in time (e.g., prior to commencing treatment) and an increased or decreased amount of PI16 or PI16 expressing cells at (i) compared to the amount of PI16 or PI16 expressing cells in the control sample indicates that the subject is responding to treatment for the condition.

In a preferred example, the condition is a Treg cell-associated condition.

For example:
(i) the Treg-associated condition is autoimmune disease which is diagnosed/prognosed by detecting reduced levels of PI16 expressing Treg cells or a reduced level of PI16 in the sample;
(ii) the Treg-associated condition is an inflammatory condition which is diagnosed/prognosed by detecting increased levels of PI16 expressing Treg cells or an increased level of PI16 in the sample; or
(iii) the Treg-associated condition is a cancer, which is diagnosed/prognosed by detecting increased levels of PI16 expressing Treg cells or an increased level of PI16 in the sample.

In one example, the Treg-associated condition is an inflammatory condition which is diagnosed/prognosed by detecting modified percentage of PI16 expressing Treg cells in a sample from the site of inflammation. The modified percentage of cells can be an increased or decreased level, and is preferably a decreased level. In this regard the percentage of PI16 expressing Treg cells is preferably expressed as the percentage of PI16$^+$ Treg cells to PI16$^-$ Treg cells.

In one example, the Treg-associated condition is an inflammatory condition which is diagnosed/prognosed by detecting a modified ratio of PI16$^+$ Treg cells to PI16$^-$ Treg cells in a sample from the site of inflammation. The modified ration of cells can be an increased (increased number of PI16$^+$ Treg cells to PI16$^-$ Treg cells) or decreased (decreased number of PI16$^+$ Treg cells to PI16$^-$ Treg cells) level, and is preferably a decreased level.

In one example, the site of inflammation comprises synovial fluid. In one example, the inflammatory condition is arthritis. In one example, the inflammatory condition is juvenile idiopathic arthritis.

The protein of the invention also facilitates imaging methods, e.g., detecting PI16 or PI16 expressing cells in vivo. Accordingly, the present invention also provides a method for localising and/or detecting and/or diagnosing and/or prognosing condition associated with a PI16 expressing cell, the method comprising detecting a compound bound to a protein of the invention in vivo, wherein detection of the bound compound localises and/or detects and/or diagnoses and/or prognoses the condition.

In one example, the invention provides a method for localising and/or detecting and/or diagnosing and/or prognosing condition associated with a PI16 expressing cell, the method comprising:
(i) administering to a subject a protein of the invention conjugated to a compound (e.g., a detectable label) such that the protein binds to the PI16 expressing cell, if present; and
(ii) detecting the compound bound to the protein in vivo, wherein detection of the bound compound localises and/or detects and/or diagnoses and/or prognoses the condition.

In one example, the method additionally comprises providing the result of a diagnostic/prognostic/localising/detecting method described herein, e.g., in paper or machine readable form.

The present invention also provides a method of treating or preventing a condition, the method comprising obtaining the results of a diagnostic or prognostic method described herein and administering a suitable therapeutic or prophylactic compound. For example, if the condition is cancer, the compound may be a chemotherapeutic compound; or if the condition is an autoimmune condition, the compound may be an anti-inflammatory, and anti-TNF compound, an anti-CD20 compound, etc.

The present invention also provides a method of treating or preventing a condition, the method comprising administering a protein of the invention or a composition of the invention or a solid or semi-solid support of the invention or the cell(s) isolated by the method of the invention or a population of cells of the invention to a subject in need thereof.

In one example, the method treats or prevents a condition associated with reduced regulatory T (Treg) cell numbers or activity, and/or induces immunosuppression, and/or reduces CTL or Thelper cell activity in a subject, the method comprising:
(i) isolating a population enriched for Treg cells by performing a method of the invention or obtaining a population of cells of the invention; and
(ii) administering the cells at (i) to the subject.

In one example, the method comprises administering a protein of the invention that activates or enhances Treg cell function.

In another example, the method treats or prevents a condition associated with reduced regulatory T (Treg) cell numbers or activity, and/or induces immunosuppression, and/or reduces CTL or Thelper cell activity in a subject, the method comprising administering or implanting the solid support or semi-solid support of the invention at a site within a subject such that the protein binds to a Treg cell and immobilizes the cell at the site. In one example, the solid or semi-solid support has Treg cells immobilized thereon prior to administration or implantation.

For example, the subject suffers from, or is at risk of developing, an autoimmune disease and/or the subject is undergoing or about to undergo or has undergone a transplant.

In another example, the condition is associated with regulatory T (Treg) cell-mediated suppression of a subject's immune system, and the method comprises administering to the subject a protein of the invention or a composition of the invention or the solid or semi-solid support of the invention.

For example, the subject suffers from a cancer, and administering the protein or composition or solid or semi-solid support reduces Treg cell numbers and/or activity in the subject and allows the subject's immune system to more effectively respond to the cancer. In one example, the protein kills Treg cells and/or delivers a toxic compound to Treg cells and/or inhibits Treg cell function.

In another example, the present invention provides a method for treating or preventing a condition, the method comprising contacting blood from a subject with the solid support or semi-solid support of the invention such that the protein binds to cells expressing PI16 and removes the cell from the blood. Such a method is useful for depleting Treg cells from the blood of a subject and inducing an immune response or allowing an immune response to occur. In this example, the solid or semi-solid support can be, for example, a support used for apheresis. Preferably, the treated blood is returned to the subject.

The present invention also provides a method for modulating an immune response in a subject, the method comprising administering to a subject in need thereof a protein of the invention or a composition of the invention or the solid or semi-solid support of the invention or the cells isolated by a method of the invention or a population of cells of the invention.

In one example, the method of the previous paragraph is for inducing, stimulating or enhancing an immune response in a subject, and the method comprises administering to a subject in need thereof a protein of the invention or a composition of the invention.

In another example, the method comprises contacting blood from a subject with the solid support or semi-solid support of the invention such that the protein binds to a regulatory T (Treg) cell and removes the cell from the blood.

In one example, the immune response is production of antibodies and/or a cytotoxic T cell-mediated immune response.

In one example of the method for inducing, stimulating or enhancing an immune response in a subject the protein is administered prior to or at the time of administration of a composition comprising an immunogenic compound.

In another example, the method comprises administering a Treg cell isolated by a method of the invention to thereby suppress or prevent an immune response. In one example, the Treg cell is administered with a cell or tissue, e.g., bone marrow to thereby reduce or prevent a graft-versus-host or a host-versus-graft response. The Treg cells can be from the subject being treated or another subject, preferably a healthy subject.

The present invention also provides a method for delivering a compound to a PI16 expressing cell, the method comprising contacting the cell with a protein of the invention which is conjugated to a compound. In one example, the cell is contacted in vivo by administering the protein to a subject.

The present invention also provides for use of a protein of the invention or a composition of the invention or the solid or semi-solid support of the invention or the cell(s) isolated by performing a method of the invention or a population of cells of the invention in medicine.

For example, the invention provides for use of the protein, composition, solid or semi-solid support or cells in the manufacture of a medicament for treating a condition associated with PI16 expression. In one example, the condition is a Treg cell-associated condition.

In one example, the medicament comprises the cell(s) isolated by performing the method of the invention and is for treating an autoimmune disease and/or the subject is undergoing or about to undergo or has undergone a transplant.

In one example, the medicament comprises the protein or the composition and the condition is associated with Treg cell-mediated suppression of a subject's immune system.

The present invention also provides for use of a protein of the invention or a composition of the invention or the solid or semi-solid support of the invention or the cell(s) isolated by performing a method of the invention in the manufacture of a medicament for modulating an immune system in a subject.

The present inventors have also shown that PI16 expressing Treg cells express chemokine receptors also expressed by $T_H17$ cells, e.g., CCR4 and/or CCR6 and migrate in response to ligands for CCR4 and/or CCR6. Accordingly, this makes PI16 expressing Treg cells particularly useful for treating $T_H17$-mediated conditions, since these cells will migrate to the same sites as $T_H17$ cells and suppress an inflammatory response.

Accordingly, the present disclosure also provides a method of treating a $T_H17$-mediated condition comprising administering a regulatory T (Treg) cell expressing PI16.

In one example, the Treg cell additionally expresses CCR4 and/or CCR6.

In one example, the Treg cells are administered systemically and migrate to the site of the $T_H17$-mediated condition.

The present inventors have also shown that Treg cells expressing PI16 (e.g., isolated using CRCBT-02-001) express CLA, indicating that the cells can or preferentially migrate to skin. Accordingly, the present disclosure also provides a method of treating a skin condition comprising administering a regulatory T (Treg) cell expressing PI16.

In one example, the Treg cell additionally expresses CCR4 and/or CCR6.

In one example, the Treg cells are administered systemically and migrate to the site of the skin condition.

In one example, the skin condition is an inflammatory skin condition, e.g., a $T_H$-17-mediated skin condition.

The present inventors have also demonstrated that PI16-expressing Treg cells maintain their ability to suppress effector T cells after exposure to inflammatory cytokines, whereas PI16$^-$ iTreg cells do not. Accordingly, PI16 expressing Treg cells can be directly administered to a site of an inflammatory response to provide therapeutic benefit.

Accordingly, the present disclosure also provides a method of treating an inflammatory condition comprising administering regulatory T (Treg) cell expressing PI16 to a site of the inflammation.

In one example, the site of inflammation is characterised by expression of interleukin (IL) 1β and/or IL6.

In one example, the inflammatory condition is juvenile idiopathic arthritis.

Suitable cells for administering to a subject include a population of cells enriched for PI16 expressing Treg cells. In one example, the population of cells is enriched for Treg cells reactive with CRCBT-02-001 deposited with the ATCC under Accession Number PTA-10685.

The present inventors have also shown that the percentage of PI16 expressing Treg cells is reduced at a site of inflammation, e.g., in juvenile idiopathic arthritis, whereas the total number of CD4$^+$CD25$^{++}$CD127$^-$ Treg cells is increased.

Accordingly, the present disclosure also provides a method of diagnosing a Treg-associated inflammatory condition, the method comprising detecting a percentage of PI16 expressing Treg cells in a sample from the site of inflammation, wherein a reduced percentage of PI16 expressing Treg cells is indicative of the condition. In this regard the percentage of PI16 expressing Treg cells is preferably expressed as the percentage of PI16$^+$ Treg cells to PI16$^-$ Treg cells.

In another example, the disclosure provides a method of diagnosing a Treg-associated inflammatory condition, the method comprising determining the ratio of PI16$^+$ Treg cells to PI16$^-$ Treg cells in a sample from the site of inflammation, wherein a reduced ratio of PI16$^+$ Treg cells to PI16$^-$ Treg cells is indicative of the condition.

In one example, the site of inflammation is synovial fluid.

In one example, the condition is arthritis.

In one example, the condition is juvenile idiopathic arthritis.

In one exemplary form of the diagnostic method, the level of PI16 expressing Treg cells is reduced compared to the level in the subject's circulation and/or in a normal or healthy subject's circulation.

The present invention also provides a method for distinguishing a natural regulatory T (nTreg) cell from an induced Treg (iTreg) cell, the method comprising detecting a Treg cell expressing an increased level of one or more proteins selected from the group consisting of LRRC32, CD33, TIGIT, IL1R1, ITGAM, NPAL2, CD88, IFNGR2 and PERP, wherein the Treg cell expressing an increased level of the protein is a nTreg cell.

The present invention also provides a method for distinguishing a natural regulatory T (nTreg) cell from an induced Treg (iTreg) cell, the method comprising detecting a Treg cell expressing a reduced level of one or more proteins selected from the group consisting of CD274, LASS6, ACVR2, CD200R1, CD82, CYBRD1, CYSLTR1, GPR174, NKG7, CD9, LRRN3, NRP2, GPR183, IER3, TMEM200A, LPCAT2, ITGA1, wherein the Treg cell expressing a reduced level of the protein is a nTreg cell.

In one example, the increased or reduced level of expression is relative to the level expressed by an iTreg cell or a CD25$^-$ cell.

The present invention also provides a method for distinguishing an induced regulatory T (iTreg) cell from a natural Treg (nTreg) cell, the method comprising detecting a Treg cell expressing an increased level of one or more proteins selected from the group consisting of TIGIT, CD88, IFNGR2, PERP, LASS6, GPR174, NKG7, CD9, LRRN3, MRP2, GPR183, IER3, TMEM200A, LPCAT2 and ITGA1 wherein the Treg cell expressing an increased level of the protein is an iTreg cell.

The present invention also provides a method for distinguishing an induced regulatory T (iTreg) cell from a natural Treg (nTreg) cell, the method comprising detecting a Treg cell expressing a reduced level of one or more proteins selected from the group consisting of LRRC32, CD33, IL1R1, ITGAM, NPAL2, CD274, CD82 and CYBRD1, wherein the Treg cell expressing a reduced level of the protein is a iTreg cell.

In one example, the increased or reduced level of expression is relative to the level expressed by a CD25$^-$ cell.

The present invention also provides an isolated protein comprising an extracellular domain of PI16 fused to an immunoglobulin Fc region. For example, the extracellular domain of PI16 fused to a Fc region from an antibody, e.g., an IgG1 antibody. In one example, the extracellular domain of PI16 comprises or consists of the sequence set forth in SEQ ID NO: 40.

BRIEF DESCRIPTION OF THE DRAWINGS

FIG. 1 is an amino acid sequence alignment of PI16 protein from *Homo sapiens* (SEQ ID NO: 1), *Mus musculus* (SEQ ID NO: 2), *Rattus novigenicus* (SEQ ID NO: 3) and *Pan troglodytes* (SEQ ID NO: 4). Asterisks indicate identical amino acids. ":" and "." Indicate conserved amino acid residues.

001 positive CD4+ T cells express CD25 (all CD4+ T cells analyzed). Panel I shows that about three quarters of the CD4+/CRCBT-002-001 positive cells express CD127 (all CD4+ T cells analyzed). Panel J shows that of all CD4+ CRCBT-002-001 positive cells approximately 20% express the Treg phenotype CD25+CD127− (all CD4+CRCBT-02-001+ cells included).

Figure 12:
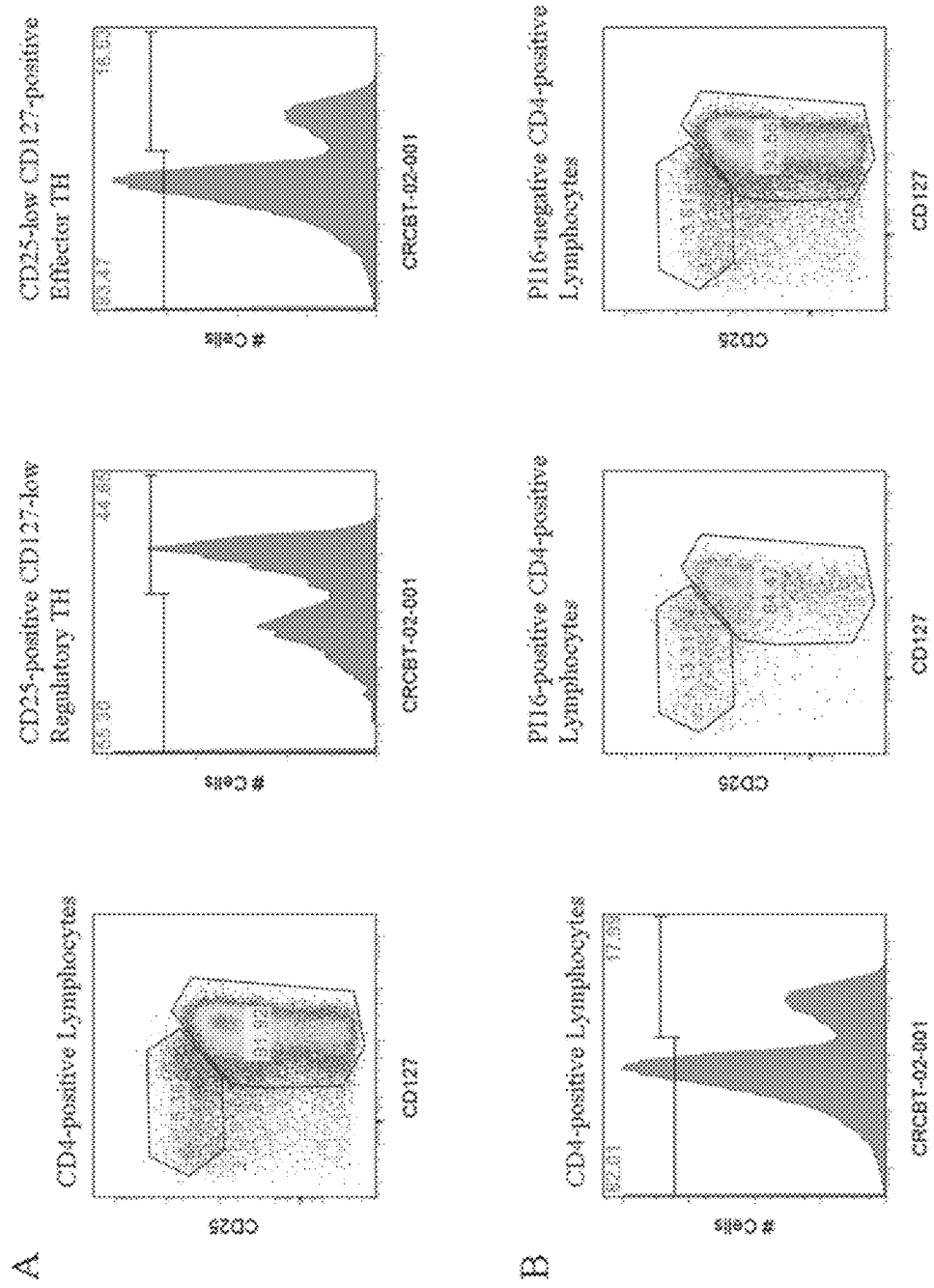

FIG. 12 includes a series of graphical representations showing expression of cell surface PI16 by Treg cell and Th cell subsets of CD4-positive lymphocytes, demonstrated using by the anti-PI16 monoclonal antibody CRCBT-02-001. Only the CD4-positive lymphocytes are shown. The panel labelled "A" shows cell surface PI16 is present on a higher proportion of CD25-bright/CD127-dim Treg (upper row, centre panel) than CD127-positive Th cells (upper row, right panel). The panel labelled "B" shows that the PI16-positive subset of CD4-positive lymphocytes contains a higher proportion of CD25-bright/CD127-dim Treg (lower row, centre panel) than the PI16-negative subset (lower row, right panel). One representative experiment shown with n>100.

Figure 13:
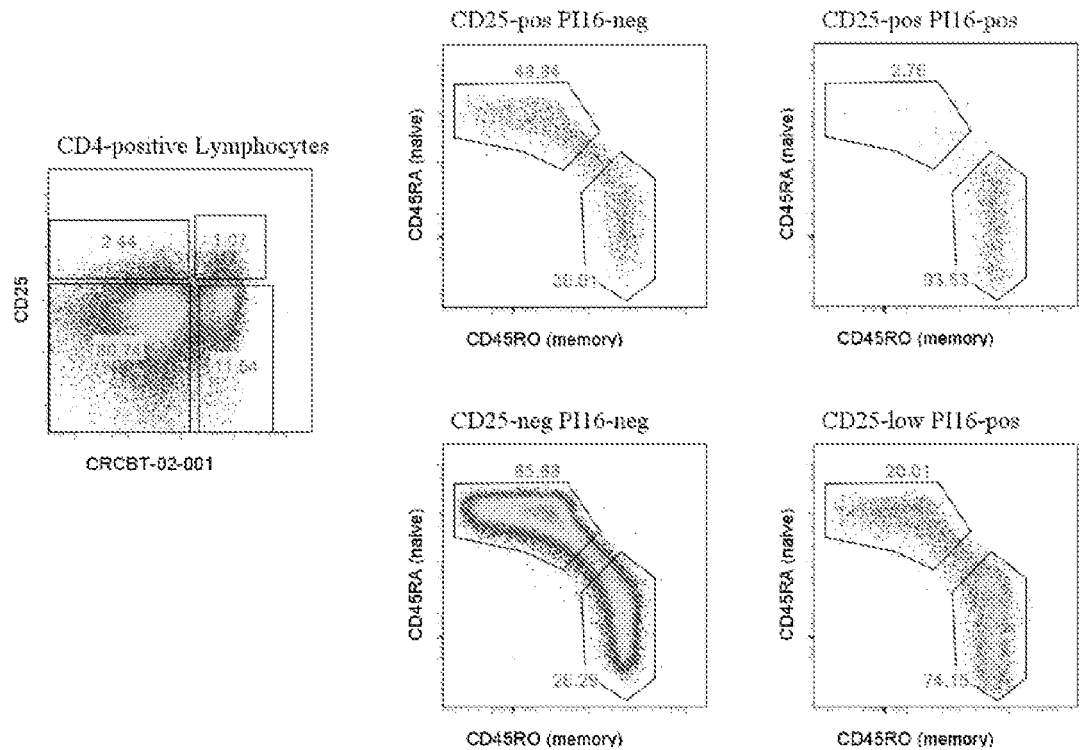

FIG. 13 includes a series of graphical representations showing expression of naive/memory phenotype by subsets of CD4-positive lymphocytes defined using the co-expression of CD25 and PI16 (CRCBT-02-001). Only the CD4-positive lymphocytes are shown. Quadrants having CD25negPI16neg, CD25posPI16neg, CD25negPI16pos and CD25posPI16pos are shown at the left hand side of the Figure. Cell surface expression of CD45RA and/or CD45RO in each quadrant is also depicted as indicated. The co-expression of CD25 and PI16 (the CD25positive/PI16-positive fraction) identifies a subset of Tregs which are cells with a "memory" (CD45RA-negative/CD45RO-positive) phenotype.

Figure 14:
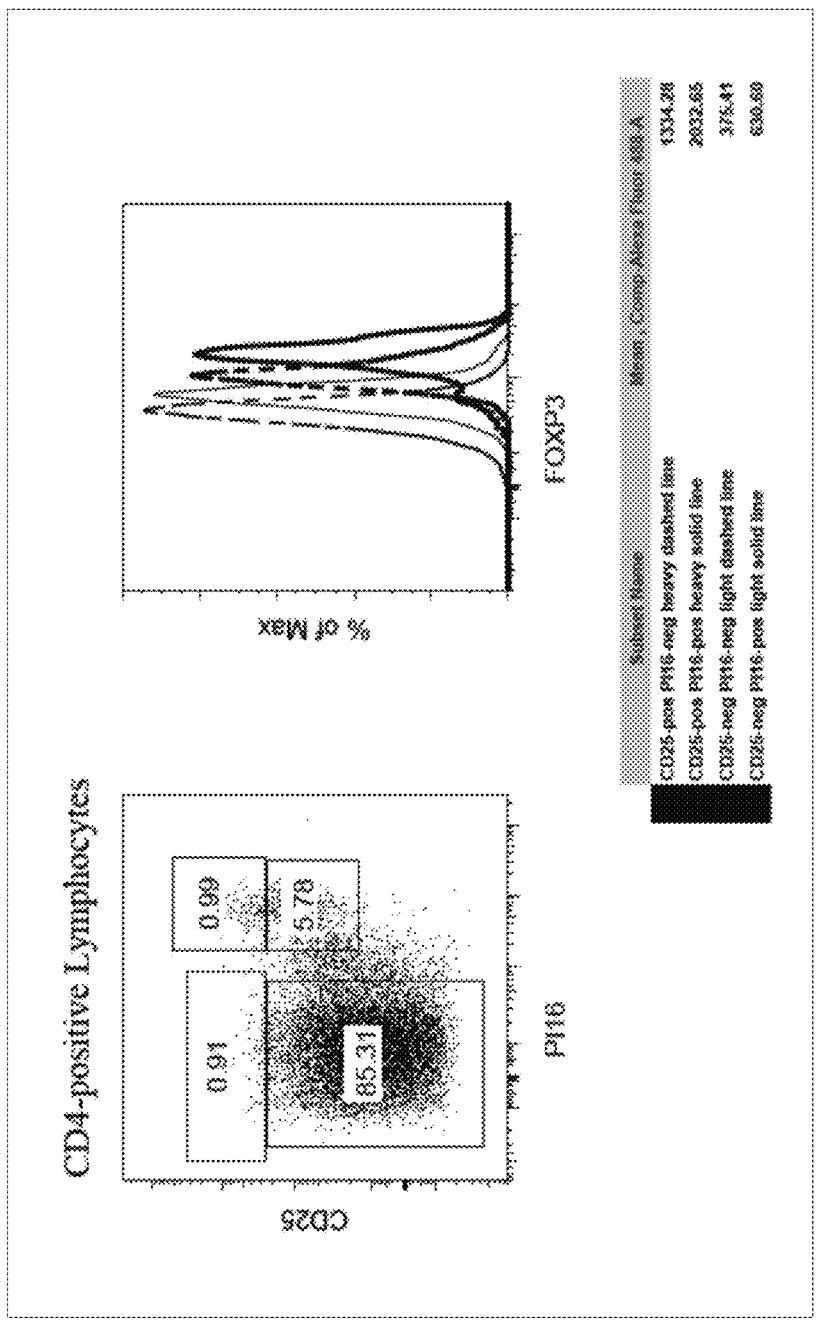

FIG. 14 is a series of graphical representations showing staining of freshly isolated adult CD4+ T cells with CRCBT-02-001 supernatant together with CD25 or FoxP3. CD25 and CRCBT-02-001 secreted antibody staining is shown in the left hand panel with boxes indicating CD25 positive or negative or CRCBT-02-001 secreted antibody positive or negative. The right hand panel indicates FoxP3 expression levels for each boxed cell population. The cells in the CD25-positive/PI16-positive Treg fraction (heavy solid line; MFI 1457) express higher levels of FoxP3 than cells in the CD25-positive/PI16-negative Treg fraction (dashed line; MFI 1062). FoxP3 staining was lowest in the CD25-negative/PI16-positive (light solid line; MFI 612) and CD25-negative/PI16-negative (dotted line; MFI 480) populations. One representative experiment shown with n>50.

Figure 15:
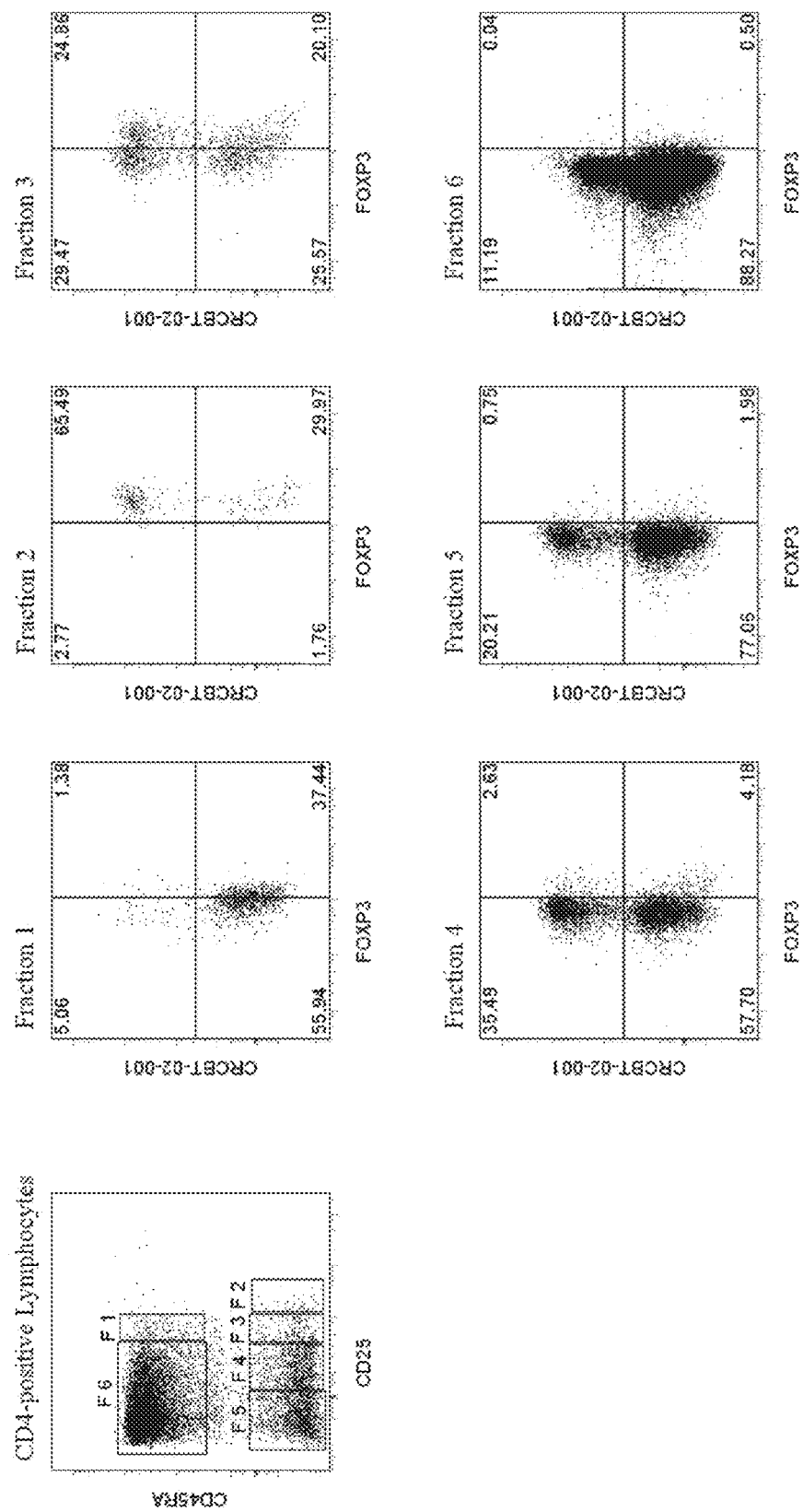

FIG. 15 includes a series of graphical representations showing expression of PI16 and FoxP3 by six fractions of naive and memory Treg using the gating strategy described by Miyara et al., 2009. Only the CD4-positive lymphocytes are shown. The fractions of CD4-positive lymphocytes (Fr 1 to Fr 6) were defined using the expression of CD45RA and CD25 as shown in the right hand panel of the Figure. The expression of PI16 (CRCBT-02-001) and FoxP3 by the cells in each of these fractions is shown as labeled. In each fraction, the PI16+ and PI16− cells express similar levels of FoxP3, with the highest levels of FoxP3 expression seen in the memory Treg (Fraction 2). One representative experiment shown with n=3.

FIG. 16 includes a series of graphical representations showing detection of memory Treg cells by CRCBT-02-001 monoclonal antibody. CD4+ cells were labelled with antibodies to CRCBT-02-001 monoclonal antibody and either CD45RA (top panel) or CD45R0 (bottom panel). Results indicate that PI16 is expressed by memory T cells (CD45R0+CD45RA−/low).

Figure 17:
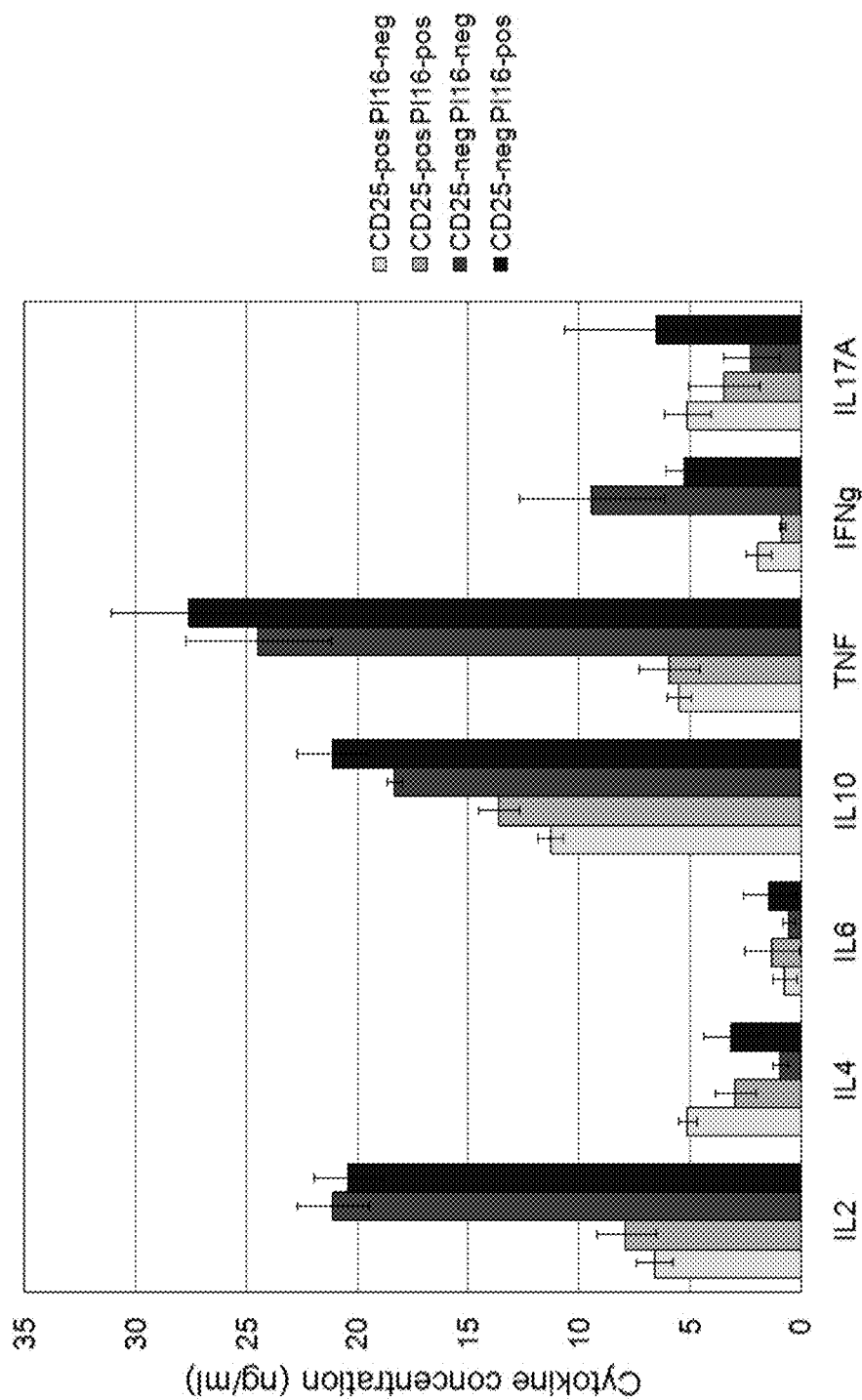

FIG. 17 is a graphical representation showing the cytokine expression profile of subsets of CD4-positive lymphocytes defined using the co-expression of CD25 and PI16, determined using a $T_H1/T_H2/T_H17$ cytometric bead array. The four populations of cells were sorted using the gates shown in FIG. 14. The graph shows the concentration of each cytokine secreted by the isolated cell population following a 3-day stimulation using CD3/CD28 beads. The error bars show the SEM for three replicate experiments.

Figure 18:
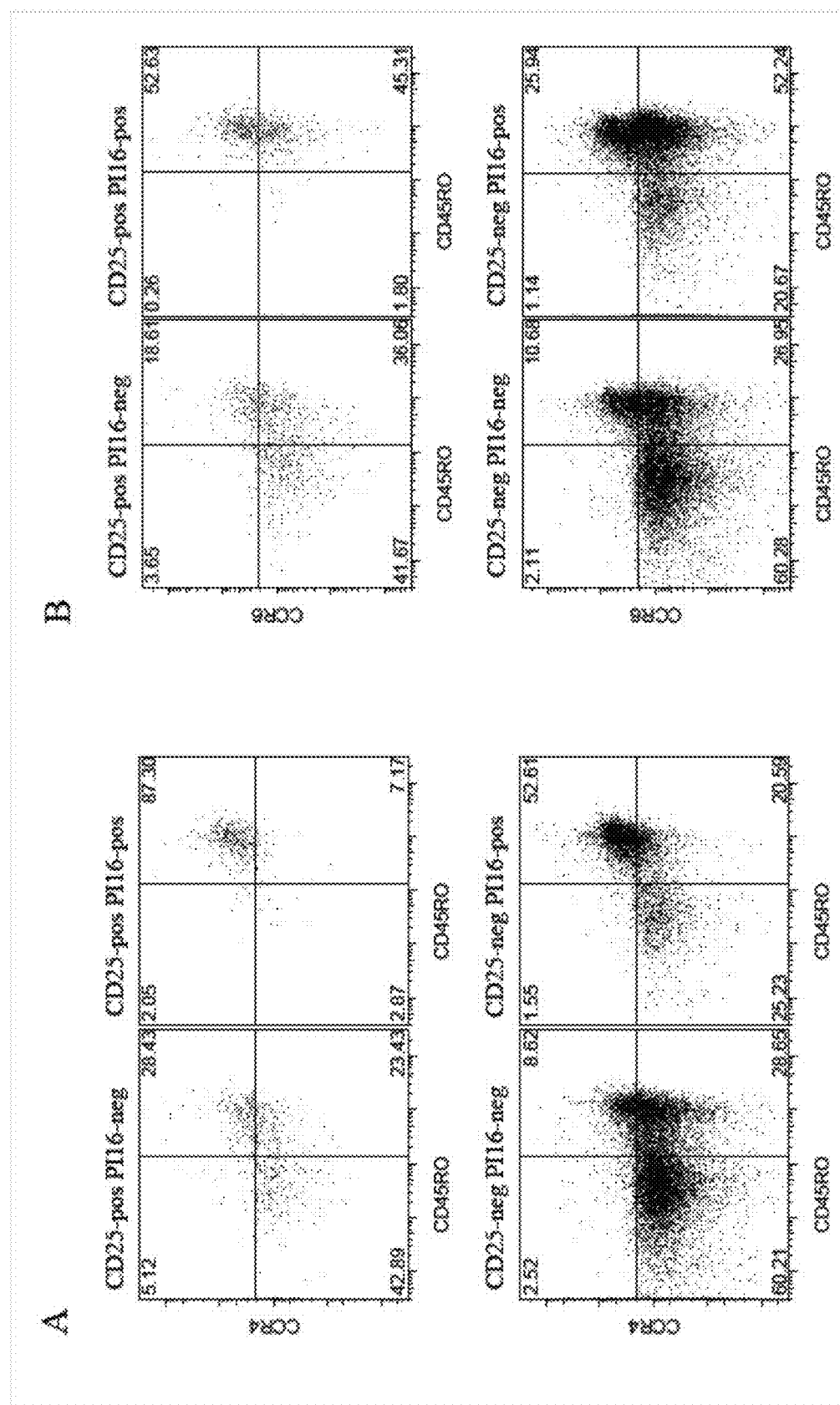

FIG. 18 includes a series of graphical representations showing expression of chemokine receptors CCR4 and CCR6 by subsets of memory CD4-positive lymphocytes defined using the co-expression of CD25 and PI16 (CRCBT-02-001). Only the CD4-positive lymphocytes are shown. The four subsets of CD4-positive lymphocytes were defined as shown in FIG. 14, and the memory fraction of each was identified by the expression of CD45RO. The panel labelled "A" shows expression of CD45RO and CCR4 by the four subsets defined using the co-expression of CD25 and PI16. The panel labelled "B" shows expression of CD45RO and CCR6 by the four subsets defined using the co-expression of CD25 and PI16. One representative experiment shown with n=3.

Figure 19:
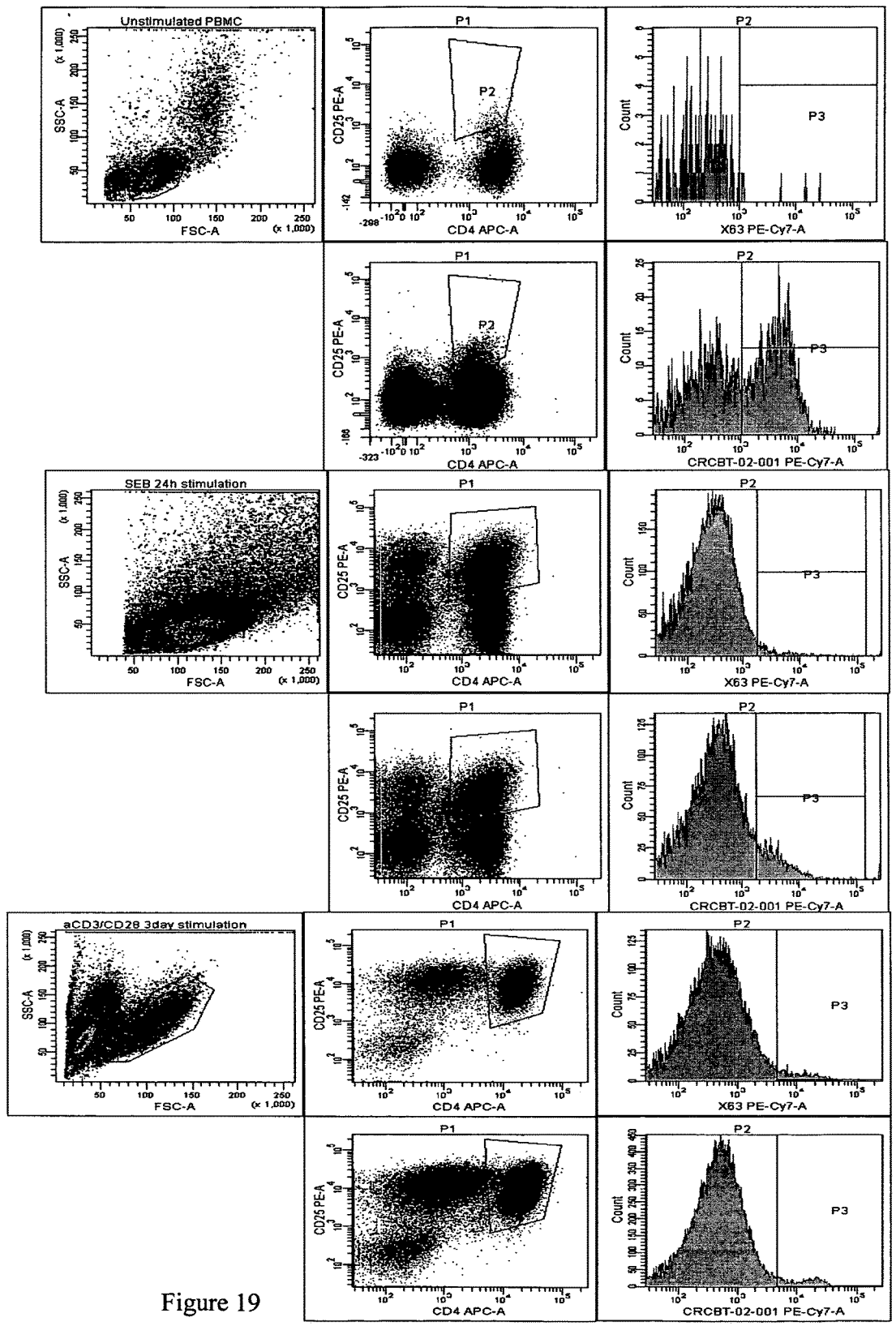

FIG. 19 is a series of graphical representations showing CRCBT-02-001 supernatant immunoreactivity on unstimulated peripheral blood mononuclear cells (PBMC) (top two rows of panels), SEB-stimulated PBMC (18 h) (centre two rows of panels) and a-CD3/a-CD28-stimulated PBMC (3 d) (bottom two rows of panels). X63 supernatant has been used as IgG1 control. All lymphocytes (P1) have been included and CD4+/CD25+ have been analyzed (P2). Expression of CD25 increases during stimulation whereas immunoreactivity of CRCBT-02-001 decreases.

Figure 20:
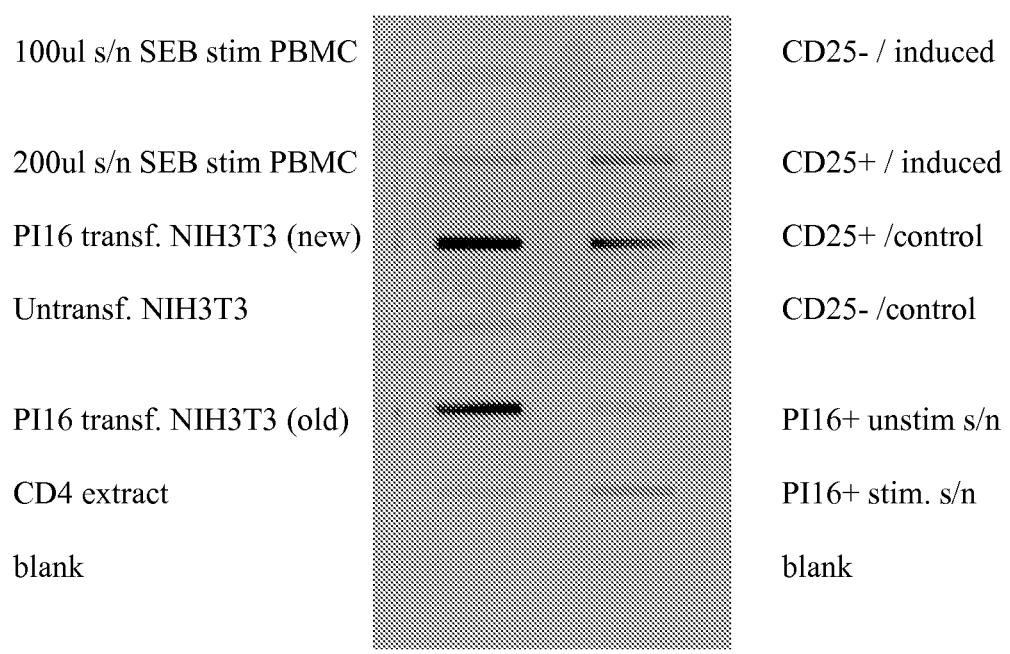

FIG. 20 is a photographic representation showing results of slot blot analysis of PI16 expression using CRCBT-02-001 supernatant. Cell lysates and supernatants of stimulated PBMC and CD4+CD25+PI16+ were incubated with CRCBT-02-001 supernatant. 100 µl s/n SEB stim=PBMC have been stimulated with SEB over night, supernatants have been collected and 100 µl have been used undiluted. 200 µl s/n SEB stim=the same with 200 µl have been used undiluted. PI16 transf. NIH3T3=NIH3T3 cells transfected with PI16 and whole cell lysate was prepared, 1:100 was used. Untransf. NIH3T3=unstranfected NIH3T3 cells were lysed in RIPA buffer, spun and extract was used 1:100. PI16 transf. NIH3T3 (old)=whole cell lysate was prepared some time ago. CD4 extract=CD4 cells were lysed in RIPA buffer, spun and extract was used 1:100. CD25−/induced=CD4+CD25− cells were stimulated with CD3/CD28 beads including TGFβ for 7 days and rested for 48 h. Cells were lysed in NP40 buffer, spun and extract was used undiluted. CD25+/induced=CD4+CD25+ cells were treated as CD25−/induced. CD25+/control=CD4+CD25+ cells were stimulated with CD3/CD28 beads without TGFβ for 7 days and rested for 48 h. Cells were lysed in NP40 buffer, spun and extract was used undiluted. CD25−/control=CD4+CD25− cells were treated as CD25+/control. PI16+ unstim s/n=CD4+CD25+ PI16+ cells were sorted and cultured without stimulation for 4 days. Supernatants were collected and used undiluted. PI16+ stim s/n=CD4+CD25+PI16+ cells were sorted and stimulated with CD3/CD28 beads for 4 days. Supernatants were collected and used undiluted.

FIG. 21 shows the amino acid sequence of the $V_H$ and the $V_L$ of CRCBT-02-001 with CDRs determined by one technique highlighted in bold.

Figure 22A:
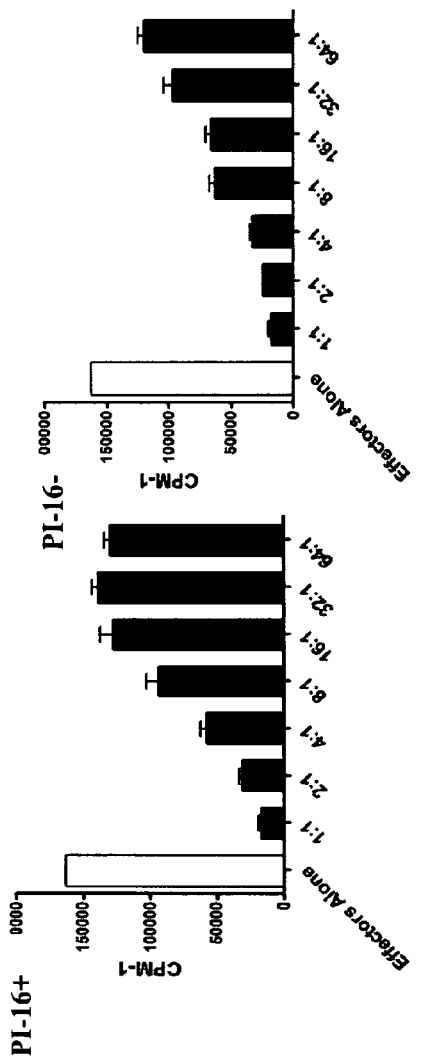

FIG. 22A includes two graphical representations showing results of a representative thymidine incorporation suppressor assay using expanded cord blood Treg cells sorted based on PI16 expression using CRCBT-02-001. The graph on the right depicts results using PI16+ Treg cells. The graph on the left depicts results using PI16- Treg cells. The ratio of the number of Treg cells to effector cell is indicated on the X-axis.

Figure 22B:
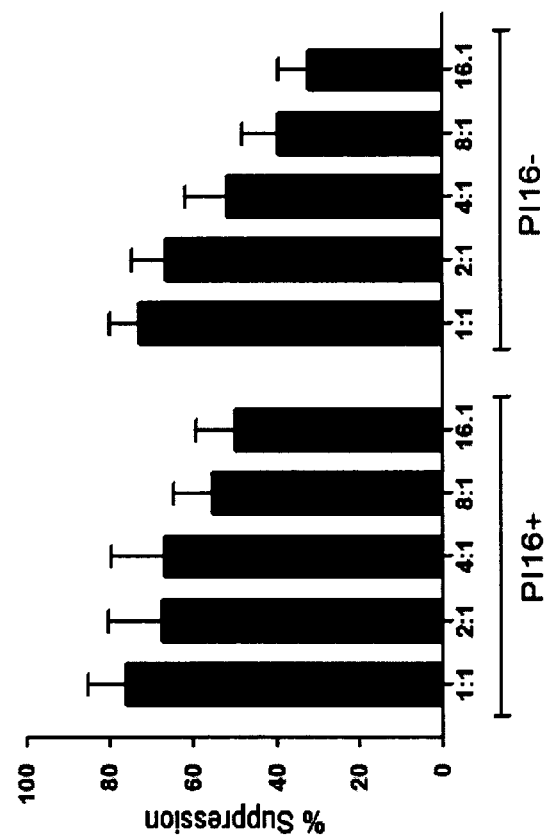

FIG. 22B is a graphical representation showing accumulative results of thymidine incorporation suppressor assays (n=6). The ratio of the number of Treg cells to effector cell is indicated on the X-axis. Treg cells isolated with CRCBT-02-001(PI-16+) and PI-16- Treg cells suppress proliferation of effector cells.

Figure 23A:
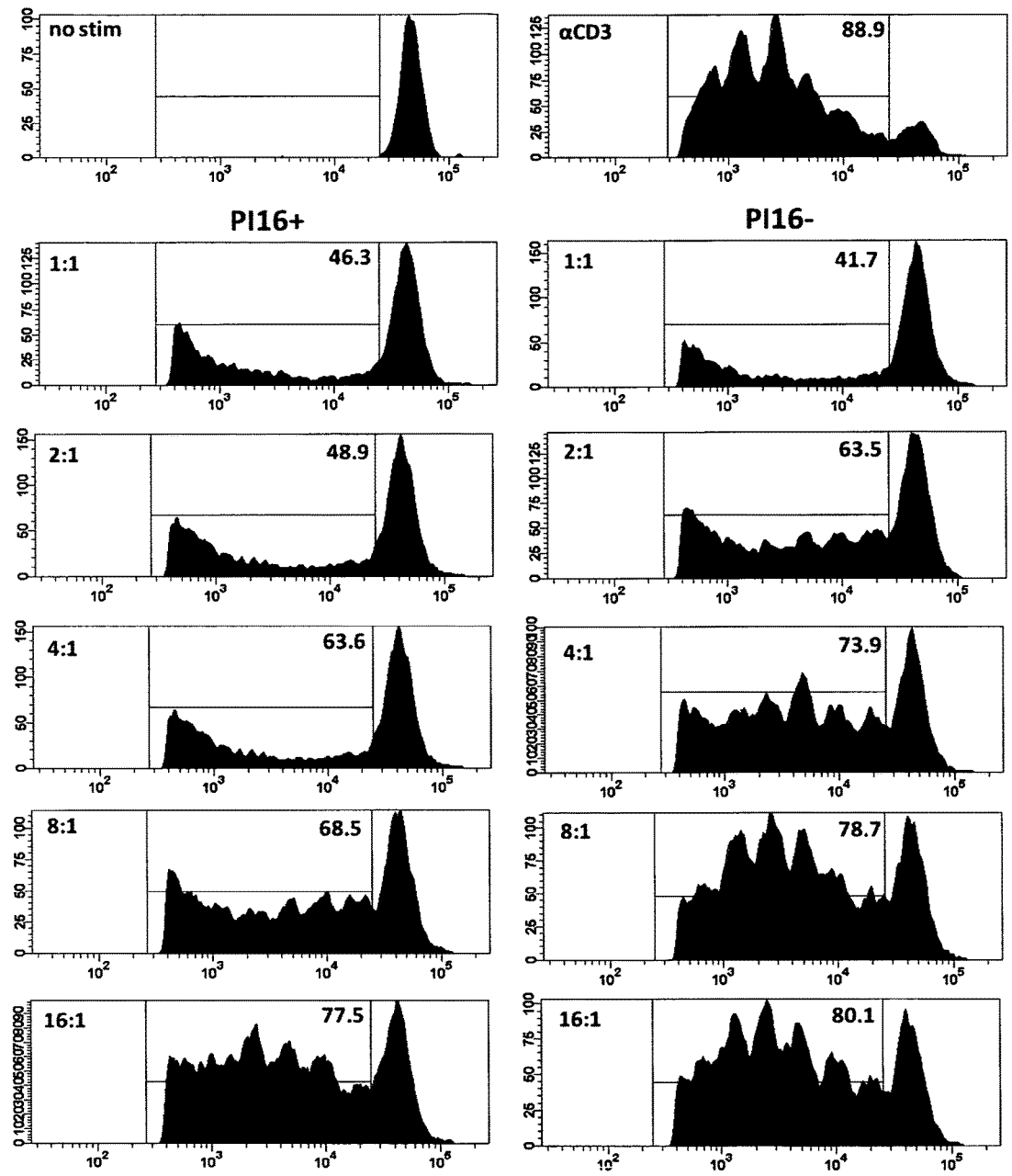

FIG. 23A includes a series of graphical representations showing results of a representative CFSE suppressor assay using expanded cord blood Treg cells sorted based on PI16 expression using CRCBT-02-001. The top two panels show negative control (left) and positive control (right). Results with PI16+ cells are shown in the left hand bottom four panels and Results with PI16- cells are shown in the right hand bottom four panels.

Figure 23B:
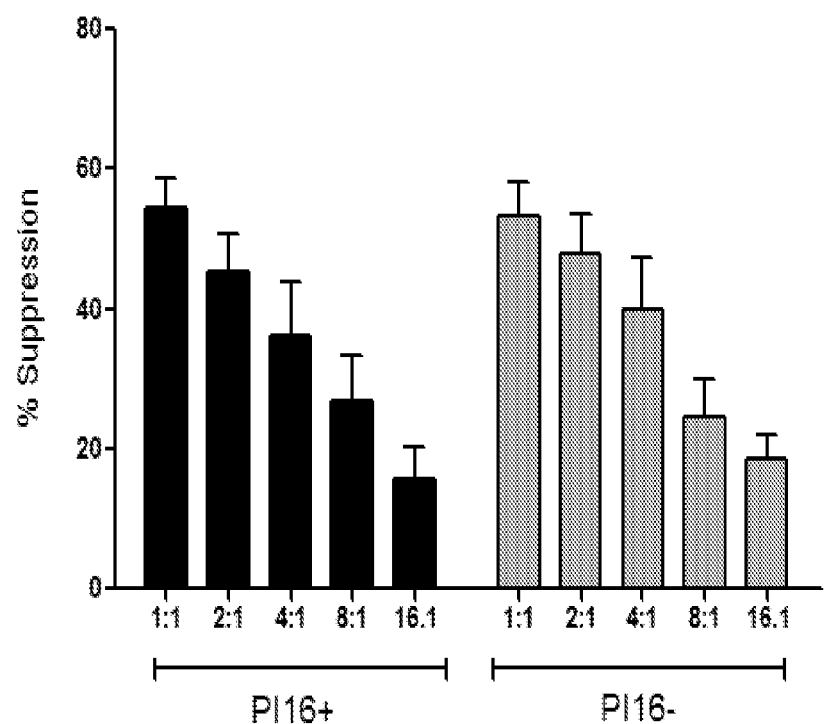

FIG. 23B is a graphical representation showing accumulative results of CFSE suppressor assays (n=6) using Treg cells from expanded cord blood. The ratio of the number of Treg cells to effector cell is indicated on the X-axis. Treg cells isolated with CRCBT-02-001(PI-16+) and PI-16- Treg cells suppress proliferation of effector cells.

Figure 23C:
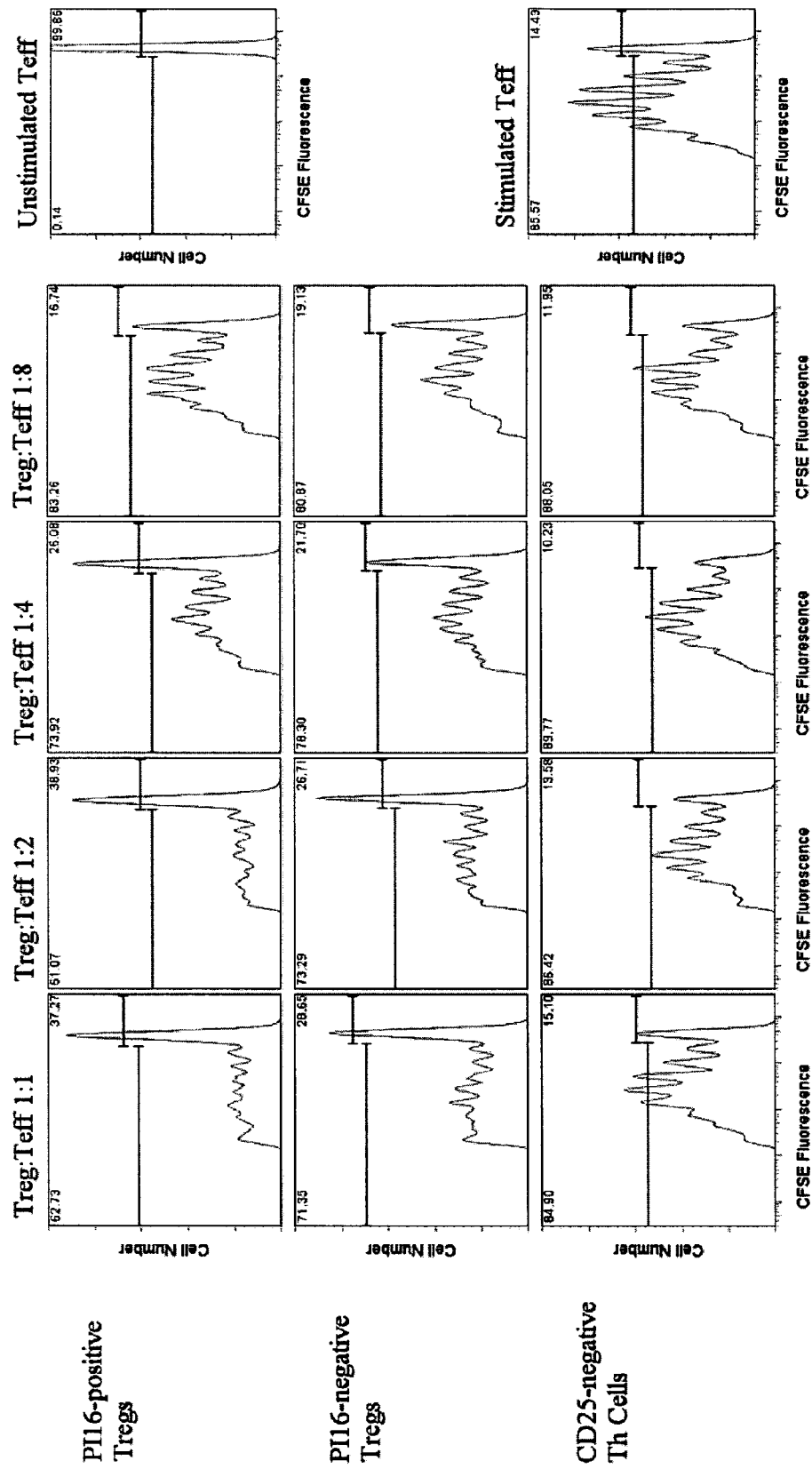

FIG. 23C includes a series of graphical representations showing results of a representative CFSE suppressor assay using Treg cells sorted based on PI16 expression using CRCBT-02-001 from fresh adult blood. The cell population studied is indicated at the left hand side of the figure and the ratio of Treg cells to effector cells is indicated at the top of the figure. Controls are included at the far right of the figure (negative control, top; and positive control, bottom).

Figure 23D:
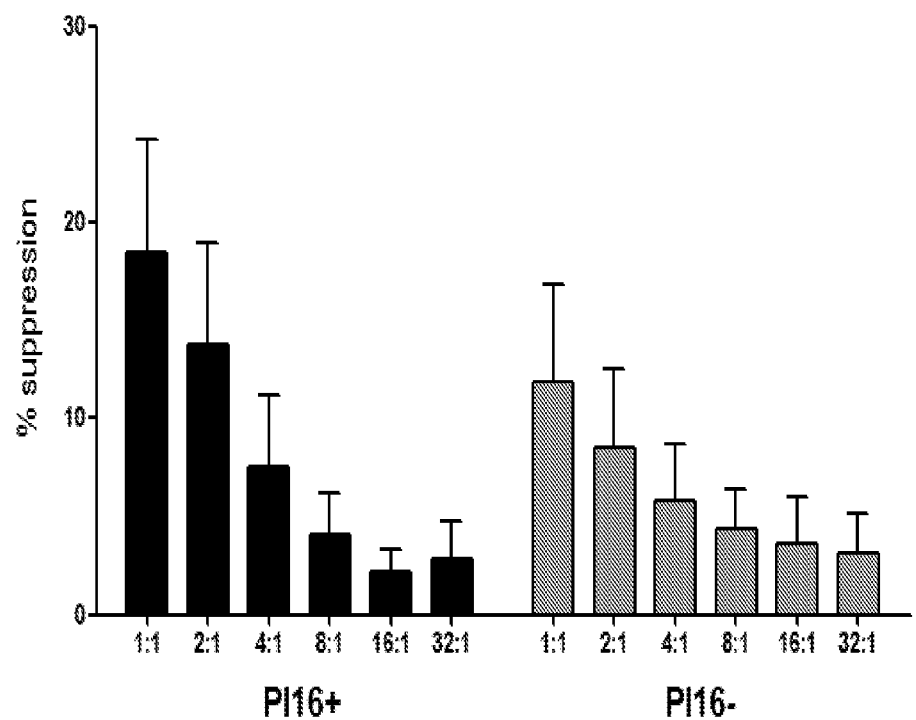

FIG. 23D is a graphical representation showing accumulative results of CFSE suppressor assays (n=4) using Treg cells from fresh adult peripheral blood. The ratio of the number of Treg cells to effector cell is indicated on the X-axis. Treg cells isolated with CRCBT-02-001 (PI-16+) and PI-16- Treg cells suppress proliferation of effector cells.

Figure 24A:
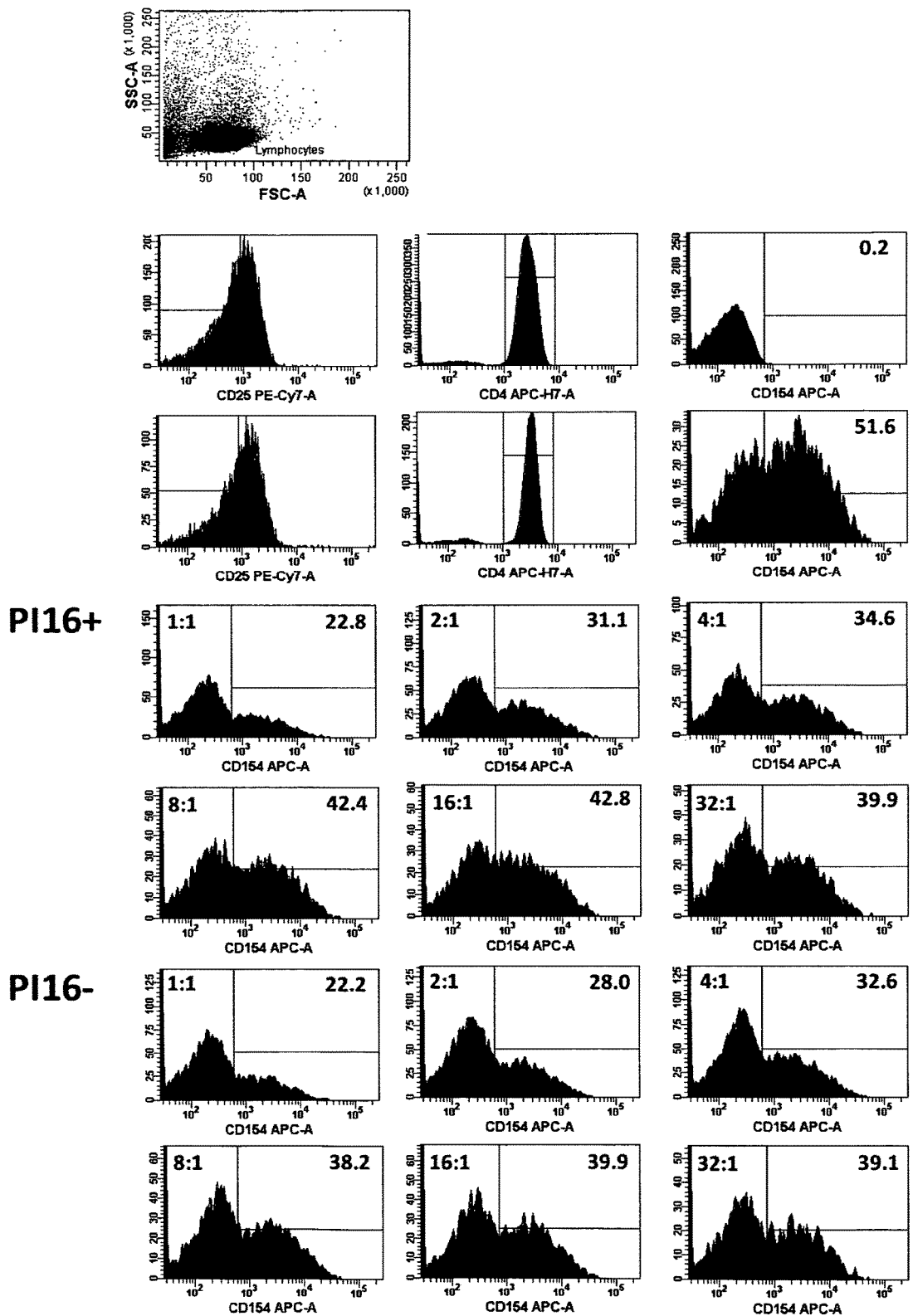

FIG. 24A includes a series of graphical representations showing results of a representative CD154 suppressor assay using Treg cells from expanded cord blood sorted based on PI16 expression using CRCBT-02-001. The cell population studied is indicated at the left hand side of the figure and the ratio of Treg cells to effector cells is indicated at the top of each graph.

Figure 24B:
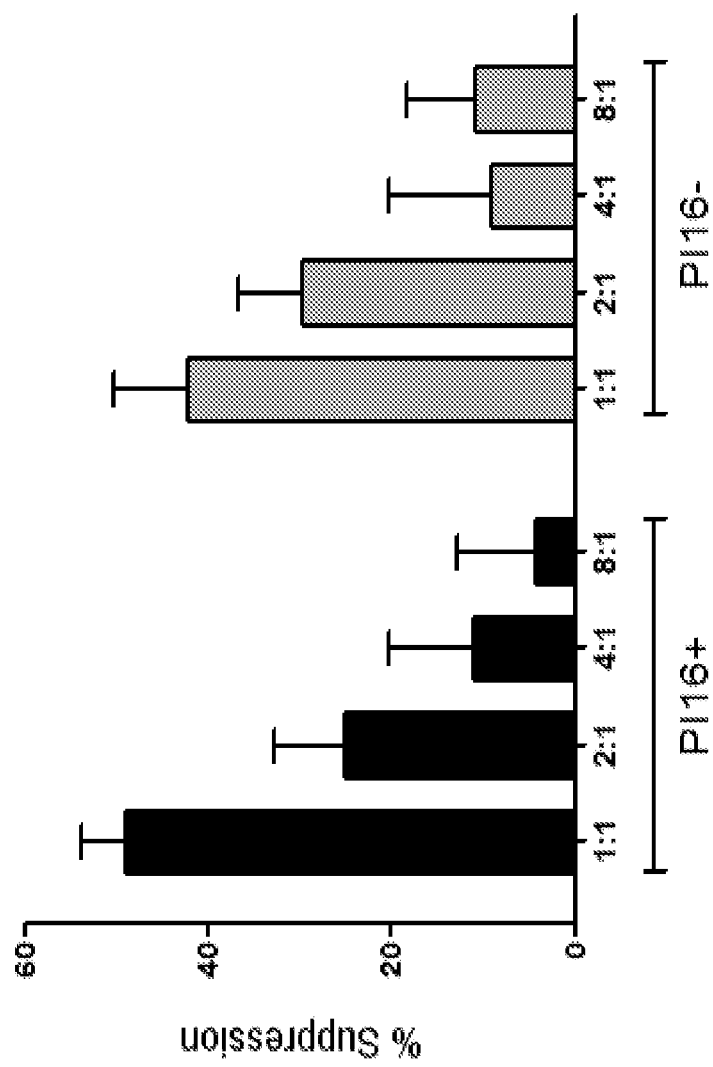

FIG. 24B is a graphical representation showing accumulative results of CD154 suppressor assays (n=4) using Treg cells from expanded cord blood. The ratio of the number of Treg cells to effector cell is indicated on the X-axis. Treg cells isolated with CRCBT-02-001(PI-16+) and PI-16- Treg cells suppress proliferation of effector cells.

Figure 25A:
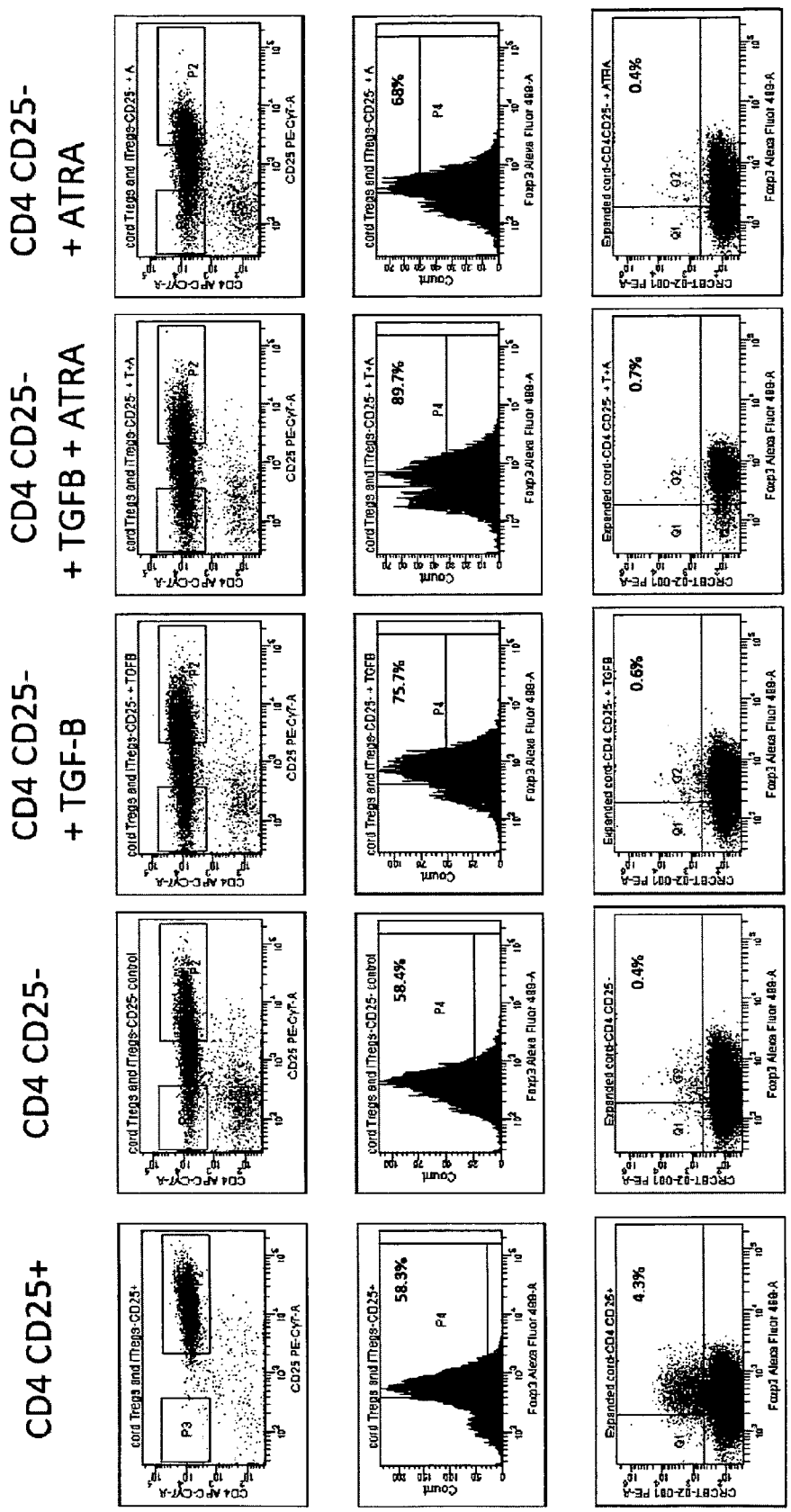

FIG. 25A includes a series of graphical representations showing representative flow cytometry data showing CD4, CD25, Foxp3 and PI16 staining (as indicated) in expanded cord nTreg cells (CD4+C25+), iTreg cells (CD4+CD25-; CD4+CD25-+TGF-B; CD4+CD25-+TGFB+ATRA; and CD4+C25-+ATRA). Both expanded nTreg cells and iTreg cells expressed high levels of CD4, CD25 and Foxp3. However, only nTreg cells expressed PI16 at significant levels.

Figure 25B:
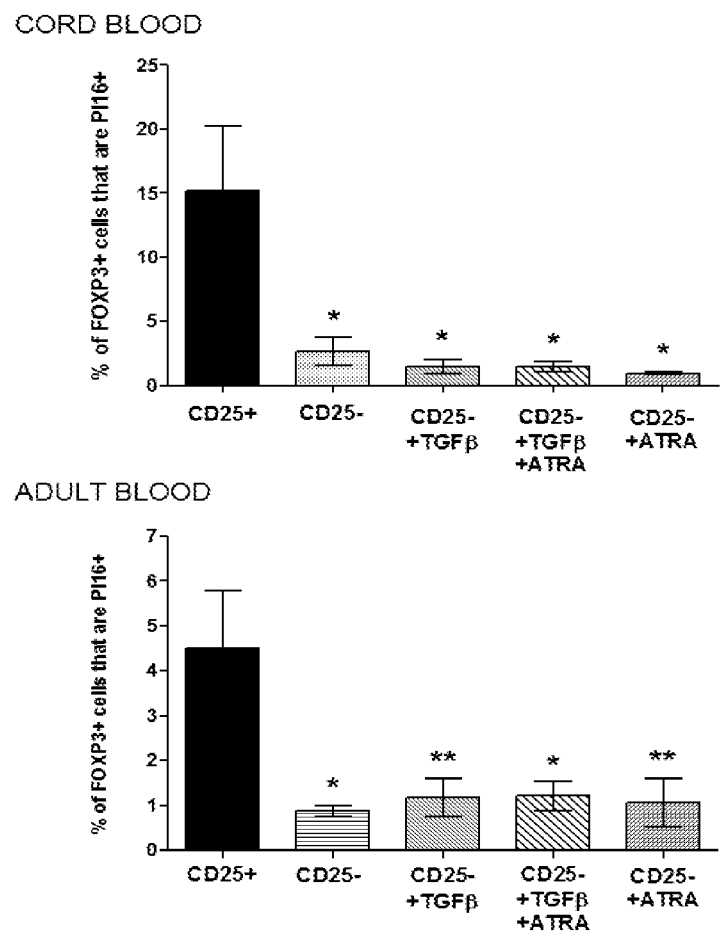

FIG. 25B includes a series of graphical representations showing accumulative results of flow cytometry for expanded cord (n=7; top panel) and adult (n=7; bottom panel) nTreg cells (CD25+) and iTreg cells (CD25-; CD25-+TGF-B; CD25-+TGFB+ATRA; and C25-+ATRA). In both cord and adult, nTreg cells expressed significantly higher levels of PI16 than iTreg cells.

Figure 26A:
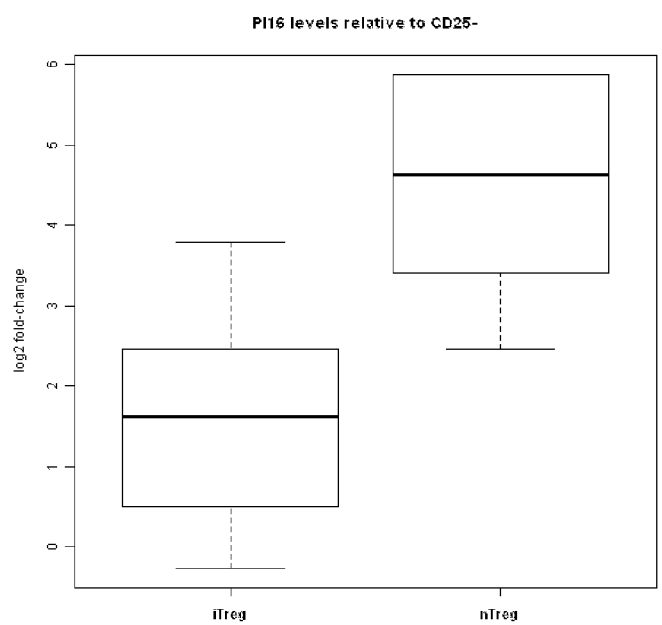

FIG. 26A is a graphical representation showing PI16 expression in expanded cord nTreg cells and iTreg cells as measured by real time PCR (n=6). ΔCt value relative to CD25- cells was estimated for both iTreg & nTreg cell populations.

Figure 26B:
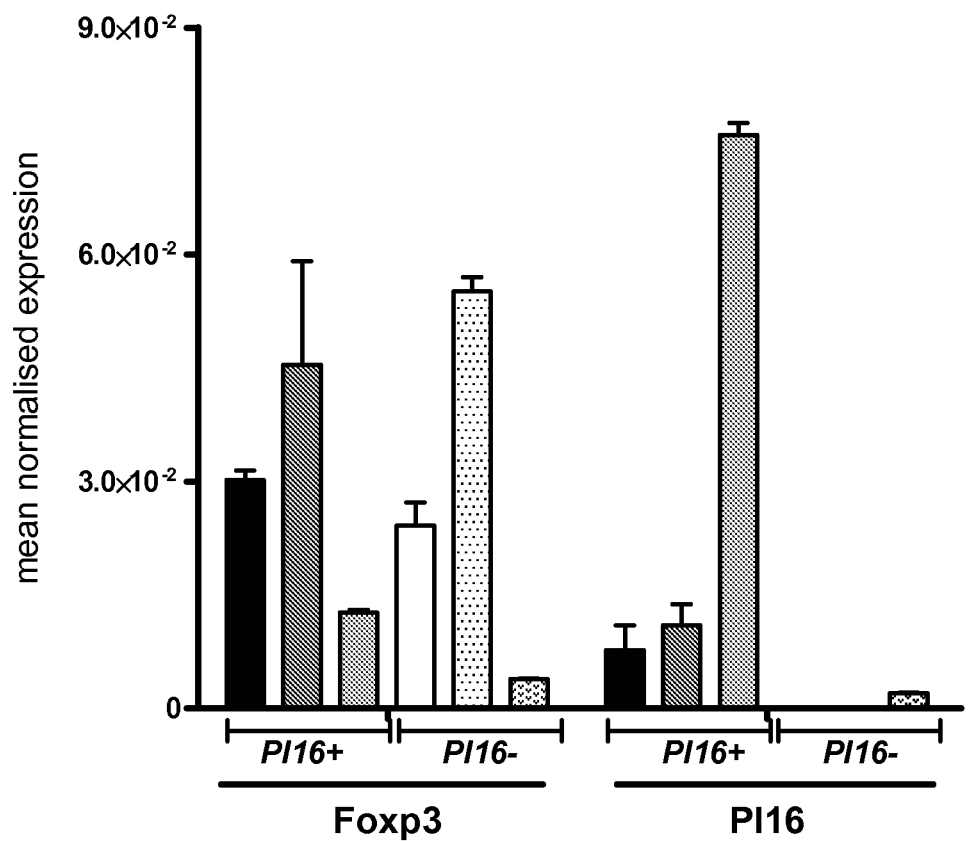

FIG. 26B is a graphical representation showing RT-PCR data of RNA extracted from freshly isolated adult peripheral blood PI16+ and PI16- Treg cells isolated using CRCBT-02-001 (n=3). Whilst Foxp3 is expressed on PI-16- Tregs, PI16 message is only expressed on cells that express PI16 at the protein level.

Figure 27A:
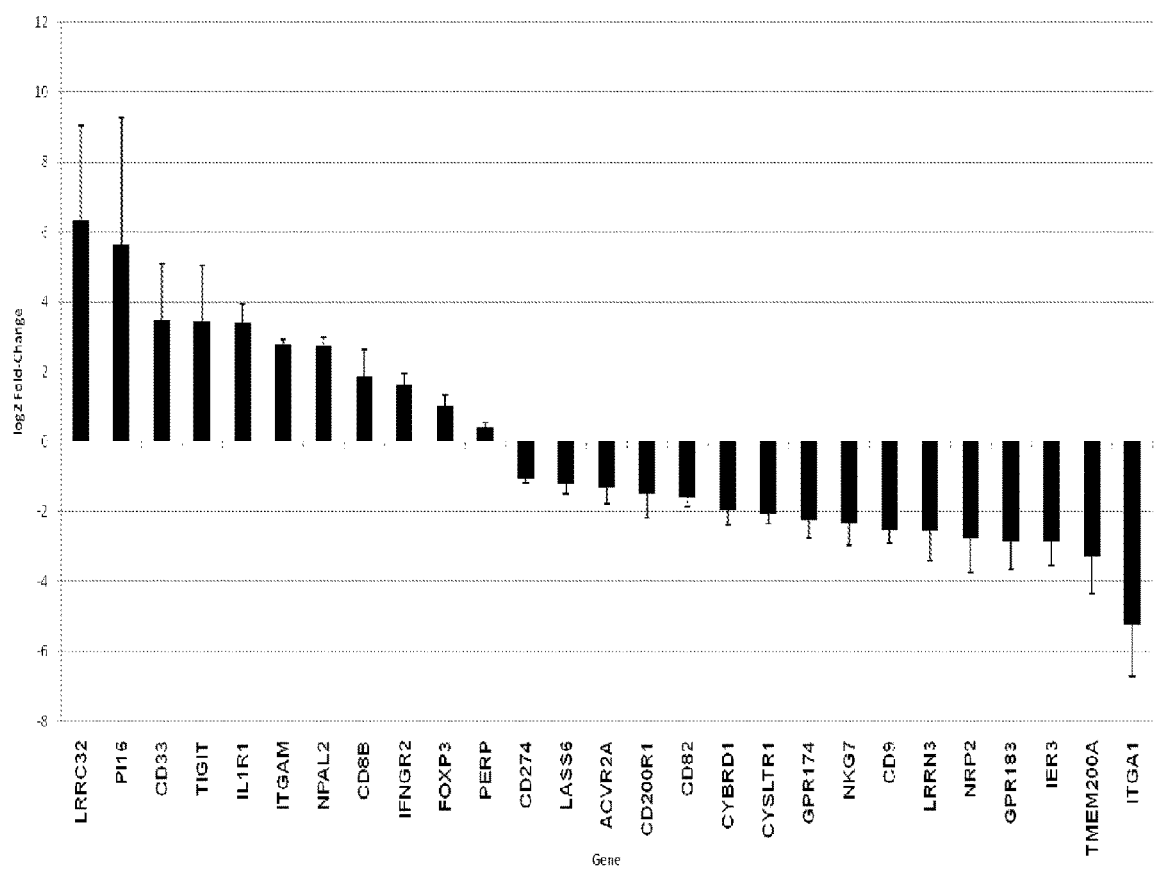

FIG. 27A is a graphical representation showing results of low density array analysis comparing the level of expression of several genes (indicated at the left of the graph) in nTreg cells compared to iTreg cells expanded from cord blood.

Figure 27B:
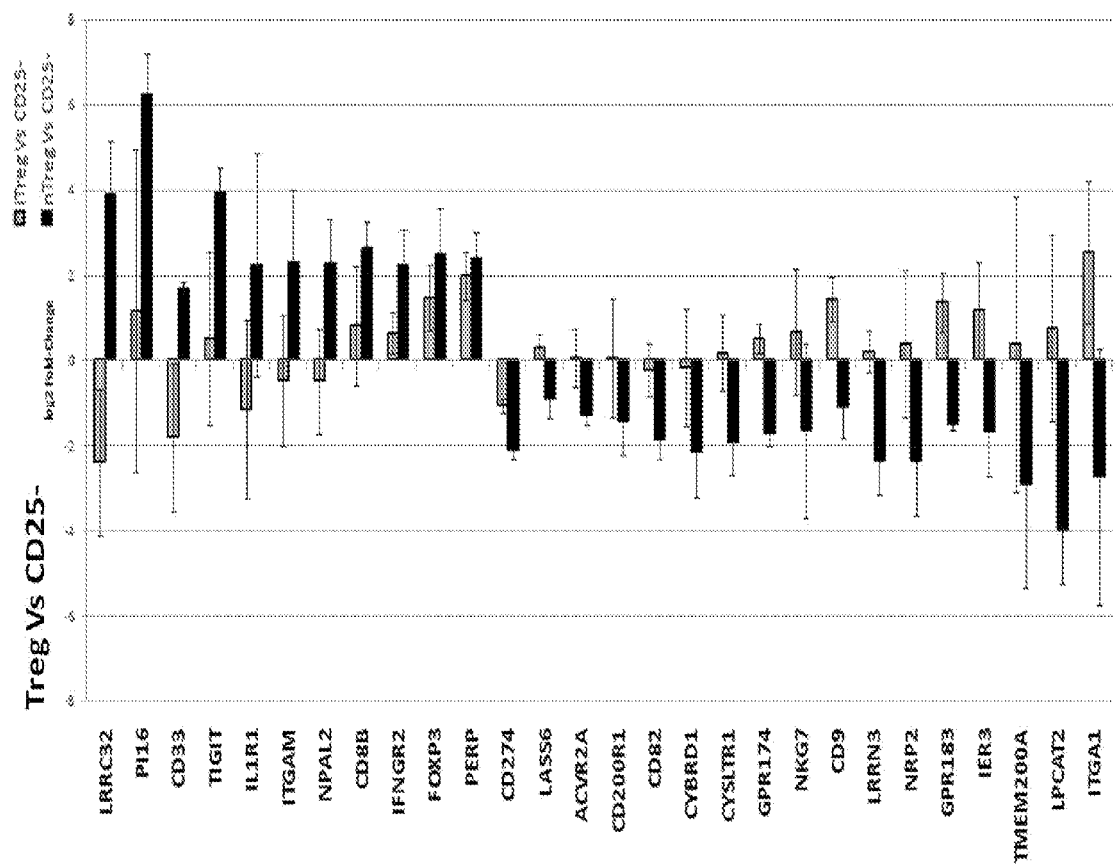

FIG. 27B is a graphical representation showing results of low density array analysis comparing the level of expression of several genes (indicated at the left of the graph) in nTreg cells compared to CD25- cells or comparing the level of expression of the genes in iTreg cells compared to CD25- cells. All cells were expanded from cord blood.

Figure 28:
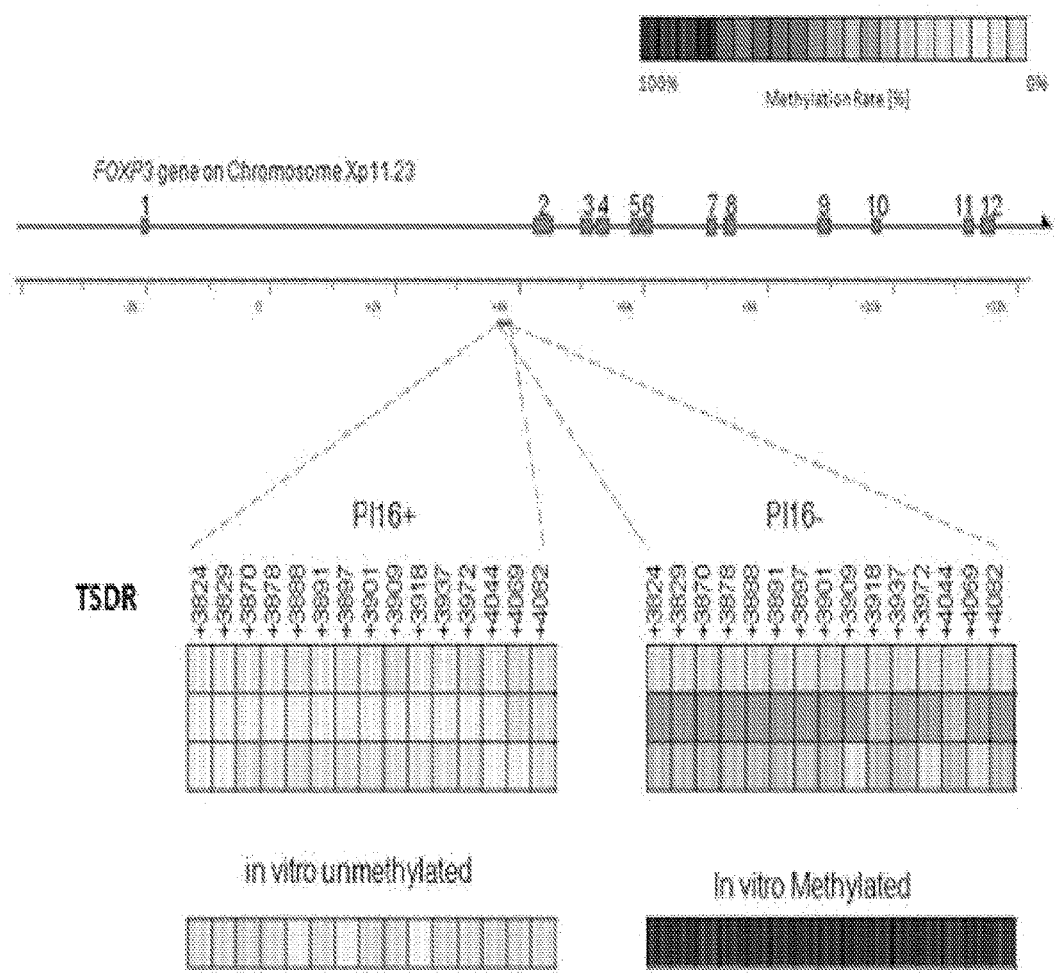

FIG. 28 is a graphical representation showing results of analysis of methylation by bisulfite sequencing of the TSDR of intron 1 of FOXP3. Three fresh adult male donor lymphocytes were sorted for CD4+CD25$^{top\ 2\%}$, and further selected by CRC-BT-02-001.

FIG. 29A includes a series of a graphical representations showing suppressive ability of PI16+ nTreg cells under normal cell culture conditions (black bars) and after exposure to IL-1 beta and IL-6 (white bars) as measured by the thymidine incorporation (top panel) and CFSE suppressor (bottom panel) assays. The ratio of Treg cells to effector cells is indicated on the X-axis.

FIG. 29B includes a series of a graphical representations showing suppressive ability of PI16- nTreg cells under normal cell culture conditions (black bars) and after exposure to IL-1 and IL-6 (white bars) as measured by the thymidine incorporation (top panel) and CFSE suppressor (bottom panel) assays. The ratio of Treg cells to effector cells is indicated on the X-axis.

Figure 29C:
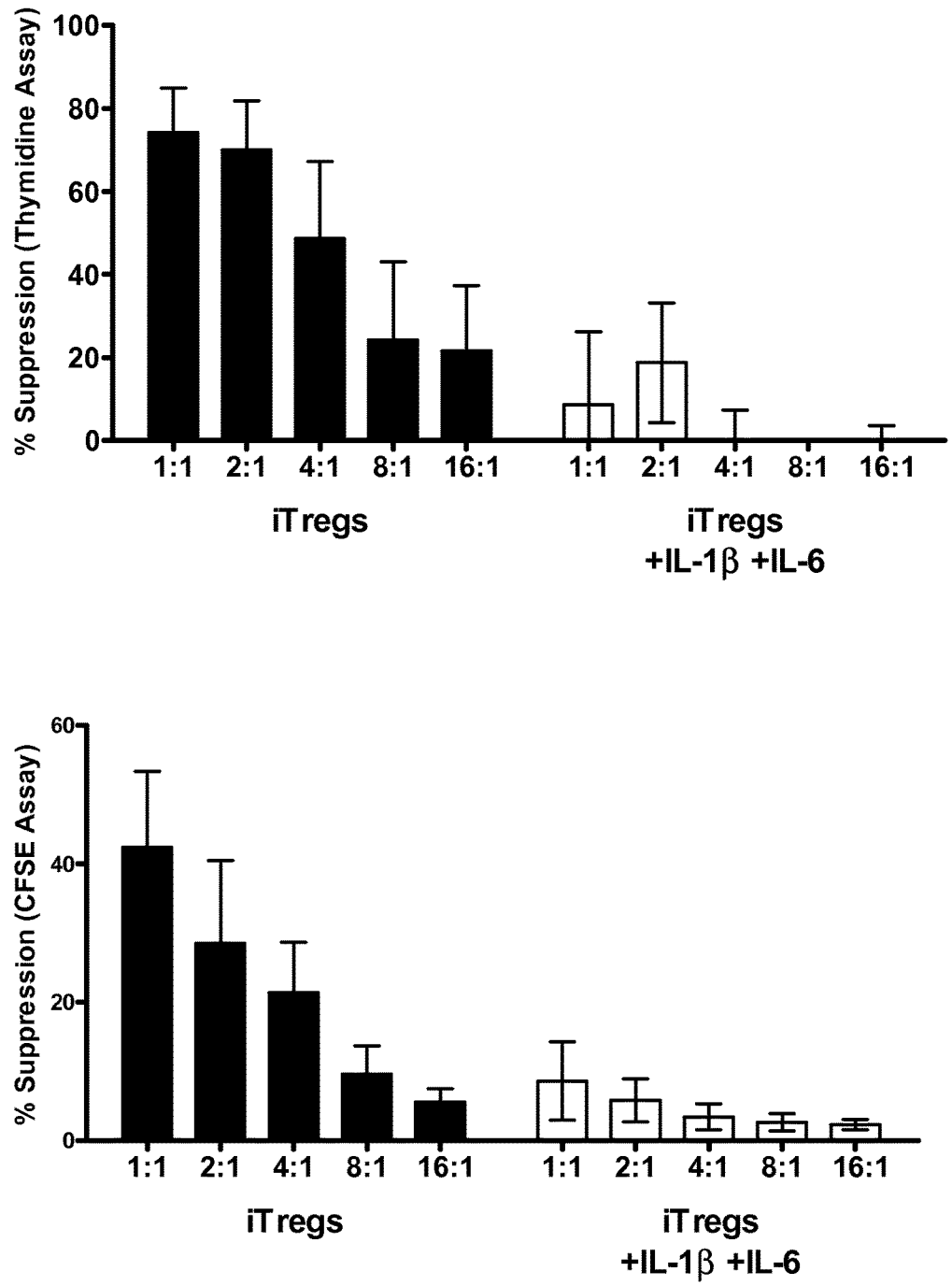

FIG. 29C includes a series of a graphical representations showing suppressive ability of PI16- iTreg cells under normal cell culture conditions (black bars) and after exposure to IL-1 and IL-6 (white bars) as measured by the thymidine incorporation (top panel) and CFSE suppressor (bottom panel) assays. The ratio of Treg cells to effector cells is indicated on the X-axis.

Figure 30:
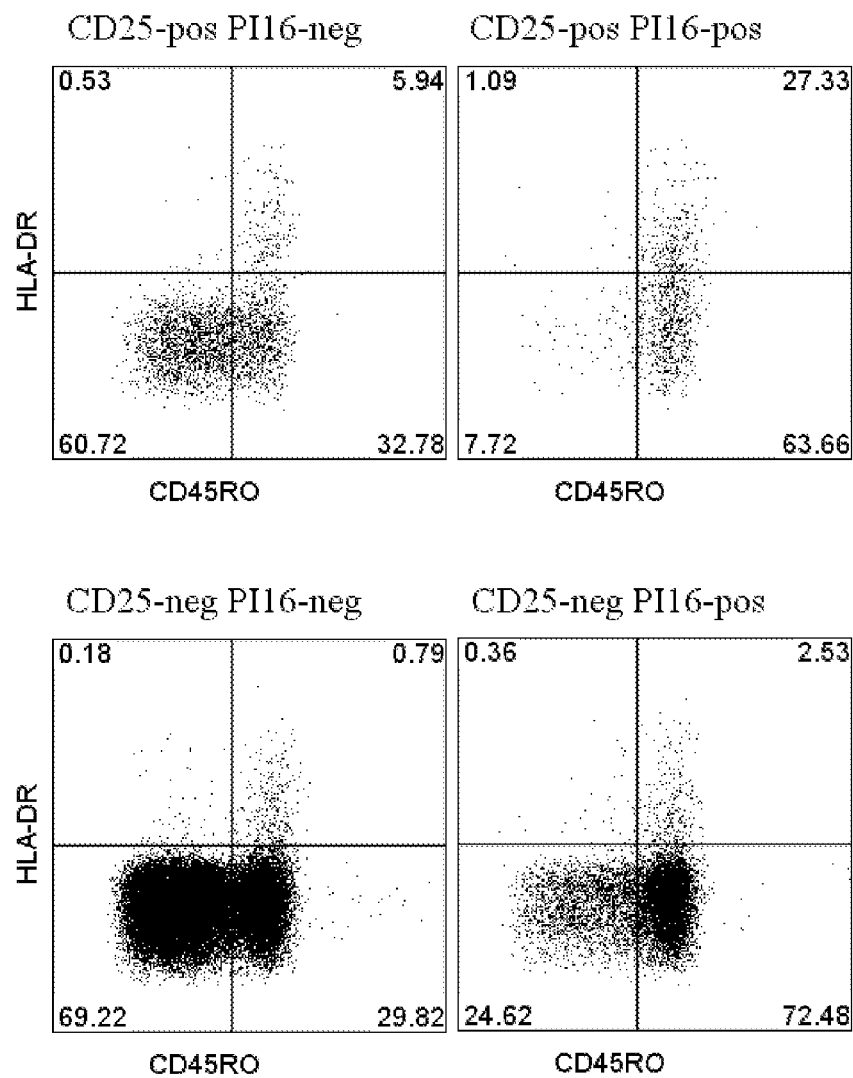

FIG. 30 is a graphical representation showing expression of HLADR on various populations of cells selected on the basis of CD25 and PI16 expression levels, as indicated using the same gating strategy as in FIG. 14.

Figure 31:
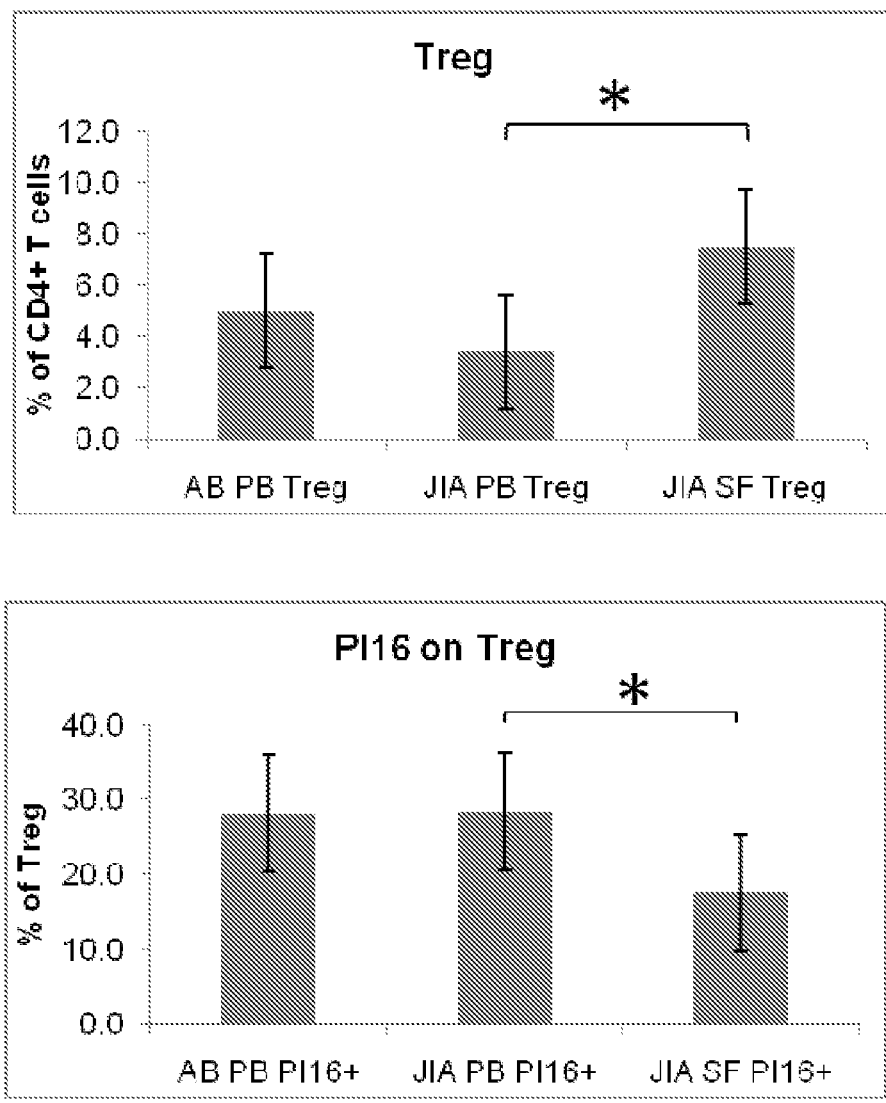

FIG. 31 includes a series of graphical representations showing analysis of Treg cells in juvenile idiopathic arthritis patients. PBMC from adults (AB PB) and JIA patients (JIA PB) and SFMC from JIA patients (JIA SF) were stained with the Treg cocktail (CD4, CD25, CD127) and CRCBT-02-001 and analysed with a FACSAria II. The top panel shows results when lymphocytes were gated on CD4+/CD25++/CD127- (Treg gate) and percentages of CD4+ T cells are displayed. (n=9) The bottom panel shows percentages of PI16-positive cells in the Treg gate. *p<0.05 (n=11).

Figure 32:
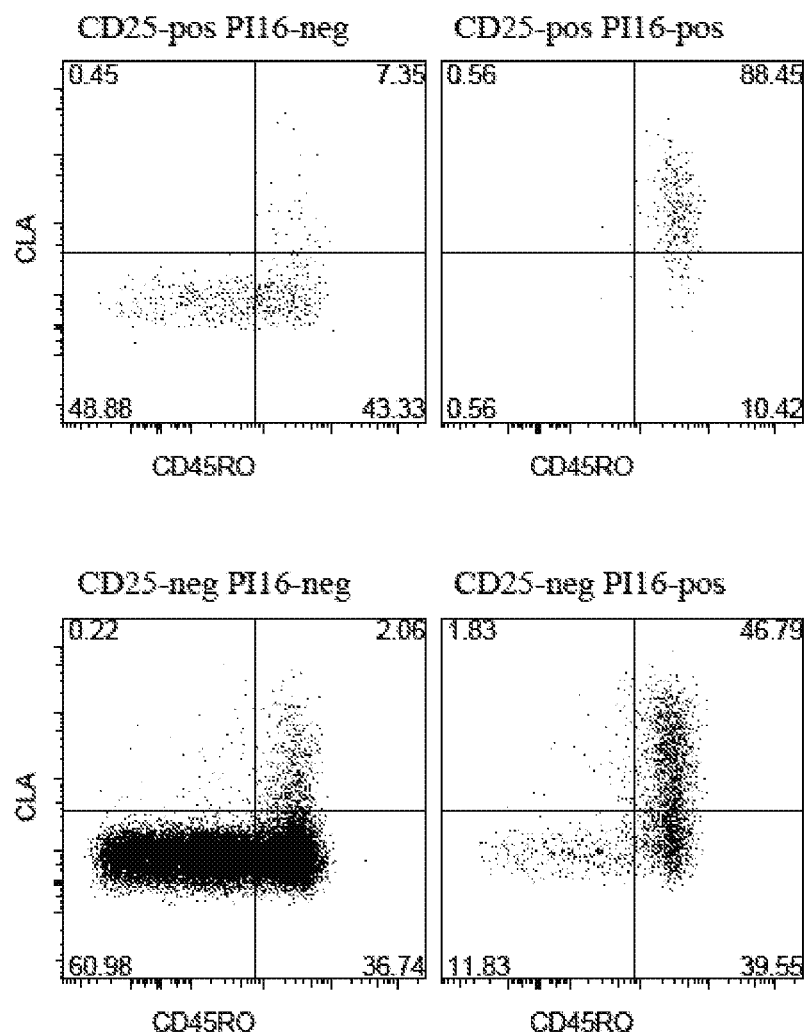

FIG. 32 includes a series of a graphical representation showing expression of CLA on various populations of cells selected on the basis of CD25 and PI16 expression levels as indicated at the top of each graph.

Figure 33A:
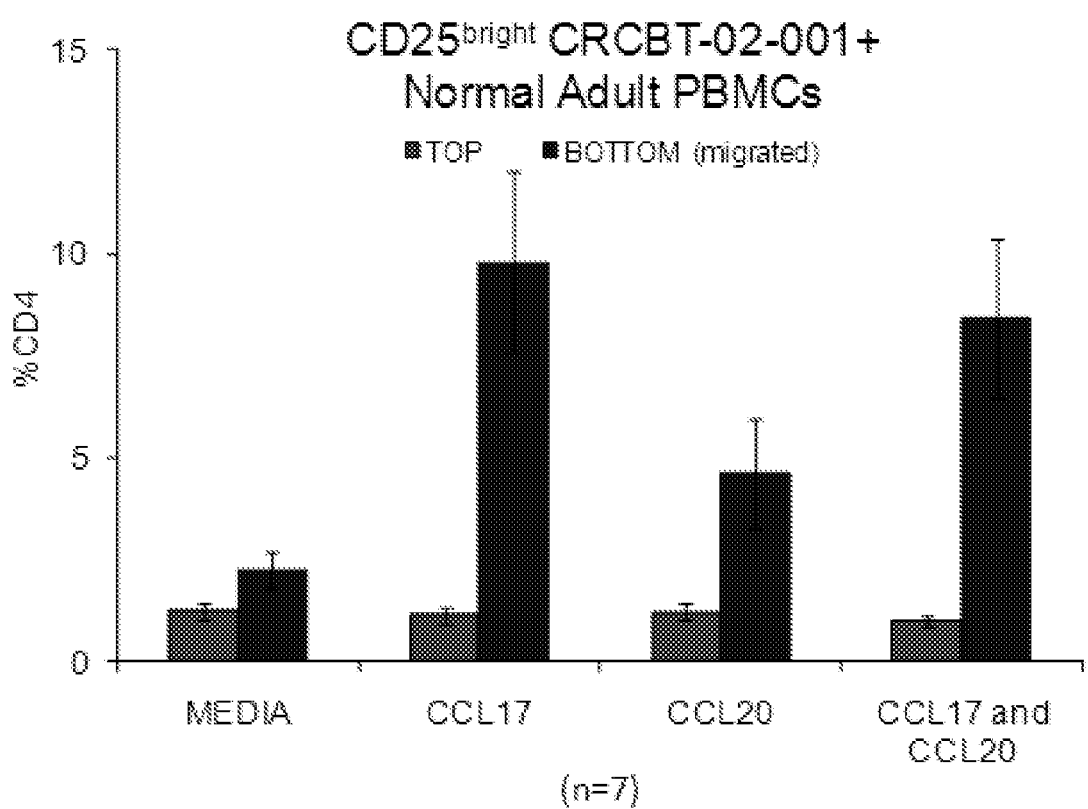

FIG. 33A is a graphical representation showing the ability of CD4$^+$ CD25$^{bright}$ CRCBT-02-001$^+$ cells from healthy adult PBMCs to migrate in response to CCR4 and CCR6 ligands, CCL17 and CCL20. CD4$^+$ CD25$^{bright}$ CRCBT-02-001 cells migrated towards CCL17, CCL20 and combined CCL17/CCL20 ligands but not to media alone.

Figure 33B:
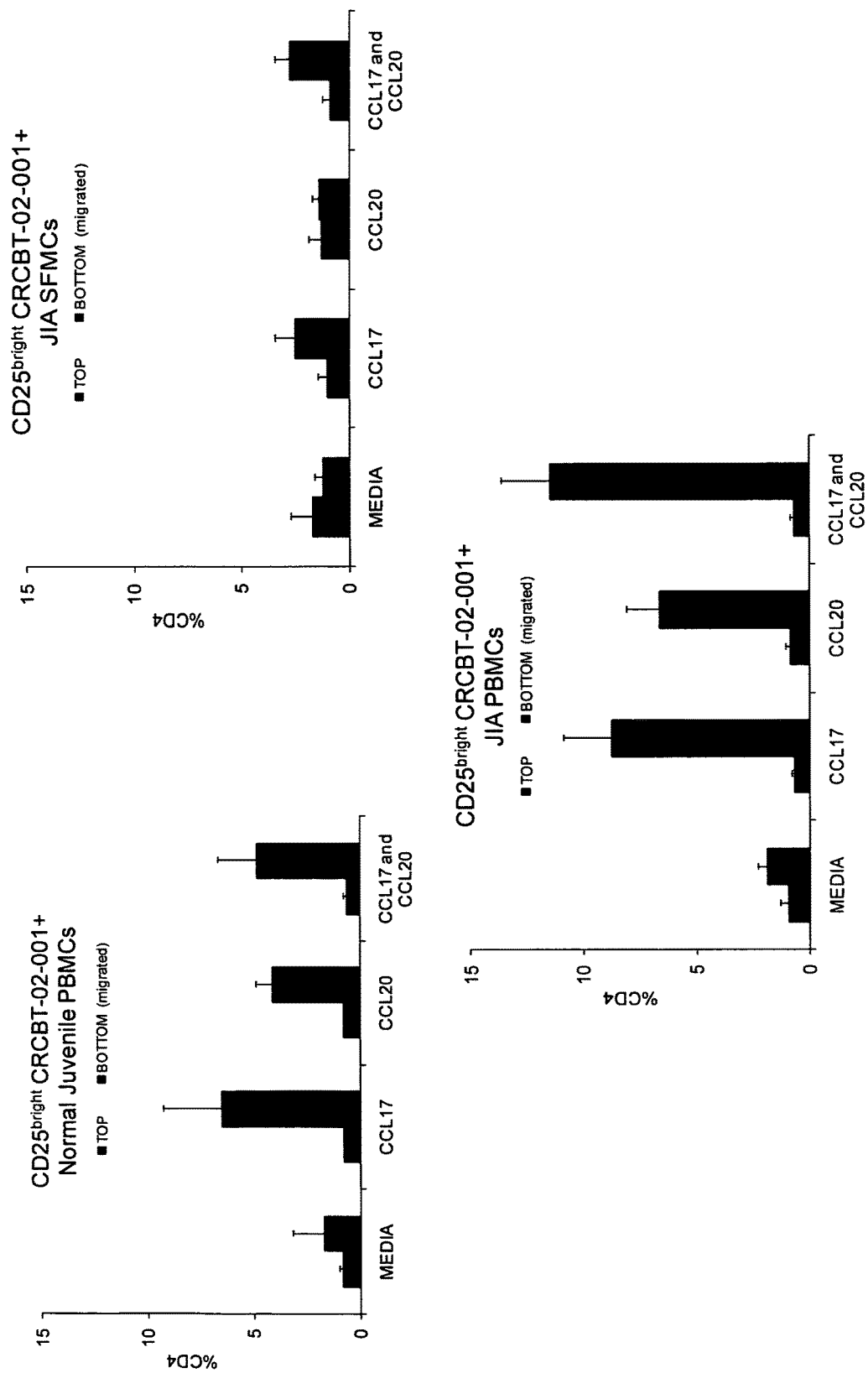

FIG. 33B includes a series of graphical representations showing the ability of CD4$^+$ CD25$^{bright}$ CRCBT-02-001$^+$ cells from PBMCs from normal juveniles (left panel), PBMCs from subjects suffering from juvenile idiopathic arthritis (JIA; centre panel) and synovial fluid mononuclear cells (SFMCs) from subjects suffering from JIA to migrate in response to CCR4 and CCR6 ligands, CCL17 and CCL20. CD4$^+$ CD25$^{bright}$ CRCBT-02-001 cells from PBMCs of healthy subjects and JIA subjects migrated towards CCL17, CCL20 and combined CCL17/CCL20 ligands, whereas cells from SFMCs from JIA subjects did not.

Figure 34A:
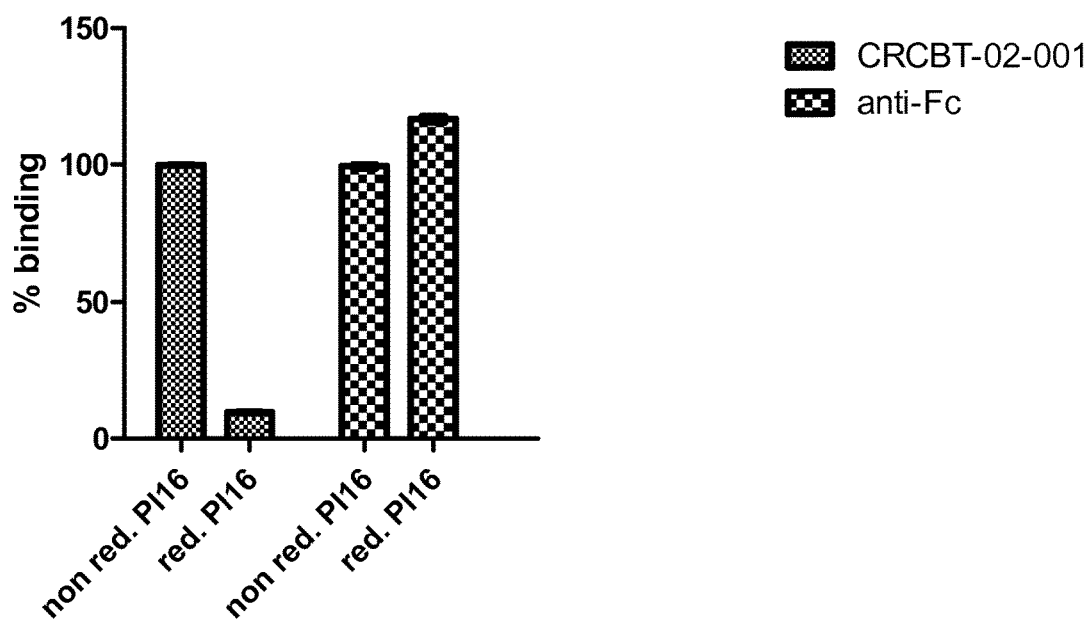

FIG. 34A is a graphical representation showing the level of binding of CRCBT-02-001 binds to native PI16-Fc and reduced and alkylated PI16-Fc (the level of binding is expressed as a percent of binding to native PI16-Fc). Reduction and alkylation (red) of PI16-Fc almost completely abolished the binding of CRCBT-02-001. The control antibody which detects the Fc portion recognized the native PI16-Fc (non red) and reduced and alkylated PI16-Fc (red) indicating the integrity of reduced and alkylated PI16 is retained independently of its redox state.

Figure 34B:
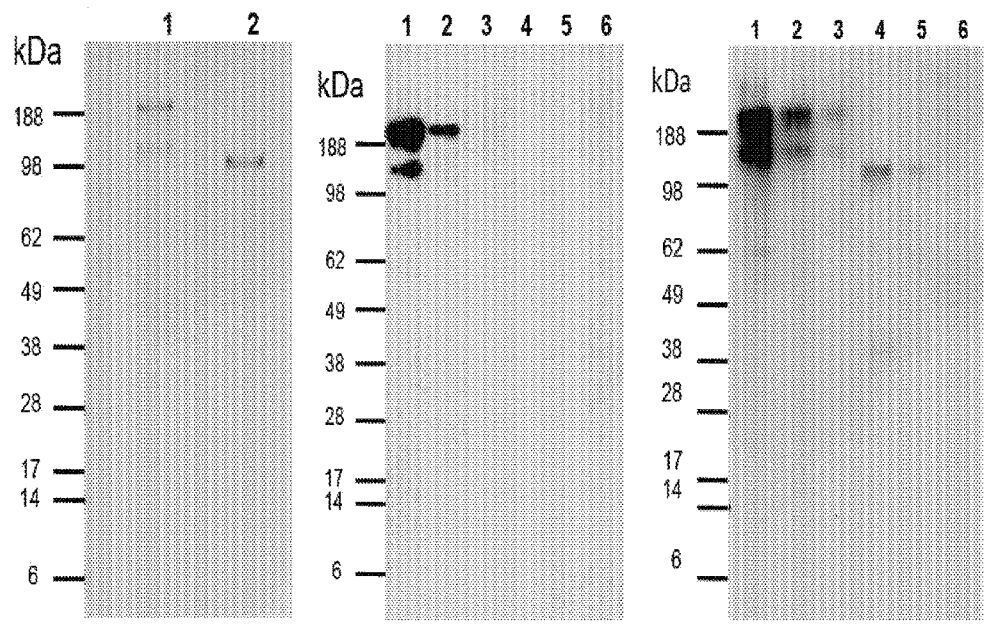

FIG. 34B includes copies of a series of photographic representations showing CRCBT-02-001 anti-PI16 monoclonal antibody recognizes a PI16-Fc in a disulphide bond-dependant manner. The left panel shows SDS PAGE analysis of native non reduced PI16-Fc (lane 1) and reduced and alkylated PI16-Fc (lane 2). The 4-12% NuPAGE gel (Invitrogen) was stained with coomassie brilliant blue. Approximately 1 µg of PI16 was loaded per lane. The centre panel shows Western blot analysis of native and reduced and alkylated PI16-Fc probed with CRCBT-02-001 and anti-mouse-HRP labelled conjugate. Lanes 1-3 correspond to 200 ng, 67 ng and 22 ng of native PI16-Fc and lanes 4-6 correspond to the same concentrations of reduced and alkylated PI16 respectively. The right panel shows results attained when the Western blot was re-probed with HRP-conjugated anti-human Fc to confirm the presence of antigens, lanes 1-3 correspond to native PI16 and lanes 4-6 reduced and alkylated PI16.

Figure 34C:
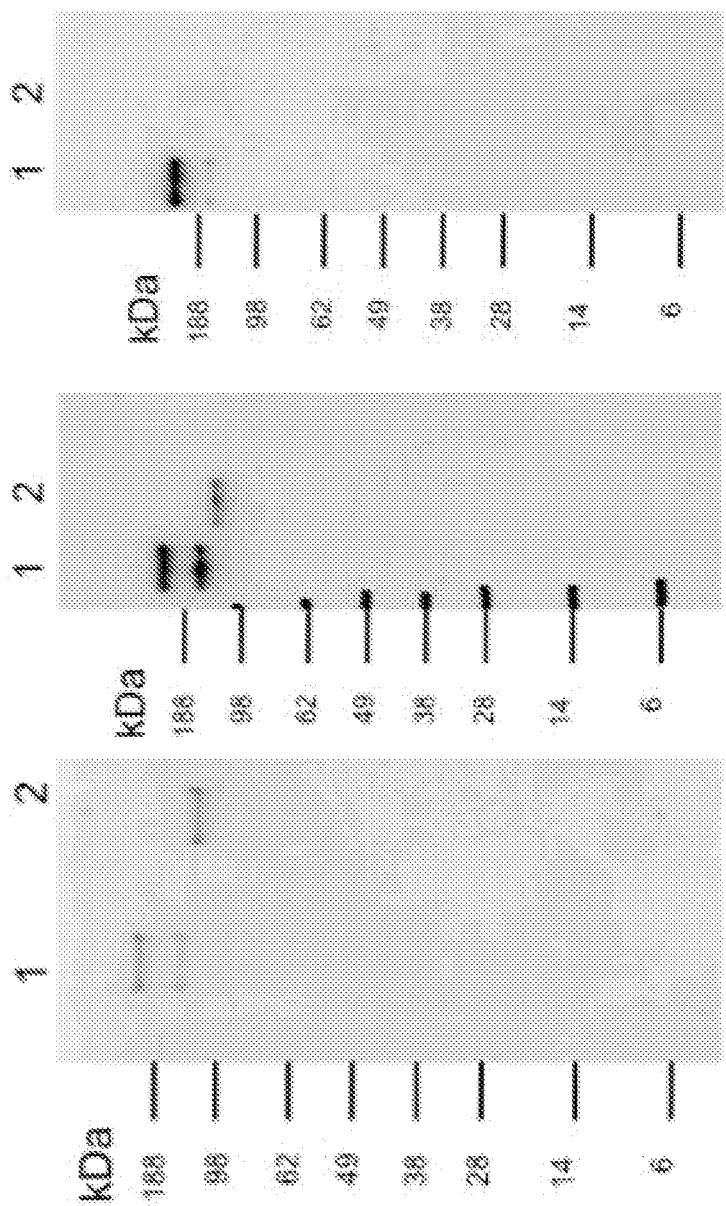

FIG. 34C includes a series of photographic representations showing that CRCBT-02-001 anti-PI16 monoclonal antibody recognises a PI16-Fc in a disulphide bond-dependant manner. The left hand panel shows results of SDS-PAGE analysis of recombinant non-reduced PI16-Fc (lane 1) and reduced and alkylated PI16-Fc (lane 2). The 4-12% NuPAGE gel (Invitrogen) was stained with coomassie brilliant blue. Approximately 1 µg of PI16 was loaded per lane. The centre panel from the left shows results of Western blot analysis of native and reduced & alkylated PI16-Fc probed with a 1/10,000 dilution of HRP-conjugated Anti-human-Fc IgG (Lanes 1 and 2 respectively). Approximately 200 ng of recombinant PI16 was loaded per lane. The right hand panel shows results of Western blot analysis of non-reduced and reduced & alkylated PI16-Fc (Lanes 1 and 2 respectively) probed with 2.5 µg/ml of CRCBT-02-001 and HRP-conjugated anti-mouse IgG. Approximately 200 ng of PI16 was loaded per lane.

Figure 35:
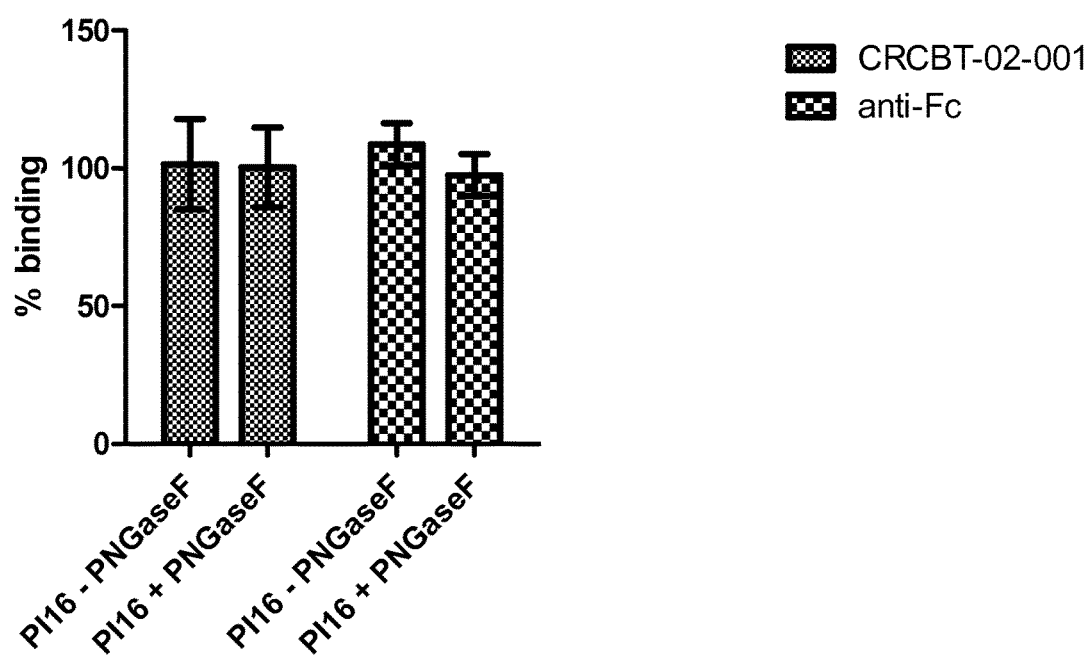

FIG. 35 is a graphical representation showing the level of CRCBT-02-001 binding to native PI16-Fc and de-glycosylated PI16-Fc (the level of binding is expressed as a percent of binding to native PI16-Fc). Treatment of PI16-Fc with PNGaseF did not have measurable influence on the binding of CRCBT-02-001. The control antibody anti-Fc recognizes the C-terminal Fc-portion of the fusion protein indicating the integrity of de-glycosylated PI16 is retained.

Figure 36:
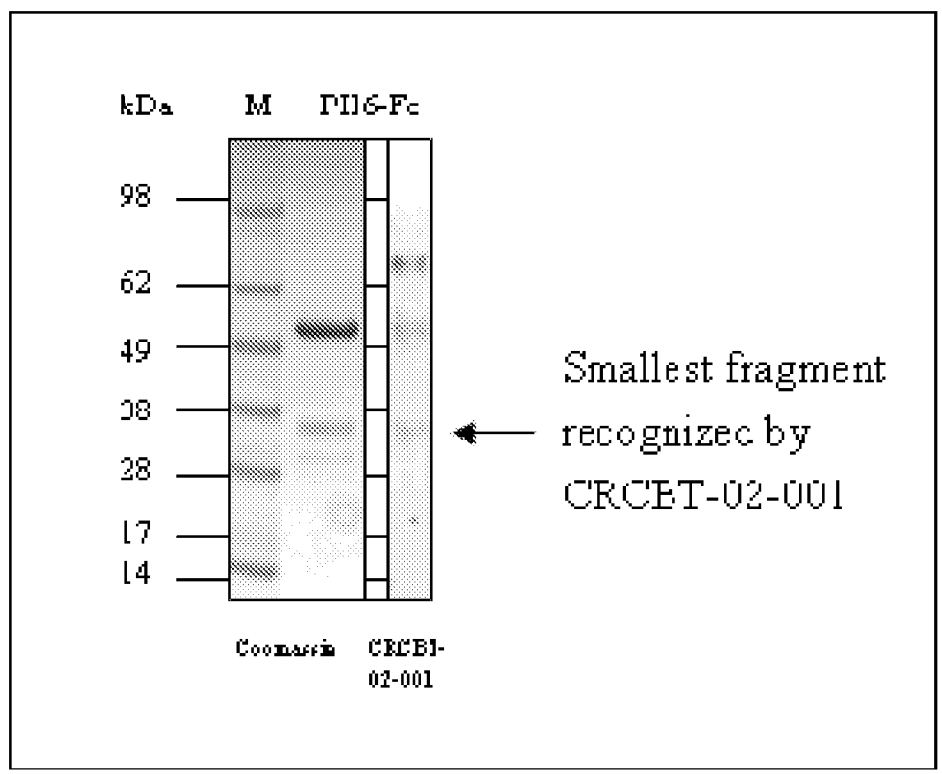

FIG. 36 is a graphical representation showing binding of CRCBT-02-001 binding to fragments of PI16-Fc containing the N-Terminal CAP-domain. Distinct degradation products of PI16-Fc were observed after heat-treatment and a fragment of about 35 kDa was still recognized by CRCBT-02-001.

Figure 37:
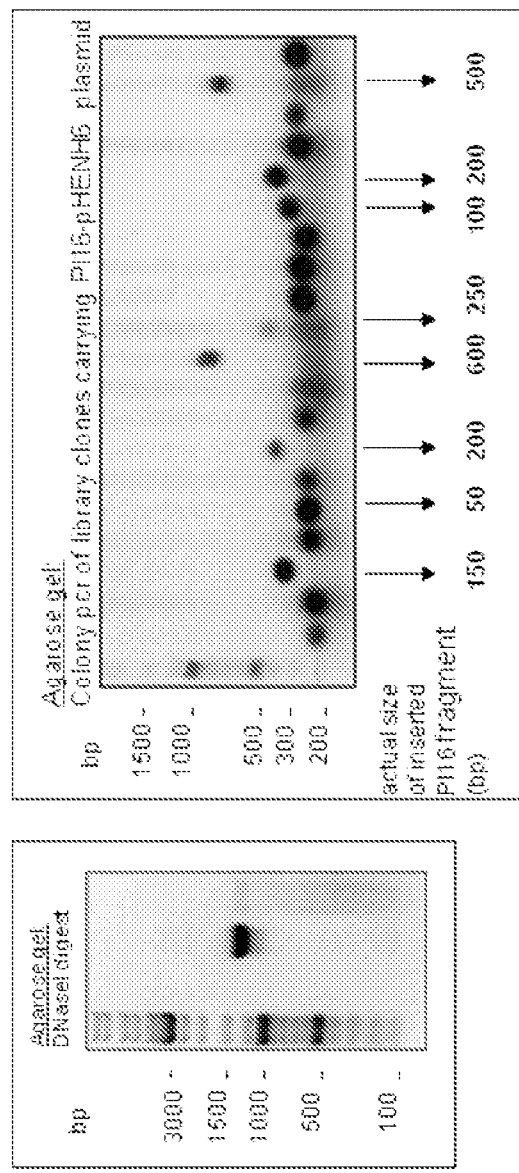

FIG. 37 includes copies of two photographic representations showing construction of a random PI16 gene fragment library displayed on phage. The level hand panel shows ethidium bromide-stained agarose gel of PI16 coding DNA digested with DNase I to generate optimal distribution of fragment sizes. The right hand panel shows ethidium bromide-stained agarose gel showing PCR amplification products representing fragments of PI16 coding DNA from randomly picked clones. The size of representative fragments is indicated at the bottom of the figure.

Figure 38A:
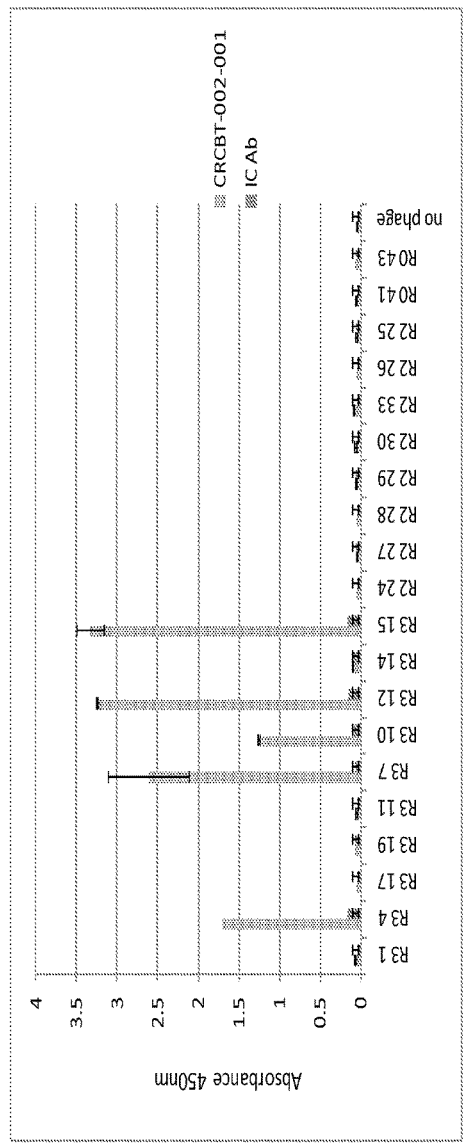

FIG. 38A is a graphical representation showing results of panning to select gene fragments from PI16 fragment library displayed on phage with specificity to CRCBT-02-001. The results shown are from an ELISA showing five gene fragments selected from Round 3 (4, 7, 10, 12 &15) bind strongly to CRCBT-02-001 and do not bind to an isotype control mAb (IC)

Figure 38B:
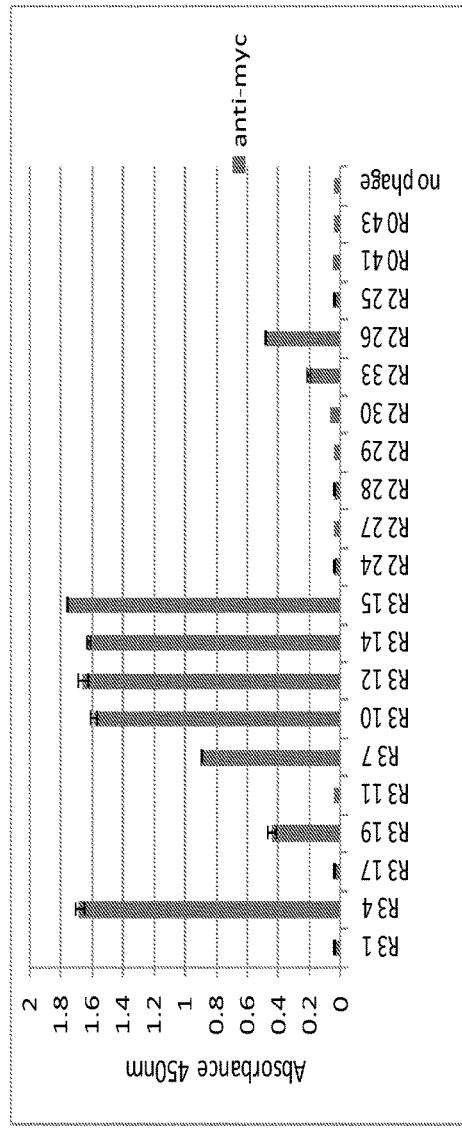

FIG. 38B is a graphical representation showing binding of the 9E10 anti-Myc antibody to fragments depicted in FIG. 38A, wherein a signal corresponds with expression of in-frame gene fragments on phage.

Figure 39:
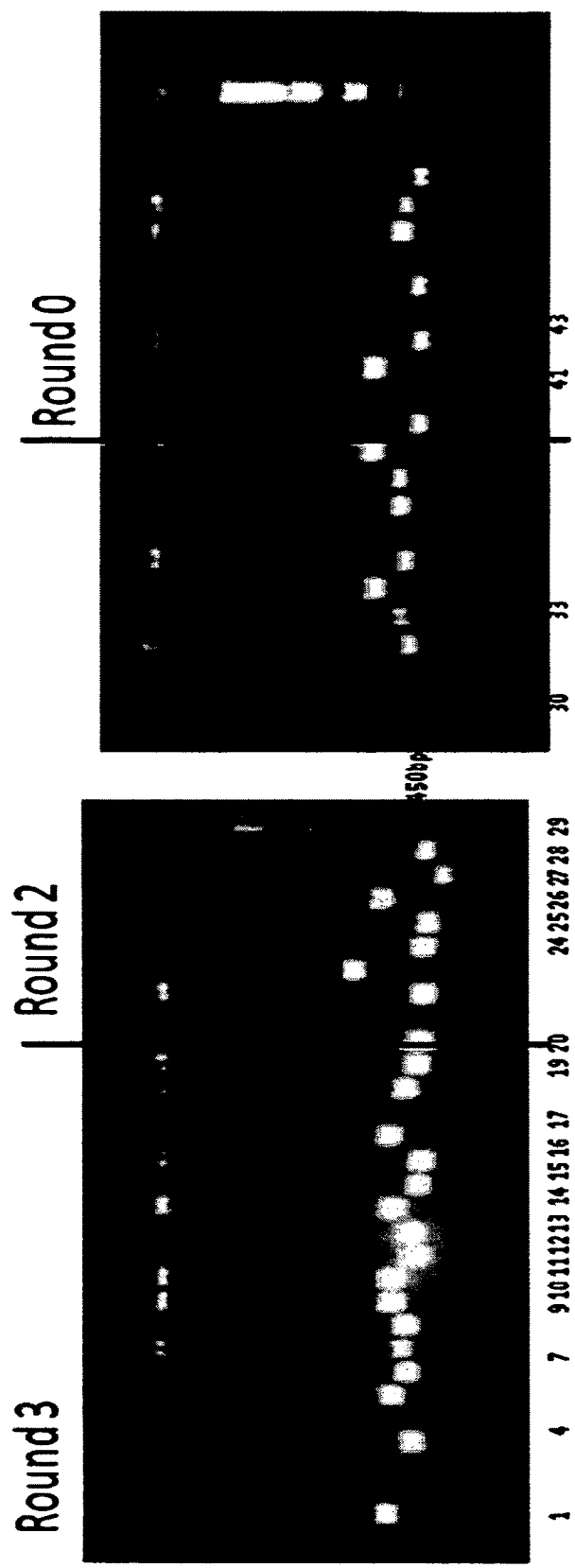

FIG. 39 includes copies of two graphical representations showing relative sizes of PI16 gene fragments isolated during phage panning. Phage clones were identified in round 0 (prior to panning) and rounds 2 and 3. Numbered clones were analysed for binding in FIG. 38. Only PI16 fragments marked with "*" were isolated after three rounds of panning and shown to bind strongly to CRCBT-02-001.

Figure 40A:
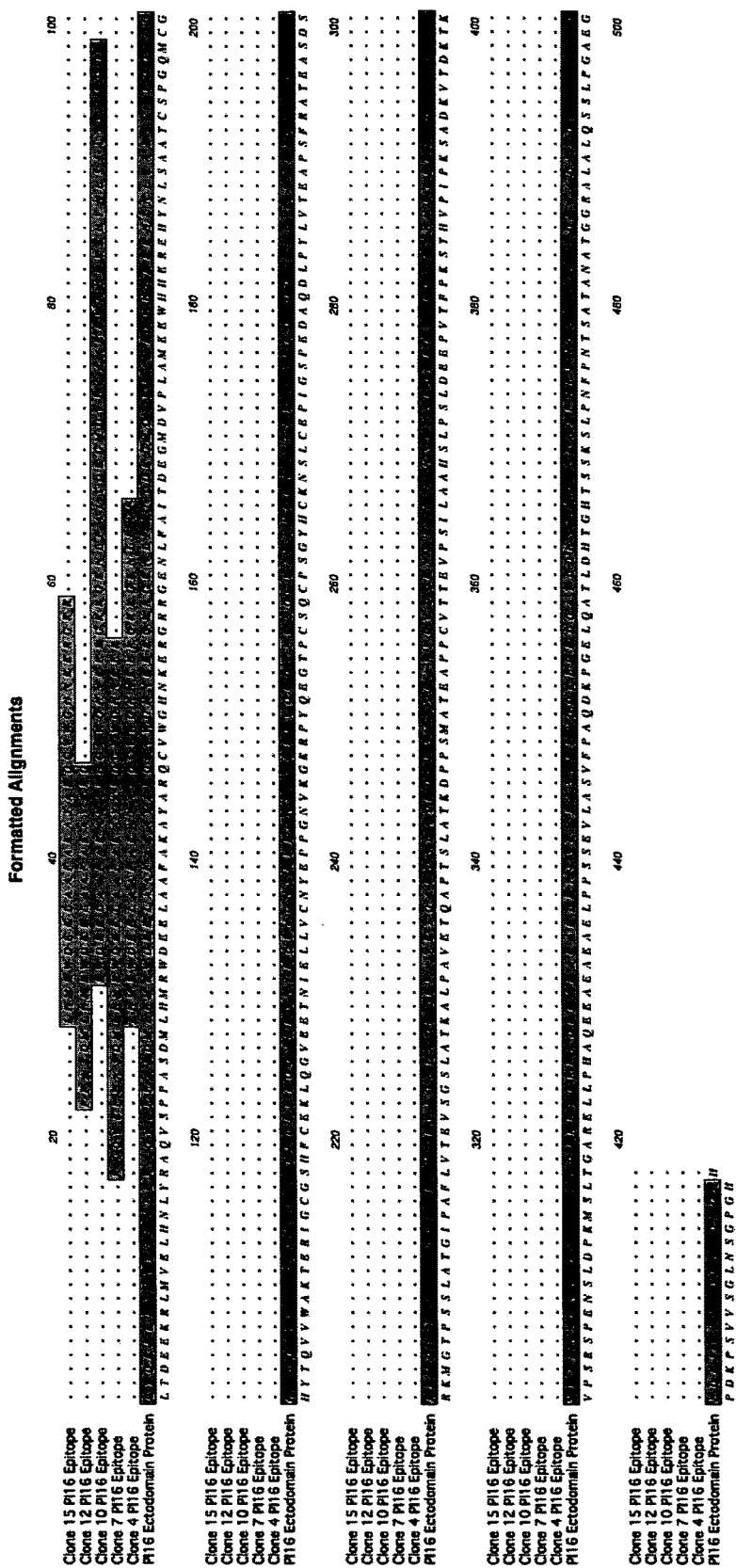

FIG. 40A is a graphical representation showing an alignment of the amino acid sequence of human PI16 (SEQ ID NO: 1) and sequences of PI16 gene fragments from round 3 panning which bind to CRCBT-02-001. Fragments depicted are clone 15 (SEQ ID NO: 33), clone 12 (SEQ ID NO: 34), clone 10 (SEQ ID NO: 35); clone 7 (SEQ ID NO: 36); and clone 4 (SEQ ID NO: 37). The results show that the sequences of the clones overlap with a region of the N-terminal portion (CAP domain) of PI16.

Figure 40B:
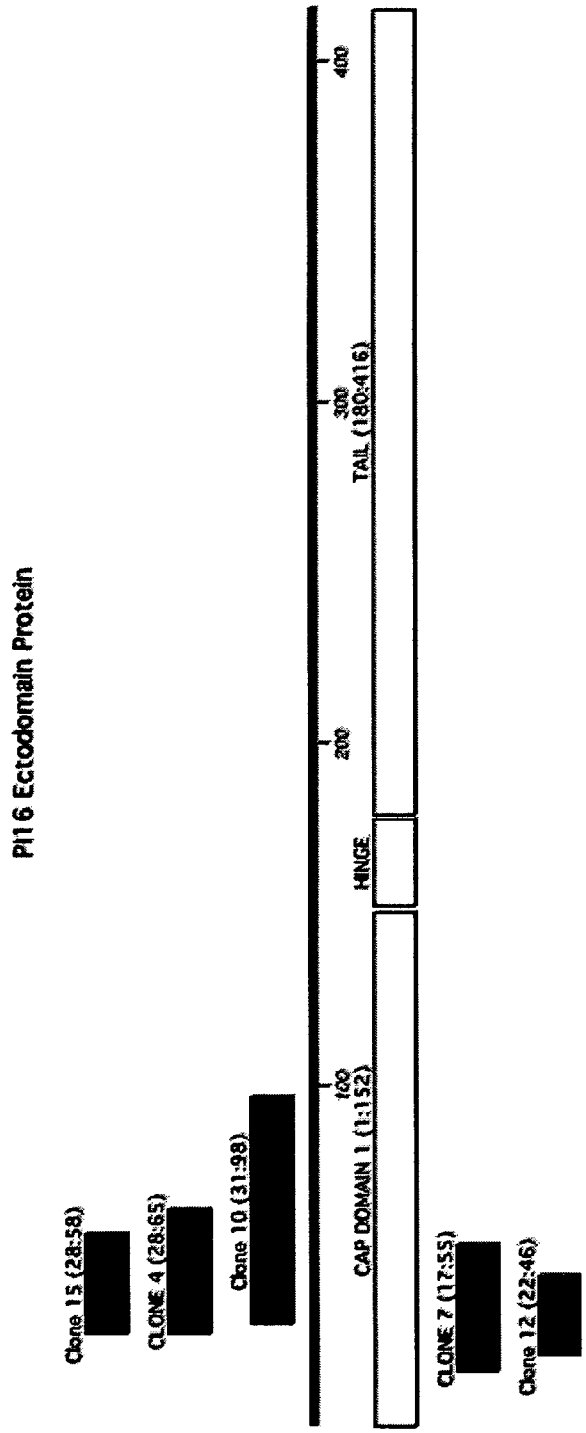

FIG. 40B shows the sequence of an overlapping region (16 amino acids) of clones R3 4, 7, 12, 10, and 15 (SEQ ID NO: 38). This is the minimum binding region of CRCBT-02-001. Below the sequence is a diagrammatic representation of the position of the sequence of the clones relative to human PI16.

Figure 40C:
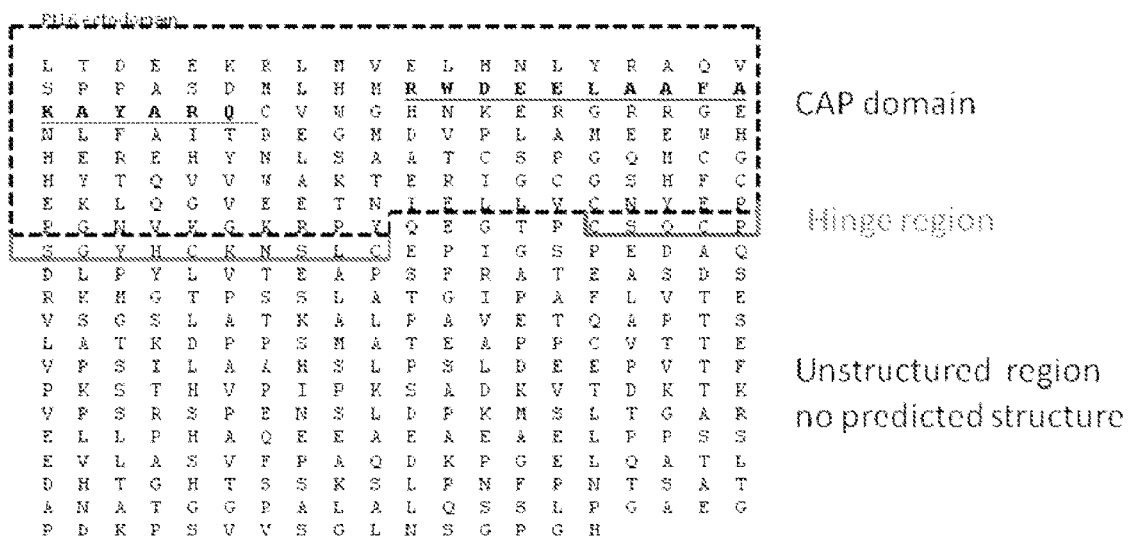

FIG. 40C shows the position of the overlapping region (16 amino acids) of clones R3 4, 7, 12, 10, and 15 (SEQ ID NO: 38) in the sequence of human PI16 (SEQ ID NO: 1). Also indicated are the boundaries of the CAP domain and hinge region.

Figure 41:
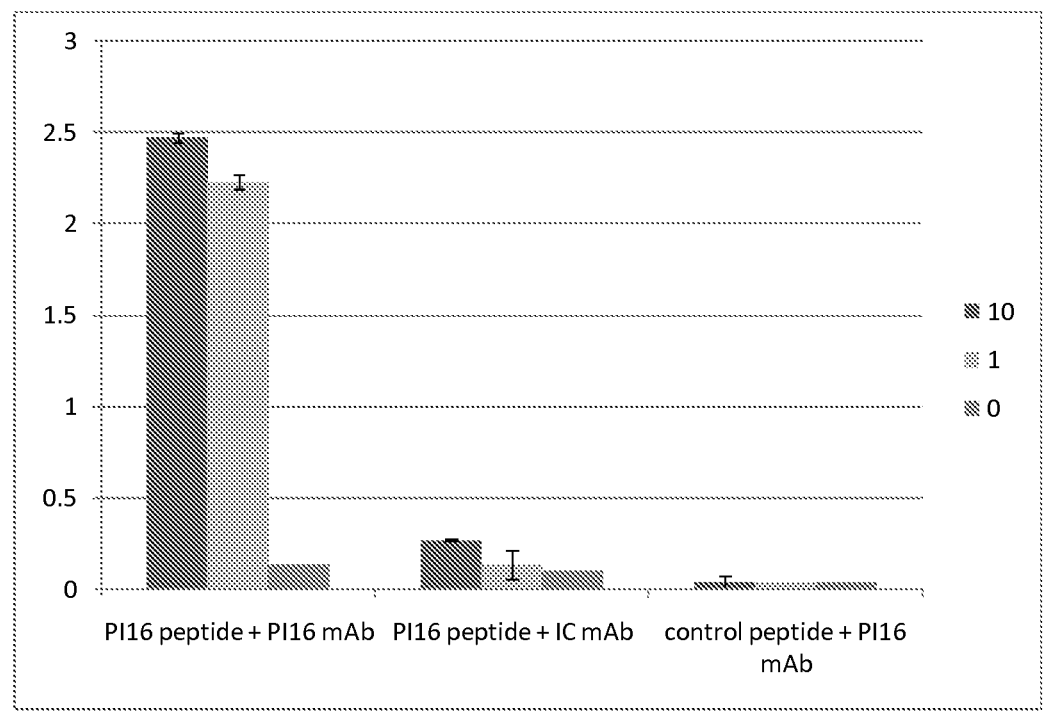

FIG. 41 is a graphical representation showing binding of CRCBT-02-001 to a peptide fragment of human PI16 or a negative control peptide. As a control another isotype control antibody (IC) was used. Concentration of antibody is shown at the right hand side of the Figure. added to wells coated with peptide.

Figure 42:
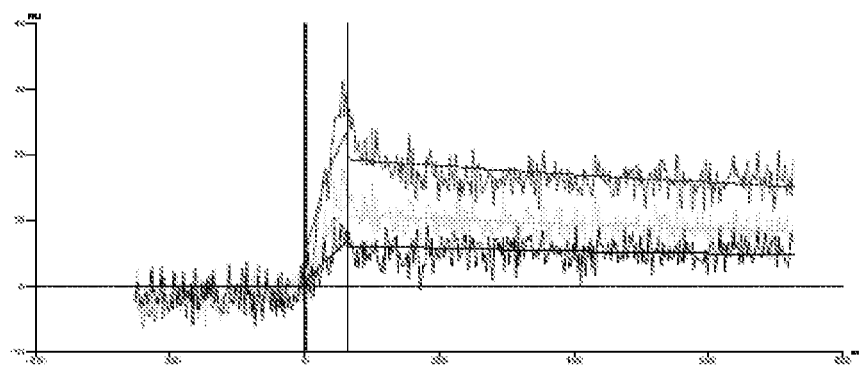

FIG. 42 is a graphical representation showing association ($K_a$) and dissociation curves ($K_d$) for PI16 Fab binding to PI16-Fc at 3 different concentrations (50 nM, 25 nM and 12.5 nM).

Figure 43:
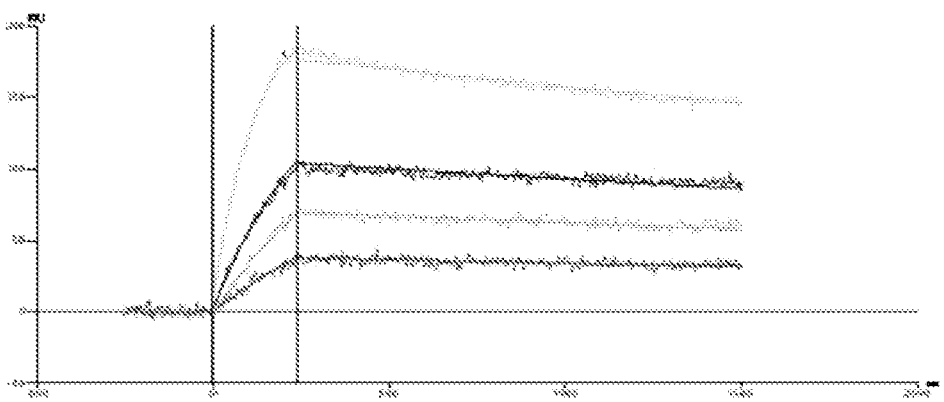

FIG. 43 is a graphical representation showing association ($K_a$) and dissociation curves ($k_d$) for PI16-fc binding to PI16 mAb at 4 different concentrations of PI16-Fc (50 nM, 25 nM, 12.5 nM and 6.25 nM).

KEY TO SEQUENCE LISTING

SEQ ID NO: 1 is the amino acid sequence of *Homo sapiens* PI16.
SEQ ID NO: 2 is the amino acid sequence of *Mus musculus* PI16.
SEQ ID NO: 3 is the amino acid sequence of *Rattus novigenicus* PI16.
SEQ ID NO: 4 is the amino acid sequence of *Pan troglodytes* PI16.
SEQ ID NO: 5 is the sequence of an oligonucleotide for amplifying *Homo sapiens* PI16 open reading frame.
SEQ ID NO: 6 is the sequence of an oligonucleotide for amplifying *Homo sapiens* PI16 open reading frame.
SEQ ID NO: 7 is a nucleotide sequence encoding the heavy chain of the antibody produced by hybridoma CRCBT-02-001.
SEQ ID NO: 8 is an amino acid sequence encoding the heavy chain of the antibody produced by hybridoma CRCBT-02-001.
SEQ ID NO: 9 is a nucleotide sequence encoding the light chain of the antibody produced by hybridoma CRCBT-02-001.
SEQ ID NO: 10 is an amino acid sequence encoding the heavy chain of the antibody produced by hybridoma CRCBT-02-001.
SEQ ID NO: 11 is a nucleotide sequence of a primer for cloning a sequence encoding a mouse immunoglobulin light chain.
SEQ ID NO: 12 is a nucleotide sequence of a primer for cloning a sequence encoding a mouse immunoglobulin light chain.
SEQ ID NO: 13 is a nucleotide sequence of a primer for cloning a sequence encoding a mouse immunoglobulin heavy chain.
SEQ ID NO: 14 is a nucleotide sequence of a primer for cloning a sequence encoding a mouse immunoglobulin heavy chain.
SEQ ID NO: 15 is a nucleotide sequence of a primer for cloning a sequence encoding a mouse immunoglobulin heavy chain.
SEQ ID NO: 16 is a nucleotide sequence of a primer for cloning a sequence encoding a mouse immunoglobulin heavy chain.
SEQ ID NO: 17 is a nucleotide sequence of a primer for cloning a sequence encoding a mouse immunoglobulin heavy chain.
SEQ ID NO: 18 is a nucleotide sequence of a primer for cloning a sequence encoding a mouse immunoglobulin heavy chain.
SEQ ID NO: 19 is a nucleotide sequence of a primer for amplifying a region of FoxP3.
SEQ ID NO: 20 is a nucleotide sequence of a primer for amplifying a region of FoxP3.
SEQ ID NO: 21 is a nucleotide sequence of a primer for amplifying a region of PI16.
SEQ ID NO: 22 is a nucleotide sequence of a primer for amplifying a region of PI16.
SEQ ID NO: 23 is a nucleotide sequence of a primer for amplifying a region of RPL13a.
SEQ ID NO: 24 is a nucleotide sequence of a primer for amplifying a region of RPL13a.
SEQ ID NO: 25 is a nucleotide sequence of a primer for amplifying a nucleic acid encoding amino acids 28-443 of PI16.
SEQ ID NO: 26 is a nucleotide sequence of a primer for amplifying a nucleic acid encoding amino acids 28-443 of PI16.
SEQ ID NO: 27 is an amino acid sequence of a peptide fragment of PI16.
SEQ ID NO: 28 is a nucleotide sequence of a primer for amplifying TSDR.
SEQ ID NO: 29 is a nucleotide sequence of a primer for amplifying TSDR.
SEQ ID NO: 30 is a nucleotide sequence of a M13 universal forward primer.
SEQ ID NO: 31 is a nucleotide sequence of a M13 universal reverse primer.
SEQ ID NO: 32 is an amino acid sequence of a peptide fragment of human PI16 bound by CRCBT-02-001.
SEQ ID NO: 33 is an amino acid sequence of a fragment of PI16 expressed by phage clone 15.
SEQ ID NO: 34 is an amino acid sequence of a fragment of PI16 expressed by phage clone 12.
SEQ ID NO: 35 is an amino acid sequence of a fragment of PI16 expressed by phage clone 10.
SEQ ID NO: 36 is an amino acid sequence of a fragment of PI16 expressed by phage clone 7.
SEQ ID NO: 37 is an amino acid sequence of a fragment of PI16 expressed by phage clone 4.
SEQ ID NO: 38 is an amino acid sequence of an overlapping region of the sequence of phage clones 15, 12, 10, 7 and 4.
SEQ ID NO: 39 is an amino acid sequence of a peptide fragment of human PI16 common to phage clones 4 and 7.
SEQ ID NO: 40 is an amino acid sequence of a human PI16 ectodomain.

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

Any embodiment herein shall be taken to apply mutatis mutandis to any other embodiment unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, Perbal (1984), Sambrook et al., (1989), Brown (1991), Glover and Hames (1995 and 1996), and Ausubel et al., (1988, including all updates until present), Harlow and Lane, (1988), Coligan et al., (including all updates until present) and Zola (1987).

The description and definitions of variable regions and parts thereof, immunoglobulins, antibodies and fragments thereof herein may be further clarified by the discussion in Kabat, 1987 and/or 1991, Bork et al., 1994 and/or Chothia and Lesk, 1987 and/or 1989 or Al-Lazikani et al., 1997.

The term "and/or", e.g., "X and/or Y" shall be understood to mean either "X and Y" or "X or Y" and shall be taken to provide explicit support for both meanings or for either meaning Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

SELECTED DEFINITIONS

The skilled artisan will be aware that an "antibody" includes an immune protein capable of specifically binding to one or a few closely related antigens (e.g., PI16) by virtue of an antigen binding site contained within at least one variable region. This term includes four chain antibodies (e.g., two light chains and two heavy chains), recombinant or modified antibodies (e.g., chimeric antibodies, humanized antibodies, primatized antibodies, de-immunized antibodies, half antibodies, bispecific antibodies) and single domain antibodies such as domain antibodies and heavy chain only antibodies (e.g., camelid antibodies or cartilaginous fish immunoglobulin new antigen receptors (IgNARs)). An antibody generally comprises constant domains, which can be arranged into a constant region or constant fragment or fragment crystallisable (Fc). Preferred forms of antibodies comprise a four-chain structure as their basic unit. Full-length antibodies comprise two heavy chains (~50-70 kD) covalently linked and two light chains (~23 kD each). A light chain generally comprises a variable region and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H$ which is—330-440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region can be identified between the $C_H1$ and Cm constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. Preferably, the antibody is a murine (mouse or rat) antibody or a primate (preferably human) antibody.

As used herein, "variable region" refers to the portions of the light and/or heavy chains of an antibody as defined herein that is capable of specifically binding to an antigen and, preferably, includes amino acid sequences of CDRs; i.e., CDR1, CDR2, and CDR3, and FRs. Preferably, the variable region comprises three or four FRs (e.g., FR1, FR2, FR3 and optionally FR4) together with three CDRs. $V_H$ refers to the variable region of the heavy chain. $V_L$ refers to the variable region of the light chain. The amino acid positions assigned to CDRs and FRs can be defined according to Kabat (1987 and 1991) or other numbering systems in the performance of this invention, e.g., the hypervariable loop numbering system of Clothia and Lesk (1987 and/or 1989 and/or Al-Lazikani et al., 1997). For example, according to the numbering system of Kabat, a $V_H$ FRs and CDRs positioned as follows residues 1-25 or 1-30 (FR1), 31-25 (CDR1), 36-49 (FR2), 50-65 (CDR2), 66-94 (FR3), 95-102 (CDR3) and 103-113 (FR4), numbered according to the Kabat numbering system. In one example, the $V_H$ is derived from an antibody comprising said heavy chain and a plurality of (preferably 3 or 4) constant domains or linked to a constant fragment (Fc). Preferably, a $V_L$ comprises FRs and CDRs positioned as follows residues 1-23 (FR1), 24-34 (CDR1), 35-49 (FR2), 50-56 (CDR2), 57-88 (FR3), 89-97 (CDR3) and 98-107 (FR4), numbered according to the Kabat numbering system. In one example, the $V_L$ is derived from an antibody comprising said $V_L$ linked to one constant domain and/or not linked to a constant fragment (Fc).

As used herein, the term "complementarity determining regions" (syn. CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat et al., (1991) and/or those residues from a "hypervariable loop" Chothia and Lesk (1987), or any other known numbering technique or combination thereof, including the IMGT numbering system (Le Franc et al., 2003). For example, in a heavy chain variable region CDRH1 is between residues 31-35, CDRH2 is between residues 50-65 and CDRH3 is between residues 95-102. In a light chain CDRL1 is between residues 24-34, CDRL2 is between residues 50-56 and CDRL3 is between residues 89-97. These CDRs can also comprise numerous insertions, e.g., as described in Kabat (1987 and/or 1991).

"Framework regions" (hereinafter FR) are those variable domain residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore an Fv of the invention (as well as any protein of the invention) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$), e.g., a domain antibody or a single domain antibody. Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. An "F(ab')2 fragment" of an antibody consists of a dimer of two Fab' fragments held together by two disulfide bonds, and is obtained by treating a whole antibody molecule with the enzyme pepsin, without subsequent reduction. An "Fab$_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker. A detailed discussion of exemplary Fv containing proteins falling within the scope of this term is provided herein below.

As used herein, the term "antigen binding site" shall be taken to mean a structure formed by a protein that is capable of specifically binding to an antigen. The antigen binding site need not be a series of contiguous amino acids, or even amino acids in a single polypeptide chain. For example, in a Fv produced from two different polypeptide chains the antigen binding site is made up of a series of regions of a $V_L$ and a $V_H$ that interact with the antigen and that are generally, however not always in the one or more of the CDRs in each variable region.

The term "constant region" (syn. CR or fragment crystallizable or Fc) as used herein, refers to a portion of an antibody comprising at least one constant domain and which is generally (though not necessarily) glycosylated and which binds to one or more F receptors and/or components of the complement cascade (e.g., confers effector functions). The heavy chain constant region can be selected from any of the five isotypes: α, δ, ε, γ, or μ. Furthermore, heavy chains of various subclasses (such as the IgG subclasses of heavy chains) are responsible for different effector functions and thus, by choosing the desired heavy chain constant region, proteins with desired effector function can be produced. Preferred heavy chain constant regions are gamma 1 (IgG1), gamma 2 (IgG2) and gamma 3 (IgG3).

A "constant domain" is a domain in an antibody the sequence of which is highly similar in antibodies/antibodies of the same type, e.g., IgG or IgM or IgE. A constant region of an antibody generally comprises a plurality of constant domains, e.g., the constant region of γ, α and δ heavy chains comprises three constant domains and the Fc of γ, α and δ heavy chains comprise two constant domains. A constant region of μ and ε heavy chains comprises four constant domains and the Fc region comprises two constant domains.

By "isolated" is meant that the protein is substantially removed from its naturally-occurring environment, e.g., is in a heterologous environment and/or that it is substantially free of contaminating agents, e.g., at least about 70% or 75% or 80% or 85% or 90% or 95% or 96% or 97% or 98% or 99% free of contaminating agents.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions. A non-covalent bond contemplated by the present invention is the interaction between a $V_H$ and a $V_L$, e.g., in some forms of diabody or a triabody or a tetrabody or a Fv.

The term "polypeptide chain" will be understood to mean from the foregoing paragraph to mean a series of contiguous amino acids linked by peptide bonds.

As used herein, the term "specifically binds" shall be taken to mean a protein of the invention reacts or associates more frequently, more rapidly, with greater duration and/or with greater affinity with a particular antigen or antigens or cell expressing same than it does with alternative antigens or cells. For example, a protein that specifically binds to an antigen binds that antigen with greater affinity, avidity, more readily, and/or with greater duration than it binds to other antigens. It is also understood by reading this definition that, for example, a protein that specifically binds to a first antigen may or may not specifically bind to a second antigen. As such, "specific binding" does not necessarily require exclusive binding or non-detectable binding of another antigen, this is meant by the term "selective binding". Generally, but not necessarily, reference to binding means specific binding, and each term shall be understood to provide explicit support for the other term.

As used herein, "does not substantially bind" shall be understood to mean that a protein does not bind to an antigen at a level greater than 20% or 15% or 10% or 9% or 8% or 7% or 6% or 5% or 4% or 3% or 2% of the level of binding to an antigen to which the protein is known to bind. In one example, the binding is detected by Western blotting and/or FACS and/or ELISA and/or antibody panning (e.g., with antibody variable regions on the surface of a particle, such as a phage) and/or Biacore analysis. For example, a protein of the present invention binds to reduced and alkyated PI16 at a level no greater than about 20% or 15% or 10% of the level bound to correctly folded and disulphide bonded PI16.

As used herein, "does not detectably bind" shall be understood to mean that a protein does not bind to an antigen at a level significantly greater than background, e.g., binds to PI16 at a level less than 10%, or 8% or 6% or 5% above background. In the case of an antibody, the antibody binds to the antigen at a level less than 10% or 8% or 6% or 5% greater than an isotype control antibody. In one example, the binding is detected by Western blotting and/or FACS and/or ELISA and/or antibody panning (e.g., with antibody variable regions on the surface of a particle, such as a phage) and/or Biacore analysis.

As used herein, the term "specifically binds to an epitope comprising a sequence" will be understood to mean that a protein binds to or makes contact with one or more residues within the recited sequence. The term does not exclude other components of PI16 being involved in the binding. For example, a protein exemplified herein binds to a sequence, however that binding is affected by the presence of disulphide bonds in PI16, which occur outside the bound sequence. In one example, the protein does not bind to any other epitope in PI16.

As used herein, the term "an epitope contained within a sequence" will be understood to mean that the sequence to which a protein binds is contained within the recited sequence. The term does not exclude other components of PI16 being involved in the binding. For example, a protein exemplified herein binds to a sequence, however that binding is affected by the presence of disulphide bonds in PI16, which occur outside the bound sequence. In one example, the protein does not bind to any other epitope in PI16.

An "epitope is dependent of disulphide bond formation within PI16" will be understood to mean an epitope that is bound by a protein when PI16 comprises disulphide bonds, however that is not substantially bound when PI16 does not comprise disulphide bonds (e.g., is reduced and/or alkylated).

As used herein, the term "reduced form" shall be taken to mean a protein treated to break disulphide bonds and/or to reduce oxidation of sulfhydryl (—SH) groups in a protein.

As used herein, the term "hybridoma designated CRCBT-02-001" shall be understood to mean the hybridoma designated with the American Type Culture Collection (ATCC) deposited with the ATCC under Accession Number PTA-10685. In some cases herein, the antibody secreted by the hybridoma designated CRCBT-02-001 is referred to as CRCBT-02-001.

As used herein, the term "peptidase inhibitor 16" or "PI16" (syn. Cysteine rich secretory protein 9, CRISP9, PSP96 binding protein or PSPBP) will be understood to mean a protein of the cysteine rich secretory protein (CRISP) family that interacts with prostate secretory protein (PSP) 94. An example of PI16 is described in Reeves et al., (2005). An exemplary sequence of a human PI16 is set forth in SEQ ID NO: 1. An exemplary sequence of mouse PI16 is set forth in SEQ ID NO: 2. An exemplary sequence of rat PI16 is set forth in SEQ ID NO: 3. An exemplary sequence of chimpanzee PI16 is set forth in SEQ ID NO: 4. As shown in the alignment depicted in FIG. 1, human, mouse, rat and chimpanzee PI16, the most diverse sequences share 52% sequence identity. Accordingly, the term "PI16" and related terms includes a protein comprising a sequence at least about 52% identity to a sequence set forth in any one or more of SEQ ID NOs: 1-4. Preferably, the PI16 is a *Homo sapiens* PI16.

As used herein, the term "epitope" (syn. "antigenic determinant") shall be understood to mean a region of PI16 to which an antibody produced by a hybridoma designated CRCBT-02-001 binds. This term is not necessarily limited to the specific residues or structure to which the antibody makes contacts. For example, this term includes the region spanning amino acids contacted by the antibody and/or 5-10 or 2-5 or 1-3 amino acids outside of this region. In some example, the epitope is a series of consecutive amino acids from PI16. However, an epitope can also comprise a series of discontinuous amino acids that are positioned close to one another when PI16 is folded, i.e., a "conformational epitope". The skilled artisan will also be aware that the term "epitope" is not limited to peptides or polypeptides. An epitope or peptide or polypeptide comprising same can be administered to an animal to generate antibodies against the epitope.

The term "competitively inhibits" shall be understood to mean that a protein of the invention reduces or prevents binding of an antibody produced by the hybridoma designated CRCBT-02-001 to PI16. It will be apparent from the foregoing that the protein need not completely inhibit binding of the antibody produced by the hybridoma designated CRCBT-02-001, rather it need only reduce binding by a statistically significant amount, for example, by at least about 10% or 20% or 30% or 40% or 50% or 60% or 70% or 80% or 90% or 95%. Methods for determining competitively inhibition of binding are known in the art and/or described herein. For example, the antibody is exposed to PI16 either in the presence or absence of the protein. If less antibody binds in the presence of the protein than in the absence of the protein, the protein is considered to competitively inhibit binding of the antibody. Preferably, the protein and antibody are exposed to PI16 substantially simultaneously.

By "overlapping" in the context of two epitopes shall be taken to mean that two epitopes share a sufficient number of amino acid residues to permit an antibody that binds to one epitope to competitively inhibit the binding of an antibody that binds to the other epitope. For example, the present invention encompasses a protein that binds to an epitope sharing a sufficient number of residues to prevent binding of an antibody produced by the hybridoma designated CRCBT-02-001 to its epitope.

As used herein, the term "Treg" or "regulatory T cell" shall be understood to mean a T cell expresses at least CD4 and/or CD25 that is capable of reducing or suppressing the activity of a T cell other than a Treg cell and/or killing a T cell. This term includes T cells which produce low levels of IL-2, IL-4, IL-5, and IL-1, and acts to suppress activation of the immune system. Regulatory T cells actively suppress the proliferation and cytokine production of $T_H1$, $T_H2$, or naive T cells which have been stimulated in culture with an activating signal (e.g., antigen and antigen presenting cells or with a signal that mimics antigen in the context of MHC, e.g., anti-CD3 antibody, plus anti-CD28 antibody). In one example, a Treg cell expresses FoxP3 (however, it not a requirement that expression of FoxP3 is detected to determine whether or not a cell is a Treg cell). This term also encompasses mutant forms of Treg cells, e.g., a cell which is derived from Treg cells but exhibits at least one difference at the phenotypic or functional or structural level. For example, the mutant or variant may have been altered to express a therapeutic protein or a protein that alters or enhances Treg cell function. Such changes can occur either spontaneously or as a result of a directed manipulation, such as would occur if a cell was deliberately transformed (for example, in order to effect the creation of a cell line) or transfected.

The term "Treg activity" includes the ability to suppress or reduce an immune response, e.g., as assessed using a mixed lymphocyte reaction (such as those described herein) and/or as assessed using an in vivo assay described herein. This term also encompasses the ability of a cell to secrete an anti-inflammatory cytokine, e.g., transforming growth factor-beta (TGF-β) and IL-10. Another activity of a Treg cell is expression of FoxP3.

The term "Treg-associated condition" shall be taken to encompass any disease or disorder or state in which modulation of Treg numbers and/or activity may provide a beneficial effect. This term encompasses conditions associated with regulatory T cell-mediated suppression of a subject's immune system, e.g., conditions associated with or caused by an excessive immune response (e.g., by a Thelper cell or a CTL or a $T_H17$ cell or other cell regulated by one or more T cells). Accordingly, this term encompasses inflammatory conditions and/or autoimmune conditions. Exemplary Treg-associated conditions include, an inflammatory disorder of the nervous system (e.g., multiple sclerosis), or a mucosal inflammatory disease (e.g., inflammatory bowel disease, asthma or tonsillitis), or an inflammatory skin disease (e.g., dermatitis, psoriasis or contact hypersensitivity) or autoimmune arthritis (e.g., rheumatoid arthritis). Preferred Treg associated conditions include rheumatoid arthritis. In one embodiment, the inflammatory disorder is an allergic inflammatory disorder. Other exemplary Treg-associated conditions include conditions characterised by excessive Treg numbers and/or activity. For example, an immune response against a graft or graft versus host disease or host versus graft disease is also a Treg-associated condition. This term also includes cancer, e.g., in which Treg cells suppress the activity of immune cells against cancerous cells, thereby permitting the disease to develop.

As used herein, the term "$T_H17$-mediated condition" shall be taken to mean any condition characterised or caused by excessive numbers or activity of $T_H17$ cells. The skilled artisan will be aware that a $T_H17$ cell is a $CD4^+$ T cell that expresses IL17. $T_H17$ cells also generally express CCR6 and/or CCR4. Exemplary $T_H17$-mediated conditions include autoimmune/inflammatory conditions (e.g., psoriasis, inflammatory bowel disease, arthritis (e.g., rheumatoid arthritis), multiple sclerosis and inflammatory bowel disease (e.g., Crohn's disease)) and graft versus host disease.

As used herein, the term "preferentially migrates" refers to cells that migrate to a specific site (e.g., a site of inflammation and/or to skin) in a subject faster or with a greater concentration than other cells in a subject, preferably faster or with a greater concentration than Treg cells that do not express PI16 (and optionally, CCR6 and/or CCR4).

As used herein, the terms "preventing", "prevent" or "prevention" include administering a therapeutically effective amount of a protein of the invention sufficient to stop or hinder the development of at least one symptom of a specified disease or condition.

As used herein, the terms "treating", "treat" or "treatment" include administering a therapeutically effective amount of a protein described herein sufficient to reduce or eliminate at least one symptom of a specified disease or condition.

As used herein, the term "subject" shall be taken to mean any animal including humans, preferably a mammal. Exemplary subjects include but are not limited to humans, primates, livestock (e.g. sheep, cows, horses, donkeys, pigs), companion animals (e.g. dogs, cats), laboratory test animals (e.g. mice, rabbits, rats, guinea pigs, hamsters), captive wild animals (e.g. fox, deer). Preferably the mammal is a human or primate. More preferably the mammal is a human.

The term "sample" shall be taken to encompass the recited sample (e.g., a blood sample) and any fraction thereof (e.g., plasma, serum or buffy coat) or cells derived therefrom (e.g., peripheral blood mononuclear cells) or processed forms thereof.

As used herein, the term "enriched" or "enrich" in the context of a cell population shall be taken to mean that the number or percentage of Treg cells is greater than the number or percentage in a naturally occurring cell population. For example, a population enriched in Treg cells is made up of at least about 0.02% of said cells, or at least about 0.05% of said cells or at least about 0.1% of said cells or at least about 0.2% of said cells or at least about 0.5% of said cells or at least about 0.5% of said cells or at least about 0.8% of said cells or at least about 1% of said cells or at least about 2% of said cells or at least about 3% of said cells or at least about 4% of said cells or at least about 5% of said cells or at least about 10% of said cells or at least about 15% of said cells or at least about 20% of said cells or at least about 25% of said cells or at least about 30% of said cells or at least about 40% of said cells or at least about 50% of said cells or at least about 60% of said cells or at least about 70% of said cells or at least about 80% of said cells or at least about 85% of said cells or at least about 90% of said cells or at least about 95% of said cells or at least about 97% of said cells or at least about 98% of said cells or at least about 99% of said cells.

PI16 Polypeptides

A preferred polypeptide PI16 comprises a sequence at least about 52% sequence identical to any one or more of SEQ ID NOs:1-4. Preferably, the degree of sequence identity is at least about 53% or 55% or 60% or 62% or 70% or 75% or 80% or 85% or 90% or 95% or 99%. As will be known to those skilled in the art, it is possible to identify naturally-occurring variants and/or mutants of said nucleic acids and/or proteins using standard techniques, including in silico analysis, e.g., using BLAST.

The % identity of a nucleic acid or polypeptide is determined by GAP (Needleman and Wunsch, 1970) analysis (GCG program) with a gap creation penalty=5, and a gap extension penalty=0.3. The query sequence is at least 50 residues in length, and the GAP analysis aligns the two sequences over a region of at least 50 residues. Even more preferably, the query sequence is at least 100 residues in length and the GAP analysis aligns the two sequences over a region of at least 100 residues. Most preferably, the two sequences are aligned over their entire length.

Variable Region Containing Proteins

The present invention contemplates any protein that comprises a protein comprising an antibody CDR, wherein the protein binds to PI16 and competitively inhibits binding of an antibody produced by the hybridoma designated CRCBT-02-001 to PI16.

The present invention also provides any protein that comprises at least three (and in some embodiments, comprises six) antibody CDRs, wherein the protein binds to PI16 and competitively inhibits binding of an antibody produced by the hybridoma designated CRCBT-02-001 to PI16

The present invention contemplates any protein that comprises an antibody variable region that binds to PI16 and competitively inhibits binding of an antibody produced by the hybridoma designated CRCBT-02-001 to PI16. Exemplary antibody variable regions are variable regions from monoclonal antibodies and modified forms thereof (e.g., humanized antibodies) and heavy chain antibodies, such as, camelid immunoglobulin and IgNAR.

Antibodies

Methods for generating antibodies are known in the art and/or described in Harlow and Lane (1988) or Zola (1987).

Generally, in such methods a PI16 protein or immunogenic fragment or epitope thereof or a cell expressing and displaying same (i.e., an immunogen), optionally formulated with any suitable or desired carrier, adjuvant, or pharmaceutically acceptable excipient, is administered to a non-human animal subject, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (Mabs).

Monoclonal antibodies are preferred. The term "monoclonal antibody" or "MAb" refers to a homogeneous antibody population capable of binding to the same antigen(s) and, preferably, to the same epitope within the antigen. This term is not intended to be limited as regards to the source of the antibody or the manner in which it is made.

For the production of Mabs any one of a number of known techniques may be used, such as, for example, the procedure exemplified in U.S. Pat. No. 4,196,265 or Harlow and Lane (1988) or Zola (1987).

For example, a suitable animal is immunized with an effective amount of the protein or immunogenic fragment or epitope thereof or cell expressing same under conditions sufficient to stimulate antibody producing cells. Rodents such as rabbits, mice and rats are preferred animals, with mice being most preferred. Mice genetically-engineered to express human immunoglobulin proteins, and preferably not express murine immunoglobulin proteins, are also preferred to generate an antibody of the present invention (e.g., as described in WO2002/066630, Lonberg et al., 1994; Tomizuka et al., 2000 and Jakobovits et al., 2007).

Following immunization, somatic cells with the potential for producing antibodies, specifically B lymphocytes (B cells), are selected for use in the MAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen. B cells and immortal cells are fused by incubating a mixtures of the cells types in the presence of an agent or agents (chemical or electrical) that promote the fusion of cell membranes. Fusion methods using Sendai virus have been described by Kohler and Milstein, (1975); and Kohler and Milstein, (1976). Methods using polyethylene glycol (PEG), such as 37% (v/v) PEG, are described in detail by Gefter et al, (1977). The use of electrically induced fusion methods is also appropriate.

Hybrids are amplified by culture in a selective medium comprising an agent that blocks the de novo synthesis of nucleotides in the tissue culture media. Exemplary and preferred agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like). The present invention also contemplates sub-cloning of antibody producing cells, e.g., as exemplified herein.

Alternatively, ABL-MYC technology (NeoClone, Madison Wis. 53713, USA) is used to produce cell lines secreting MAbs (e.g., as described in Largaespada et al, 1996; and Kumar et al, 1999).

Antibodies can also be produced or isolated by screening a display library, e.g., a phage display library, e.g., as described in U.S. Pat. No. 6,300,064 EP0368684 and/or U.S. Pat. No. 5,885,793.

Chimeric Antibodies and Proteins

In one example an antibody of the invention is a chimeric antibody. The term "chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass, as well as fragments of such antibodies, so long as they exhibit the desired biological activity. Typically chimeric antibodies utilize rodent or rabbit variable regions and human constant regions, in order to produce an antibody with predominantly human domains. Methods for producing chimeric antibodies are described in, e.g., U.S. Pat. No. 4,816,567; and Morrison et al., 1984.

The present invention also includes a chimeric protein, e.g., in which a variable region from one species or antibody subtype is fused to a region of a protein from another species or antibody subtype. For example, the invention contemplates a protein comprising a variable region from one species fused to a single constant domain from a separate species.

Humanized and Human Antibodies/Proteins

The antibodies or proteins of the present invention may be humanized or human.

The term "humanized antibody" shall be understood to refer to a chimeric molecule, generally prepared using recombinant techniques, having an antigen binding site or variable region derived from an antibody from a non-human species and the remaining antibody structure of the molecule based upon the structure and/or sequence of a human antibody. The antigen-binding site preferably comprises the complementarity determining regions (CDRs) from the non-human antibody grafted onto appropriate framework regions in the variable domains of a human antibody and the remaining regions from a human antibody. Antigen binding sites may be wild type or modified by one or more amino acid substitutions. In some instances, Fv framework residues of the human immunoglobulin are replaced by corresponding non-human residues. Humanized antibodies may also comprise residues which are found neither in the recipient antibody nor in the imported CDR or framework sequences.

Methods for humanizing non-human antibodies or parts thereof (e.g., variable regions) are known in the art. Humanization can be essentially performed following the method of U.S. Pat. No. 5,225,539, or U.S. Pat. No. 5,585,089, by substituting rodent CDRs or CDR sequences for the corresponding sequences of a human antibody. Other methods for humanizing an antibody are not excluded.

The term "human antibody" as used herein in connection with antibody molecules and binding proteins refers to antibodies having variable (e.g. $V_H$, $V_L$, CDR and FR regions) and, optionally constant antibody regions derived from or corresponding to sequences found in humans, e.g. in the human germline or somatic cells. The "human" antibodies can include amino acid residues not encoded by human sequences, e.g. mutations introduced by random or site directed mutations in vitro (in particular mutations which involve conservative substitutions or mutations in a small number of residues of the antibody, e.g. in 1, 2, 3, 4 or 5 of the residues of the antibody, preferably e.g. in 1, 2, 3, 4 or 5 of the residues making up one or more of the CDRs of the antibody). These "human antibodies" do not actually need to be produced by a human, rather, they can be produced using recombinant means and/or isolated from a transgenic animal (e.g., mouse) comprising nucleic acid encoding human antibody constant and/or variable regions (e.g., as described above). Human antibodies can also be produced using various techniques known in the art, including phage display libraries (e.g., as described in Hoogenboom and Winter, 1991; Marks et al., 1991; U.S. Pat. No. 5,885,793).

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope (Jespers et al, 1988).

A human protein of the invention comprises a variable region of a human antibody.

De-Immunized Antibodies and Proteins

The present invention also contemplates a de-immunized antibody or protein. De-immunized antibodies and proteins have one or more epitopes, e.g., B cell epitopes or T cell epitopes removed (i.e., mutated) to thereby reduce the likelihood that a subject will raise an immune response against the antibody or protein. Methods for producing de-immunized antibodies and proteins are known in the art and described, for example, in WO00/34317, WO2004/108158 and WO2004/064724.

Methods for introducing suitable mutations and expressing and assaying the resulting protein will be apparent to the skilled artisan based on the description herein.

Heavy Chain Antibodies

Heavy chain antibodies differ structurally from many other forms of antibodies, in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain antibodies are generally referred to as "$V_{HH}$ domains" in camelid antibodies and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

A general description of heavy chain antibodies from camelids and the variable regions thereof and methods for their production and/or isolation and/or use is found inter alia in the following references WO94/04678, WO97/49805 and WO 97/49805.

A general description of heavy chain immunoglobulins from cartilaginous fish and the variable regions thereof and methods for their production and/or isolation and/or use is found inter alia in WO2005/118629; Shao et al., (2007); and/or Dooley and Flajnik (2006).

Variable Region Containing Proteins

Single-Domain Antibodies

In some examples, a protein of the invention is a single-domain antibody (which is used interchangeably with the term "domain antibody" or "dAb"). A single-domain antibody is a single polypeptide chain comprising all or a portion of the heavy chain variable domain of an antibody. In certain embodiments, a single-domain antibody is a human single-domain antibody (Domantis, Inc., Waltham, Mass.; see, e.g., U.S. Pat. No. 6,248,516; WO90/05144; WO2003/002609 and/or WO2004/058820).

Diabodies, Triabodies, Tetrabodies

Exemplary preferred proteins comprising an antibody variable region are diabodies, triabodies, tetrabodies and higher order protein complexes such as those described in WO98/044001 and WO94/007921.

For example, a diabody is a protein comprising two associated polypeptide chains, each polypeptide chain comprising the structure $V_L$-X-$V_H$ or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

The skilled artisan will be aware of diabodies, triabodies and/or tetrabodies and methods for their production. Exemplary publications describing diabodies, triabodies and/or tetrabodies include WO94/07921; WO98/44001; Holliger et al., (1993); Hudson and Kortt (1999); Holliger and Hudson (2005); and references cited therein.

Single Chain Fv (scFv) Fragments

The skilled artisan will be aware that scFvs comprise $V_H$ and $V_L$ regions in a single polypeptide chain. Preferably, the polypeptide chain further comprises a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favoured linkers for a scFv.

The present invention also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv (see, for example, Brinkmann et al., 1993).

Alternatively, or in addition, the present invention provides a dimeric scFv, i.e., a protein comprising two scFv molecules linked by a non-covalent or covalent linkage, e.g., by a leucine zipper domain (e.g., derived from Fos or Jun) (see, for example, Kruif and Logtenberg, 1996). Alternatively, two scFvs are linked by a peptide linker of sufficient length to permit both scFvs to form and to bind to an antigen, e.g., as described in US20060263367.

For a review of scFv, see Plückthun (1994).

Minibodies

The skilled artisan will be aware that a minibody comprises the $V_H$ and $V_L$ domains of an antibody fused to the $C_H2$ and/or $C_H3$ domain of an antibody. Optionally, the minibody comprises a hinge region between the $V_H$ and a $V_L$, sometimes this conformation is referred to as a Flex Minibody (Hu et al., 1996). A minibody does not comprise a $C_H1$ or a $C_L$. Preferably, the $V_H$ and $V_L$ domains are fused to the hinge region and the $C_H3$ domain of an antibody. At least one of the variable regions of said minibody binds to PI16 in the manner of the invention. Exemplary minibodies and methods for their production are described, for example, in WO94/09817.

Other Variable Region Containing Proteins

The present invention also contemplates other variable region containing proteins, such as:
(i) "key and hole" bispecific proteins as described in U.S. Pat. No. 5,731,168;
(ii) heteroconjugate proteins, e.g., as described in U.S. Pat. No. 4,676,980;
(iii) heteroconjugate proteins produced using a chemical cross-linker, e.g., as described in U.S. Pat. No. 4,676,980 or Brennan (1985);
(iv) Fab'-SH fragments, e.g., as described in Shalaby (1992);
(v) single chain Fab (e.g., Hust et al., 2007); or
(vi) $Fab_3$ (e.g., as described in EP19930302894).

Constant Domain Fusions

The present invention encompasses proteins comprising a variable region and a constant region (e.g., Fc) or a domain thereof, e.g., $C_H2$ and/or $C_H3$ domain. The skilled artisan will be aware of the meaning of the terms constant region and constant domain based on the disclosure herein and references discussed herein.

Constant domain sequences useful for producing the proteins of the present invention may be obtained from a number of different sources. In some examples, the constant domain or portion thereof of the protein is derived from a human antibody. Moreover, the constant domain or portion thereof may be derived from any antibody class, including IgM, IgG, IgD, IgA and IgE, and any antibody isotype, including IgG1, IgG2, IgG3 and IgG4. In a preferred example, the human isotype IgG1 is used.

A variety of constant domain gene sequences (e.g. human constant domain gene sequences) are available in the form of publicly accessible deposits or the sequence thereof is available from publicly available databases. Constant domains can be selected having a particular effector function (or lacking a particular effector function) or with a particular modification to reduce immunogenicity.

As used herein, the term "effector function" refers to the functional ability of the Fc region or portion thereof (e.g., $C_H2$ domain) to bind proteins and/or cells of the immune system and mediate various biological effects. Effector functions may be antigen-dependent or antigen-independent. "Antigen-dependent effector function" refers to an effector function which is normally induced following the binding of an antibody to a corresponding antigen. Typical antigen-dependent effector functions include complement dependent cytotoxicity, antibody-dependent phagocytosis (ADCP), antibody-dependent cell-mediated cytotoxicity (ADCC), release of inflammatory mediators, regulation of immune system cell activation, placental transfer and control of antibody production.

As used herein, the term "antigen-independent effector function" refers to an effector function which may be induced by an immunoglobulin, regardless of whether it has bound its corresponding antigen. Typical antigen-independent effector functions include cellular transport, circulating half-life and clearance rates of antibodies, and facilitation of purification.

In one example, an altered protein of the invention comprises an altered synthetic constant regions wherein or more constant region domains are partially or entirely deleted ("domain-deleted constant regions"). The present invention also encompasses modified Fc regions or parts there having altered, e.g., improved or reduced effector function. Many such modified Fc regions are known in the art and described, for example, in WO2005/035586, WO2005/063815 or WO2005/047327.

Affinity Maturation

In a further example, an existing antibody, e.g., that secreted by the hybridoma designated CRCBT-02-001 or a humanized form thereof is affinity matured to produce an antibody capable of binding to PI16 with increased affinity. For example, the sequence encoding the $V_L$ and/or $V_H$ is isolated and the CDR encoding region (e.g., the region encoding CDR3 of the $V_L$ and/or $V_H$) is mutated such that one or more amino acid substitutions is introduced. The resulting mutant protein is then screened for binding to PI16, e.g., in a competitive assay.

The proteins according to the invention may be soluble secreted proteins or may be presented as a fusion protein on the surface of a cell, or particle (e.g., a phage or other virus, a ribosome or a spore). Exemplary phage display methods are described, for example, in U.S. Pat. No. 5,821,047; U.S. Pat. No. 6,248,516 and U.S. Pat. No. 6,190,908. Phage display particles produced using these methods are then screened to identify a displayed protein having a conformation sufficient for binding to a target antigen e.g., PI16.

Protein Production

In one example, a protein of the invention is produced by culturing a hybridoma of the invention under conditions sufficient to produce the protein, e.g., as described herein and/or as is known in the art.

Recombinant Expression

In the case of a recombinant protein, nucleic acid encoding same is preferably placed into expression vectors, which are then transfected into host cells, preferably cells that can produce a disulphide bridge or bond, such as *E. coli* cells, yeast cells, insect cells, or mammalian cells, such as simian COS cells, Chinese Hamster Ovary (CHO) cells, or myeloma cells that do not otherwise produce immunoglobulin protein, to obtain the synthesis of proteins in the recombinant host cells. Review articles on recombinant expression in bacteria of DNA encoding the immunoglobulin include Skerra et al, (1993) and Plückthun, (1992). Molecular cloning techniques to achieve these ends are known in the art and described, for example in Ausubel or Sambrook. A wide variety of cloning and in vitro amplification methods are suitable for the construction of recombinant nucleic acids. Methods of producing recombinant antibodies are also known in the art. See U.S. Pat. No. 4,816,567; and Queen et al., (1989).

Following isolation, the nucleic acid encoding a protein of the invention is preferably inserted into an expression construct or replicable vector for further cloning (amplification of the DNA) or for expression in a cell-free system or in cells. Preferably, the nucleic acid is operably linked to a promoter.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Preferred promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Cell free expression systems are also contemplated by the present invention. For example, a nucleic acid encoding a protein of the invention is operably linked to a suitable promoter, e.g., a T7 promoter, and the resulting expression construct exposed to conditions sufficient for transcription and translation. Typical expression vectors for in vitro expression or cell-free expression have been described and include, but are not limited to the TNT T7 and TNT T3 systems (Promega), the pEXP1-DEST and pEXP2-DEST vectors (Invitrogen).

Many vectors for expression in cells are available. The vector components generally include, but are not limited to, one or more of the following: a signal sequence, a sequence encoding protein of the present invention (e.g., derived from the information provided herein), an enhancer element, a promoter, and a transcription termination sequence. The skilled artisan will be aware of suitable sequences for expression of a protein. For example, exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters include those active in prokaryotes (e.g., phoA promoter, β-lactamase and lactose promoter systems, alkaline phosphatase, a tryptophan (trp) promoter system, and hybrid promoters such as the tac promoter).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid molecule or a gene construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

The host cells used to produce the protein of this invention may be cultured in a variety of media, depending on the cell type used. Commercially available media such as Ham's F10 (Sigma), Minimal Essential Medium ((MEM), (Sigma), RPMl-1640 (Sigma), and Dulbecco's Modified Eagle's Medium ((DMEM), Sigma) are suitable for culturing mammalian cells. Media for culturing other cell types discussed herein are known in the art.

Isolation of Proteins

A protein of the present invention is preferably isolated. Methods for purifying a protein of the invention are known in the art and/or described herein.

When using recombinant techniques, the protein of the invention can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Where the protein is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Zola (1997).

The skilled artisan will also be aware that a protein of the invention can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. Preferably, the tag is a hexa-his tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilised on a solid or semi-solid support, washing the sample to remove unbound protein, and subsequently eluting the bound protein. Alternatively, or in addition a ligand or antibody that binds to a tag is used in an affinity purification method.

Conjugates

The present invention also provides conjugates of proteins described herein according to any embodiment. Examples of compounds to which a protein can be conjugated are selected from the group consisting of a radioisotope, a detectable label, a therapeutic compound, a colloid, a toxin, a nucleic acid, a peptide, a protein, a compound that increases the half life of the protein in a subject and mixtures thereof. Exemplary therapeutic agents include, but are not limited to an anti-angiogenic agent, an anti-neovascularization and/or other vascularization agent, an anti-proliferative agent, a pro-apoptotic agent, a chemotherapeutic agent or a therapeutic nucleic acid.

A toxin includes any agent that is detrimental to (e.g., kills) cells. For a description of these classes of drugs which are known in the art, and their mechanisms of action, see Goodman et al., (1990). Additional techniques relevant to the preparation of immunoglobulin-immunotoxin conjugates are provided in for instance Vitetta (1993) and U.S. Pat. No. 5,194,594. Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO93/21232.

Suitable chemotherapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)).

In one example, a protein as described herein according to any embodiment is conjugated or linked to another protein, including another protein of the invention or a protein comprising an antibody variable region, such as an antibody or a protein derived therefrom, e.g., as described herein. Other proteins are not excluded. Additional proteins will be apparent to the skilled artisan and include, for example, an immunomodulator or a half-life extending protein or a peptide or other protein that binds to serum albumin amongst others.

Exemplary serum albumin binding peptides or protein are described in US20060228364 or US20080260757.

A variety of radionuclides are available for the production of radioconjugated proteins. Examples include, but are not limited to, low energy radioactive nuclei (e.g., suitable for diagnostic purposes), such as $^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like. Preferably, the radionuclide is a gamma, photon, or positron-emitting radionuclide with a half-life suitable to permit activity or detection after the elapsed time between administration and localization to the imaging site. The present invention also encompasses high energy radioactive nuclei (e.g., for therapeutic purposes) such as $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic. Alternatively, high-energy isotopes may be generated by thermal irradiation of an otherwise stable isotope, for example as in boron neutron-capture therapy (Guan et al., 1998).

In another embodiment, the protein is conjugated to a "receptor" (such as streptavidin) for utilization in cell pretargeting wherein the conjugate is administered to the patient, followed by removal of unbound conjugate from the circulation using a clearing agent and then administration of a "ligand" (e.g., avidin) that is conjugated to a therapeutic agent (e.g., a radionucleotide).

The proteins of the present invention can be modified to contain additional nonproteinaceous moieties that are known in the art and readily available. Preferably, the moieties suitable for derivatization of the protein are physiologically acceptable polymer, preferably a water soluble polymer. Such polymers are useful for increasing stability and/or reducing clearance (e.g., by the kidney) and/or for reducing immunogenicity of a protein of the invention. Non-limiting examples of water soluble polymers include, but are not limited to, polyethylene glycol (PEG), polyvinyl alcohol (PVA), or propropylene glycol (PPG).

In one example, a protein as described herein according to any embodiment comprises one or more detectable markers to facilitate detection and/or isolation. For example, the compound comprises a fluorescent label such as, for example, fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7, fluorescein (5-carboxyfluorescein-N-hydroxysuccinimide ester), rhodamine (5,6-tetramethyl rhodamine). The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm).

Alternatively, or in addition, the protein as described herein according to any embodiment is labeled with, for example, a fluorescent semiconductor nanocrystal (as described, for example, in U.S. Pat. No. 6,306,610).

Alternatively, or in addition, the protein is labeled with, for example, a magnetic or paramagnetic compound, such as, iron, steel, nickel, cobalt, rare earth materials, neodymium-iron-boron, ferrous-chromium-cobalt, nickel-ferrous, cobalt-platinum, or strontium ferrite.

Immobilized Proteins

In one example a protein is immobilized on a solid or semi-solid matrix. The term "immobilization" is to be understood to involve various methods and techniques to fix proteins onto specific matrices, e.g. as described in WO99/56126 or WO02/26292. For example, immobilization can serve to stabilize the proteins so that their activity is not reduced or adversely modified by biological, chemical or physical exposure, especially during storage or in single-batch use.

A protein can be immobilized on a matrix that permits implantation into a subject, e.g., so as to capture Treg cells and/or to retain Treg cells implanted on the matrix.

Alternatively, a sample, preferably a blood sample is reacted with the matrix, e.g., in a continuous fashion.

In the meaning of the invention, three basic methods can be used for immobilization:

Various methods for immobilizing a protein on a matrix are known in the art and include crosslinking, binding to a carrier, retention within a semi-permeable matrix.

Exemplary matrices include porous gels, aluminium oxide, bentonite, agarose, starch, nylon or polyacrylamide.

Assaying Activity of a Protein of the Invention

Determining Competitive Binding

Assays for determining a protein that competitively inhibits binding of an antibody secreted by CRCBT-02-001 will be apparent to the skilled artisan. For example, an antibody secreted by CRCBT-02-001 is conjugated to a detectable label, e.g., a fluorescent label or a radioactive label. The labelled antibody and the test protein are then mixed and contacted with PI16 or an epitope thereof or a cell expressing same. The level of labelled antibody is then determined and compared to the level determined when the labelled antibody is contacted with the PI16, epitope or cells in the absence of the protein. If the level of labelled antibody is reduced in the presence of the test protein compared to the absence of the protein, the protein competitively inhibits binding of an antibody secreted by CRCBT-02-001.

Optionally, the test protein is conjugated to different label to the antibody secreted by CRCBT-02-001. This permits detection of the level of binding of the test protein to the protein, epitope or cell.

In another example, the epitope of the protein is mapped to determine if it is the same or overlaps with the epitope bound by the antibody secreted by CRCBT-02-001. Epitope mapping methods will be apparent to the skilled artisan. For example, a series of overlapping peptides spanning the PI16 sequence, e.g., peptides comprising 10-15 amino acids are produced. The protein is then contacted to each peptide and the peptide(s) to which it binds is determined. This permits determination of peptide(s) comprising the epitope to which the protein binds. If multiple non-contiguous peptides are bound by the protein, the protein may bind a conformational epitope.

Alternatively, or in addition, amino acid residues within PI16 are mutated, e.g., by alanine scanning mutagenesis, and mutations that reduce or prevent protein binding are determined. Any mutation that reduces or prevents binding of the protein is likely to be within the epitope bound by the protein.

Alternatively, or in addition, the protein is produced using the epitope to which the antibody secreted by CRCBT-02-001 binds, and thus is likely to bind to the same epitope.

Optionally, the dissociation constant (Kd) of a protein for PI16 or an epitope thereof. The "Kd" or "Kd value" for a PI16 binding protein of the invention is in one example measured by a radiolabeled PI16 binding assay (RIA). This assay equilibrates the protein with a minimal concentration of radioactive PI16 in the presence of a titration series of unlabeled PI16. Following washing to remove unbound PI16, the amount of radioactivity is determined, which is indicative of the Kd of the protein. According to another example the Kd or Kd value is measured by using surface plasmon resonance assays using BIAcore surface plasmon resonance (BIAcore, Inc., Piscataway, N.J.) with immobilized PI16. Preferably, proteins having a similar Kd or a higher Kd than the antibody secreted by CRCBT-02-001 are selected, because they are likely to compete for binding to PI16.

In Vitro Functional Assays

An exemplary in vitro method for determining the effect of a cell isolated using a protein of the invention on Treg activity or of the protein of the invention is, for example, a mixed lymphocyte reaction (MLR) or a mixed lymphocyte culture (MLC). Such a method involves culturing a mixture of cells, e.g., Treg cells as isolated by a method described herein and allotypically different T cells are cultured together. Several measures may then be performed to measure Treg activity, e.g., cell proliferation is then measured using a standard method, e.g., $^{13}$H thymidine incorporation (which indicates proliferation of active T cells indicating that the Treg cells are not active); and/or cytokine secretion by either Treg cells or other T cells which can indicate Treg activity or inactivity. Such a method is useful for identifying Treg cells having regulatory ability and/or for identifying compounds that induce/enhance or suppress/prevent Treg activity. An exemplary MLR is described in Wang et al., 2008.

Alternatively, or in addition an in vitro method for determining the effect of a protein on Treg cells is a 5,6-carboxy fluorescein diacetate succinimidyl ester (CFSE) suppressor assay, e.g., as described herein in the examples. In such an assay $CD4^+CD25^-$ cells are labeled with CFSE. $CD4^+CD25^-$ CFSE labeled T cells are then cultured with irradiated PBMCs in the presence of varying amounts of cells isolated according to the present invention. After a sufficient time, proliferation of the CD4 $CD25^-$ CFSE labeled T cells is analysed by flow cytometry. Each CFSE signal peak represents one division cycle. The ability of Treg cells to suppress cell proliferation is assessed by comparing CFSE signal peaks of $CD4^+CD25^-$ CFSE labeled T cells with and without the presence of a regulatory cell population. An exemplary CFSE suppressor assay is described in Venken et al., (2007).

In a further example, Treg cells isolated according to the invention are cultured in the presence of effector T cells and the number of effector T cells ($CD4^+CD25^-$) expressing CD154 (CD40L) is determined. Cells that reduce the number of cells expressing CD154 (i.e., activated T cells) compared to the number of $CD154^+$ cells in the absence of Treg cells, are considered to have Treg activity. This assay is described in more detail below.

Alternatively, or in addition, Treg cells are isolated, cultured in the presence or absence of a test compound and activated, e.g., as described herein. Secretion of IL-10 and/or TGF-β is then assessed using standard techniques, e.g., ELISA or FLISA.

An exemplary method for assessing activity of a protein of the invention on a metastatic cell is a cell migration assay or colony formation, e.g., in matrigel. In a migration assay a population of metastatic cells expressing PI16 is placed in a chamber of a cell culture device that is in liquid communication with another chamber comprising a compound that attracts the metastatic cell (a chemoattractant). The two chambers are separated by a membrane, e.g., a membrane that mimics the extracellular matrix found in a subject. The amount of cell migration from one chamber to the other through the membrane is assessed in the presence or absence of the protein and a protein that reduces the amount of migration compared to a control sample (containing no protein) is considered to inhibit metastasis. Exemplary methods are described in Albini et al., (1987); and Repesh, (1989).

An exemplary method for assessing activity of a protein of the invention on cardiomyocytes is to contact a population of cardiomyocytes overexpressing PI16 with the protein. PI16 overexpression induces hypotrophy (or prevents growth) of cardiomyocytes. Accordingly, a protein that results in cardiomyocytes larger then the cardiomyocytes overexpressing PI16 is considered to be useful for treating cardiac disorders.

As will be apparent to the skilled artisan, methods of screening may involve detecting levels of cell death, cell proliferation and/or cell survival. Such methods are known in the art.

In one embodiment, death of cells in the activity of a protein is assayed (e.g., to isolate a compound that kills cells), e.g., using a method for the detection of cellular components associated with cell death, such as, for example apoptosis. Methods for detecting cell death in a cell are known in the art. For example, APOPTEST (available from Immunotech) stains cells early in apoptosis, and does not require fixation of the cell sample. This method utilizes an annexin V antibody to detect cell membrane re-configuration that is characteristic of cells undergoing apoptosis. Apoptotic cells stained in this manner can then be sorted either by fluorescence activated cell sorting (FACS), ELISA or by adhesion and panning using immobilized annexin V antibodies. Alternatively, a terminal deoxynucleotidyl transferase-mediated biotinylated UTP nick end-labeling (TUNEL) assay is used to determine the level of cell death. The TUNEL assay uses the enzyme terminal deoxynucleotidyl transferase to label 3'-OH DNA ends, generated during apoptosis, with biotinylated nucleotides. The biotinylated nucleotides are then detected by using streptavidin conjugated to a detectable marker. Kits for TUNEL staining are available from, for example, Intergen Company, Purchase, N.Y. Such assays can be performed with other cells, e.g. T helper cells and/or CTLs to identify and/or isolate compounds that selectively kill Treg cells.

Alternatively, cell viability or cell metabolism may be detected and/or assayed. By way of example, non-fluorescent resazurin is added to cells cultured in the presence of a protein of the present invention. Viable cells reduce resazurin to red-fluorescent resorufin, easily detectable using, for example, microscopy or a fluorescent plate reader. This marker of cell viability is useful for a variety of different cell types, from bacteria to higher eukaryotes. Kits for analysis of cell viability are available, for example, from Molecular Probes, Eugene, Oreg., USA. Other assays for cell viability include, for example, assays that detect Water-Soluble Tetrazolium GLT008 (WST-8) reduction to formazan salt in live cells (Alexis Biochemicals), staining of live cells with cell-permeable calcein acetoxymethyl (calcein AM) which is converted to fluorescent calcein by intracellular esterases, detection of reduction of 3'-{1-[(phenylamino)carbonyl]-3, 4-tetrazolium}-bis(4-methoxy-6-nitro)benzenesulfonic acid hydrate] (XTT) to formazan salt (Intergen), or (4,5-dimethylthiazol-2-yl)-5-(3-carboxymethoxyphenyl)-2-(4-sulfophenyl)-2H-tetrazolium) PES: phenazine ethosulfate (MTS) reduction to formazan salt (Promega Corporation).

In Vivo Functional Assays

A protein of the invention can be tested for their ability to suppress Treg function and/or numbers (e.g., by killing Treg cells) can be administered to a test subject and the number of Treg cells detected/isolated using standard methods or methods described herein. A reduction in the number of Treg cells compared to the number of Treg cells from an untreated subject indicates that the protein reduces Treg numbers.

Alternatively, or in addition, a protein is administered to a test subject at the time of, prior to or following administration of tumor cells. The presence/absence and/or size of any resulting tumor is then assessed and compared to subjects to which the cells but not the protein has been administered. A protein that reduces tumor size and/or prevents tumor formation is considered to reduce Treg function and permit induction of an immune response against the tumor cells. Exemplary methods are described in Jones et al., (2002).

In another example, a test protein of the invention is administered at the time of or prior to administration of a composition comprising an immunogenic compound. The immune response is then measured against the immunogenic compound, e.g., antibody response (e.g., by ELISA/FLISA) or a T cell response (e.g., by ELISPOT or Fluorospot). Alternatively, or in addition, the compound and composition are administered to a subject suffering from or developing a condition treatable by an immune response, e.g., an infection or a tumor. Suitable models are known in the art and/or described herein.

In another example, a population of cells isolated using a protein of the invention is determined by administering the cells to an animal model of a condition associated with Treg cells. For example, the cells are administered to an animal lacking Treg cells e.g., as a result of myeloablation or mice lacking FoxP3 expression e.g., as described in (Asano (1996); Suri-Payer (1998); and McHugh (2002). Cells that suppress, prevent, reduce or delay an autoimmune response are considered to have regulatory T cell function.

Alternatively, or in addition, cells isolated by a method as described herein according to any embodiment are administered to nude mice at the time of, prior to or after transfer of CD4$^+$CD25$^-$ (which induce autoimmune disease), e.g., as described in Sakaguchi et al., (1995). Cells that suppress, prevent, reduce or delay an autoimmune response are considered to have regulatory T cell function.

Isolated cells can also be administered to NOD mice to test their ability to suppress, prevent, treat or delay diabetes (e.g., as described in Tang et al., (2004)) and/or to a mouse model of GVHD (e.g., as described in Trenado (2002)) and/or to a mouse model of psoriasis (e.g., Wang et al., 2008) and/or to a model of rheumatoid arthritis e.g., a SKG strain of mouse (Sakaguchi et al., 1995), rat type II collagen arthritis model, mouse type II collagen arthritis model or antigen induced arthritis models in several species (Bendele, 2001) and/or a model of multiple sclerosis (for example, experimental autoimmune encephalomyelitis (EAE; Bradl and Linington, 1996)) and/or inflammatory airway disease (for example, OVA challenge or cockroach antigen challenge (Chen et al., 2007; Lukacs et al., 2001) and/or models of inflammatory bowel disease (e.g., dextran sodium sulphate (DSS)-induced colitis or Muc2 deficient mouse model of colitis (Van der Sluis et al., 2006) or CD45Rb adoptive transfer model of colitis (e.g., Kanai et al., 2006)). Each of the previously listed models are preferably produced using mice irradiated and having their hetamopoietic system repopulated with human hematopoietic cells to thereby provide a "humanized" model. These models are also useful for testing compounds for their ability to enhance or increase Treg function.

In a further example, the effect of a protein of the invention is assessed in a model of metastasis. For example, a metastatic cell is injected into a mouse, e.g., intravenously or intraperitoneally or in the vicinity of an organ such as the lung, and the number of tumors growing in an organ (e.g., lung) is assessed. The cells may be labelled, e.g., with a fluorescent dye, to facilitate detection. A protein of the invention that reduces the number of tumors growing in the organ compared to the number in an animal that has not been treated with the protein is considered to reduce metastasis. Exemplary methods are described in Price (1990); and Kerbel (1998).

Pharmaceutical Compositions and Methods of Treatment

The proteins of the invention (syn. active ingredients) are useful for formulations into a pharmaceutical composition for parenteral, topical, oral, or local administration, aerosol administration, or transdermal administration, for prophylactic or for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the pharmaceutical compositions of this invention, when administered orally, must be protected from digestion. This is typically accomplished either by complexing the compound with a composition to render it resistant to acidic and enzymatic hydrolysis or by packaging the compound in an appropriately resistant carrier such as a liposome. Means of protecting proteins from digestion are known in the art.

The pharmaceutical compositions of this invention are particularly useful for parenteral administration, such as intravenous administration or administration into a body cavity or lumen of an organ or joint. The compositions for administration will commonly comprise a solution of the protein of the invention dissolved in a pharmaceutically acceptable carrier, preferably an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of compounds of the present invention in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

The protein of the invention can be formulated for parenteral administration, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains the compounds of the present invention as an active ingredient will be known to those of skill in the art.

Suitable pharmaceutical compositions in accordance with the invention will generally include an amount of the protein of the present invention admixed with an acceptable pharmaceutical diluent or excipient, such as a sterile aqueous solution, to give a range of final concentrations, depending on the intended use. The techniques of preparation are generally known in the art as exemplified by Remington's Pharmaceutical Sciences, 16th Ed. Mack Publishing Company, 1980, incorporated herein by reference.

Upon formulation, compounds of the present invention will be administered in a manner compatible with the dosage formulation and in such amount as is therapeutically/prophylactically effective. Suitable dosages of compounds of the present invention will vary depending on the specific compound, the condition to be treated and/or the subject being treated. It is within the ability of a skilled physician to determine a suitable dosage, e.g., by commencing with a sub-optimal dosage and incrementally modifying the dosage to determine an optimal or useful dosage.

PI16 has also shown to be involved in tumor metastasis and in reducing or preventing cardiomyocyte hypertrophy following cardiac arrest. Accordingly, the present invention additionally provides a method for treating metastasis in a subject, the method comprising administering to a subject suffering from metastasis or likely to develop metastasis a protein of the invention. In one example, the subject suffers from breast cancer, prostate cancer, lung cancer, colon cancer. Preferably, the subject suffers from breast cancer or a metastasis thereof.

The present invention also provides a method for treating cardiac dysfunction, the method comprising administering to a subject suffering from cardiac dysfunction or likely to develop cardiac dysfunction a protein of the invention. Alternatively, or in addition, the invention provides a method for improving cardiac function the method comprising administering to a subject in need thereof a protein of the invention. Alternatively, the present invention provides a method for inducing cardiomyocyte hypertrophy in a subject, the method comprising administering to a subject in need thereof a protein of the invention.

Isolation or Enrichment of Cells

The present invention also contemplates detection and/or isolation of cells based on PI16 expression.

In one example, the cells are Treg cells, such as nTreg cells, preferably, memory nTreg cells, preferably, resting memory nTreg cells.

In one example, the method comprises detecting marker of another marker, e.g., of a Treg cell. Exemplary additional proteins or nucleic acids include, CD4, CD25, FoxP3, cytotoxic T-lymphocyte-associated antigen 4 (CTLA-4), CD62 ligand (CD62L), CD134 (OX40), glucocorticoid-induced tumor necrosis factor receptor (GITR), membrane-bound TGF-β, CD196 (CCR6), programmed cell death ligand 1 (PD-L1), $\alpha_4\beta_7$ integrin or $\alpha_4\beta_1$ integrin. Preferred additional proteins or nucleic acids are CD4 and/or CD25. Preferably, CD25 is expressed at a high level.

In another example, a method for detecting or isolating Treg cells additionally comprises detecting a low or undetectable level of expression of a nucleic acid or protein expressed by a non-Treg cell. Exemplary nucleic acids and/or proteins include CD19 and/or CD20 and/or CD14 and/or CD56 and/or CD127. Preferably, the method comprises detecting or isolating a cell that does not detectably express CD127 ($CD127^{neg}$) or that expresses low levels of CD127 ($CD127^{lo}$).

As used herein, the term "positive expression" or "+" shall be taken to mean expression above the level of background, e.g., as detected using an isotype control compound, e.g., antibody.

As used herein, the term "isotype control compound" shall be taken to mean a compound, preferably an antibody of the same isotype as that used to detect expression of a protein, however having no relevant specificity to a protein and conjugated to the same detectable moiety as the compound used to detect expression of the protein. Such a control aids in distinguishing non-specific "background" binding from specific binding.

Reference to a "high" or "hi" level of expression means the 50% of cells, preferably 40%, 30% or more preferably 20%, more preferably 10% of cells within a population of cells expressing the highest level of the recited marker (e.g., PI16), e.g., as determined using FACS analysis.

As used herein, the term "negative expression" or "−" shall be taken to mean expression equal to or less than the level of background expression, e.g., as detected using an isotype control compound, e.g., antibody.

Reference to a "low" or "lo" level of expression, e.g., in the context of CD127 expression shall be taken to mean the 50% or 60% or 70% or 80% or 90% of cells with lowest level of expression of the recited nucleic acid or protein in a population of cells.

One exemplary approach to enrich for the desired cells is magnetic bead cell sorting (MACS) or any other cell sorting method making use of magnetism, e.g., Dynabeads®. A conventional MACS procedure is described by Miltenyi et al., (1990). In this procedure, cells are labeled with magnetic beads bound to an antibody or other compound that binds to a cell surface marker or protein and the cells are passed through a paramagnetic separation column or exposed to another form of magnetic field. The separation column is placed in a strong magnet, thereby creating a magnetic field within the column. Cells that are magnetically labeled are trapped in the column; cells that are not pass through. The trapped cells are then eluted from the column.

Cells of the invention can be enriched, for example, from a suitable sample using MACS to separate cells expressing a suitable protein. The sample is incubated with immunomagnetic beads that bind to the protein. Following incubation, samples are washed and resuspended and passed through a magnetic field to remove cells bound to the immunomagnetic beads, and cells bound to the beads collected. These techniques are equally applicable to negative selection, e.g., removal of cells expressing an undesirable marker, e.g., in the case of Treg cells, CD8.

In another example, a compound that binds to a protein or cell surface marker is immobilized on a solid surface and a population of cells is contacted thereto. Following washing to remove unbound cells, cells bound to the compound can be recovered, e.g., eluted, thereby isolating or enriching for cells expressing the protein to which the compound binds. Alternatively, cells that do not bind to the compound can be recovered if desired.

In a preferred example, cells are isolated or enriched using fluorescence activated cell sorting (FACS). FACS is a known method for separating particles, including cells, based on the fluorescent properties of the particles and described, for example, in Kamarch, 1987. Generally, this method involves contacting a population of cells with compounds capable of binding to one or more proteins or cell surface markers, wherein compounds that bind to distinct markers are labeled with different fluorescent moieties, e.g., fluorophores. The cells are entrained in the center of a narrow, rapidly flowing stream of liquid. The flow is arranged so that there is a separation between cells relative to their diameter. A vibrating mechanism causes the stream of cells to break into individual droplets. The system is adjusted so that there is a low probability of more than one cell being in a droplet. Just before the stream breaks into droplets the flow passes through a fluorescence measuring station where the fluorescent character of interest of each cell is measured, e.g., whether or not a labeled compound is bound thereto. An electrical charging ring is placed at the point where the stream breaks into droplets. A charge is placed on the ring based on the immediately prior fluorescence intensity measurement and the opposite charge is trapped on the droplet as it breaks from the stream. The charged droplets then fall through an electrostatic deflection system that diverts droplets into containers based upon their charge, e.g., into one container if a labeled compound is bound to the cell and another container if not. In some systems the charge is applied directly to the stream and the droplet breaking off retains charge of the same sign as the stream. The stream is then returned to neutral after the droplet separates.

Cell Culture

Following isolation cells of the invention can be maintained under standard cell culture conditions. For example, the cells can be maintained in Dulbecco Minimal Essential Medium (DMEM) or any other appropriate cell culture medium known in the art, e.g., as described above. Other appropriate media include, for example, MCDB, Minimal Essential Medium (MEM), IMDM, and RPMI.

Cell cultures are preferably incubated at about 37° C. in a humidified incubator. Cell culture conditions can vary considerably for the cells of the present invention. Preferably, the cells are maintained in an environment suitable for cell growth, e.g., comprising 5% $O_2$, 10% $CO_2$, 85% $N_2$ or comprising 10% $CO_2$ in air.

In one example, Treg cells are grown in the presence of anti-CD3 antibodies to facilitate expansion, optionally in the presence of IL-2 and/or TGF-β. In one example, cells are cultured in the presence of beads (e.g., magnetic iron-dextran beads-Dynabeads) coated with antibodies to CD3 and CD28. The anti-CD28 antibody provides signals for augmented activation and growth of the hypo-proliferative Treg cells. $CD4^+CD25^+$ cells grown with the beads with low ratio (low anti-CD3 compared to anti-CD28) are much more stable, and less likely to be overgrown with conventional T cells. The beads can easily be removed by passing the cultured cells through a magnetic column. Cell sorting is not required.

Treg cells can also be cultured in the presence of cytokines, e.g., IL-4 and/or IL-7, which increase survival of T cells and/or IL-10, which is partially responsible for production of regulatory T cells and/or IL-15, which has been shown to synergize with IL-2 and induce proliferation of $CD4^+CD25^+$ T cells.

In some examples, autologous $CD4^+$ T cells are used as feeder cells. Alternatively, feeder-free cultures can be performed, e.g., using the beads described above together with IL-2. Moreover culture-expansion can be accomplished with or without host APCs, e.g., DCs.

Cellular Compositions

In one example, cells isolated according to the present invention (e.g., Treg cells and/or progeny cells thereof) are administered in the form of a composition. Preferably, such a composition comprises a pharmaceutically acceptable carrier.

Suitable carriers for this invention include those conventionally used, e.g., water, saline, aqueous dextrose, lactose, Ringer's solution, a buffered solution, hyaluronan and glycols are preferred liquid carriers, particularly (when isotonic) for solutions. Suitable pharmaceutical carriers also include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. Preferably, such a media composition does not induce any adverse effects in a subject to whom it is administered.

Preferred carriers do not adversely affect the viability of a cell and/or the activity of a cell, e.g., ability of a cell to reduce, prevent or delay a Treg-associated condition.

In one example, the carrier provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors. In such a case, the composition of the invention may be produced as a liquid for direct application to the blood stream or into a tissue or a region surrounding or adjacent to a tissue, e.g., by injection.

Cells isolated according to the invention (e.g., Treg cells and/or progeny cells thereof) can also be incorporated or embedded within scaffolds that are recipient-compatible and which degrade into products that are not harmful to the recipient. Exemplary scaffolds include polyglycolic acid scaffolds, e.g., as described by Vacanti, et al., 1988; Cima, et al., 1991; Vacanti, et al., 1991; or synthetic polymers such as polyanhydrides, polyorthoesters, and polylactic acid.

Preferably, the composition comprises an effective amount or a therapeutically or prophylactically effective amount of cells. For example, the composition comprises about $1 \times 10^5$ cells/kg to about $1 \times 10^9$ cells/kg or about $1 \times 10^6$ cells/kg to about $1 \times 10^8$ cells/kg or from about $1 \times 10^6$ cells/kg to about $1 \times 10^7$ cells/kg. The exact amount of cells to be administered is dependent upon a variety of factors, including the age, weight, and sex of the patient, and the extent and severity of the condition to be treated or prevented.

The cellular compositions of this invention can be administered to the subject by any recognized methods, either systemically or at a localized site.

Stimulating or Enhancing an Immune Response

As will be apparent to the skilled artisan based on the description herein, the present invention also contemplates methods for enhancing an immune response in a subject by reducing or depleting Treg cells in the subject. In one example, reducing or depleting Treg cells in the subject is sufficient to induce an immune response, e.g., against a tumor and/or against an infectious agent (e.g., without administration of an immunogenic composition). In another example, a method for inducing an immune response against a subject involves reducing or depleting Treg cells in the subject and administering a composition comprising an immunogenic compound.

As used herein, the term "immunogenic compound" means any substance or organism that provokes an immune response (produces immunity) when introduced to a subject. In some embodiments, an immunogen can be used in therapeutic settings in a form of a vaccine. As used herein, and unless otherwise specified, the term "enhanced immune response" means that, when an immunogen is administered in combination with a protein of the invention, there is an increased immunological response, preferably T cell response and/or antibody response, measured using any standard methods known in the art or described herein, in a subject that receives such an administration as compared to a subject to which a compound of the invention is not administered.

Immunogenic compounds used in methods of this invention may be a cancer antigen or a tumor antigen. Any cancer or tumor antigen known to one skilled in the art may be used in accordance with the immunogenic compositions of the invention including, but not limited to, KS 1/4 pan-carcinoma antigen (Perez and Walker, 1990), ovarian carcinoma antigen (CA125) (Yu et al, 1991), prostatic acid phosphate (Tailor et al, 1990), prostate specific antigen (Henttu and Vihko, 1989), melanoma-associated antigen p97 (Estin et al, 1989), melanoma antigen gp75 (Vijayasardahl et al, 1990), high molecular weight melanoma antigen (HMW-MAA) (Natali et al, 1987), prostate specific membrane antigen, carcinoembryonic antigen (CEA) (Foon et al, 1994), TAG-72 (Yokata et al, 1982), CO17-1A (Ragnhammar et al, 1993); human B-lymphoma antigen-CD20 (Reff et al, 1994), GD2 (Saleh et al, 1993), ganglioside GM2 (Livingston et al., 1994), EGFR (Epidermal growth factor receptor), HER2 antigen. Additional tumor antigens are described, for example, in Novellino et al., 2005.

In another example, the immunogen is a cancer cell or a lysate thereof.

In one example, the cancer is breast cancer.

In another example, the cancer is brain cancer, e.g., glioma.

In a further example, the cancer is gastric cancer.

In another example, the cancer is prostate cancer.

In another example, the cancer is melanoma.

In another example, the cancer is lymphoma, e.g., Hodgkin's lymphoma.

Immunogens used in methods of this invention may also be an infectious disease agent including, but not limited to, influenza virus hemagglutinin (Genbank Accession No. JO2132; Air, 1981), hepatitis B surface antigen (Itoh et al, 1986), hepatitis B virus core protein and/or hepatitis B virus surface antigen or a fragment or derivative thereof (see, e.g., GB 2034323).

In one example, the immunogenic compound is a DNA encoding a polypeptide antigen.

In one example, the immunogenic composition additionally comprises an adjuvant. Adjuvants are molecules and preparations that improve the immunogenicity of antigens. Suitable adjuvants include all acceptable immunostimulatory compounds, such as cytokines, toxins or synthetic compositions. Exemplary, often preferred adjuvants include, but are not limited to, complete Freund's adjuvant (a non-specific stimulator of the immune response containing killed *Mycobacterium tuberculosis*), incomplete Freund's adjuvants, and aluminum hydroxide adjuvant.

Suppressing and Immune Response

The present invention also provides a method of treating or preventing a condition associated with reduced Treg cell numbers or activity, and/or inducing immunosuppression, and/or reducing CTL or Thelper cell activity in a subject, said method comprising:

(i) isolating a population of Treg cells by performing a method as described herein according to any embodiment; and (ii) administering the cells at (i) to the subject.

In another example, the method comprises administering a protein of the invention that activates Treg function (e.g., as assessed using a method described hereon).

In another example, the method comprises implanting a solid or semi-solid support having a protein of the invention immobilized thereon and, optionally Treg cells bound thereto.

In one example, the subject suffers from or is at risk of developing a condition associated with reduced Treg numbers and/or activity and/or requires a reduction in CTL or Thelper cell activity (e.g., the subject suffers from or is at risk of developing an autoimmune disease) and/or the subject requires immunosuppression (e.g., is undergoing or about to undergo a transplant or suffers from graft-versus-host disease). Methods for determining a subject suffering from a condition will be apparent to the skilled artisan based on the description herein.

In one example, the subject suffers from type 1 diabetes.

In another example, the subject suffers from multiple sclerosis.

In a further example, the subject suffers from inflammatory bowel disease.

In a preferred example, the subject suffers from arthritis, e.g., rheumatoid arthritis.

In a further example, the cells are administered with a graft (e.g., a cell graft or a tissue graft or an organ graft) to thereby suppress or reduce a graft-versus-host or host-versus-graft immune response.

Methods for identifying and/or isolating and/or culturing and/or formulating Treg cells for therapy are described herein.

Diagnostic/Prognostic Assays

It will be apparent from the description herein that the present invention provides various methods for diagnosing/prognosing conditions associated with PI16 expression, particularly Treg-associated conditions. PI16 has been shown to be dysregulated in metastasis, prostate cancer and cardiac arrest. Accordingly, the methods of the invention are to be understood to apply mutatis mutandis to methods for diagnosing or prognosing metastasis (e.g., breast cancer metastasis), wherein an increased level of PI16 or PI16 expressing cells is indicative of metastasis. The methods of the invention are to be understood to apply mutatis mutandis to methods for diagnosing or prognosing cardiac hypotrophy or cardiac arrest, wherein an increased level of PI16 or PI16 expressing cells is indicative of cardiac hypotrophy or cardiac arrest. The methods of the invention are to be understood to apply mutatis mutandis to methods for diagnosing or prognosing prostate cancer, wherein a reduced level of PI16 or PI16 expressing cells is indicative of prostate cancer.

Protein Detection Assays

One example of the invention detects the presence of PI16 or a cell expressing same. The amount, level or presence of a protein or cell is determined using any of a variety of techniques known to the skilled artisan such as, for example, a technique selected from the group consisting of flow cytometry, immunohistochemistry, immunofluorescence, an immunoblot, a Western blot, a dot blot, an enzyme linked immunosorbent assay (ELISA), radioimmunoassay (RIA), enzyme immunoassay, fluorescence resonance energy transfer (FRET), matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or protein chip technology.

In one embodiment the assay used to determine the amount or level of a protein is a semi-quantitative assay.

In another embodiment the assay used to determine the amount or level of a protein is a quantitative assay.

Preferably, the protein is detected with an immunoassay. Preferably, using an assay selected from the group consisting of, immunohistochemistry, immunofluorescence, enzyme linked immunosorbent assay (ELISA), fluorescence linked immunosorbent assay (FLISA), Western blotting, radioimmunoassay (RIA), a biosensor assay, a protein chip assay and an immunostaining assay (e.g. immunofluorescence). Preferably, the detection method is a flow cytometry method, e.g., detection of the number of Treg cells using fluorescence activated cell sorting (FACS), e.g., as is known in the art and/or described herein.

Standard solid-phase ELISA or FLISA formats are particularly useful in determining the concentration of a protein from a variety of samples.

In one form, an ELISA or FLISA comprises of immobilizing a protein of the invention or a protein that binds to a different epitope of PI16 on a solid matrix, such as, for example, a membrane, a polystyrene or polycarbonate microwell, a polystyrene or polycarbonate dipstick or a glass support. A sample is then brought into physical relation with the immobilized protein, PI16 is bound or 'captured'. The bound PI16 is then detected using a second labeled compound that binds to a different epitope of PI16 (e.g., the protein of the invention). Alternatively, a third labeled antibody can be used that binds the second (detecting) antibody.

In another form, a protein of the invention is used to capture a cell expressing PI16. A second protein that binds to a different protein is then used to detect the cell. For example, in the case of a Treg cell, the second protein could bind to CD4 or CD25. Of course, a third protein that binds to the second protein can be used as a detection reagent.

It will be apparent to the skilled person that the assay formats described herein are amenable to high throughput formats, such as, for example automation of screening processes or a microarray format as described in Mendoza et al., 1999. Furthermore, variations of the above-described assay will be apparent to those skilled in the art, such as, for example, a competitive ELISA.

In an alternative embodiment, a polypeptide is detected within or on a cell, using methods known in the art, such as, for example, immunohistochemistry or immunofluorescence. Methods using immunofluorescence are preferable, as they are quantitative or at least semi-quantitative. Methods of quantitating the degree of fluorescence of a stained cell are known in the art and described, for example, in Cuello, 1984.

Biosensor devices generally employ an electrode surface in combination with current or impedance measuring elements to be integrated into a device in combination with the assay substrate (such as that described in U.S. Pat. No. 5,567,301). A protein of the invention is incorporated onto the surface of a biosensor device and a biological sample contacted to said device. A change in the detected current or impedance by the biosensor device indicates protein binding to said protein. Some forms of biosensors known in the art also rely on surface plasmon resonance to detect protein interactions, whereby a change in the surface plasmon resonance surface of reflection is indicative of a protein binding to a ligand or antibody (U.S. Pat. No. 5,485,277 and U.S. Pat. No. 5,492,840).

Biosensors are of particular use in high throughput analysis due to the ease of adapting such systems to micro- or nano-scales. Furthermore, such systems are conveniently adapted to incorporate several detection reagents, allowing for multiplexing of diagnostic reagents in a single biosensor unit. This permits the simultaneous detection of several proteins or peptides in a small amount of body fluids.

Imaging Methods

As will be apparent to the skilled artisan from the foregoing, the present invention also contemplates imaging methods using a protein of the invention. For imaging, a protein is generally conjugated to a detectable label, which can be any molecule or agent that can emit a signal that is detectable by imaging. However, a secondary labeled compound that specifically binds to a protein of the invention may also be used. Exemplary detectable labels include a protein, a radioisotope, a fluorophore, a visible light emitting fluorophore, infrared light emitting fluorophore, a metal, a ferromagnetic substance, an electromagnetic emitting substance a substance with a specific magnetic resonance (MR) spectroscopic signature, an X-ray absorbing or reflecting substance, or a sound altering substance.

The protein of the invention (and, if used the labeled secondary compound) can be administered either systemically or locally to an organ, or tissue (or tumor, in the case of a cancer) to be imaged, prior to the imaging procedure. Generally, the protein is administered in doses effective to achieve the desired optical image of a tumor, tissue, or organ. Such doses may vary widely, depending upon the particular protein employed, condition to be imaged, tissue, or organ subjected to the imaging procedure, the imaging equipment being used, and the like.

In some examples of the invention, the protein is used as in vivo optical imaging agents of tissues and organs in various biomedical applications including, but not limited to, imaging of tumors, tomographic imaging of organs, monitoring of organ functions, coronary angiography, fluorescence endoscopy, laser guided surgery, photoacoustic and sonofluorescence methods, and the like.

Examples of imaging methods include magnetic resonance imaging (MRI), MR spectroscopy, radiography, computerized tomography (CT), ultrasound, planar gamma camera imaging, single-photon emission computed tomography (SPECT), positron emission tomography (PET), other nuclear medicine-based imaging, optical imaging using visible light, optical imaging using luciferase, optical imaging using a fluorophore, other optical imaging, imaging using near infrared light, or imaging using infrared light.

In some examples, an imaging agent is tested using an in vitro or in vivo assay prior to use in humans, e.g., using a model described herein.

Samples

To the extent that the method of the present invention is performed in vitro, on an isolated tissue sample, rather than as an in vivo based screen, reference to "sample" should be understood as a reference to any sample of biological material derived from an animal such as, but not limited to, a body fluid (e.g., blood or synovial fluid or cerebrospinal fluid), cellular material (e.g. tissue aspirate), tissue biopsy specimens or surgical specimens. Preferably, the sample comprises Treg cells or is likely to comprise Treg cells.

The sample which is used according to the method of the present invention may be used directly or may require some form of treatment prior to use. For example, a biopsy or surgical sample may require homogenization or other form of cellular dispersion prior to use. Furthermore, to the extent that the biological sample is not in liquid form, (if such form is required or desirable) it may require the addition of a reagent, such as a buffer, to mobilize the sample.

As will be apparent from the preceding description, such an assay may require the use of a suitable control, e.g. a normal or healthy individual or a typical population, e.g., for quantification.

As used herein, the term "normal individual" shall be taken to mean that the subject is selected on the basis that they do not have abnormal numbers of PI16 expressing cells, e.g., Treg cells in a sample derived therefrom.

A "healthy subject" is one that has not been diagnosed as suffering from a condition, e.g., a Treg-associated condition and/or is not at risk of developing the condition.

Alternatively, or in addition, a suitable control sample is a control data set comprising measurements of the marker being assayed for a typical population of subjects known not to suffer from a condition.

In one embodiment, a reference sample is not included in an assay. Instead, a suitable reference sample is derived from an established data set previously generated from a typical population. Data derived from processing, analyzing and/or assaying a test sample is then compared to data obtained for the sample population.

Kits

The present invention also provides therapeutic/prophylactic/diagnostic kits comprising compounds of the present invention for use in the present detection/isolation/diagnostic/prognostic/treatment/prophylactic methods. Such kits will generally contain, in suitable container means, a protein of the present invention. The kits may also contain other compounds, e.g., for detection/isolation/diagnosis/imaging or combined therapy. For example, such kits may contain any one or more of a range of anti-inflammatory drugs and/or chemotherapeutic or radiotherapeutic drugs; anti-angiogenic agents; anti-tumor cell antibodies; and/or anti-tumor vasculature or anti-tumor stroma immunotoxins or coaguligands or vaccines.

In one example, the kit is for detecting PI16 and additionally comprises a reagent to facilitate detection (a detectable label and/or a substrate of a detectable label. Such kits may additionally comprise a positive control.

In another example, the kit is for isolating a cell or a population of cells. In such kits a protein of the invention may be labeled with a detectable label to facilitate FACS. The protein may also be labeled with a magnetic or paramagnetic particle to facilitate MACS. The protein may also be immobilized on a solid or semi-solid substrate to facilitate isolation.

In a further example, the kit is for treatment or prevention of a condition. In such kits the protein may be provided in solution or in a lyophilized form, optionally with a solution for resuspension. The protein may be conjugated to a therapeutic compound or the kit may include a therapeutic compound for conjugation thereto. As discussed above, the kit may also comprise additional therapeutic or prophylactic compounds.

Microorganism Deposit Details

The hybridoma designated CRCBT-02-001 was deposited on 24 Feb. 2010 with the American Type Culture Collection (ATCC) under Deposit Reference PTA10685.

These deposits were made under the provisions of the Budapest Treaty on the International Recognition of the Deposit of Microorganisms for the Purpose of Patent Procedure and the Regulations thereunder. This assures maintenance of viable cultures for 30 years from the date of deposit. The organisms will be made available by the ATCC under the terms of the Budapest Treaty which assures permanent and unrestricted availability of the progeny of the culture to the public upon issuance of the pertinent patent.

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

The present invention is described further in the following non-limiting examples.

Example 1

Identification of PI16 on Treg Cells 1.1 Materials and Methods
1.1.1 Isolation and In Vitro Expansion and Characterization of Cord Blood T Cell Populations Cord blood was obtained with informed maternal consent as approved by the Children's, Youth and Women's Health Service Research Ethics Committee. Mononuclear cells (MNC) were isolated from cord blood post partum into blood collection bags (Fenwell) containing anticoagulant. Cord blood $CD4^+CD25^+$ (Treg) and $CD4^+CD25^-$ (Thelper) cells were isolated from MNC using a Dynabeads Regulatory $CD4^+CD25^+$ T cell kit (Invitrogen). The purity for each cell type was routinely greater than 90% by two colour flow cytometry for CD4 and CD25 expression. Ex vivo expansion of isolated T cell populations ($1 \times 10^6$ cells/well in a 24 well plate) were performed in X-Vivo 15 media (BioWhitticker) supplemented with 20 mM HEPES, pH 7.4, 5% heat inactivated pooled human serum (Lonza), 2 mM 1-glutamine and 500 U/ml recombinant human interleukin-2 (rhIL2; R&D research) in the presence of Dynabeads CD3/CD28 T cell expander beads (Invitrogen; Cat#111-41D) at a bead to cell ratio of 3:1. Cells were expanded for 8 days in the presence of Dynabeads prior to magnetic removal of the beads and culture in X-Vivo 15 media supplemented as above except with 100 U/ml rhIL2. On the day of use the phenotype of expanded cells were characterised by surface expression of CD4 (PEcy5, ebioscience clone RPA-T4), CD25 (PE, BD clone M-A251) and CD127 (PE, ebioscience clone ebioRDR73) in combination with intracellular detection of FoxP3 (FoxP3-Alexa 488, BD clone 259D/C7; Human FoxP3 Buffer Set, BD cat#560098) by three colour flow cytometry on a Beckman Coulter Epics Elite ESP flow cytometer.

1.1.2 RNA Preparation and Expression Array

Differential expression analysis was carried out using Affymetrix Human Exon 1.0ST arrays. Total RNA was isolated from expanded $CD4^+25^-$ (Thelper) and $CD4^+25^+$ (Treg) cells that were rested for approximately 60 hours following an 8 day expansion protocol prior to either vehicle (DMSO) or Ionomycin treatment (2 hours). Total RNA, including small molecular weight RNA, was isolated using QIAshredder and a miRNeasy mini kit (QIAGEN). Labelling and hybridisation to Affymetrix Human Exon 1.0ST arrays was carried out essentially according to the manufacturers' protocols at the Biomolecular Resource Facility (John Curtin School of Medical Research, Australian National University) RNA quality was assayed for using an Agilent Systems Bioanalyzer prior to array experiments.

1.1.3 RNA Expression Array Data Normalisation

Probe level data was processed using the RMA model (Irizarry et al., 2003) with final transcript level estimates obtained using probe-level modelling (Bolstad et al., 2003) based on v11.0 of an EntrezGene centric cdf (Dai et al., 2004). All processing was conducted using the statistical software R(R Development Core Team) under the aroma.affymetrix framework (Bengtsson et al., 2006; and Bengtsson and Hossjer, 2006). Hybridisation quality for each array was assessed using pseudo-image plots, NUSE, RLE (Bolstad et al., 2001) and histograms of probe-level data. Log fold-change in a four way comparison between resting and stimulated treatments of $CD4^+CD25^+$ Treg cells vs. $CD4^+CD25^-$ Thelper cells was estimated within individual donors after loess normalisation. Final expression analysis was performed using array level weights and the R package limma (Smyth et al., 2005; and Wettenhall and Smyth, 2004). Raw p-values for each term were adjusted globally to provide an estimate of the FDR (Hochberg and Benjamini, 1990).

1.1.4 Semi-Quantitative Real Time PCR

Validation of differentially regulated target genes identified by expression array analysis was performed on RNA isolated from expanded $CD4^+CD25^+$ and $CD4^+CD25^-$ cells from five separate donors. Expansion, stimulation and RNA isolation conditions were identical to those used in the expression array experiments. Random primed cDNA was prepared from total RNA using a QuantiTect reverse transcriptase kit (QIAGEN). cDNA was used in a 25 µl qPCR reactions consisting of 1.25 Units FastTaq DNA polymerase (Roche), 2.5 mM $MgCl_2$, 200 µM each primer, 200 µM dNTP mix, 1.1×SYBR green (Molecular Probes, Invitrogen) in 1× FastTaq PCR buffer. Gene specific primers pairs for qPCR were selected from Primerbank (Wang and Seed *Nucleic Acids Res* 31: e154, 2003). A primer set specific for RPL13a was used as an internal control. Cycling conditions comprised 40 cycles of: 50 seconds at 94° C., 25 seconds at 60° C., and 50 seconds at 72° C. followed by melt curve using a Rotorgene 6000 PCR machine (Corbet Research). Results were analyzed using Rotor-Gene 6000, Q-gene software (Muller et al., 2002) and R.

1.1.5 Validation of Cell Surface Molecule Expression

For surface molecule analysis adult peripheral blood $CD4^+CD25^+$ Treg or $CD4^+CD25^-$ Thelper cells were either freshly isolated or isolated and stimulated overnight in the presence of CD3/CD28 beads (bead to cell ratio, 1:1) and 100 U/ml IL2, prior to 4 colour flow cytometry using antibodies against CD4, CD25, FoxP3 and PI16.

1.2 Results 1.2.1 Isolation and Validation of Human Cord Blood Treg

To generate sufficient human Treg for expression profiling studies, approx $1×10^6$ $CD4^+CD25^{hi}$ cells isolated from human cord blood were expanded in vitro using anti-CD3/CD28 beads. Following a single round of ex vivo expansion, 100-200 fold expansion of the cord blood Treg was routinely obtained. These cells maintained a Treg phenotype upon expansion, with >90% of the expanded cells staining $CD4^+$, $CD25^{hi}$, and FoxP3 positive. These cells were also $CD127^{dim}$. Post expansion, the cells retained regulatory function as they were able to robustly suppress the proliferation of $CD4^+CD25^-$ cells in vitro in an unmatched donor mixed leukocyte suppression assay. The expanded functional Treg cells were used for the expression profiling experiments.

1.2.2 Differential Gene Expression in Resting and Activated Treg Cells

Expression profiling was carried out on cord blood Treg isolated and expanded in vitro. A four way Treg gene expression array experiment was designed to reveal the expression profile of Treg and matched Thelper cells in a stimulated or resting state. This four way comparison identified genes with a Treg intrinsic expression pattern, genes which contribute to Treg-specific activation signature and genes that display common responses to T cell activation. In total 1851 genes were identified as displaying significant differences in behaviour in a Treg compared to a Thelper with a further 746 genes showing a similar response to activation in both cell types. One of the genes identified PI16 was expressed on a significant proportion of both resting and activated human Treg cells.

In order to confirm the gene expression profiles in the Treg arrays, gene specific semi-quantitative real time PCR (qPCR) was performed. A group of the differentially expressed candidate genes including PI16 were selected and tested their expression on 5 biological replicates of Treg vs Thelper cells. Quantitative RT-PCR and Low Density Array confirmed the differential expression of PI16, and results were relatively consistent with the gene behaviour identified in the array analysis.

1.2.3 Analysis of PI16 Cell Surface Molecule on Treg

Figure 2:
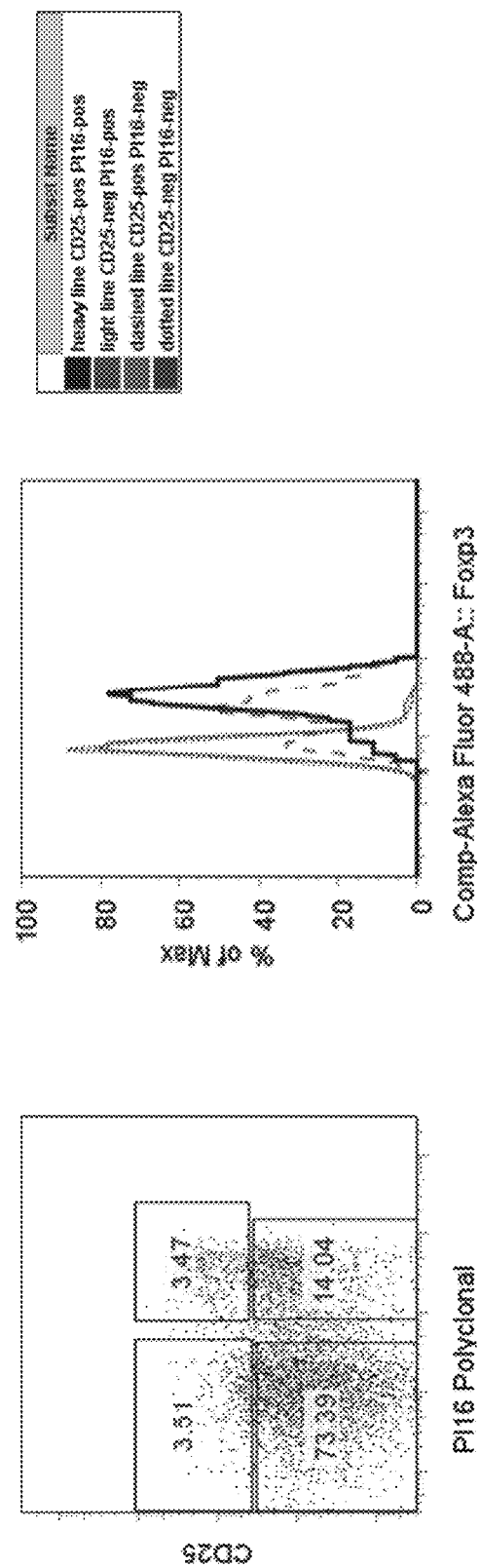
FIG. 2 is a series of graphical representations showing staining of freshly isolated adult CD4$^+$ T cells with a polyclonal PI16 antibody (Abnova) together with CD25 or FoxP3. CD25 and PI16 staining is shown in the left hand panel with boxes indicating CD25 positive or negative or PI16 positive or negative. The right hand panel indicates FoxP3 expression levels for each boxed cell population. Results reveal that CD4$^+$CD25$^+$PI16$^+$ cells show the highest FoxP3 expression levels whereas the CD4$^+$CD25$^+$PI16$^-$ cells show a lower mean expression level. CD4$^+$CD25$^-$ cells are FoxP3$^-$.

Array data discussed above was analyzed to identify a biomarker that could be used as a surrogate for FoxP3 expression to identify Treg cells. From these data PI16 was identified as one such biomarker. CD25 positive adult $CD4^+$ cells were screened for co-expression of PI16 and FoxP3 using a polyclonal anti-PI16 antibody and PI16 was found to have a positive correlation with FoxP3 (FIG. 2).

Figure 3:
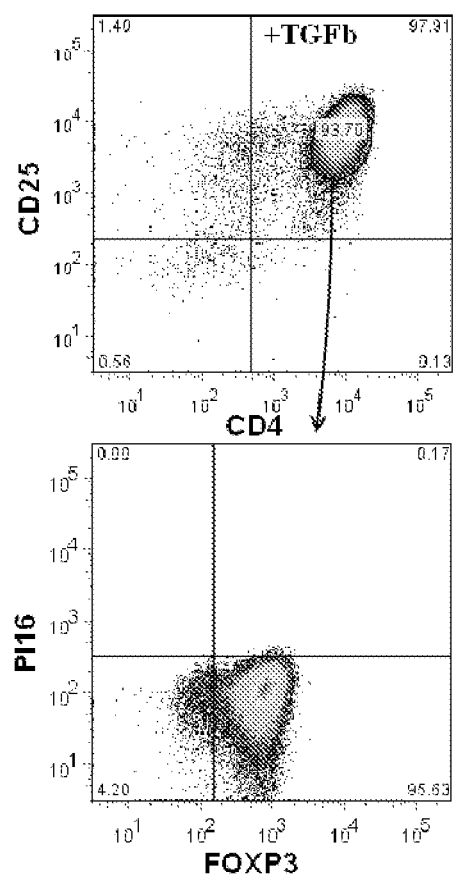
FIG. 3 is a series of graphical representations showing the expression of PI16 on induced Treg cells (iTreg). Cord blood CD4$^+$CD25$^-$ cells were expanded in the presence of recombinant human TGFβ-1 and CD3/CD28 T cell expander beads for a total of eight days before beads were removed and analyzed for CD25, FoxP3 and PI16 expression. The induced Treg cells expressed FoxP3 but are not positive for PI16 suggesting that PI16 may serve as a marker for natural but not induced Treg.

The expression of PI16 was also tested on TGFβ induced Treg (iTreg; FIG. 3). While TGFβ substantially up-regulated CD25 and FoxP3 expression, PI16 was not substantially expressed on these transiently induced cells, suggesting that PI16 expression may discriminate natural Treg from induced Treg.

Example 2

Production and Characterization of Antibodies Against PI16

2.1 Materials and Methods
2.1.1 Peripheral Blood Mononuclear Cell Isolation Peripheral blood mononuclear cells (PBMC) were isolated from whole blood (obtained from healthy subjects with informed consent, under Ethics clearance from the Research Ethics Committee of the Children's, Youth and Women's Health Service, South Australia) by density centrifugation over Lymphoprep (Nycomed, Oslo) and washed twice with PBS-Azide. Blood was collected using lithium-heparin anticoagulant.

2.1.2 Generation of PI16-Expressing Cells

A construct containing the full-length PI16 coding sequence in the pCMV-SPORT6 was purchased from Open Biosystems (Thermo, MHS1010-708293). To generate an insert that was compatible with the Gateway vector system (Invitrogen), the PI16 coding sequence was amplified from this vector using the primers: PI16-F: 5'-ggggacaagtttgtacaaaaaagcaggctgccaccATGCACGGCTCC-TGCAGTT-3' (SEQ ID NO: 5); which corresponds to nucleotides 329 to 347 of the NCBI RefSeq NM_153370 and PI16-R: 5'-ggggaccactttgtacaagaaagctgggtcGAAG-ATTCCAGCCAACACCA-3' (SEQ ID NO: 6); which corresponds to the reverse and complement of nucleotides 1698 to 1717 of the reference sequence. The capitalised portions of the primers are specific to the PI16 coding sequence, while the underlined portions of the primers are adapters for Gateway vector. The PCR product was purified and cloned into the Gateway vector pDONR201 (Invitrogen) to create an "Entry Clone" pDONR201/PI16. The identity of the cloned insert was confirmed by sequencing of the pDONR201/PI16 using the forward and reverse sequencing primers described in the Gateway Technology Instruction Manual. The PI16 insert was transferred from the pDONR201 vector to the pDEST40 vector, using the procedure described in the Gateway Technology Instruction Manual. Single colonies were isolated and screened by PCR to confirm the insert was present. Plasmid DNA of the pDEST40/PI16 construct was prepared using the Qiagen Midi-Prep kit (Qiagen).

The pDEST40/PI16 vector was used to generate transiently transfect L929 mouse fibroblast cells (ATCC) and stably transfected NIH3T3 cells (ATCC) for immunization. Cells were maintained in DMEM medium supplemented with 2 mM L-glutamine (Glutamax, Gibco), 0.5 U/ml penicillin (Sigma), 0.5 µg/ml streptomycin (Sigma), and 10% FCS (SAFC Bioscience). A mixture of 20 µg of plasmid DNA, 20 µl of Lipofectamine LTX (Invitrogen), 20 ul of PLUS reagent was made up to 4000 µl using Opti-MEM. This mixture was used to transfect sub-confluent (60-80% confluent) L929 and NIH3T3 cells in a T75 flask (75 cm$^2$). After 6 h, the transfection mixture was removed and replaced with DMEM. Transfected cells containing the pDEST40/PI16 plasmid were selected by adding G418 (Invitrogen) to the culture medium at a concentration of 500 n/ml. To generate stable transfected cells, PI16-expressing NIH3T3 cells were sorted three times (FACSAria II; BD Biosciences).

2.1.3 Immunization and Hybridoma Generation

To generate monoclonal antibodies to the PI16 protein, 6-to-8 week old female Balb/c mice were immunized with L929 cells expressing the PI16 protein. Non-immune serum samples were taken from all mice prior to the first immunization. Groups of two mice were initially immunized by the sub-cutaneous injection of 50 million cells in 500 ul of PBS. Four weeks later, the mice were boosted by injection with sub-cutaneous injection of 50 million cells in 500 ul of PBS. A test bleed was taken six days after the second injection, and was screened for reactivity as described below. Fourteen days later the mice were given a final boost with 50 million cells in 500 ul of PBS, and four days later they were sacrificed and the spleens collected for preparing hybridomas.

For fusions, SP2/0 myeloma cells were obtained from ATCC. Hybridoma cells were generated following the instructions of Macardle and Bailey (2006) using $10^8$ mouse spleen cells and $10^7$ SP2/0 myeloma cells (ratio 10:1).

Hybridoma cells from selected wells were screened on PBMC and PI16-transfected NIH3T3 cells, expanded and cloned by single-cell sorting using a FACSAria II cell sorter equipped with an ACDU (BD Biosciences). Colonies arising from the sorted cells were screened by flow cytometry again.

As the commercially available PI16 polyclonal antibody showed a distinct staining pattern on peripheral blood, flow cytometry was used to screen hybridoma colonies for antibodies that reacted with a similar fraction of peripheral blood lymphocytes. The staining was performed as described below. Hybridoma cells from selected wells were expanded and re-cloned by single-cell sorting. Colonies arising from the sorted cells were screened by flow cytometry for the expression of antibodies with similar reactivity with PBMC as the parent hybridoma. The CRCBT-02-001 hybridoma was identified as expressing a monoclonal antibody with reactivity that was similar to the polyclonal PI16 antibody.

2.1.4 Flow Cytometry

Analysis of the reactivity of CRCBT-02-001 were performed using a three-step "high sensitivity" staining protocol (Mavrangelos et al., 2004) on peripheral blood mononuclear cells (PBMC) and PI16-transfected NIH3T3 cells. Peripheral blood mononuclear cells were isolated from whole blood (obtained from healthy volunteers) by density centrifugation over Lymphoprep (Nycomed, Oslo) and were washed twice with PBS-Azide (Sigma). Blood was collected using lithium-heparin anticoagulant.

A mouse polyclonal antibody raised to full-length recombinant PI16 protein was purchased from Abnova (Taipei City, Taiwan). Monoclonal antibodies to CD3, CD4, CD8, CD19, CD25, CD27, CD127, FoxP3, CD154, CD45RA, CD45RO, CD73, CD95, CD69, CD44, HLA-DR, CLA, CCR4, CCR5, CCR6, CXCR3, CXCR4 staining buffers, the Treg cocktail (an optimised mixture of CD4-APC, CD127-FITC and CD25-PE/Cy7) and fluorophore-streptavidin conjugates were obtained from BD Biosciences (San Jose, Calif.). A monoclonal antibody to CD39 was purchased from eBioscience (San Diego, Calif.), biotinylated horse anti-mouse Ig from VECTOR Laboratories (Burlingame, Calif.), and normal mouse serum from Dako (Glostrup, Denmark).

Multi-parameter flow cytometry experiments to characterise PI16 expression by PBMC were analysed using a FACSAria II cell sorter. Experiments using an unconjugated antibody were performed using a three-step "high sensitivity" staining protocol essentially as described in Zola et al., (1990). Briefly, PBMC were incubated with the unconjugated primary antibody for 30 min on ice and washed. Biotinylated horse anti-mouse Ig reagent was added, incubated for 30 min on ice. After washing normal mouse serum was added (to block free Ig-binding sites on the anti-mouse Ig reagent) and incubated for 10 min, prior to the addition of the fluorophore-streptavidin conjugate detection reagent and any directly conjugated antibodies. No wash step was performed between the incubation of the mouse Ig and the addition of the final reagents. The cells were incubated as above and washed twice. In experiments where antibodies directed against intracellular antigens were used, the surface staining as described above was performed first, and the cells were then permeabilised and stained according to the manufacturer's instructions.

2.1.5 Validation of Surface Staining of CRCBT-02-001 by Immunofluorescence

Cells were cultured on 8-wells chamber slides (Lab-Tek, Naperville, Ill.), washed with PBS, fixed in 2% paraformaldehyde solution (pH 7.4) for 15 min and subsequently washed and permeabilized in PBS containing 0.2% Triton X-100. Following blocking with 1% bovine serum in PBS for 30 min, the cells were immunostained with primary antibodies either mouse control IgG (1 µg/ml) (BD Biosciences, San Jose, Calif.), IgG1 control X-63 (neat, 100 µl/well) (in-house), PI16 mouse polyclonal antibody (1 µg/ml) (Abnova, Taipei, Taiwan), mouse anti-V5 antibody (1:300) (Invitrogen, Carsbad, Calif.) and CRCBT-02-001 culture supernatant (neat, 100 µl/well) (in-house) for 1 hr at RT. Then, cells were washed and incubated with Biotinylated Horse anti-Mouse IgG (1:50) (Vector, Burlingame, Calif.), followed by labelling with Streptavidin Alexa Flour 488 conjugate (1:500) (Molecular Probes, Eugene, Oreg.) for 1 hr at RT. Finally, the cells were incubated with DAPI solution for nuclear staining and mounted with mounting medium (Dako Cytomation, Carpinteria, Calif.) to prepare for microscopic examination. The images were acquired with a fluorescence microscopy (Leica, Germany) using an Olympus DP-72 camera with Olympus Cell$^F$ Imaging Software for Life Science Microscopy.

2.1.6 Stimulation of PBMC

PBMC were cultured in RPMI 1640 supplemented with 2 mM L-glutamine (Glutamax, Gibco), 0.5 U/ml penicillin (Sigma), 0.5 µg/ml streptomycin (Sigma), and 10% FCS (SAFC Bioscience). Cells were stimulated in 96 U-well culture plates (0.5-1×10$^6$/well) with *Staphylococcus* enterotoxin B (Sigma; 1 µg/ml) for 18 h or immobilized anti-CD3 and anti-CD28 antibodies according to the manufacturer's instructions (Dynabeads® CD3/CD28 T Cell Expander, Dynal/Invitrogen) for 3 days. After stimulation, cells were harvested, washed with PBS and analyzed by flow cytometry.

2.1.7 Determination of Antibody Subclass

The Mouse Monoclonal Antibody Isotyping Kit (Roche) was used to determine the subclass of CRCBT-02-001 essentially according manufacturer's instructions.

2.1.8 Purification of Antibody Secreted by CRCBT-02-001

CRCBT-02-001 was grown in RPMI-1640 with 10% FCS, 0.5 U penicillin/ml, 0.5 µg streptomycin/ml, and 200 mM Glutamax (Gibco). The supernatant was centrifuged at 500×g to remove cell debris and large material, before being filtered with 0.45 µm, then 0.22 µm syringe filters (Millex; Millipore).

Purification was performed using a BioLogicLP chromatography machine (Biorad), the column (5 ml Protein G column; BioRad using Invitrogen rProteinG Agarose) was washed with more than 10 column volumes of PBS pH 7.4 at 1 mL/min. CRCBT-02-001 supernatant was applied over the column twice at 1 mL/min. The flowthrough was collected for later analysis. The column was washed back to baseline UV absorbance with PBS pH 7.4. To elute the bound IgG, 0.1M Glycine HCl pH 2.8 (Amresco) was applied over the column in a gradient from 0%-100% in 20-40 column volumes at 1 ml/min. The eluted antibody was collected in tubes with 1M Tris HCl pH 7.4 to equal 20% of the volume of the collected fraction. The fractions to be collected were found within the UV peak from the readout. The selected fractions were then pooled, a volume measurement taken and a small sample to analyze further. The remaining sample was desalted/buffer exchanged into PBS pH 7.4 using GE spin columns 100 kDa MWCO (GE Healthcare). The antibody was then quantitated, diluted 30 to 1-2 mg/ml with 1% BSA and 0.05% sodium azide (Sigma) in PBS final volume.

2.1.9 Effect of CRCBT-02-001 on Proliferation and Cell Survival

PBMC were stimulated for 18 hours and 3 days as described above. Purified (azide-free) antibody secreted by CRCBT-02-001 was added to the culture with 2 ug/ml, 5 ug/ml and 10 ug/ml as well as unpurified CRCBT-02-001-containing supernatants (serum-free and serum-containing) In addition, purified IgG (BD Biosciences), CD28 mAb and CD49d mAb (BD Biosciences) and media were added as negative controls. SEB and CD3/CD28 beads were added as positive controls. The stimulated cells were stained for activation markers CD25 and CD69 (as described above). To determine cell death, cells have been incubated with 7-Aminoactinomycin D (7AAD; Sigma Aldrich) for 15 min before acquisition and analyzed by flow cytometry.

To test if immobilized antibody secreted by CRCBT-02-001 has any effect on proliferation and cell survival, purified 2 µg/ml, 5 g/ml and 10 g/ml antibody (azide-free) was incubated in media over night, media was discarded and PBMC were added. After 1 and 3 days cells were harvested and stained for apoptosis and activation marker.

2.1.10 Slot Blot

100 µl of samples (as indicated) were loaded into each slot onto nitrocellulose membrane (Protran; Schleicher & Schuell) under vacuum. After loading, the blot was blocked for 1 hour at RT with 3% skim milk powder (Diploma) in PBS Tween 0.05% (block buffer). The primary Ab (secreted by CRCBT-02-001 or the polyclonal PI16 antibody from Abnova) was diluted in block buffer one in two and incubated on a platform rocker for 1 hour at RT. The blot was washed 3×5 minutes with PBS tween. Biotinylated horse anti mouse (Vector) 1/1000 diluted in block buffer was added and incubated for one hour at RT on rocking platform. The blot was washed 3×5 minutes with PBS tween. A dilution of 1/1000 SA:HRP (GE Healthcare) in block buffer was added and incubated for one hour at RT on rocking platform. The blot was washed 3×5 minutes with PBS tween. An appropriate volume of ECL solutions A and B (enough to cover membrane surface; ECL Advance Western Blotting Kit, GE Healthcare) was added and incubated for one minute with constant shaking. The blot was read immediately in a G:Box (Syngene) upon 15 seconds UV-exposure.

2.1.11 Characterization of Cytokine Secretion

To identify the profile of cytokines secreted by subsets of CD4-positive cells defined using PI16 and CD25, the $T_H1/T_H2/T_H17$ Cytometric Bead Array (CBA; BD Biosciences) was used to measure the levels of the cytokines IL2, IL4, IL6, IL10, IL17A, TNFalpha, IFNgamma in the supernatant of cells following in vitro stimulation. CD4-positive lymphocytes were isolated from a buffy coat using the RosetteSep CD4$^+$ T cell enrichment kit and were stained with antibodies to CD25 and PI16. The four CD4-positive subsets defined by CD25 and PI16 were sorted under aseptic conditions using a FACSAria II cell sorter.

To stimulate the cells, 5.0×10$^5$ of a population of sorted cells were incubated with CD3/CD28 beads (Dynal T cell expander kit; Invitrogen) for 3 days. Unstimulated control cells were incubated without beads. After incubation, the supernatant was collected and assayed for the cytokines using the $T_H1/T_H2/T_H17$CBA kit, according to the manufacturer's instructions. For each subset, the cytokine concentrations were calculated by subtracting the concentration value for unstimulated cells from the value for stimulated cells.

2.1.12 Sequencing CRCBT-02-001

Messenger RNA (mRNA) was isolated from CRCBT-02-001 hybridoma cells using RNeasy midi kit (Qiagen, Germany). RT-PCR was done using one-step RT PCR kit (Qiagen) according to the manufacturer's instructions. Briefly, 1 μg of mRNA was used as template for cDNA synthesis and variable mouse light and heavy chains were amplified with degenerate primers as described in: Zang et al, 2005.

The light chain was amplified using 10 pM of 5'-GG GAGCTC GAY ATT GTG MTS ACM CAR WCT MCA-3' (SEQ ID NO: 11) and 5'-GGT GCATGC GGA TAC AGT TGG TGC AGC ATC-3' (SEQ ID NO: 12) respectively forward and reverse primers. The heavy chain was amplified using equimolar concentration (10 pM final) of the following forward primers:

MH3
(SEQ ID NO: 13)
5'-CTT CCG GAA TTC CAG GTT ACT CTG AAA GWG TST G-3'

MH4
(SEQ ID NO: 14)
5'-CTT CCG GAA TTC GAG GTC CAR CTG CAA CAR TC-3'

MH5
(SEQ ID NO: 15)
5'-CTT CCG GAA TTC CAG GTC CAA CTV CAG CAR CC-3'

MH6
(SEQ ID NO: 16)
5'-CTT CCG GAA TTC GAG GTG AAS STG GTG GAA TC-3'

MH7
(SEQ ID NO: 17)
5'-CTT CCG GAA TTC GAT GTG AAC TTG GAA GTG TC-3' with the IgG1 specific reverse primer: IgG1: 5'-gga aga tct ATA GAC AGA TGG GGG TGT CGT TTT GGC-3' (SEQ ID NO: 18). The RT-PCR product was run on a 1% agarose gel, bands were excized and DNA purified using Promega SVgel extraction (Promega, A9282) before sequencing.

2.2 Results

A mouse polyclonal antibody to human PI16 (Abnova) was used in multi-colour flow cytometry (FIG. 2). This antibody stained approximately 18% of lymphocytes, the majority of which were also CD4-positive. To confirm that PI16 was expressed by Treg cells, cells were stained with antibodies against CD4, CD25 and FoxP3 in addition to the PI16 antibody. As shown in FIG. 2, more than 50% of $CD25^{bright}$ $PI16^+$ cells also expressed FoxP3.

To avoid specificity issues with using a polyclonal antibody, a mouse monoclonal antibody to human PI16 protein was generated. A comparison of the human and mouse amino acid sequences (FIG. 1) indicated that there was likely sufficient divergence to elicit an immune response.

Figure 4:
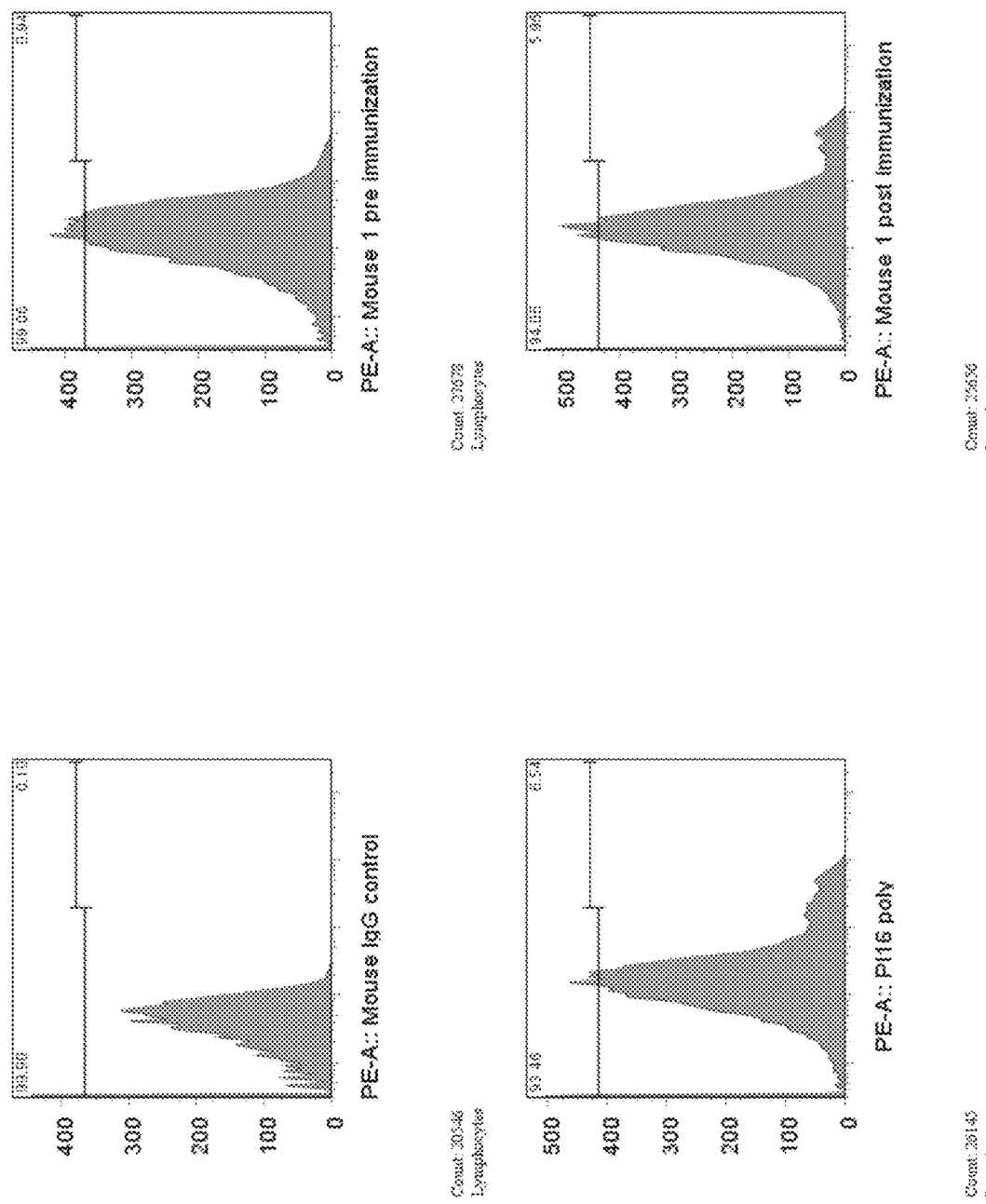
FIG. 4 is a series of graphical representations showing reactivity of serum from mice for PI16 expressing cells before (pre; right hand top panel) and after (post; right hand bottom panel) immunization with those cells. Binding of serum antibodies was analyzed by flow cytometry. Mouse IgG isotype was used as negative control (left hand top panel), the polyclonal mouse PI16 antibody (Abnova) was used as positive control (left hand bottom panel).

Mice were immunized with L929 cells expressing PI16 and screened for antibody production using flow cytometry (FIG. 4). Mice producing antibodies reactive with PI16 expressing L929 cells were selected for hybridoma generation.

Figure 5:
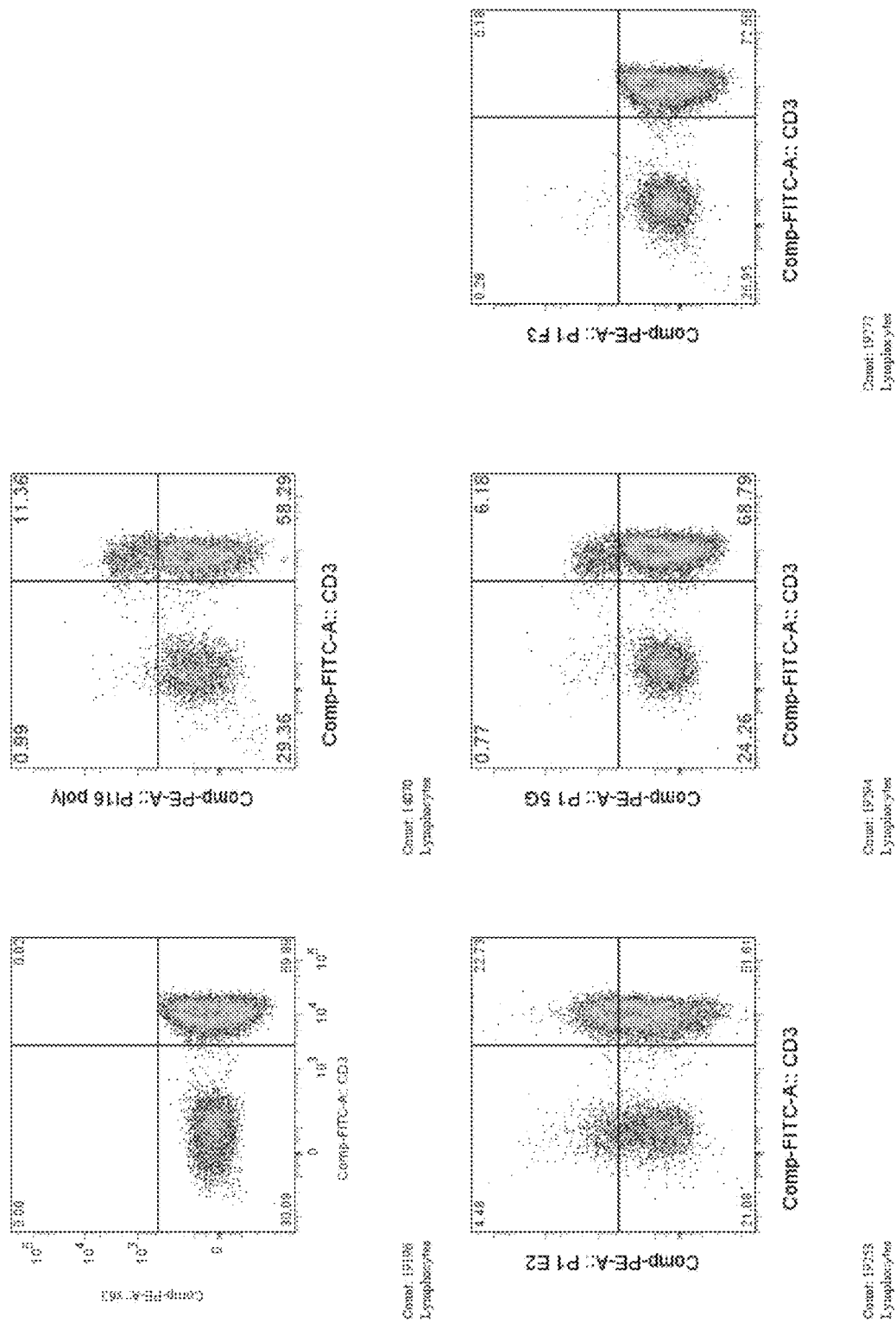
FIG. 5 is a series of graphical representation showing screening of hybridoma cell culture supernatant on CD3$^+$ lymphocytes. X63 supernatant was used as IgG control (top left panel). Abnova polyclonal mouse PI16 antibody (PI16 poly) was used as positive control (top right panel). Hybridoma well P1G5 (P1 5G) showed similar staining to the positive control (bottom centre panel), and two other hybridomas (P1 E2 and P1 F3) showed different staining (bottom left and right panels, respectively).

Following fusion, hybridoma culture supernatant was screened using flow cytometry to detect binding to PI16 expressing L929 cells. As shown in FIG. 5, cells in hybridoma well P1G5 (P1 5G) secreted antibodies that stained C3+ cells in a similar fashion to the previously tested polyclonal antibody.

Figure 6:
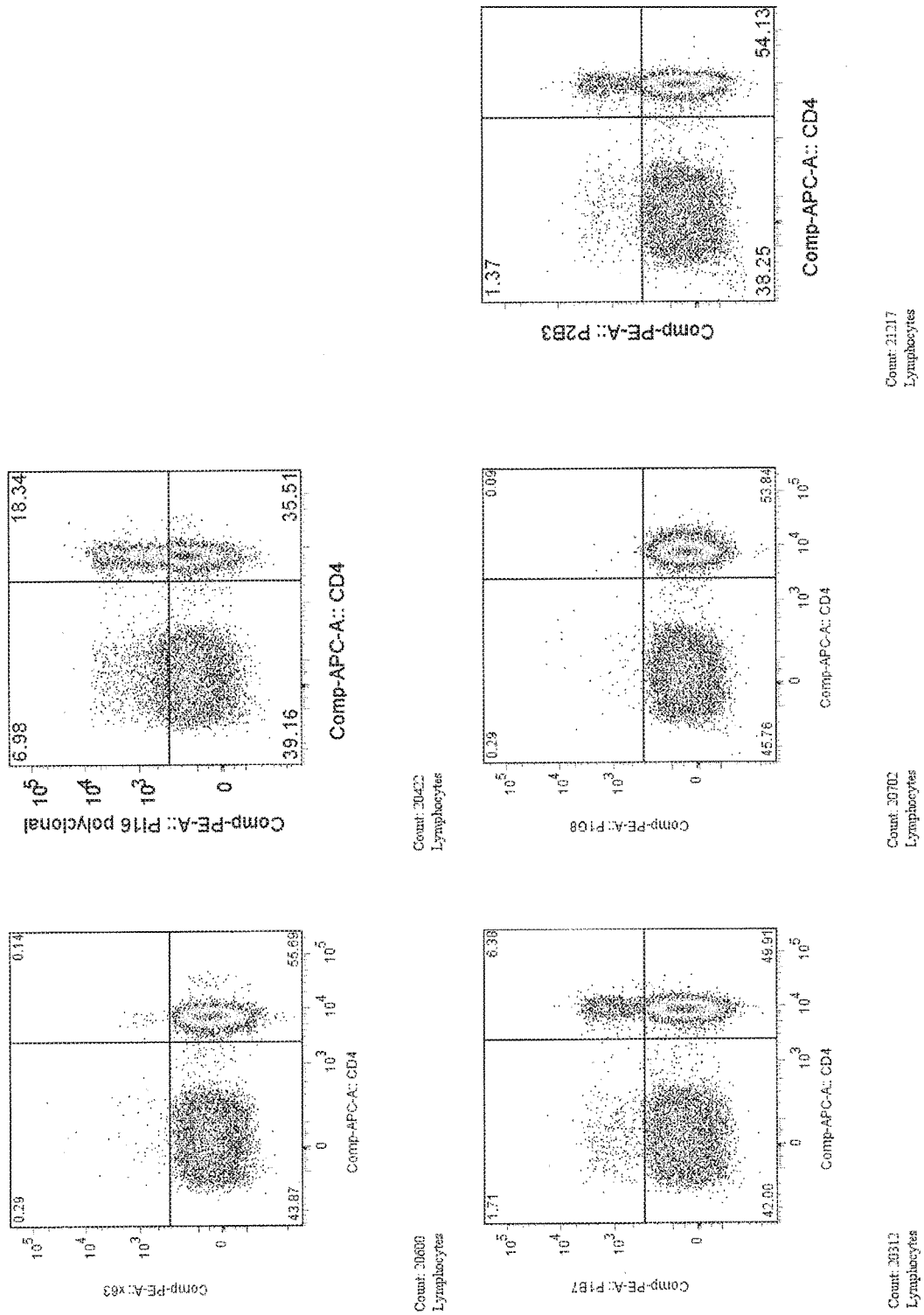
FIG. 6 is a series of graphical representations showing reactivity of cell culture supernatant from subclones of hybridoma P1G5. X63 supernatant was used as IgG control (top left panel). Abnova polyclonal mouse PI16 antibody (PI16 poly) was used as positive control (top right panel). Subclone P2B3 (designated CRCBT-02-001; bottom right panel) shows similar staining to the positive control, while subclone P1B7 shows similar staining to P2B3 and P1G8 is negative for PI16 reactivity (bottom left and centre panels).

P1G5 was then recloned by single cell sorting and tested for binding to CD4+ T cells using flow cytometry. As shown in FIG. 6, clone P1G5-P2B3 showed a similar binding pattern to the previously tested polyclonal antibody, while clones P1G5-P1B7 and P1G5-P1G8 did not. P1G5-P2B3 was selected for expansion and was designated CRCBT-02-001. CRCBT-02-001 was determined to be murine IgG1κ.

Figure 7:
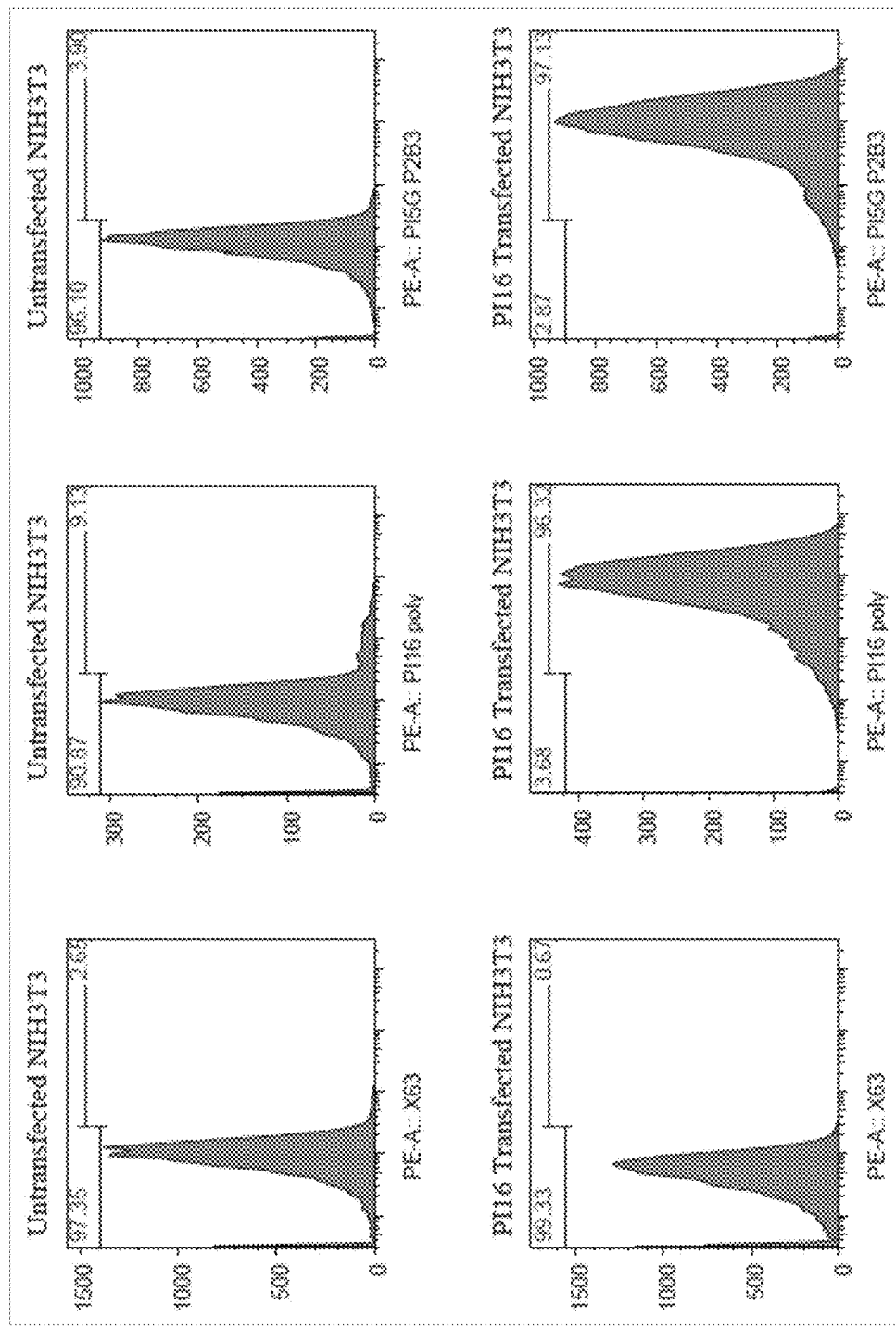
FIG. 7 is a series of graphical representations showing comparison of the staining of CRCBT-02-001 supernatant (P1G5 P2B3; right panels), Abnova polyclonal PI16 antibody (PI16 poly) (centre panels) and X63 negative control body (left panels) on stable PI16-transfected NIH3T3 cells (bottom panels) as well as on untransfected NIH3T3 cells (top panels).

PI16 expressing NIH3T3 cells were used to confirm the reactivity of hybridoma culture supernatant produced by CRCBT-02-001 and to compare that of the previously tested commercial polyclonal antibody. As shown in FIG. 7, the polyclonal antibody and the hybridoma supernatant demonstrated a similar staining pattern.

Figure 8:
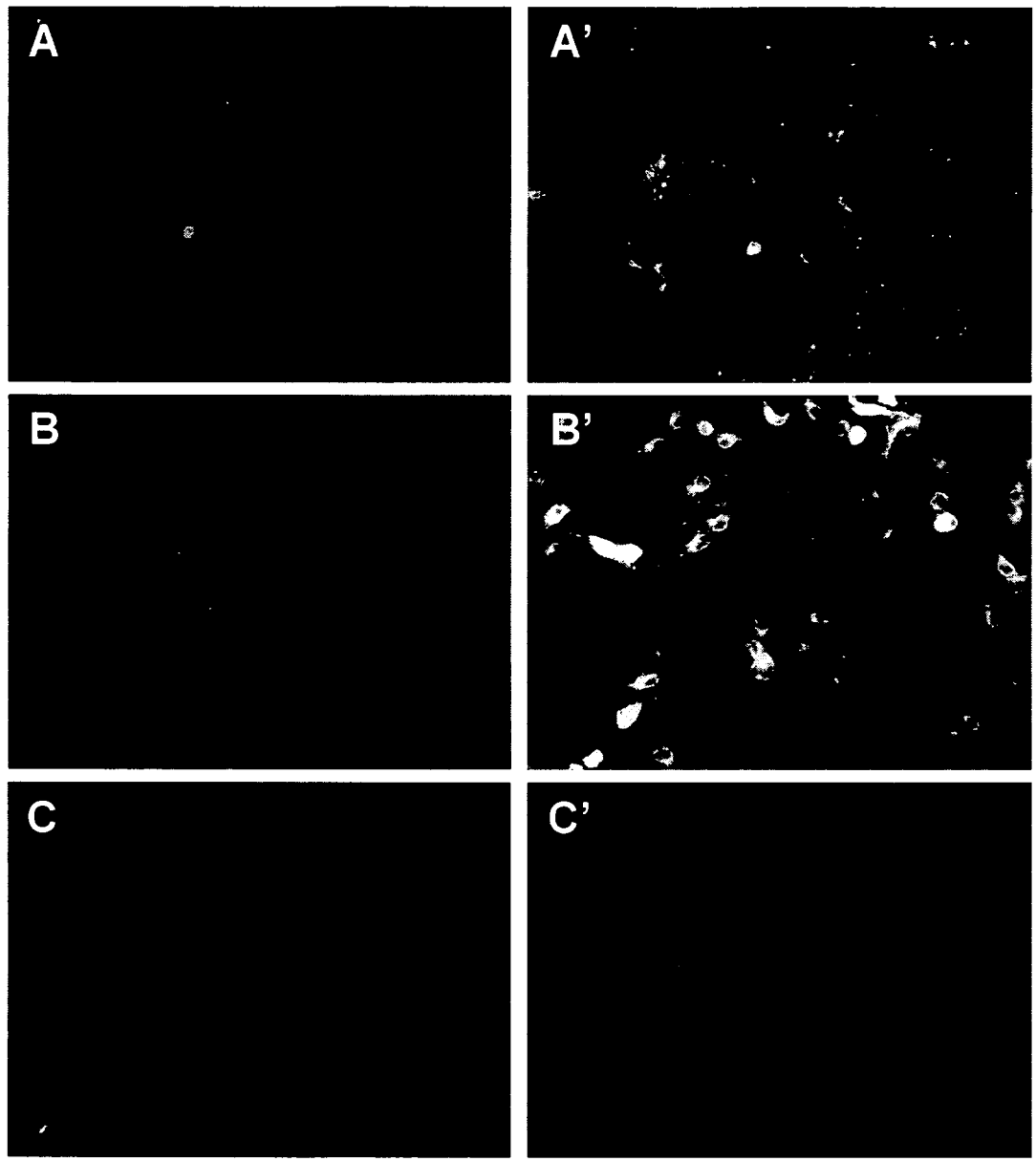
FIG. 8 is a series of photomicrographs showing immunoreactivity of antibodies for untransfected control (A, B and C) and stable transfected NIH3T3 cells expressing PI16 fused to a V5 epitope (A', B' and C'). Cells were stained with CRCBT-02-001 culture supernatant (A and A'), anti-V5 antibody (B and B') and the Abnova PI16 mouse polyclonal antibody (C and C') followed by incubating with biotinylated horse anti-mouse antibodies. Then, the cells were incubated with streptavidin AF488 conjugate (green) and DAPI (blue) for visualization (DAPI stains the nucleus). Panel A' shows an accumulation of green fluorescence along the plasma membranes confirming surface staining of CRCBT-02-001. Staining of the V5-tag in Panel B' confirms the successful transfection of NIH3T3 cells. Panel C' shows surface staining of the polyclonal PI16 antibody in comparison.

To confirm sub-cellular localisation of PI16 detected with CRCBT-02-001 supernatant, untransfected or stably transfected NIH3T3 cells were grown in Chamber Slides. As shown in FIG. 8, CRCBT-02-001 supernatant accumulated at the plasma membrane, confirming cell surface staining FIG. 8 also shows that CRCBT-02-001 supernatant (FIG. 8A') stains the surface of transfected cells to a greater degree than the commercially available anti-PI16 polyclonal antibody (FIG. 8C').

Figure 9:
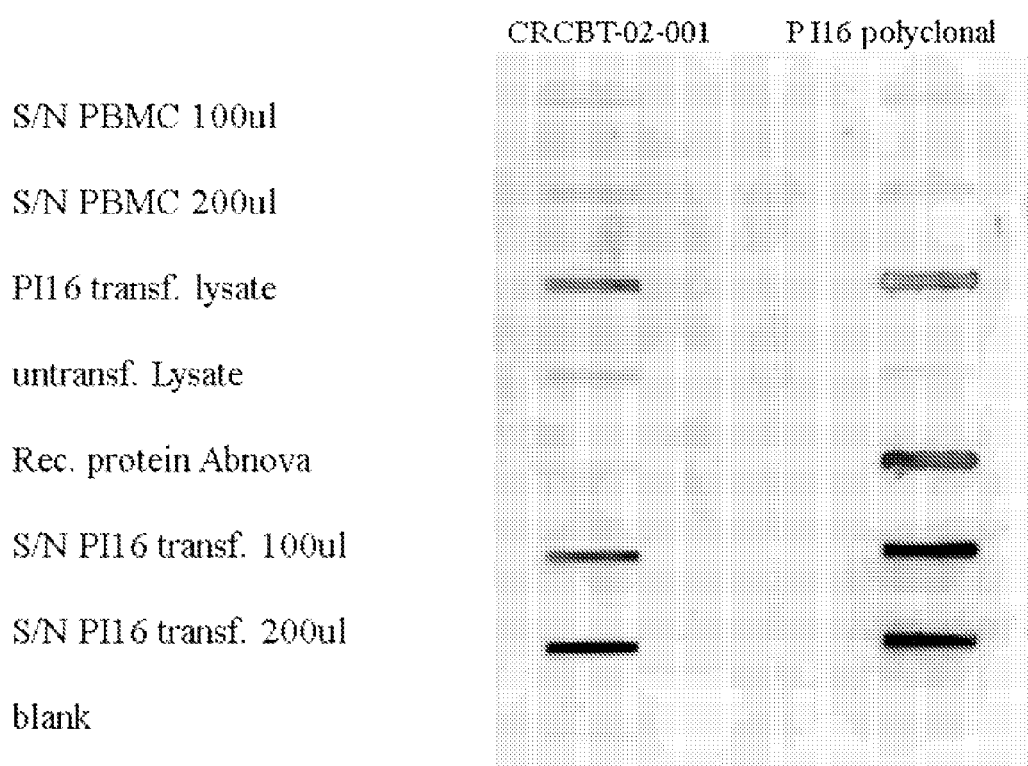
FIG. 9 is a photographic representation showing results of a slot blot demonstrating that both, CRCBT-02-001 antibody and the PI16 polyclonal antibody (Abnova) bind the PI16 stable transfectant NIH3T3 cells (PI16 transf. lysate) but not the untransfectant NIH3T3 cells (untransf. lysate). Both antibodies also bind to supernatant of the PI16 stable transfectant NIH3T3 cells (S/N PI16 transf.) suggesting that the transfected cells secrete or shed PI16 from their surface. CRCBT-02-001 does not bind the Abnova recombinant protein (Rec. protein Abnova). These results suggest that both, CRCBT-02-001 and the PI16 polyclonal antibody (Abnova) bind PI16. The failure of the CRCBT-02-001 monoclonal antibody to bind the Abnova recombinant PI16 protein suggests that the monoclonal antibody may bind more selectively to PI16 produced by a cell (e.g., a mammalian cell) as opposed to in a cell-free system.

To determine the protein to which the monoclonal antibody binds, slot blots were performed. FIG. 9 shows a slot blot demonstrating that both CRCBT-02-001 supernatant and the PI16 polyclonal antibody (Abnova) bind the PI16 stable transfectant NIH3T3 cells (PI16 transf. lysate) but not the untransfectant NIH3T3 cells (untransf. lysate). Both antibodies also bind to supernatant of the PI16 stable transfectant NIH3T3 cells (S/N PI16 transf.) suggesting that the transfected cells secrete or shed PI16 from their surface. CRCBT-02-001 does not bind the Abnova recombinant protein (Rec. protein Abnova). These results suggest that both, CRCBT-02-001 and the PI16 polyclonal antibody (Abnova) bind PI16. The failure of the CRCBT-02-001 monoclonal antibody to bind the Abnova recombinant PI16 protein (which is expressed using a wheat germ cell free system) suggests that the monoclonal antibody is more selective for PI16 made in cells, e.g., eukaryotic cells than the polyclonal antibody. These data indicate that the monoclonal antibody is reactive with native mammalian PI16 and has limited cross-reactivity with PI16 which has not been processed and/or folded in a manner yielding a protein similar to native mammalian protein, e.g., native human protein.

Figure 10:
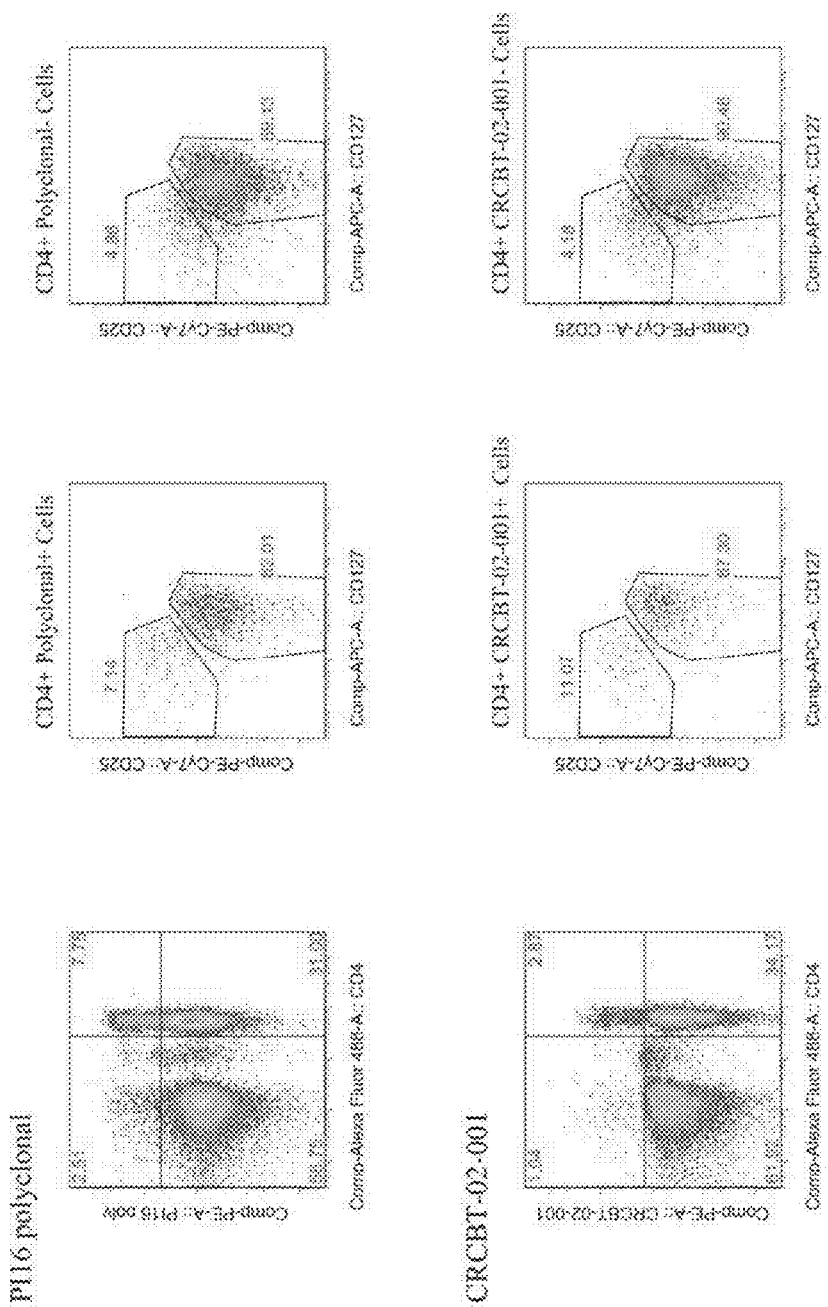
FIG. 10 is a series of graphical representations showing the proportion of PI16$^+$ cells (identified with CRCBT-02-001 supernatant or PI16 polyclonal antibody) that are in the population of cells isolated based on Treg cell surface markers (CD4$^+$CD25$^{bright}$CD127$^-$). Cells isolated with CRCBT-02-001 supernatant are shown in the bottom panels; cells isolated with the polyclonal PI16 antibody are shown in the top panels. This figure shows that CRCBT-02-001 supernatant binds to a more specific population of CD4$^+$ cells (2.8%) than the polyclonal antibody (7.9%). CRCBT-02-001 supernatant also identifies a larger proportion of cells expressing the Treg phenotype than the polyclonal PI16 antibody.

To confirm that CRCBT-02-001 supernatant is capable of binding to Treg cells, the supernatant was used to analyze CD4+ cells for CD25 and CD127 co-expression. As shown in FIG. 10, CRCBT-02-001 detected a larger degree of $CD4^+CD25^{hi}CD127^-$ (Treg) cells than the commercially available polyclonal antibody.

Figure 11:
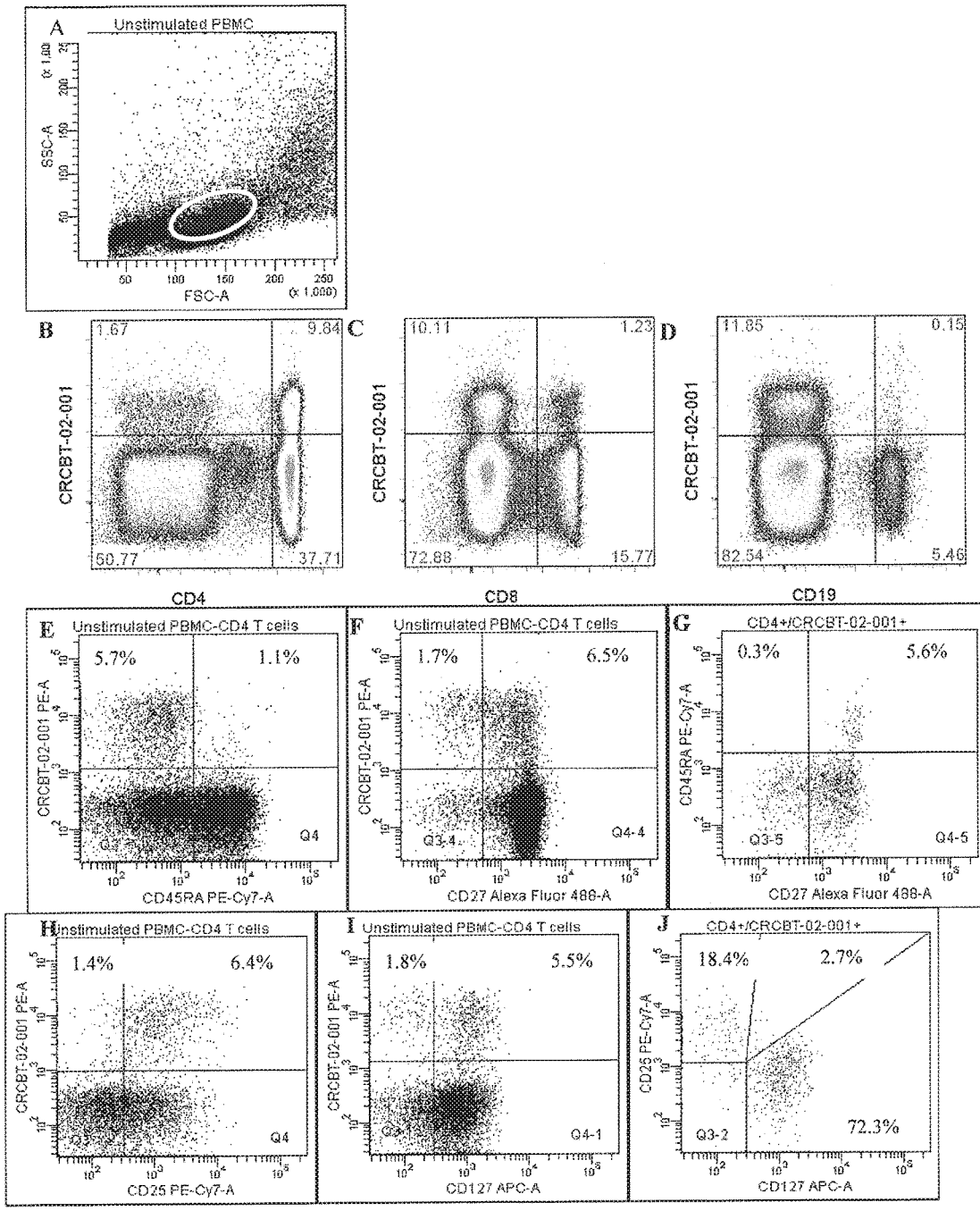
FIG. 11 is a series of graphical representations showing immunoreactivity of various populations of peripheral blood leukocytes with CRCBT-02-001. Panel A shows the gate used to identify lymphocytes for the subsequent analyses (all PBMC included; white oval indicates lymphocytes). Panel B shows that CRCBT-02-001 supernatant binds to CD4$^+$ T cells (only lymphocytes analyzed). Panel C shows that CRCBT-02-001 supernatant binds very few CD8$^+$ T cells (only lymphocytes analyzed). Panel D shows that CRCBT-02-001 supernatant binds a minority of B cells (only lymphocytes analyzed). Panel E shows that the majority of CRCBT-02-001 positive CD4$^+$ T cells have a memory phenotype (CD45RA−) (all CD4$^+$ T cells analyzed). Panel F shows that about three quarters of CRCBT-02-001 positive CD4$^+$ T cells also express CD27 (all CD4$^+$ T cells analyzed). Panel G shows that only a minority of CRCBT-02-001- positive cells belong to the effector memory cell subset (CD45RA−/CD27−) (all CD4$^+$CRCBT-02-001$^+$ cells included). Panel H shows that the majority of CRCBT-02-

Various lymphocyte subsets from fresh PBMC were also stained for CRCBT-02-001 supernatant immunoreactivity. This staining indicated that the majority of PI16-expressing cells were CD4-positive lymphocytes (approximately 20% of CD4-positive subset; FIG. 11B), with the remaining cells being CD8-positive T cells (approximately 10% of the CD8-bright subset; FIG. 11C). Very few CD19-positive lymphocytes (B cells) react with CRCBT-02-001 supernatant (FIG. 11D)

The majority of CRCBT-02-001 supernatant immunoreactive CD4+ T cells have a memory phenotype (CD45RA−) (FIG. 11E) with a majority also expressing CD27 (FIG. 11F). Furthermore, a small proportion of CRCBT-02-001-immunoreactive cells belong to the effector memory cell subset (CD45RA−/CD27−; FIG. 11G).

The majority of CRCBT-02-001 supernatant immunoreactive CD4+ T cells express CD25 (FIG. 11H) and about three quarters of the CD4+/CRCBT-002-001 supernatant positive cells express CD127 (FIG. 11I). Of all CD4+/CRCBT-002-001 supernatant positive cells approximately 20% express the Treg phenotype CD25+/CD127− (FIG. 11J).

To further characterize the expression of PI16 by Treg cells and other $T_H$ cells, peripheral blood mononuclear cells were stained with the CRCBT-002-01 monoclonal antibody and antibodies to CD4, CD25 and CD127, and used the gating strategy of Seddiki et al (2006) to identify the CD25-bright/CD127-dim Tregs and CD127-positive Th cell subsets (FIG. 12). The staining indicates that PI16 is expressed by a fraction of both the Treg and Th subsets of CD4-positive lymphocytes, with a higher proportion of Tregs expressing PI16.

Additional characterization of PI16-positive Treg cells was performed by staining lymphocytes with monoclonal antibodies to CD4, CD25, PI16 (CRCBT-02-001), CD45RA and CD45RO. The majority of the CD4-positive lymphocytes which expressed both PI16 and CD25 had a CD45RO-positive/CD45RA-negative "memory" phenotype (FIG. 13).

Treg are defined by the expression of the transcription factor FoxP3. Antibodies to CD4, CD25, PI16 (CRCBT-02-001) and FoxP3 were also to examine the expression of FoxP3 by Treg subsets defined by the presence or absence of PI16 (FIG. 14). Higher levels of FoxP3 expression were detected in the PI16-positive/CD25-positive fraction (population mean fluorescence intensity (MFI) of 1457) compared to the PI16-negative/CD25-positive fraction (MFI of 1062). The level of FoxP3 in the PI16-positive/CD25-negative fraction (MFI of 613) was similar to the background levels of the PI16-negative/CD25-negative Effector cell fraction (MFI of 480).

Using the gating strategy essentially as described by Miyara et al (2009), PI16-positive memory Treg were also shown to express the FoxP3 transcription factor (FIG. 15).

CD4+CD25+ cells were further analyzed for co-staining with CRCBT-02-001 supernatant and Treg subset markers by flow cytometry. Results of this analysis are presented in Table 2.

TABLE 2

Representative expression of T cell markers by subsets of CD4-positive lymphocytes identified using the co-expression of CD25 and PI16 (CRCBT-02-001) as shown in FIG. 14. The values shown are the percentage of cells in each quadrant that express the particular marker.

| Marker | CD25-pos PI16-neg | CD25-pos PI16-pos | CD25-neg PI16-neg | CD25-neg PI16-pos |
|---|---|---|---|---|
| isotype | 0 | 1 | 0 | 0 |
| CD45RA | 34 | 10 | 86 | 19 |
| CD45RO | 69 | 96 | 14 | 92 |

TABLE 2-continued

Representative expression of T cell markers by subsets of CD4-positive lymphocytes identified using the co-expression of CD25 and PI16 (CRCBT-02-001) as shown in FIG. 14. The values shown are the percentage of cells in each quadrant that express the particular marker.

| Marker | CD25-pos PI16-neg | CD25-pos PI16-pos | CD25-neg PI16-neg | CD25-neg PI16-pos |
|---|---|---|---|---|
| CD95 | 86 | 99 | 17 | 97 |
| CD39 | 10 | 23 | 1 | 1 |
| CD73 | 9 | 9 | 3 | 12 |
| CD44 | 99 | 99 | 99 | 99 |
| CD69 | 0 | 0 | 0 | 0 |
| CCR6 | 17 | 42 | 2 | 37 |
| HLADR | 21 | 60 | 2 | 8 |

The differential staining with CD45RO, CD45RA, CD39 and CCR6 indicates that the PI16-positive Treg population is a subset of memory Treg which is phenotypically distinct from both the PI16-negative Treg population and from the other PI16-positive $T_H$ cells.

FIG. 16 further supports the ability of CRCBT-02-001 secreted antibody to bind to memory Treg cells. Briefly, CD4+ cells were labelled with CRCBT-02-001 supernatant and antibodies to either CD45RA or CD45RO. Staining of CD45RA is widely used to distinguish memory cells from naïve cells with CD45RA− cells belonging to the memory cell subset (CD45RO+). Thus, CRCBT-02-001 appears to identify a population of CD4+CD25+CD45RA−CD45RO+ memory Treg cells.

A Cytometric Bead Array (CBA) was used to determine which cytokines were expressed by PI16-expressing Treg following stimulation through the T cell receptor (FIG. 17). These experiments indicate that the cytokine expression profile of the PI16-positive Treg cells is the same as the PI16-negative Treg cells, and that the PI16-positive $T_H$ cells express the same cytokines as their PI16-negative counterparts.

To further characterise the PI16-positive memory Treg, the expression of several chemokine receptors by the PI16-positive memory Treg was compared to PI16-negative memory Treg and other PI16-positive memory $T_H$ cells (see Table 3). CCR4 and CCR6 chemokine receptors are expressed by a higher proportion of memory PI16-positive Treg and memory PI16-positive $T_H$ cells compared to the memory component of the PI16-negative Treg or $T_H$ fractions (FIG. 18). The differential expression of chemokine receptors can be used to predict the migration of subsets of $T_H$ cells, and also to identify functional subsets of Th cells. The data presented herein show that the profile of chemokine receptors expressed by the PI16-positive memory Treg is different to both the PI16-negative memory Treg and the other PI16-positive $T_H$ cells. Their expression of chemokine receptors such as CCR4 and CCR6 indicates that the PI16-positive memory Treg can migrate to the same sites of inflammation as can $T_H17$ cells.

TABLE 3

Representative expression of chemokine receptors by subsets of memory CD4-positive lymphocytes identified using the co-expression of CD25 and PI16 (CRCBT-02-001) as shown in FIG. 14, and the memory fraction of each was identified by the expression of CD45RO. The values shown are the percentage of cells in each quadrant that express the particular marker.

| Marker | Memory CD25-pos PI16-neg | Memory CD25-pos PI16-pos | Memory CD25-neg PI16-neg | Memory CD25-neg PI16-pos |
|---|---|---|---|---|
| isotype | 0.4 | 1.5 | 0.9 | 1.2 |
| CCR4 | 26.7 | 71.8 | 11.1 | 47.6 |
| CCR5 | 29.4 | 45.9 | 22.2 | 21.3 |

TABLE 3-continued

Representative expression of chemokine receptors by subsets of memory CD4-positive lymphocytes identified using the co-expression of CD25 and PI16 (CRCBT-02-001) as shown in FIG. 14, and the memory fraction of each was identified by the expression of CD45RO. The values shown are the percentage of cells in each quadrant that express the particular marker.

| Marker | Memory CD25-pos PI16-neg | Memory CD25-pos PI16-pos | Memory CD25-neg PI16-neg | Memory CD25-neg PI16-pos |
|---|---|---|---|---|
| CCR6 | 23.8 | 41.7 | 22.1 | 31.6 |
| CXCR3 | 26.2 | 29.1 | 37.8 | 34.4 |
| CXCR4 | 34.4 | 39.4 | 42.0 | 40.4 |

As shown in FIG. 19, despite up-regulation of CD25, there is no correspondent upregulation of PI16.

PBMC were stimulated over night and 3 days. Purified antibody secreted by CRCBT-02-001 (azide-free) was added to the culture with 2 µg/ml, 5 µg/ml and 10 µg/ml or cells were contacted with immobilized antibody and stained for activation markers CD25 and CD69. To determine cell death, cells were incubated with 7AAD for 15 min before acquisition and analyzed by flow cytometry. Results are shown in Tables 4 and 5.

TABLE 4

Effect of soluble CRCBT-02-001 on proliferation and cell survival

| | Overnight Stimulation | | | 3 days | | |
|---|---|---|---|---|---|---|
| Soluble CRCBT-02-001 | 7AAD+ (%) | CD25+ (%) | CD69+ (%) | 7AAD+ (%) | CD25+ (%) | CD69+ (%) |
| Media alone | 11.4 | 16.4 | 12.5 | 22.3 | 20.2 | 24.4 |
| IgG1 control | 9.8 | 17.5 | 15.6 | 27.1 | 21 | 24.2 |
| CD28/CD49d | 8.9 | 14.3 | 9.1 | 20.8 | 20.2 | 23.1 |
| 2 ug/ml CRCBT-02-001 | 5.4 | 17.7 | 9.9 | 23.1 | 22.8 | 26 |
| 5 ug/ml CRCBT-02-001 | 6.8 | 17.4 | 11.2 | 22.5 | 22.6 | 24.8 |
| 10 ug/ml CRCBT-02-001 | 8.8 | 18.6 | 12.2 | 23.3 | 21.1 | 25.3 |
| Serum free CRCBT-02-001 s/n | 10.8 | 19.4 | 12 | 37 | 30.5 | 28.4 |
| CRCBT-02-001 s/n | 6.6 | 18.3 | 20.4 | 83.9 | 57.9 | 45.8 |
| SEB (o/n) resp. anti-CD3/CD28 (3 days) | 18.1 | 46.4 | 57.9 | 74.3 | 71.4 | 85.7 |

TABLE 5

Effect of immobilized CRCBT-02-001 on proliferation and cell survival

| | Overnight Stimulation | | | 3 days | | |
|---|---|---|---|---|---|---|
| Immobilized CRCBT-02-001 | 7AAD+ (%) | CD25+ (%) | CD69+ (%) | 7AAD+ (%) | CD25+ (%) | CD69+ (%) |
| Media alone | 11.7 | 16.2 | 13.1 | 23.6 | 25.4 | 22.6 |
| Media and PBS | 13.7 | 24.6 | 15.8 | 18.3 | 23.1 | 17 |
| IgG1 control | 10 | 19.1 | 14.4 | 19.4 | 22.4 | 20.3 |
| CD28/CD49d | 25.8 | 23.7 | 17.3 | 16.5 | 22.7 | 16.3 |
| 2 ug/ml CRCBT-02-001 | 7.8 | 18.8 | 16.6 | 14.9 | 15.3 | 16.3 |
| 5 ug/ml CRCBT-02-001 | 14.8 | 24.5 | 15.9 | 11.9 | 22.1 | 16.7 |
| 10 ug/ml CRCBT-02-001 | 9.9 | 20.3 | 13.5 | 13.5 | 22.4 | 15.7 |
| Serum free CRCBT-02-001 s/n | 8.9 | 21.7 | 15.3 | 17.9 | 23.5 | 18.8 |
| CRCBT-02-001 s/n | 11.8 | 25.1 | 35.1 | 17.3 | 23.1 | 18.9 |
| SEB (o/n) resp. aCD3/CD28 (3 days) | 45.1 | 57.3 | 74.8 | 33.7 | 65.3 | 74 |
| New SEB | 35 | 54.3 | 77.8 | | | |

The results presented in Tables 3 and 4 show that CRCBT-02-001 does not kill or cause differentiation of cells having a Treg phenotype in the absence of effector cells. This is useful for isolating Treg cells using this antibody or a protein that binds to the same epitope without significantly affecting the cells.

As shown in FIG. 20, the antibody secreted by CRCBT-02-001 detects PI16 in supernatants of stimulated PBMC suggesting that PI16 may be shed or secreted upon stimulation. There was no signal detected on CD4 cell lysates. However, because PI16 is only on about 5% of CD4 cells, this extract was most likely too dilute for detection of PI16 (1:100). CRCBT-02-001 secreted antibody bound only to CD4$^+$CD25$^+$ stimulated and rested cell lysates, not to CD4$^+$ CD25$^-$ cell lysates. CRCBT-02-001 secreted antibody detected PI16 in supernatants of stimulated Treg (CD4$^+$ CD25$^+$PI16$^+$) suggesting that PI16 may be shed or secreted upon stimulation of Treg cells.

The antibody secreted by CRCBT-02-001 was also found to bind to human PI16 but did not detectably bind to mouse PI16.

The sequence of the nucleic acids encoding the variable regions of CRCBT-02-001 and the encoding amino acid deduced. The sequence encoding the heavy chain variable region is set forth in SEQ ID NO: SEQ ID NO: 7 and the encoded amino acid in SEQ ID NO: 8. The sequence encoding the light chain variable region is set forth in SEQ ID NO: SEQ ID NO: 9 and the encoded amino acid in SEQ ID NO: 10. FIG. 21 shows these sequences with CDRs highlighted. CDRs in the $V_H$ were found by comparison with AB089648.1 as published in Komatsu et al., (2003).

Example 3

Suppression of Immune Response by Tregs Isolated Using CRCBT-02-001

3.1. Isolation of Fresh Adult Treg and Teffector Subsets for Suppression Assays

Treg cells were isolated from a buffy coat after first enriching for CD4$^+$ T cells using the RosetteSep CD4$^+$ T cell enrichment kit (Stem Cell Technologies, Vancouver, Canada). CD4$^+$ CD25$^{bright}$ PI16$^+$ and CD4$^+$ CD25$^{bright}$ PI16$^-$ were sorted under aseptic conditions using a FACSAria II cell sorter, essentially as described in Example 2. CD4$^+$CD25$^-$ effector cells were isolated from a second donor buffy coat and purified using magnetic-activated cell-sorting (MACS) beads (Miltenyi Biotech).

3.1.2. Expansion of Human Cord nTreg Cells and iTreg Cells

CD4$^+$ CD25$^+$ and CD4$^+$CD25$^-$ T cells were extracted and purified from fresh cord blood using the Invitrogen Dynal Bead Regulatory T cell kit (cat #113.63D). Isolated CD4$^+$ CD25$^+$ Treg cells were incubated for 7 days with Dynal Bead Human T Expander CD3/CD28 beads at a 3:1 ratio (cat #111.41D) and 500 U/ml IL-2 in complete X-vivo 15 media (Lonza cat #04-418Q). CD4$^+$CD25$^-$ T cells were expanded under the same conditions representing a Treg control group. iTreg cells were generated by incubating CD4$^+$ CD25$^-$ T cells with CD3/CD28 beads (3:1 beads to cells ratio), 500 U/ml IL-2 and 5 ng/ml TGF-β with 10 μM all-trans-retinoic acid (ATRA)(Sigma). All Treg cell subsets were expanded for 7 days. At day 7, CD3/CD28 beads were removed and cells were allowed to rest for a further 7 days in complete X-vivo media with 100 U/ml IL-2.

3.2 Thymidine Incorporation

PI16$^+$ nTregs (CRCBT-02-001$^+$) and PI16$^-$ nTregs (CRCBT-02-001$^-$) from expanded cord were tested for their suppressive activity in a mixed lymphocyte reaction (MLR). CD4$^+$CD25$^-$ effector T-cells (approximately 2×10$^4$) were cultured in 96 well plates and grown in the presence of 1×10$^5$ irradiated (30 Gy) PBMCs. CD4$^+$CD25$^+$PI16$^+$ cells isolated by the method essentially as described in Example 2. Cells were added at ratios of 1:1, 2:1, 4:1, 8:1, 16:1, 32:1, 64:1. Cells were activated with 100 ng/ml anti-CD3 (OKT3) monoclonal antibody (eBioscience). Wells were pulsed on day 4 with $^3$H-thymidine for the last 16 hours of culture. All time points were measured in triplicate. Results were expressed in scintillation counts per minute. FIG. 22A shows a representative thymidine assay from expanded cord demonstrating suppression of effector cells by PI-16$^+$ and PI-16$^-$ nTregs.

As shown in FIG. 22B, PI16$^+$ Treg cells isolated with CRCBT-02-001 suppress proliferation of effector cells at ratios of 1:1-16:1 with the same efficacy as PI-16$^-$ nTregs (n=6).

3.3 5,6-Carboxyfluorescein Diacetate Succinimidyl Ester (CFSE) Suppressor Assay

Cell division of effector cells in a mixed lymphocyte reaction was also analysed by CFSE dilution (Venken et al., 2009). Effector CD4$^+$CD25$^-$ cells were isolated as described in 3.1, and labelled with 1 mM CFSE (Invitrogen, Carlsbad, Calif.) in PBS for 10 minutes at 37° C. 2×10$^4$ CFSE labelled effector cells were incubated with Treg cells at Teffector/Treg ratios of 1:1, 2:1, 4:1, 8:1, 16:1, 32:1. Effector and Treg cells were incubated with 1×10$^5$ irradiated (30 Gy) PBMCs and 100 ng/ml anti-CD3 (OKT3) monoclonal antibody (eBioscience) in 200 μl cRPMI in a 96-well U-bottom plate. Co-cultures were harvested after 5 days of incubation and the proliferation of the responder population was visualised by the dilution of CFSE fluorescence with cell division by flow cytometry. FIG. 23A provides a representative CFSE suppressor assay using expanded cord Tregs (PI-16$^+$ and PI-16$^-$). The accumulative results for six expanded cord Tregs (PI-16$^{+/-}$) is shown in FIG. 23B. PI-16$^+$ and PI-16$^-$ Tregs suppress with equal potency under normal culture conditions.

Freshly-isolated PI16-expressing Treg cells from peripheral blood were able to suppress the proliferation of stimulated CD25$^-$ T effector cells (FIG. 23C). These data confirm that the PI16$^+$/CD25$^+$ cells isolated with CRCBT-02-001 are functional Treg cells with the same suppressive abilities as PI-16$^-$ Tregs. Accumulative CFSE suppressor assay results in fresh adult nTregs (PI-16$^+$ and PI-16) confirm the suppressive capacity of PI-16$^+$ Tregs isolated from peripheral blood (n=4) (FIG. 23D). There is no difference in suppressive abilities between PI-16$^+$ and PI-16$^-$ Tregs from adult blood under normal cell culture conditions.

3.4 CD154 Suppression Assay

PI16$^+$ nTregs (CRCBT-02-001$^+$) and PI16$^-$ nTregs (CRCBT-02-001) subsets from expanded cord were isolated essentially as described in Example 2 and rested overnight at 37° C. in complete X-Vivo 15 media (Lonza) before being added to the assay. Freshly collected or previously cryopreserved MACS or FACS isolated CD4$^+$CD25$^-$ cells were used as effector cells in this assay. Freshly collected CD4$^+$ CD25$^-$ effector cells are used within 12 hours of collection, cryopreserved CD4$^+$CD25$^-$ effector cells are rested for 12-20 hours at 37° C. in complete RPMI media prior to use in the assay.

Treg cell subsets were plated in 96 well plates at 1:1, 2:1, 4:1, 8:1, 16:1 and 32:1 Effector/Treg cell ratios. CD4$^+$ CD25$^-$ effector cells were plated at 5×10$^4$ cells/50 μl/well, Tregs were plated at 5×10$^4$ cells/50 μl/well (1:1) and serially diluted to 1.56×10$^3$ cells/50 ul/well. Control wells of approximately 5×10$^4$ Treg only and CD4$^+$CD25$^-$ effectors only (both stimulated and unstimulated) were included. Unstimulated wells received a cocktail containing CD154-APC (BDBiosciences (BD); 5 μl per well), stimulated wells received a cocktail containing CD154$^-$APC (5 ul per well) and CD3/CD28 T cell expander beads at a 0.25:1 bead/cell ratio. The cultures were incubated in the dark for 7-8 hours at 37° C. Following the incubation period the 96 well plates were refrigerated for a maximum of 15 hours prior to staining Cells were stained in the 96 well plate for surface expression of CD4 (FITC, BD) and CD25 (PECy7, BD) at room temperature for 30 minutes then washed. Cells were analysed for CD154 expression by three colour flow cytometry on a BD FACS Canto flow cytometer. During analysis the Treg (CD4$^+$ CD25$^{bright}$) cell response is excluded by gating on the CD4$^+$CD25$^-$ cells. Suppression of T cell activation was assessed by comparing CD154 expression in stimulated CD4$^+$CD25$^-$ effectors alone with CD154 expression in stimulated CD4$^+$CD25$^-$ effectors co-cultured with Tregs (FIG. 24A).

As shown in FIG. 24B, Treg cells isolated using CRCBT-02-001 from four expanded cord blood samples are capable of suppressing CD154 expression indicating that these cells suppress T cell activation. There is no difference in suppressive abilities between PI-16+ and PI-16− Tregs under normal conditions.

Example 4

Characterization of nTreg Cell and iTreg Cell Subsets 4.1 Flow Cytometry of Expanded nTregs and iTregs nTreg and iTreg cell subsets (essentially as described in 3.1.2) were analyzed by multi-colour flow cytometry and real time RT-PCR after 7 days of expansion and 7 days of rest in low levels of IL-2. In vitro generated nTreg cells and iTreg cells were profiled by FACS analysis, essentially as described in Example 2, to compare the expression of CD4, CD25, PI16 and FoxP3.

FIG. 25A shows that both nTreg cells and iTreg cells expressed high levels of CD4, CD25 and FoxP3, however expanded nTregs express significantly more PI16 than expanded cord iTregs. This was confirmed in seven expanded cord blood samples and seven expanded adult blood samples (FIG. 25B, n=7, p<0.05).

4.2 Quantitative Real Time PCR of Expanded nTregs and iTregs

RNA was also extracted from the Treg subsets described in Section 4.1 and real time RT-PCR was performed to investigate the relative expression of PI16 and FoxP3. Total RNA was extracted using the RNeasy kit (Qiagen, Hilden Germany) and subsequently converted to cDNA using the Quantitect Reverse Transcription kit (Qiagen). Semi-Quantitative RT-PCR was performed using the KAPA SYBR Fast Universal qPCR kit (KAPA Biosystems, Cambridge, Mass. USA) in triplicate. PCR reactions were performed on a Corbett real time PCR machine (Rotorgene 6000). Results from six independent experiments were analyzed using Rotor-Gene 6000 software and normalized to the expression of reference transcript ribosomal protein L13a (RPL13a).

Sequence of RT PCR primers were as follows; FoxP3 forward -5'-ATGGCCCAGCGGATGAG-3' (SEQ ID NO:19) and reverse 5'-GAAACAGCACATTCCCAGAGT TC-3' (SEQ ID NO: 20); PI16 forward 5'-GAGAATCTGT TCGCCATCACA-3' (SEQ ID NO: 21) and reverse 5'-GAAACAGCACATTCCCAGAGTTC-3' (SEQ ID NO: 22); and RPL13a forward 5'-CGAGGTTGG CTGGAAG-TACC-3' (SEQ ID NO: 23) and reverse 5'-CTTCTCGGC-CTGTTTCCGTAG-3' (SEQ ID NO: 24).

FIG. 26A confirms the expression of PI16 in nTreg cell populations at the message levels. nTregs express a 2.2 log 2-fold increase in Foxp3 (p<0.01) and a 4.48 log 2-fold increase in PI-16 (P<0.01) when compared to CD25$^-$ cells (Table 6). While, FOXP3 and PI16 are present in both nTreg and iTregs, there is statistically less FOXP3 (p<0.001) and PI16 (p<0.05) in iTregs than nTregs (Table 7). FIG. 26B represents RT-PCR data of RNA extracted from three freshly isolated adult peripheral blood PI16$^+$ and PI16$^-$ Tregs isolated using CRCBT-02-001. This demonstrates that in adult blood Treg PI16 is not present in cells that are cell surface PI16 negative. This is important as it suggests that there is a distinct PI16$^+$ subset of Treg and a PI16$^-$ subset that can be isolated using CRCBT-02-001.

TABLE 6

Results from single sample t-tests for both FOXP3 and PI16 in iTreg and nTreg. Estimates of log2 fold-change relative to CD25$^-$ cells are provided.

| | | | | | | | |
|---|---|---|---|---|---|---|---|
| FOXP3 | iTreg | 1.281 | 4.355 | 5 | 0.0073 | 0.0146 | * |
| | nTreg | 2.274 | 8.325 | 5 | 0.0004 | 0.0016 | ** |
| PI16 | iTreg | 1.616 | 2.737 | 5 | 0.0410 | 0.0410 | * |
| | nTreg | 4.480 | 7.625 | 5 | 0.0006 | 0.0019 | ** |

Adjusted p-values <0.01 are denoted with a double asterisk (**), whilst those below 0.05 are denoted with a single asterisk (*).

TABLE 7

Results from the paired t-test for both FOXP3 and PI16. The estimated difference in the relative levels between iTreg and nTreg is provided.

| | | | | | | | |
|---|---|---|---|---|---|---|---|
| FOXP3 | −0.9933 | −7.247 | 5 | 0.0008 | −1.346 | −0.641 | *** |
| PI16 | −2.8647 | −3.659 | 5 | 0.0146 | −4.877 | −0.852 | * |

P-values <0.001 are denoted with a triple asterisk (***), whilst those below 0.05 are denoted with a single asterisk.

4.3 RNA Preparation and Expression Analysis by Custom TaqMan® Low Density Array

Total RNA was isolated from expanded cord blood CD25$^-$ Thelper, nTreg and iTreg cells that were rested for 7 days following a 7 day expansion protocol. Total RNA was isolated using QIAshredder and a RNeasy mini kit (QIAGEN). Total RNA (2 µg) was converted to cDNA using a High Capacity cDNA Transcription Kit (Applied Biosystems). Each cDNA synthesis reaction was combined with TaqMan® Universal PCR master mix and loaded equally into 4 sample fill-reservoirs of a Custom TaqMan® Low Density Array (Format 96b). Amplification and data acquisition was carried out on a 900HT Real-Time PCR System (Applied Biosystems). Donor matched control Thelper, nTreg and iTreg samples were loaded on the same array. The Custom TaqMan® Low Density Array was built using validated TaqMan® gene expression assays. Data was analysed using the AACT method with normalization to RPL13a. Fold change was calculated between cell types and T-tests were performed for each gene.

The comparison of nTreg with iTreg (FIG. 27A), and nTreg with CD25$^-$ (FIG. 27B) demonstrates that although iTregs express FOXP3, they do not express PI16 or a number of genes that are coexpressed with PI16 on nTreg. This suggests that PI16 is a strong surrogate marker for nTreg but not iTreg.

4.4 Methylation

Genomic DNA was isolated from fresh adult Tregs labelled with CRCBT-02-001 and sorted into CD4$^+$ CD25$^{bright}$ PI16$^+$ and CD4+CD25$^{bright}$ PI16$^-$ populations, essentially as described in Example 2. DNA from both populations were extracted using the QIAamp DNA Blood Mini kit (Qiagen), followed by the conversion and clean up of DNA for methylation analysis using the EpiTect Bisulfite kit (Qiagen). PCR for Treg-specific demethylated region (TSDR) was performed essentially as described in Baron et al (2007). PCR primers were as follows; Forward -5'-TGTTTGGGGGTAGAGGATTT-3' (SEQ ID NO: 28) and Reverse -5'-TATCACCCCACCTAAACCAA-3' (SEQ ID NO: 29). PCR products were gel extracted, and cleaned up using Qiaquick Gel Extraction Kit (Qiagen). PCR fragments were then cloned into pCR4-TOPO using TOPO TA Cloning Kit for Sequencing (Invitrogen), and transformed into One Shot Top10 Chemically competent *E. Coli* and plated onto ampicillin agar plates. Colonies were picked grown overnight in Luria Broth containing ampicillin, followed by DNA isolation using QuickLyse Mini-prep Kit (Qiagen). Plasmid DNA were sequenced applying the M13 universal forward and reverse primers, Forward 5'-GTAAAAC-GACGGCCAG-3' (SEQ ID NO: 30) and Reverse 5'-GTTTTCCCAGTCACGAC-3' (SEQ ID NO: 31), followed by ABI Big Dye Terminator labelling (Applied Biosystems) and capillary separation on AB 3730x1. Sequence files were then analysed for G to A changes at CpG motifs. As shown in FIG. 28, PI16$^+$ Tregs isolated using CRCBT-02-001 show a demethylated phenotype at the TSDR of intron 1 of FOXP3. Conversely, Tregs lacking in PI16 expression are partially methylated, a phenotype consistent with induced Tregs.

Example 5

Functional Characterization of nTreg and iTreg Subsets Following Exposure to Inflammatory Cytokines To determine whether expanded cord Treg subsets isolated based on surface expression of PI16 show altered functional characteristics relative to matched comparator populations following exposure to pro-inflammatory cytokines, a mixed leukocyte reaction assay using anti-CD3 OKT3 stimulation of CD25$^-$ responder cells was used. Thymidine suppressor assays were performed substantially as described in Example 3. Expanded cord nTregs (PI16$^+$ and PI16$^-$) and iTregs (PI16) were isolated by flow cytometry and then rested for 3 days in complete X-vivo media. A subgroup of PI16$^+$, PI16$^-$ nTreg and PI16$^-$ iTregs were incubated for 3 days in 10 ng/ml IL-10 and 50 ng/ml IL-6. Cells were washed thoroughly prior to their inclusion to a suppressor assay.

FIG. 29A shows the level of suppression of effector cells by PI16$^+$ nTreg cells under normal cell culture conditions compared with exposure to the inflammatory cytokines IL1β and IL6 for 3 days prior to addition to the suppressor assay. The function of PI16$^+$ nTregs was measured by thymidine and CFSE suppressor assays. Suppression did not vary when exposed to a proinflammatory environment and these cells maintained their suppressive function (n=2).

FIG. 29B compares the suppressive function of PI16$^-$ nTregs under normal cell culture conditions and under inflammatory conditions in the presence of IL1β and IL6, using the thymidine and CFSE suppressor assays. PI16$^-$ nTregs maintain a suppressive capacity under an inflammatory environment (n=2).

FIG. 29C similarly compares the functional characteristics of iTregs (PI16) expanded from cord blood with TGF-β and ATRA, substantially as described in Example 3.1.2. These cells were either rested in media for 3 days under normal conditions or under inflammatory conditions in the presence of IL1β and IL6. Suppressive function was measured using the thymidine and CFSE suppressor assays. Unlike nTreg populations, the expanded iTregs suppressed well under normal conditions, however lost all suppressive function after prior exposure to IL1β and IL6.

These data demonstrate that PI16$^+$ Treg cells are a robust cell type that retain suppressive activity even after exposure to proinflammtory cytokines commonly encountered at sites of inflammation. PI16$^-$ iTreg cells do not retain suppressive activity in the presence of proinflammatory cytokines.

Example 6

PI16$^+$ Treg Cells Express HLADR

Expression of MHC Class 2 protein HLADR by subsets of memory CD4-positive cells defined using the co-expression of CD25 and PI16 (CRCBT-02-001) was assessed. The subsets of CD4-positive lymphocytes were defined as shown in FIG. 14, and the memory fraction of each was identified by the expression of CD45RO. The data presented in FIG. 30 indicate that proportionally more of the PI16-positive Treg cells (CD25-pos PI16-pos) express HLADR, which is involved in antigen-specific cognate interaction between CD4-positive T cells and antigen-presenting cells. Without being bound by any theory or mode of action, the expression of HLADR by Treg cells would allow those cells to interfere with normal cognate interaction between CD4-positive T cells and antigen-presenting cells, thereby disrupting the normal antigen-specific activation of effector T cells.

Example 7

PI16+ Treg Cells in Juvenile Idiopathic Arthritis

PBMC from adults and patients suffering from juvenile idiopathic arthritis (JIA) and synovial fluid from JIA patients were stained with the Treg cocktail (CD4, CD25, CD127) and CRCBT-02-001 and analysed with a FACSAria II.

As shown in FIG. 31, there is a significant increase of Treg in synovial fluid of patients suffering from JIA compared to matching blood samples and blood samples from healthy adult donors. In contrast, there is a significant decrease of PI16-positive Treg in the inflamed joint compared to matching blood and blood samples from healthy adult donors.

Although there is an enrichment of Treg cells in inflamed joints of JIA patients, significantly fewer of these Treg express PI16 than the Treg cells in the periphery. Without being bound by any theory or mode of action, the results presented herein indicate that in a healthy person PI16-positive Treg cells and $T_H17$ cells may home to the same inflammatory sites, with the Treg cells controlling the $T_H17$ immune response. A defect in, or the lack of, or reduction in PI16-positive Treg cells on the other hand, might contribute to autoimmunity.

Without being bound by any theory or mode of action, the results presented herein indicate that in a healthy person PI16-positive Treg cells and $T_H17$ cells home to the same inflammatory sites, with the Treg cells controlling the $T_H17$ immune response. A defect in PI16-positive Treg cells on the other hand, might contribute to autoimmunity.

Example 8

PI16$^+$ Treg Cells Express CLA

Expression of cutaneous lymphocyte antigen (CLA) by subsets of memory CD4$^+$ cells defined using the co-expression of CD25 and PI16 (CRCBT-02-001) was assessed. The data presented in FIG. 32 indicate that proportionally more of the PI16$^+$ Treg cells (CD25$^+$PI16$^+$) express CLA, which is involved in migration of cells to skin. Without being bound by any theory or mode of action, the expression of CLA by PI16$^+$ Treg cells would allow those cells to migrate to inflammation in the skin, whereas PI16$^-$ Treg cells do not express CLA and may not migrate to the skin.

Example 9

Chemotaxis of PI16 Expressing Treg Cells Isolated Using CRCBT-02-001

9.1 Chemotaxis Assay

Recombinant human thymus and activation regulated chemokine (CCL17, ligand to CCR4) and Recombinant Human Macrophage Inflammatory protein-3 alpha (CCL20, ligand to CCR6) were purchased from Raybiotech (Norcross, Ga.). Chemotaxis assays were performed using Transwell plates with 5-µm pores (Corning). Bottom wells contained either media alone, 100 ng/ml CCL17, 100 ng/ml CCL20 or 100 ng/ml of both CCL17 and CCL20. Peripheral blood mononuclear cells (PBMC) and synovial blood mononuclear cells (SFMC) were isolated by standard density gradient centrifugation. Upper wells were loaded with 1×10$^6$ cells per well and the cells were allowed to migrate for 2 h at 37° C. After chemotaxis, cells in the top and bottom (migrated) wells were collected and stained with monoclonal antibodies against CD4, CD25, CCR4, CCR6 and CRCBT-02-001.

The ability of CD4$^+$CD25$^{bright}$CRCBT-02-001$^+$ cells from healthy adult PBMCs to migrate in response to CCR4 and CCR6 ligands, CCL17 and CCL20 was tested using 5 µm pore Transwells™. CD4+CD25$^{bright}$ CRCBT-02-001 cells migrated towards CCL17, CCL20 and combined CCL17/CCL20 ligands (FIG. 33A).

The ability of PI16$^+$ Treg from subjects suffering from juvenile idiopathic arthritis was also assessed. Similar to adults, CD4$^+$CD25$^{bright}$CRCBT-02-001$^+$ Treg cells from healthy children (Normal Juvenile PBMCs) and CD4$^+$ CD25$^{bright}$CRCBT-02-001$^+$ Treg cells from JIA patients were able to migrate to ligands CCL17, CCL20 and CCL17 and CCL20 (FIG. 33B). In contrast, synovial fluid mononuclear cells (SFMCs) from JIA patients showed no ability to migrate to ligands CCL17, CCL20 and CCL17 and CCL20.

The data presented above indicate that PI16 (in this case as detected by CRCBT-O$_2$-001) identifies a distinct subset of functional stable memory Treg which is capable of migrating towards the chemokines CCL17 and CCL20 and therefore most likely to the same sites of inflammation as pro-inflammatory T$_H$17 cells.

In the case of JIA, although the inflamed joint is enriched in PI16$^-$ Treg cells (and enriched in T$_H$17 cells), it is not enriched in PI16$^+$ Treg cells.

Mass spectrometry was also used to confirm that CRCBT-02-001 binds to PI16. CRCBT-02-001 was found to bind to a protein comprising a peptide having an ion mass matching the expected molecular weight of a peptide from the sequence of PI16 having the mass 2926.31 Da. This peptide corresponds to the expected mass of peptide $^{80}$GENLFAITDEGMDVPLAMEEWHHER$^{105}$ (SEQ ID NO: 27). Subsequent MALDI-tof/tof-MS analysis confirmed the peptide sequence.

Example 11

Mapping the Epitope Bound by CRCBT-02-001

11.1 Summary of Approach:
Characterisation of the Epitope

Firstly determine if the epitope is conformational (discontinuous, dependant on 3-D structure) or linear (sequential amino acids). A reduction and alkylation (R&A) step was performed to dissemble the disulphide bonding structure of the PI16 recombinant antigen. If the mAb still binds to the R&A protein then the disulphides are not required and the epitope is most likely to be predominantly contained within a linear stretch of amino acids.

To determine if the epitope is glycosylated, PI16 was treated with an enzyme Peptide-N4-acetyl-β-glucosaminyl (PNGase F) which cleaves asparagine-linked high mannose as well as hybrid and complex oligosaccharides from glycoproteins. If the mAb binds to de-glycosylated PI16 then the epitope is not dependant on carbohydrate structures linked to the epitope.

Determine Minimal Binding Regions of the mAb to PI16.

A phage display approach was used to construct a gene fragment library by fragmenting the human PI16 ORF and expressing the fragments on the surface of bacteriophage. Using a selection process referred to as panning the aim is to select from the library the minimum binding part of the gene which binds to the antibody or the minimal-binding fragment which is also defined as the "epitope".

11.2 Methods:
Cloning of the Extracellular Domain of Human PI16 as Soluble Fc-Fusion (PI16-Fc)

The DNA coding for the extracellular domain minus signal peptide (aa 28-443) of human PI16 was amplified using the following primers:

```
PI16_pFUSE_EcoRVFnew:
                                            (SEQ ID NO: 25)
5' ttgatatcactcacagatgaggagaaacgtttgat 3'

PI16_pFUSE_BglII_R:
                                            (SEQ ID NO: 26)
5' aaagatctaccctgaaaatacaggttttcatgaccagggcccgagttcagccct 3'
```

Example 10

Confirming CRCBT-02-001 Binds to PI16

10.1 Identification of Protein Bound by CRCBT-02-001 Using Mass Spectrometry

Protein purified using CRCBT-02-001 was reduced with 10 mM DTT in 50 mM Tris pH 8.0 for 1 h at 60° C. and alkylated with 50 mM iodoacetamide for 30 minutes at RT followed by addition of 0.5 µg trypsin and the protein was digested for 2 h at 40° C. The digest was injected onto a RP column (150 mm×150 µm Vydac everest C18) and the eluent was spotted onto the MALDI-MS target plate together with a saturated solution of 2,4α-cyano cinnamic acid and left to dry. The sample was then analysed using mass spectrometry.
10.2 Results A 5' EcoRV-site, a 3' tev-protease cleavage site and BglII-site was added. The amplified sequence was subsequently cloned into vector pFUSE-hIgG1-Fc2 (INVIVOGEN) resulting in a construct comprising an N-terminal secretion peptide, PI16(aa28-443) a tev-protease cleavage site and a C-terminal human Fc portion. The construct is referred to as PI16-Fc.

Expression and Purification of PI16-Fc.

The created construct coding for PI16-Fc was transfected into HEK293T cells using Lipofectamine 2000 (Invitrogen) according to the manufacturer's instructions. 16 hours after transfection the culture medium was changed to incomplete DMEM without FCS and cells were cultured for 6 days at 37° C. 5% CO$_2$. Culture supernatant was collected and 0.22 µm sterile filtered. Supernatant was diluted with ⅓ volume binding buffer (20 mM sodium phosphate pH 7.0/150 mM sodium chloride) and incubated with 200 µl Protein A Sepharose 6 MB slurry (GE Healthcare, prewashed with distilled water and binding buffer) at 4° C. for 16 hours. The mixture was applied to an empty column (Econo, 1.5×15 cm, BIO-RAD) and flowthrough was discarded. After washing with 3×15 ml binding buffer elution of bound protein was performed by addition of 3×0.5 ml 0.1 M glycine (pH 2.2). 25 µl 1.5 M Tris (pH 11.0)/0.5 ml elution fraction were added immediately to balance pH of sample. SDS-PAGE analysis followed by Coomassie staining revealed a protein band present in all elution fractions that was confirmed to be the target PI16-Fc construct by mass spec analysis. CRCBT-02-001 mAb similarly recognized the same band after SDS-PAGE and Western transfer of the obtained elution fractions in an immuno-detection assay (data not shown).

Binding of CRCBT-02-001 to Native and Reduced and Alkylated (R&A) PI16-Fc.

The purified construct PI16-Fc was used to analyse binding to CRCBT-02-001 using western blot analysis. To establish the nature of the CRCBT-02001 epitope a sample of purified PI16-Fc was reduced and alkylated as stated previously in section 8. Native and R&A PI16 samples were separated using a 4-12% NuPAGE gel and stained with Coomassie brilliant blue stain, or electroblotted onto PVDF membrane. The membrane was blocked with 5% skim milk and developed using CRCBT-02-001 antibody followed by peroxidase-conjugated anti-mouse or anti-human antibodies and ECL.

Binding of CRCBT-02-001 to Native and De-Glycosylated PI16-Fc

The purified construct PI16-Fc was also used to analyse whether binding to CRCBT-02-001 is dependent of any N-glycosylated residues. To address this question a sample of purified PI16-Fc was treated with PNGaseF as follows: 8 µg PI16-Fc were incubated with 80 ng PNGaseF (SIGMA) in a final volume of 300 µl PBS at 35° C. for 3 hours. A control sample containing the same amount of PI16-Fc but no enzyme was incubated the same way. Both, the PNGaseF treated and the non-treated sample of PI16-Fc were used in parallel to coat an ELISA plate (Nunc Maxisorp flat bottom 96 well) at a protein concentration of 3 µg/ml in PBS at 4° C. for 16 hours. Afterwards the coated wells were washed twice with PBS and blocked in a solution of 5% milk powder in PBS for 2 hours (all wash and block steps involved 200 µl buffer volume if not stated differently). Non coated control wells were blocked accordingly. After washing with PBS twice a CRCBT-02-001 solution was added to the wells at a concentration of 5 µg/ml in PBS and incubated at 22° C. for 60 min. Non-coated control wells were incubated with CRCBT-02-001 accordingly. After washing twice with PBS the wells were incubated with secondary anti-mouse antibody (HRP-conjugated, 1:2000 in PBS). Control wells coated with PI16-Fc PNGase treated/non-treated were probed with anti-Fc antibody (HRP-conjugated, 1:4000 in PBS) directed against the C-terminal Fc portion of the purified fusion protein. After 1 hour 30 min incubation at 22° C. the wells were washed 3× with PBS and each well was probed with 100 µl of substrate solution (120 mM citrate, 1 mM ABTS, 0.03% hydrogen peroxide) and incubated at 22° C. for 30 min. Subsequently the plate was read in a plate reader at 414 nm. (Samples processed in quadruplicate).

Construction and Panning of a Human PI16 Gene Fragment Library Displayed on Bacteriophage.

A variation of the method (Coley et al., 2001) was used to prepare a human PI16 gene fragment library expressed on M13 bacteriophage. The phagemid vector pHENH6 (Hoogenboom et al., 1991) contains a copy of the M13 bacteriophage gene III, coding for the pIII protein on the surface of phage particles, and a multiple cloning site between the periplasmic targeting sequence and the functional gene III sequence. Ligation of dsDNA into the multiple cloning site results in expression of the inserted fragment fused to the gene III product and subsequent display of the fusion protein on M13 bacteriophage surface.

Oligonucleotide primers flanking the coding region for human PI16 were used to amplify the extracellular reading frame by polymerase chain reaction using PI16 ORF DNA as template. The PI16 PCR product was subsequently digested with DNase I and digestion products at different time points assayed by agarose gel electrophoresis to determine optimal reaction conditions. The conditions showing the broadest fragment size distribution were chosen to digest 5 µg of DNA using 20 ng of DNAse I in reaction buffer (50 mM Tris, pH 7.6, 10 mM $MnCl_2$, 0.1 mg/ml BSA) for 2 minutes. The reaction was stopped by adding EDTA to a final concentration of 50 mM and heat inactivated at 70° C. for 10 minutes. The digested DNA was purified and ends blunted using Vent DNA polymerase. 5.4 µg pHENH6 phagemid vector was digested using PstI and subsequently blunted using Vent DNA polymerase. To avoid re-circularization of the vector it was treated with alkaline phosphatase (CIP). The blunted PI16 gene fragments generated by random digest were then ligated into the prepared pHENH6 vector using a vector to insert ratio of 1:9. Ligated products were purified using Wizard® SV Gel and PCR Clean-Up System (PROMEGA) and transformed into competent *E. coli* TG1 cells (Stratagene) by electroporation.

Using serial dilutions of the transformed bacterial cells the size of the gene library was estimated to be of about $1×10^7$ individual clones. Due to the unidirectional cloning it was estimated that approximately 1 in 6 clones were in frame (40%) and the approximate working library size is $1×10^6$. The fragment size diversity in the library was assayed by polymerase chain reaction (PCR) and sequencing of individual clones. Coverage appeared to be random.

A library glycerol stock was amplified in a 200 ml 2YT culture and the phage particles rescued with helper phage substantially as described in Coley et al., 2001. Three rounds of panning were performed by coating an immunotube (NUNC maxisorp) with 10 µg/ml of mAb CRC-BT-02-001 overnight at 4° C. The tube was blocked with 5% skim milk powder in PBS and the library ($10^{11}$ phagemid particles) was allowed to bind to the mAb. After 1 hour the tube was washed with PBS to remove phages which do not bind to the mAb, and the adherent phage were eluted with 0.1M glycine pH 2.2 and neutralised with 1.5M TRIS buffer. The eluted phage was re-infected in TG1 *E. coli* cells, rescued, amplified and PEG precipitated for the next round of panning substantially as described in Coley et al., 2001. For the second round of panning 2 washes with PBS containing 0.1% TWEEN20 (PBST) were performed followed by 2 PBS washes, and in round 3, 2 additional washes with PBST were added. Clones from round 3 were DNA sequenced in order to establish the identity of the fragments of PI16 binding to CRC-BT-02-001 mAb and compared with clones from earlier rounds of panning To determine whether binding of the pI16 gene fragment occurs out of the context of phage a biotinylated peptide consisting of the overlapping region of R34 and R3 7 was synthesised (GL Biochem, China) (SEQ ID NO: 39). The peptide was solubilised in PBS and coupled to microtiter plates pre-coated with neutrAvidin (Pierce). Wells were washed and monoclonal antibody CRCBT-02-001 was added to the wells coupled with peptide and a control peptide. As a control another isotype control antibody (IC) was added to wells coated with peptide. Anti-mouse HRP was used to detect bound antibody and the ELISA was developed with TMB substrate.

11.3 Results

The CRCBT-02-001 Epitope on PI16 is Dependent on the Presence of Disulphide Bonds.

Reduction and alkylation of human PI16-Fc was performed in order to assess whether the CRCBT-02-001 mAb requires the presence of disulphide bonds (3-D structure) within the PI16 antigen for binding.

The data in FIGS. 34A-C illustrate that CRCBT-02-001 mAb binds to native PI16 and not R&A PI16. FIGS. 34A-C confirm the Fc-portion of the recombinant protein PI16-Fc can be detected confirming the integrity of the PI16 is retained after R&A. The ELISA, SDS PAGE gel and Western blot in FIGS. 34A-C confirm that CRCBT-02-001 does not bind to R&A PI16.

Binding of CRCBT-02-001 is Independent of the Antigen's N-Glycosylation Status

De-glycosylation of PI16-Fc with PNGase F to remove asparagine-linked carbohydrate structures did not have measurable influence on the binding of CRCBT-02-001. The control antibody (anti-human Fc) recognizes the Fc-portion of the fusion protein (FIG. 35). This indicates the epitope of CRCBT-02-001 is not dependent on the N-glycosylation status of the antigen.

Both PNGaseF treated and untreated PI16-Fc were analysed by SDS PAGE and Western transfer: there was a clear shift in molecular weight (minus ~5 kDa) observed for PI16-Fc after PNGaseF treatment (data not shown).

Characterization of CRCBT-02-001 Binding to PI16, Narrowing Down the Epitope

Purified PI16-Fc was showing distinct degradation products after heat-treatment of the sample (FIG. 36). When analysed using SDS-PAGE and immuno-decorated with CRCBT-02-001a fragment of PI16-Fc was recognized by the antibody at a molecular weight of about 35 kDa. The control antibody anti-Fc directed against the C-terminal Fc tag fused to the ectodomain of PI16 in the used protein construct did not show any binding to the mentioned degradation product (data not shown).

The sample was subjected to SDS-PAGE and after Coomassie staining the corresponding protein band was excised from the gel. After an in-gel digest of the gel piece with trypsin, the extracted tryptic peptides were analysed and a peptide belonging to the N-Terminal CAP domain of PI16 was sequenced using the MALDI-tof/tof-MS technology: PI16 aa 59-68 (sequence: WDEELAAFAK (SEQ ID NO: 32).

These results indicate an involvement of the N-terminal CAP domain of PI16 in the actual binding site for mAb CRCBT-02-001.

Generation of a Phage Library Expressing Random PI16 Fragments

The coding region for PI16(aa28-443) ectodomain was amplified and digested with DNase I. Conditions that yielded fragments between 1200-100 bp were used to produce a mixture of PI16 gene fragments (FIG. 37) which were cloned into phagemid vector pHENH6 to create a gene fragment library. Several randomly picked clones showed a broad size distribution for gene fragments (FIG. 37).

Panning the PI16 Gene Fragment Library on mAb CRC-BT-02-001

Three rounds of panning were performed to select gene fragments of PI16 which bound to mAb CRC-BT-02-001.

The binding of PI16 gene fragment clones to the mAb was analysed by ELISA and results are shown in FIG. 38A. Five of the clones selected in round 3 (R3 4, 7, 10, 12 &15) bound strongly to the anti-PI16 mAb indicated by the high ELISA signal, in contrast none of the clones in round 2 and round 0 bound to the mAb. These sequences maybe out of frame a summary of the sequence data is shown in FIG. 40. The 9E10 or anti-myc signal shown in FIG. 38B reflects the comparative amounts of phage as there is a myc tag present at the C-terminus of the gene fragments (N-terminus of gene III). A high binding signal to the anti-myc antibody is an indicator of good expression on the surface of phage (FIG. 38B). Some of the fragments were expressed on phage shown by a positive anti-Myc signal but did not bind to anti-PI16 mAb.

Individual clones were picked in round 3, a PCR was performed and the gene fragments sequenced. In the unpanned library (round 0) and in round 1 there was a wide spread of fragment sizes whereas by round 3 many of the fragments were of very a similar size (FIG. 39). The sequence identity of round 3 selected PI16 gene fragments is shown in FIG. 40. These fragments are overlapping in the sequence of PI16 indicating a minimum binding region of CRCBT-01-001, which indicates this region forms the epitope of PI16 to which the antibody binds.

The overlapping sequence of CRCBT-02-001 binding clones from the gene fragment library is shown underlined in FIG. 40C.

The data presented above indicate that epitope for CRCBT-02-001 is dependent on the presence of intramolecular disulfide bonds but is independent on N-linked carbohydrates. The data suggest that the epitope for CRCBT-02-001 has been located to the N-terminal CAP domain and the short sequence identified by phage display, RWDEELAAFAKAYARQ (SEQ ID NO: 38), either comprises or contains the epitope.

The minimum binding region identified by phage display does not contain cysteines or a disulphide bond. It is possible that the epitope may rely on disulphide bonds out of the context of phage. However peptide LHM RWDEELAAFFAKAYARQCVWGHNKER-biotin (SEQ ID NO: 39) was synthesised and was shown to bind to mAb CRCBT-02-001 by ELISA (FIG. 41). This peptide contains the minimum binding region identified (underlined). This demonstrates that mAb CRCBT-02-001 binds to this region of PI16 in isolation but requires additional structural components present within the antigen in order to react with its cognate epitope when presented in the context of the entire PI16 antigen.

We conclude that the epitope of CRCBT-02-001 is contained within the primary sequence of RWDEELAAFAKA-YARQ and the integrity of the disulphide bond(s) confer accesibilty to the mAb when presented in the context of the entire PI16 antigen.

Example 12

Affinity of CRCBT-02-001

Two methods were compared to measure the affinity of CRCBT-02-001. Analysis was performed using a BIO-RAD Proteon XPR36™ protein interaction array system based on surface plasmon resonance:

Method 1: Direct coupling of antigen PI16-Fc to the chip and flow over the analyte CRCBT-02-001 Fab.

Method 2: Anti-mouse capture method to capture anti-PI16 Mab and flow over PI16-Fc as the analyte.

12.1 Methods

Method 1: Interaction of PI16-Fc Coupled to a Sensor Chip with CRCBT-02-001 (Fab)

A ProteOn sensor chip (GLC) was activated by flowing a mixture of 0.2 M N-ethyl-N'-(3-dimethylaminopropyl) carbodiimide (EDC) and 0.05 M sulfo-N-hydroxysuccinimide (sulfo-NHS) over the chip (150 µL at 30 µL/min for 5 minutes). Recombinant PI16-Fc was coupled to the chip in the vertical orientation by flowing 150 µL of a 50 µg/mL solution in 10 mM acetate buffer (pH 4.5) at 30 µL/min. The remaining activated carboxyl group were then deactivated by flowing 150 µL of 1 M ethanolamine-HCl (pH 8.5) at 30 µL/min. Anti-PI16 Fab fragment diluted in PBS Tween 20 (0.005%) was passed over ligand (100 µL, 100 µL/min) contact time 60 seconds and dissociation time of 600 seconds) in the horizontal direction in 5 channels at the following concentrations: 50 nM, 25 nM, 12.5 nM, 6.25 nM and 3.125 nM. PBS Tween 20 (0.005%) alone was passed over the remaining channel. Binding sensorgrams were collected and analysed with the ProteOn Manager 2.1×PR36 software using the Langmuir kinetic model to fit the data and determine the affinity constant (KD).

Method 2: Interaction of CRCBT-02-001 Mab with PI16-Fc Using Anti-Mouse Capture Reagent.

A proteOn sensor chip (GLM) was activated by flowing a mixture of 0.2 M EDC and 0.05 M sulpho-NHS over the chip (150 µA at 30 µL/min for 5 minutes). Rabbit anti-mouse IgG whole molecule (Sigma M-7023) was then coupled to the chip in the vertical orientation by flowing 150 µL of a 50 µg/mL solution in 10 mM acetate buffer (pH 4.5) at 30 µL/min. The remaining coupling sites were then deactivated by flowing 150 µL of 1 M ethanolamine-HCl (pH 8.5) at 30 µL/min. Mouse monoclonal anti PI16 IgG was then allowed to flow over and be captured by the coupled anti-mouse IgG antibody by flowing 150 µL of 100 µg/mL IgG at 25 µL/min over a single channel of the sensor chip in the horizontal direction. Recombinant PI16-Fc diluted in PBS Tween 20 (0.005%) was then passed over the GLM sensor chip (150 µL, 25 µL/min, contact time 240 seconds and dissociation time of 1200 seconds) in the vertical direction in 5 channels at the following concentrations: 50 nM, 25 nM, 12.5 nM, 6.25 nM and 3.125 nM. PBS Tween 20 (0.005%) alone was passed over the remaining channel and served as a reference. Binding sensorgrams were collected and analysed with the ProteOn Manager 2.1×PR36 software using the Langmuir kinetic model to fit the data and determine the affinity constant (KD).

12.2 Results

Method 1

This coupling method was performed using various pHs to optimise the coupling of PI16-Fc to the GLC chip. The optimal coupling pH was 4.5. The association and dissociation curves and affinity measurement was performed with 3 dilutions of the PI16 Fab shown in FIG. 42 and Table 8. The data fitted well to a Langmuir kinetic model using global fit (all the curves fitted simultaneously).

TABLE 8

Summary of parameters used to analysed the data and kinetic measurements. The Chi2 is a measure of best fit to the Langmuir model (a value of <50 is considered a good model fit).

| Parameter | Ka | Kd | KD | Chi2 |
|---|---|---|---|---|
| Units | 1/Ms | 1/s | | RU |
| Scope | Global | Global | Auto defined | |

TABLE 8-continued

Summary of parameters used to analysed the data and kinetic measurements. The Chi2 is a measure of best fit to the Langmuir model (a value of <50 is considered a good model fit).

| Parameter | Ka | Kd | KD | Chi2 |
|---|---|---|---|---|
| Type | Fitted | Fitted | Fitted | |
| Kinetic-Langmuir | 2.97E+05 | 3.72E−04 | 1.25E−09 | 4.98 |

Method 2

The published method (Nahshol et al., 2008) was used to measure the kinetics of the PI16 mab by anti-mouse capture. This is a relatively mild method coupling method and the association and dissociation curves and affinity measurement was performed with 4 dilutions of the PI16-Fc (FIG. 43 and Table 9). The data fitted well to a Langmuir kinetic model using global fit (all the curves fitted simultaneously).

TABLE 9

Summary of parameters used to analysed the data and kinetic measurements. The Chi2 is a measure of best fit to the Langmuir model (a value of <50 is considered a good model fit).

| Parameter | Ka | Kd | KD | Chi2 |
|---|---|---|---|---|
| Units | 1/Ms | 1/s | | RU |
| Scope | Global | Global | Auto defined | |
| Type | Fitted | Fitted | Fitted | |
| Kinetic-Langmuir | 5.82E+04 | 1.49E−04 | 2.56E−09 | 8.29 |

The affinity of CRCBT-02-001 for PI16-fc has been measured using 2 methods. The affinity (KD) using both methods is comparable 1.25-2.56 nM.

Example 13

Treatment of GVHD

Subjects requiring a bone marrow transplant are irradiated. Following a suitable time, subjects receive a bone marrow transplant or a transplant of hematopoietic stem cells. In test patients, the transplants additionally comprise Treg cells isolated as described in Examples 2 and 3. Survival is then determined, with prolonged survival in subjects receiving Treg cells indicating that the cells are functional.

Example 14

Treatment of Autoimmune Disease

Subjects suffering from autoimmune disease are administered purified Treg cells are isolated as described in Examples 2 and 3 or carrier alone. Levels of auto-antibodies, cytokines and autoimmune symptoms are determined. Detection of reduced symptoms and/or decreased serum levels of inflammatory cytokines indicates that the isolated Treg cells are capable of treating or preventing autoimmune disease.

An exemplary autoimmune disease is rheumatoid arthritis. In the case of this disease, subjects are administered purified Treg cells are isolated as described in Examples 2 and 3 or carrier alone. Levels of anti-collagen antibodies, cytokines and/or symptoms of arthritis are determined. Detection of reduced symptoms of arthritis and/or decreased serum levels of cytokines, such as TNF-alpha and/or IL-6 indicates that the isolated Treg cells are capable of treating or preventing rheumatoid arthritis.

Example 15

Treatment of Diabetes

Subjects suffering from a pre-diabetic phenotype (e.g., impaired glucose tolerance albeit not to the level detected in symptomatic type I diabetes, and preferably autoreative B and/or T cells) are treated with purified Treg cells isolated as described in Examples 2 and 3 or carrier alone. Following treatment, subjects are assessed for symptoms of diabetes, including increased blood glucose levels, impaired insulin response, impaired glucose tolerance or autoantibody levels. Prevention or delay in the onset of one or more symptoms of diabetes is indicative that the isolated Treg cells are capable of treating autoimmune diabetes.

Example 16

Cloning and Sequencing of Variable Regions of Antibody Secreted by CRCBT-02-001

Messenger RNA is prepared from CRCBT-02-001 hybridoma cells producing and reverse-transcribed using an oligo-dT primer to produce cDNA. Several independent PCR reactions are performed with primers that bind to and facilitate amplification of cDNA that encodes leader sequence, variable region and some downstream sequence. PCR amplicons are separated on an agarose gel. Amplicons are isolated from the gel, cloned and sequenced.

Example 17

Production of Chimeric Antibodies Comprising Variable Regions of Antibody Secreted by CRCBT-02-001

Variable regions of the antibody secreted by CRCBT-02-001 are converted into whole antibody by fusion to a human IgG1 Fc region. The variable regions are PCR-amplified from the cloning vector described in Example 1 or 16 and in-frame cloned into an antibody expression vector with leader sequences in front of the antibody sequences. In the vector, genomic DNA sequences for all constant regions for light and heavy chains are already engineered in the vectors. The expression is driven by a human cytomegalovirus (CMV) early promoter and followed by an SV40 polyadenylation signal. In-frame fusion of variable regions allows the proper expression of whole antibody. By design, leader sequences from mouse light and heavy chains are included in front of the antibody open reading frames.

Either combined light chain and heavy chain plasmid DNA or a 1:1 ratio mixture of corresponding light and heavy chain plasmid DNA are transfected into CHO cells by lipofection. Culture medium is harvested, filtered and concentrated using by low speed Millipore Centricon® centrifugation concentrator.

Example 18

Humanization of Antibody Secreted by CRCBT-02-001

Humanized forms of the antibody secreted by CRCBT-02-001 are produced essentially as described in WO92/22018. Briefly, to produce humanized antibody retain binding affinity for PI16 human antibodies having a high degree of sequence homology to the antibody secreted by CRCBT-02-001 are selected to provide both the acceptor light and heavy chain human frameworks.

Using the sequence determined herein, the computer programs ABMOD and ENCAD (Levitt, 1983 and Zilber et al., 1990) are used to construct a model of the variable region of each mouse antibody. The model is used to determine the amino acids in each framework that were close enough to the CDRs to potentially interact with them.

In designing each humanized antibody, at each position the amino acid was selected to be the same as in the human acceptor sequence, unless the position fell into one or more of categories (1)-(4) as follows:

Category 1: The amino acid position is in a CDR is defined by Kabat et al.;

Category 2: If an amino acid in the framework of the human acceptor immunoglobulin is unusual (i.e., "rare", which as used herein indicates an amino acid occurring at that position in less than about 20% but usually less than about 10% of human heavy (respectively light) chain V region sequences in a representative data bank), and if the donor amino acid at that position is typical for human sequences (i.e., "common", which as used herein indicates an amino acid occurring in more than about 25% but usually more than about 50% of sequences in a representative data bank), then the donor amino acid rather than the acceptor may be selected;

Category 3: In the positions immediately adjacent to one or more of the 3 CDRs in the primary sequence of the humanized immunoglobulin chain, the donor amino acid(s) rather than acceptor amino acid may be selected.

Category 4: A 3-dimensional model, typically of the original donor antibody, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected.

Amino acids in the mouse donor sequence falling into any of the above categories is used.

For the construction of genes encoding the humanized antibodies, nucleotide sequences are selected that encode the protein sequences of the humanized heavy and light chains, including signal peptides typically from the mouse antibody chains, generally utilizing codons found in the mouse sequence. Several degenerate codons are changed to create restriction sites or to remove undesirable ones. The nucleotide sequences also included splice donor signals typical for immunoglobulin genes. Each gene as constructed from overlapping synthetic oligonucleotides. For each variable domain gene, two pairs of overlapping oligonucleotides on alternating strands are synthesized that encompassed the entire coding sequences as well as the signal peptide and the splice donor signal. Double stranded DNA fragments are synthesized with Klenow or Taq polymerase or sequenase from each pair of oligonucleotides, digested with restriction enzymes, ligated to pUC 18 vector and sequenced. Two fragments with the respectively correct half-sequences are then ligated into expression vectors in the appropriate orientations to produce the complete heavy and light chain genes.

The heavy chain and light chain plasmids are transfected into CHO cells by lipofection.

Clones are screened by assaying human antibody production in the culture supernatant by ELISA using recombinant PI16 as a capture reagent or using FACS as described in Example 1 or 2, and antibody is purified from the best producing clones. Antibody is purified by passing tissue culture supernatant over a Protein A column. The bound antibodies are eluted with an acidic elution buffer, which is then exchanged into PBS by passing over a PD10 column (Pharmacia).

The binding of the humanized antibodies to cell types expressing the corresponding antigens is then tested as described in Example 3.

Example 19

Affinity Maturation of Humanized Antibodies

The DNA encoding variable heavy and the variable light chains of the humanized antibodies described in Example 18 are cloned in a Fab phage-display vector or a scFv phage display vector. Cloned DNA is then randomly mutated in the variable heavy and light CDR3 regions (each library possessing >$10^8$ functional diversity). The resultant mutants are then panned against cells expressing PI16 (described in Example 2) using standard phage display panning protocols (see, e.g., Phage Display: A Laboratory Manual, 2001, Cold Spring Harbor Laboratory Press). By lowering the concentration of target cells in each subsequent round of panning, the stringency of panning is effectively increased, thereby enriching for higher and higher affinity phage with each subsequent round. Phage ELISA is used as the primary assay to determine the ability of the phage-bound recombinant Fabs or scFv to recognize the PI16 expressing cells.

Fragments capable of binding to PI16 expressing cells are converted into full-length antibodies of human subclass IgG1 for expression, production and characterization.

Example 20

Competitive Binding Assay

Antibody produced by CRCBT-02-001 is labelled with a fluorescent label and mixed 1:1 with chimeric antibody (Example 17), humanized antibodies (Example 18), affinity matured antibodies (Example 19) or a naïve fully human phage display library displaying scFv. For controls, labelled CRCBT-02-001 is used alone.

Approximately equal numbers of NIH3T3 cells stably expressing PI16 (Example 2) are cultured in 94 well plates. Cells are cultured in the presence of antibodies for sufficient time for the antibodies to bind. Supernatant is isolated and cells are washed. The level of fluorescence bound to the cells and/or in the supernatant is then determined.

Antibodies that reduce the level of fluorescence bound to the cells and/or increase fluorescence in the supernatant are considered to competitively inhibit binding of an antibody secreted by CRCBT-02-001.

Any competitive phage displayed scFv are engineered into a human isotype IgG1 full antibody.

Example 21

Inducing an Immune Response

Subjects are administered tumor cell lines, e.g., Neuro-2A or CT26 colorectal cancer cells. Following cell administration or at the time of administration, subjects are administered a competitive antibody identified in Example 20. Alternatively, subjects are treated by leucapharesis using an antibody secreted by CRCBT-02-001 to capture Treg cells. A subset of subjects is also administered killed cancer cells. Immune response against tumor cells is also determined using ELISA and/or ELISPOT. Survival, tumor presence, the size of tumors and/or the degree of immune response against tumors in mice administered tumor cells without antibody treatment versus subjects treated with antibody alone or antibody and cell vaccine is determined. A further increase in survival or immune response and/or reducing in tumor presence or size in mice administered cells and antibodies or receiving leucapharesis treatment versus antibody alone or no antibody/leucapharesis indicates that treatment permits a stronger response to vaccine treatment.

REFERENCES

Albini et al., Cancer Research 47: 3239-3245, 1987;
Al-Lazikani et al., J Mol Biol 273, 927-948, 1997;
Andersson-Engels et al, Phys. Med. Biol, 42:815-824, 1997;
Asano et al, J. Exp. Med. 184:387-396, 1996;
Ausubel et al., (editors), Current Protocols in Molecular Biology, Greene Pub. Associates and Wiley-Interscience (1988, including all updates until present);
Baecher-Allan et al, J. Immunol. 167:1245-1253, 2001;
Baron et al., Eur. J. Immunol., 37: 2378-2389, 2007;
Bassuny et al., Immunogenetics, 55: 149-156, 2003;
Bendele J Musculoskel Neuron Interact; 1(4):377-385, 2001;
Bengtsson et al., BMC Bioinformatics 7: 96, 2006;
Bengtsson and Hossjer BMC Bioinformatics 7: 100, 2006;
Bluestone et al., Nat. Rev. Immunol., 3: 253, 2000;
Bolstad et al., Bioinformatics (Oxford, England) 19: 185-193, 2003;
Bork et al., J Mol. Biol. 242, 309-320, 1994;
Boyer et al., Blood, 103: 3428-3430, 2004;
Brinkmann et al., Proc. Natl. Acad. Sci. USA, 90: 7538-7542, 1993;
Brown (editor), Essential Molecular Biology: A Practical Approach, Volumes 1 and 2, IRL Press (1991);
Cao et al., Arthritis Res. Ther., 6: R35-R46, 2004;
Chen et al., Nature, 446:203-207, 2007;
Chothia and Lesk J. Mol. Biol. 196:901-917, 1987;
Chothia et al., Nature 342, 877-883, 1989;
Cima, et al., Biotechnol. Bioeng. 38:145 1991;
Cohen et al., Hum. Gene Ther. 10:2701-2707, 1999;
Coley et al., Protein Engineering 14: 691-698, 2001;
Coligan et al., (editors) Current Protocols in Immunology, John Wiley & Sons (including all updates until present);
Crispin et al., J. Autoimmun., 21: 273-276, 2003;
Curiel et al., Nat. Med., 10: 942-949, 2004;
Dai et al., J Bioinform Comput Biol 1: 627-645, 2004;
De Kleer et al., J. Immunol., 172: 6435-6443, 2004;
Dejaco et al., Immunology, 117: 289-300, 2005;
Dooley and Flajnik, Dev Comp Immunol. 30:43-56, 2006;
Estin et al, J Natl. Cancer Instil 81(6): 445-446, 1989;
Foon et al, Proc. Am. Soc. Clin. Oncol. 13: 294, 1994;
Gefter et al, Somatic Cell Genet. 3, 231-236, 1977;
Glover and Hames (editors), DNA Cloning: A Practical Approach, Volumes 1-4, IRL Press (1995 and 1996);
Goforth et al., Cancer Immunol Immunother. 2008;
Goodman et al., Goodman and Gilman's The Pharmacological Basis of Therapeutics, 8th Ed., Macmillan Publishing Co., 1990;
Gregori et al., J Immunol. 167: 1945-1953, 2001;

Harlow and Lane (editors) Antibodies: A Laboratory Manual, Cold Spring Harbour Laboratory, (1988);
Henttu and Vihko, *Biochem. Biophys. Res. Comm.* 160(2): 903-910, 1989;
Hochberg and Benjamini *Stat Med* 9: 811-818, 1990;
Holliger et al., *Proc. Natl. Acad Sci. USA* 90: 6444-6448, 1993;
Hollinger and Hudson *Nature Biotechnology*, 23: 1126-1136, 2005;
Hoogenboom and Winter *J Mol Biol*, 227:381, 1991;
Hoogenboom et al., *Nucl. Acids Res.*, 19: 4133-4137, 1991
Hu et al., *Cancer Res.*, 56: 3055-3061, 1996;
Hudson and Kortt *J. Immunol. Methods*, 231: 177-189, 1999;
Itoh et al, *Nature* 308: 19, 1986;
Irizarry et al., *Biostatistics* 4: 249-264, 2003;
Jakobovits et al., *Nature Biotechnology* 25, 1134-1143 2007;
Jespers et al, *Bio/technology* 12:899-903, 1988;
Jones et al., *Nature*, 321:522-525, 1989;
Jones et al., *Cancer Immun.* 22; 2:1, 2002;
Kabat *Sequences of Proteins of Immunological Interest*, National Institutes of Health, Bethesda, Md., 1987 and 1991;
Kamarch, *Methods Enzymol*, 151:150-165, 1987;
Kanai et al., *Inflamm Bowel Dis.*, 12: 89-99, 2006;
Kerbel *Cancer Metastasis Rev.*, 17: 301-304, 1998;
Kingsley et al, *J. Immunol.* 168:1080, 2002;
Koenecke et al., *Eur J Immunol.* 39):3091-3096, 2009
Kohler and Milstein, *Nature* 256, 495-497, 1975;
Kohler and Milstein, *Eur. J. Immunol.* 6, 511-519, 1976;
Komatsu et al., *J Immunol Methods.* 272:161-175, 2003;
Kruif and Logtenberg *J. Biol. Chem.*, 271: 7630-7634, 1996;
Kumar et al, *Immuno. Letters* 65, 153-159, 1999;
Largaespada et al, *J. Immunol. Methods.* 197(1-2), 85-95, 1996;
Le Franc et al., *Dev. Comp. Immunol.*, 27: 55-77, 2003;
Levitt, *J. Mol. Biol.* 168: 595, 1983;
Lonberg et al., *Nature* 368 (1994): 856-859;
Lonberg, N. "Transgenic Approaches to Human Monoclonal Antibodies." Handbook of Experimental Pharmacology 113 (1994): 49-101;
Liu et al., *Scand. J. Immunol.*, 59: 198-202, 2004;
Livingston et al., *J Clin. Oncol.* 12: 1036-1044, 1994;
Longhi et al., *J. Hepatol.*, 41: 31-37, 2004;
Lukacs et al., *J. Exp. Med.*, 194: 551-555, 2001;
Macardle and Bailey Cell Biology: A Laboratory Handbook. Chapter 57: Preparation of Monoclonal Antibodies. 2006;
Marks et al, *J. Mol. Biol.*, 222:581-597, 1991;
Mavrangelos et al., *J Immunol Methods.* 289:169-178 2004;
McHugh et al., *J. Immunol.*, 168: 5979-5983, 2002;
Miltenyi et al., *Cytometry* 11:231-238, 1990;
Miyara et al., *Immunity* 30:899-911, 2009;
Morrison et al., *Proc. Natl. Acad. Sci. USA* 81:6851-6855, 1984;
Mottet et al., *J. Immunol.*, 170: 3939-3943, 2003;
Muller et al., *BioTechniques* 32: 1372-1374, 1376, 1378-1379, 2002;
Nakamura et al, *J. Exp. Med.* 194:629-644, 2001;
Nahshol et al., *Anal. Biochem.* 383: 52-60, 2008;
Natali et al, *Cancer* 59: 55-63, 1987;
Novellino et al., *Cancer Immunol Immunother.* 54(3):187-207, 2005;
Perbal, A Practical Guide to Molecular Cloning, John Wiley and Sons (1984);
Perez and Walker, *J. Immunol.* 142: 3662-3667, 1990;
Plückthun, *Immunol. Revs.*, 130:151-188, 1992;
Plückthun in The Pharmacology of Monoclonal Antibodies, vol. 113, Rosenburg and Moore eds., Springer Verlag, New York, pp. 269-315, 1994;
Presta *Curr Op Struct Biol*, 2:593-59, 1992;
Price *Prog. Clin. Biol. Res.*, 354A: 237-255, 1990;
Queen et al., *Proc. Natl. Acad. Sci. USA* 86: 10029 10033, 1989;
Ragnhammar et al, *Int. J. Cancer* 53: 751-758, 1993;
Ramanujam et al, *IEEE Transactions on Biomedical Engineering*, 48:1034-1041, 2001;
Reeves et al., *Biochem J* 385: 105-114, 2005;
Reff et al, *Blood* 83: 435-445, 1994;
Repesh, *Invasion Metastasis.* 9:192-208, 1989;
Riechmann et al., *Nature*, 332:323-329, 1988;
Robb et al., *J Exp Med* 154: 1455-1474, 1981;
Roux et al., *J. Immunol.* 161:4083, 1998;
Sakaguchi et al., *Nature*, 426: 454-460, 1995;
Sakaguchi et al, *Immunol. Rev.* 182:18-32, 2001;
Saleh et al, *J. Immunol.*, 151, 3390-3398, 1993;
Salomon et al, *Immunity* 12:431-440, 2000;
Sambrook et al., Molecular Cloning: A Laboratory Manual, Cold Spring Harbour Laboratory Press (1989);
Seddiki et al., *J Exp Med* 203:1693-1700, 2006;
Shalaby et al, *J. Exp. Med.*, 175: 217-225, 1992;
Shao et al., *Mol Immunol.* 44:656-65, 2007;
Shevach, *Annu. Rev. Immunol.* 18:423-449, 2000;
Shevach, *Nature Rev. Immunol* 2:389, 2002;
Skerra et al, *Curr. Opinion in Immunol.*, 5:256-262, 1993;
Smyth et al., *Bioinformatics* (Oxford, England) 21: 2067-2075, 2005;
Stephens et al, *Eur. J. Immunol.* 31:1247-1254, 2001;
Suri-Payer et al, *J. Immunol.* 157:1799-1805, 1996;
Suri-Payer et al., *J. Immunol.*, 160: 1212-1218, 1998;
Taams et al, *Eur. J. Immunol.* 31:1122-1131, 2001;
Tang et al., *J. Exp. Med.*, 199: 1455-1465, 2004;
Tomizuka et al., *Proc. Natl. Acad. Sci. USA* 97: 722-727, 2000;
Trenado et al., *J. Clin. Invest.*, 112: 1688-1696, 2002;
Vacanti, et al., *J. Ped. Surg.* 23:3-9 1988;
Vacanti, et al., *Plast. Reconstr. Surg.* 88:753-9 1991;
Van der Sluis et al., *Gastroenterology* 131: 117-129, 2006;
Van Maurik *J. Immunol.* 169: 5401-5404, 2002;
Venken et al., *J. Immunol. Methods*, 322: 1-11, 2007;
Vijayasardahl et al, *J Exp. Med.* 171(4): 1375-1380, 1990;
Wang et al., *Immunity* 20: 107-118, 2004;
Wang et al., *J Clin Invest.* 118(7): 2629-2639, 2008;
Wettenhall and Smyth *Bioinformatics* (Oxford, England) 20: 3705-3706, 2004;
Willerford et al, *Immunity* 3:521-530, 1995;
Wing and Sakaguchi, *Nature Immunology*, 11: 7-13, 2010;
Yu et al, *Cancer Res.* 51(2): 468-475, 1991;
Zilber et al., *Biochemistry* 29: 10032, 1990;
Zang et al, *Journal of Immunological Methods* 233: 167-177, 2005;
Zola, "Monoclonal Antibodies: A Manual of Techniques", CRC Press, 1987;
Zola et al., *Immunol Cell Biol.*, 67: 233-237, 1989;
Zola et al., *J Immunol Methods* 135:247-255, 1990

We claim:

1. An isolated protein comprising two monoclonal antibody variable regions capable of binding to peptidase inhibitor 16 (PI16), wherein one of the variable regions is an antibody heavy chain variable region (VH) and the other variable region is an antibody light chain variable region (VL), wherein the protein is also capable of competitively inhibiting binding of an antibody produced by a hybridoma designated CRCBT-02-001 deposited with the ATCC under Accession Number PTA-10685 to PI16, and wherein
   (i) the variable s are from the antibody produced by a hybridoma designated CRCBT-02-001 deposited with the ATCC under Accession Number PTA-10685; or
   (ii) the variable regions comprise CDRs of a heavy chain variable region comprising a sequence set forth in SEQ ID NO: 8 and CDRs of a light chain variable re ion comprising a sequence set forth in SEQ ID NO: 10.

2. The protein of claim 1, which binds to a conformational epitope in PI16.

3. The protein of claim 1 wherein the protein does not substantially bind to PI16 in reduced form.

4. The protein of claim 1, which is a chimeric antibody, de-immunized antibody or a humanized antibody.

5. The protein of claim 1, which is an antibody produced by a hybridoma designated CRCBT-02-001 deposited with the ATCC under Accession Number PTA-10685.

6. The protein of claim 1 having a compound conjugated thereto.

7. A method for detecting peptidase inhibitor 16 (PI16) or a PI16 expressing cell in a sample, the method comprising contacting the sample with the protein of claim 1 such that the protein binds to PI16 in the sample, if present, and detecting the bound protein, or for distinguishing a natural regulatory T (nTreg) cell from an induced Treg (iTreg) cell, the method comprising contacting a sample comprising Treg cells with the protein of claim 1 such that the protein binds to Treg cells expressing PI16 in the sample and detecting a Treg cell expressing PI16, wherein the Treg cell expressing PI16 is a nTreg cell.

8. The method of claim 7, wherein the cell is a regulatory T (Treg) cell.

9. The method of claim 8 additionally comprising isolating the detected cell or isolating the distinguished nTreg cell.

10. A method for producing a population of cells enriched for cells expressing PI16, the method comprising contacting a population of cells comprising PI16 expressing cells with the protein of claim 1 such that the protein binds to a PI16 expressing cell in the sample and selecting cells to which the protein is bound.

11. The method of claim 10, wherein the enriched cells are regulatory T (Treg) cells.

* * * * *

SEQUENCE LISTING

<160> NUMBER OF SEQ ID NOS: 40

<210> SEQ ID NO 1

<211> LENGTH: 463
<212> TYPE: PRT
<213> ORGANISM: Homo sapiens

<400> SEQUENCE: 1

```
Met His Gly Ser Cys Ser Phe Leu Met Leu Leu Pro Leu Leu Leu
1               5                   10                  15

Leu Leu Val Ala Thr Thr Gly Pro Val Gly Ala Leu Thr Asp Glu Glu
            20                  25                  30

Lys Arg Leu Met Val Glu Leu His Asn Leu Tyr Arg Ala Gln Val Ser
            35                  40                  45

Pro Thr Ala Ser Asp Met Leu His Met Arg Trp Asp Glu Glu Leu Ala
50                  55                  60

Ala Phe Ala Lys Ala Tyr Ala Arg Gln Cys Val Trp Gly His Asn Lys
65                  70                  75                  80

Glu Arg Gly Arg Arg Gly Glu Asn Leu Phe Ala Ile Thr Asp Glu Gly
                85                  90                  95

Met Asp Val Pro Leu Ala Met Glu Glu Trp His His Glu Arg Glu His
            100                 105                 110

Tyr Asn Leu Ser Ala Ala Thr Cys Ser Pro Gly Gln Met Cys Gly His
            115                 120                 125

Tyr Thr Gln Val Val Trp Ala Lys Thr Glu Arg Ile Gly Cys Gly Ser
130                 135                 140

His Phe Cys Glu Lys Leu Gln Gly Val Glu Glu Thr Asn Ile Glu Leu
145                 150                 155                 160

Leu Val Cys Asn Tyr Glu Pro Pro Gly Asn Val Lys Gly Lys Arg Pro
                165                 170                 175

Tyr Gln Glu Gly Thr Pro Cys Ser Gln Cys Pro Ser Gly Tyr His Cys
            180                 185                 190

Lys Asn Ser Leu Cys Glu Pro Ile Gly Ser Pro Glu Asp Ala Gln Asp
            195                 200                 205

Leu Pro Tyr Leu Val Thr Glu Ala Pro Ser Phe Arg Ala Thr Glu Ala
        210                 215                 220

Ser Asp Ser Arg Lys Met Gly Thr Pro Ser Ser Leu Ala Thr Gly Ile
225                 230                 235                 240

Pro Ala Phe Leu Val Thr Glu Val Ser Gly Ser Leu Ala Thr Lys Ala
                245                 250                 255

Leu Pro Ala Val Glu Thr Gln Ala Pro Thr Ser Leu Ala Thr Lys Asp
            260                 265                 270

Pro Pro Ser Met Ala Thr Glu Ala Pro Cys Val Thr Thr Glu Val
            275                 280                 285

Pro Ser Ile Leu Ala Ala His Ser Leu Pro Ser Leu Asp Glu Glu Pro
        290                 295                 300

Val Thr Phe Pro Lys Ser Thr His Val Pro Ile Pro Lys Ser Ala Asp
305                 310                 315                 320

Lys Val Thr Asp Lys Thr Lys Val Pro Ser Arg Ser Pro Glu Asn Ser
                325                 330                 335

Leu Asp Pro Lys Met Ser Leu Thr Gly Ala Arg Glu Leu Leu Pro His
            340                 345                 350

Ala Gln Glu Glu Ala Glu Ala Glu Leu Pro Ser Ser Glu
            355                 360                 365

Val Leu Ala Ser Val Phe Pro Ala Gln Asp Lys Pro Gly Glu Leu Gln
        370                 375                 380

Ala Thr Leu Asp His Thr Gly His Thr Ser Ser Lys Ser Leu Pro Asn
```

```
        385                 390                 395                 400
   Phe Pro Asn Thr Ser Ala Thr Asn Ala Thr Gly Gly Arg Ala Leu
                       405                 410                 415

Ala Leu Gln Ser Ser Leu Pro Gly Ala Glu Gly Pro Asp Lys Pro Ser
                   420                 425                 430

Val Val Ser Gly Leu Asn Ser Gly Pro Gly His Val Trp Gly Pro Leu
                   435                 440                 445

Leu Gly Leu Leu Leu Leu Pro Pro Leu Val Leu Ala Gly Ile Phe
       450                 455                 460

<210> SEQ ID NO 2
<211> LENGTH: 498
<212> TYPE: PRT
<213> ORGANISM: Mus musculus

<400> SEQUENCE: 2

Met His Gly Ser Cys Ser Pro Trp Val Met Leu Pro Pro Leu Leu
1               5                   10                  15

Leu Leu Leu Leu Ile Ala Thr Gly Pro Thr Thr Ala Leu Thr Glu
                20                  25                  30

Asp Glu Lys Gln Thr Met Val Asp Leu His Asn Gln Tyr Arg Ala Gln
                35                  40                  45

Val Ser Pro Pro Ala Ser Asp Met Leu Gln Met Arg Trp Asp Asp Glu
    50                  55                  60

Leu Ala Ala Phe Ala Lys Ala Tyr Ala Gln Lys Cys Val Trp Gly His
65                  70                  75                  80

Asn Lys Glu Arg Gly Arg Arg Gly Glu Asn Leu Phe Ala Ile Thr Asp
                85                  90                  95

Glu Gly Met Asp Val Pro Leu Ala Val Gly Asn Trp His Glu Glu His
                100                 105                 110

Glu Tyr Tyr Asn Phe Ser Thr Ala Thr Cys Asp Pro Asn Gln Met Cys
        115                 120                 125

Gly His Tyr Thr Gln Val Val Trp Ser Lys Thr Glu Arg Ile Gly Cys
    130                 135                 140

Gly Ser His Phe Cys Glu Thr Leu Gln Gly Val Glu Glu Ala Asn Ile
145                 150                 155                 160

His Leu Leu Val Cys Asn Tyr Glu Pro Pro Gly Asn Val Lys Gly Arg
                165                 170                 175

Lys Pro Tyr Gln Glu Gly Thr Pro Cys Ser Gln Cys Pro Leu Gly Tyr
                180                 185                 190

Ser Cys Glu Asn Ser Leu Cys Glu Pro Met Arg Asn Pro Glu Lys Ala
        195                 200                 205

Gln Asp Ser Pro Pro Arg Val Thr Glu Val Pro Ser Thr Arg Ala Thr
    210                 215                 220

Glu Ala Pro Ser Ser Arg Glu Thr Gly Thr Pro Ser Leu Ala Thr Ser
225                 230                 235                 240

Glu Thr Leu His Phe Ser Val Thr Lys Val Ser Asp Ser Leu Ala Thr
                245                 250                 255

Glu Ser Ser Pro Ala Val Glu Thr Lys Ala Pro Ser Ser Leu Ala Thr
                260                 265                 270

Glu Gly Pro Ser Ser Met Ala Thr Glu Ala Gln Ala Phe Val Thr Glu
        275                 280                 285

Val Pro Leu Val Ser Ala Arg His Met Gln Pro Ser Val Asp Glu Gly
    290                 295                 300
```

```
Pro Val Asn Phe Leu Thr Ser Thr His Ile Pro Val Pro Lys Ser Met
305                 310                 315                 320

Asp Glu Glu Ala Ser Lys Ser Ser Ala Thr Ser Val Ser Pro Lys Lys
                325                 330                 335

Ser Leu Tyr Pro Lys Met Ser Leu Thr Glu Ser Gly Glu Ser Val Pro
            340                 345                 350

Gln Ile Gln Glu Glu Ala Glu Pro Lys Asp Glu Leu Ser Glu Pro Glu
        355                 360                 365

Ala Ile Leu Pro Glu Ala Glu Ala Pro Thr Glu Ala Glu Val Glu
    370                 375                 380

Leu Arg Glu Pro Glu Ala Glu Ser Pro Lys Ala Glu Ser Pro Glu Ala
385                 390                 395                 400

Glu Ala Glu Ser Pro Leu Ser Ser Glu Ala Leu Val Pro Val Leu Pro
                405                 410                 415

Ala Gln Glu Arg Gly Gly Gln Lys Ala Ser Leu Glu His Ser Gly His
                420                 425                 430

Pro Ala Ser Pro Ser Leu Pro Thr Phe Pro Ser Ala Ser Gly Asn Ala
            435                 440                 445

Thr Gly Gly Arg Thr Leu Ala Leu Gln Ser Ser Trp Thr Gly Ala Glu
450                 455                 460

Asn Pro Glu Lys Ala Asp Trp Asp Leu Lys Asn Ser Ala His Val Trp
465                 470                 475                 480

Gly Pro Phe Leu Gly Leu Leu Pro Ser Leu Leu Leu Ala Gly
            485                 490                 495

Met Val

<210> SEQ ID NO 3
<211> LENGTH: 483
<212> TYPE: PRT
<213> ORGANISM: Rattus norvegicus

<400> SEQUENCE: 3

Met His Ser Ser Cys Ser Pro Trp Val Met Leu Pro Gln Leu Pro Leu
1               5                   10                  15

Leu Leu Leu Leu Leu Leu Leu Leu Thr Ala Thr Gly Pro Ala Thr
                20                  25                  30

Ala Leu Thr Glu Asp Glu Lys Gln Thr Met Val Glu Leu His Asn His
            35                  40                  45

Tyr Arg Ala Gln Val Ser Pro Pro Ala Ser Asp Met Leu Gln Met Arg
    50                  55                  60

Trp Asp Asp Glu Leu Ala Ala Phe Ala Lys Ala Tyr Ala Gln Lys Cys
65                  70                  75                  80

Val Trp Gly His Asn Lys Glu Arg Gly Arg Arg Gly Glu Asn Leu Phe
                85                  90                  95

Ala Ile Thr Asp Glu Gly Met Asp Val Pro Leu Ala Val Gly Asn Trp
            100                 105                 110

His Glu Glu His Glu Tyr Tyr Asn Leu Ser Thr Ala Thr Cys Asp Pro
        115                 120                 125

Gly Gln Met Cys Gly His Tyr Thr Gln Val Val Trp Ser Lys Thr Glu
    130                 135                 140

Arg Ile Gly Cys Gly Ser His Phe Cys Glu Thr Leu Gln Gly Val Glu
145                 150                 155                 160

Glu Ala Asn Ile His Leu Leu Val Cys Asn Tyr Glu Pro Pro Gly Asn
                165                 170                 175
```

Val Lys Gly Arg Lys Pro Tyr Gln Glu Gly Thr Pro Cys Ser Gln Cys
            180                 185                 190

Pro Leu Gly Tyr Ser Cys Val Asn Ser Leu Cys Glu Pro Glu Arg Lys
            195                 200                 205

Pro Glu Lys Ala Gln Asp Ser Pro Pro Arg Val Thr Glu Val Pro Gly
            210                 215                 220

Ser Arg Glu Thr Gly Ile Pro Ser Leu Ala Thr Ser Glu Ser Leu His
225                 230                 235                 240

Phe Ser Ser Val Thr Lys Val Ser Asp Ser Leu Ala Thr Glu Pro Ser
                    245                 250                 255

Pro Ala Val Glu Thr Lys Ala Pro Pro Ser Leu Ala Thr Glu Gly Pro
            260                 265                 270

Ser Ser Met Ala Thr Glu Ala Gln Ser Phe Leu Thr Glu Val Pro Ser
            275                 280                 285

Val Ser Ala Thr His Ile Gln Pro Ser Leu Asp Glu Gly Pro Val Asn
            290                 295                 300

Phe Leu Thr Ser Thr His Ile Pro Val Pro Lys Ser Thr Asp Lys Glu
305                 310                 315                 320

Ala Ser Ser Lys Ser Arg Ala Ala Ser Val Ser Pro Glu Lys Ser Leu
                    325                 330                 335

Tyr Pro Lys Met Ser Pro Thr Glu Thr Gly Glu Ser Pro Pro Gln Ile
            340                 345                 350

Gln Glu Glu Ala Glu Pro Lys Ala Glu Leu Pro Glu Arg Glu Asp Glu
            355                 360                 365

Leu Pro Glu Ala Glu Val Glu Leu Pro Glu Ala Glu Ala Glu Leu Pro
            370                 375                 380

Glu Ala Lys Ala Glu Leu Pro Val Ser Ser Glu Ala Leu Val Pro Val
385                 390                 395                 400

Leu Pro Ala Gln Glu Arg Gly Gly Pro Lys Ala Ser Leu Glu His Ser
                    405                 410                 415

Ser Tyr Pro Val Pro Thr Tyr Leu Pro Asn Phe Pro Ser Ala Ser Gly
            420                 425                 430

Asn Ala Thr Gly Gly Arg Thr Leu Ala Leu Gln Ser Ser Arg Thr Gly
            435                 440                 445

Ala Glu Asp Pro Glu Lys Ala Ser Trp Asp Ser Lys Asn Ser Ala Pro
450                 455                 460

Val Trp Gly Pro Phe Pro Gly Leu Leu Leu Pro Leu Leu Leu Leu Ala
465                 470                 475                 480

Gly Ile Phe

<210> SEQ ID NO 4
<211> LENGTH: 465
<212> TYPE: PRT
<213> ORGANISM: Pan troglodytes

<400> SEQUENCE: 4

Met His Gly Ser Cys Ser Phe Leu Met Leu Leu Pro Leu Leu Leu Leu
1               5                   10                  15

Leu Leu Val Ala Thr Thr Gly Pro Val Gly Ala Leu Thr Asp Glu Glu
            20                  25                  30

Lys Arg Leu Met Val Glu Leu His Asn Leu Tyr Arg Ala Gln Val Ser
            35                  40                  45

Pro Pro Ala Ser Asp Met Leu His Met Arg Trp Asp Glu Glu Leu Ala
        50                  55                  60

-continued

```
Ala Phe Ala Lys Ala Tyr Ala Arg Gln Cys Val Trp Gly His Asn Lys
 65                  70                  75                  80

Glu Arg Gly Arg Arg Gly Glu Asn Leu Phe Ala Ile Thr Asp Glu Gly
                 85                  90                  95

Met Asp Val Pro Leu Ala Met Glu Glu Trp His His Glu Arg Glu His
            100                 105                 110

Tyr Asn Leu Ser Ala Ala Thr Cys Ser Pro Gly Gln Met Cys Gly His
            115                 120                 125

Tyr Thr Gln Val Val Trp Ala Lys Thr Glu Arg Ile Gly Cys Gly Ser
        130                 135                 140

His Phe Cys Glu Lys Leu Gln Gly Val Glu Glu Thr Asn Ile Glu Leu
145                 150                 155                 160

Leu Val Cys Asn Tyr Glu Pro Pro Gly Asn Val Lys Gly Lys Arg Pro
                165                 170                 175

Tyr Gln Glu Gly Thr Pro Cys Ser Gln Cys Pro Ser Gly Tyr His Cys
            180                 185                 190

Lys Asn Ser Leu Cys Glu Pro Ile Gly Ser Ser Glu Asp Ala Gln Asp
            195                 200                 205

Leu Pro Tyr Leu Val Thr Glu Ala Pro Ser Phe Arg Ala Thr Glu Ala
        210                 215                 220

Ser Asp Ser Arg Lys Met Gly Thr Pro Ser Ser Leu Ala Thr Gly Ile
225                 230                 235                 240

Pro Ala Phe Leu Val Thr Glu Val Ser Gly Ser Leu Ala Thr Lys Ala
                245                 250                 255

Leu Pro Ala Val Glu Thr Gln Ala Pro Thr Ser Leu Ala Thr Lys Asp
            260                 265                 270

Pro Pro Ser Met Ala Thr Glu Ala Pro Cys Val Thr Thr Glu Val
            275                 280                 285

Pro Ser Ile Leu Ala Ala His Ser Leu Pro Ser Leu Asp Glu Glu Pro
    290                 295                 300

Val Thr Phe Pro Lys Ser Thr His Val Pro Ile Pro Lys Ser Ala Asp
305                 310                 315                 320

Lys Val Thr Asp Lys Thr Lys Val Pro Ser Arg Ser Pro Glu Asn Ser
                325                 330                 335

Leu Asp Pro Lys Met Ser Leu Thr Gly Ala Arg Glu Leu Leu Pro His
            340                 345                 350

Ala Gln Glu Glu Ala Glu Ala Glu Ala Glu Leu Pro Pro Ser
            355                 360                 365

Ser Glu Val Leu Ala Ser Val Phe Pro Ala Gln Asp Lys Pro Gly Glu
    370                 375                 380

Leu Gln Ala Thr Leu Asp His Thr Gly His Thr Ser Ser Lys Ser Leu
385                 390                 395                 400

Pro Asn Phe Pro Asn Thr Ser Ala Thr Ala Asn Ala Thr Gly Gly Arg
                405                 410                 415

Ala Leu Ala Leu Lys Ser Ser Leu Pro Gly Ala Glu Gly Pro Asp Lys
            420                 425                 430

Pro Ser Val Val Ser Gly Leu Asn Ser Gly Pro Gly His Val Trp Gly
            435                 440                 445

Pro Leu Leu Gly Leu Leu Leu Pro Pro Leu Val Leu Ala Gly Ile
        450                 455                 460

Phe
465
```

<210> SEQ ID NO 5
<211> LENGTH: 54
<212> TYPE: DNA
<213> ORGANISM: artificial
<220> FEATURE:
<223> OTHER INFORMATION: Sequence of oligonucleotide for amplifying Homo sapiens PI16 open reading frame

<400> SEQUENCE: 5
ggggacaagt ttgtacaaaa aagcaggctg ccaccatgca cggctcctgc agtt      54

<210> SEQ ID NO 6
<211> LENGTH: 50
<212> TYPE: DNA
<213> ORGANISM: artificial
<220> FEATURE:
<223> OTHER INFORMATION: Sequence of oligonucleotide for amplifying Homo sapiens PI16 open reading frame

<400> SEQUENCE: 6
ggggaccact ttgtacaaga aagctgggtc gaagattcca gccaacacca            50

<210> SEQ ID NO 7
<211> LENGTH: 367
<212> TYPE: DNA
<213> ORGANISM: Mus musculus

<400> SEQUENCE: 7
tttggaggag gcttggtgca acctggagga tccatgaaac tctcctgtgt tgcctctgga      60 ttcacttttta gttattactg gatgaactgg gtccgccaat ctccagaaca gggacttgag    120
tggattgctg aaattagatt gcaatctaat gattatccaa cacattacgc ggagtctgtg    180
aaagggaggt tcaccatctc aagagatgat tccaaaaata gtgtctacct gcaaatgaac    240
aacctaagac ctgaagacac tggcatttat tactgtgcct gccggtatgc ggactacttt    300
gaccactggg gccaaggaac cactctcaca gtctcttcag ccaaaacgac acccccatct    360
gtctata                                                              367

<210> SEQ ID NO 8
<211> LENGTH: 122
<212> TYPE: PRT
<213> ORGANISM: Mus musculus

<400> SEQUENCE: 8

Phe Gly Gly Gly Leu Val Gln Pro Gly Gly Ser Met Lys Leu Ser Cys
1               5                   10                  15

Val Ala Ser Gly Phe Thr Phe Ser Tyr Tyr Trp Met Asn Trp Val Arg
            20                  25                  30

Gln Ser Pro Glu Gln Gly Leu Glu Trp Ile Ala Glu Ile Arg Leu Gln
        35                  40                  45

Ser Asn Asp Tyr Pro Thr His Tyr Ala Glu Ser Val Lys Gly Arg Phe
    50                  55                  60

Thr Ile Ser Arg Asp Asp Ser Lys Asn Ser Val Tyr Leu Gln Met Asn
65                  70                  75                  80

Asn Leu Arg Pro Glu Asp Thr Gly Ile Tyr Tyr Cys Ala Cys Arg Tyr
                85                  90                  95

Ala Asp Tyr Phe Asp His Trp Gly Gln Gly Thr Thr Leu Thr Val Ser
            100                 105                 110

Ser Ala Lys Thr Thr Pro Pro Ser Val Tyr
        115                 120

<210> SEQ ID NO 9
<211> LENGTH: 337
<212> TYPE: DNA
<213> ORGANISM: Mus musculus

<400> SEQUENCE: 9
gtgatgaccc aatctccagc aatcctgtct gtatatccag gggagaaggt cacaatgact      60
tgcagggcca gtttaagtgt aagttacatg cactggtgcc aacagaagcc aggatcctcc     120
cccaaatcct ggatttatgc cacatccaac ctggcttctg gagtccctgc tcgcttcagt     180
ggcagtgggt ctgggacctc ttactctctc acaatcagca gagtggaggc tgaagatgct     240
gccacttatt actgccagca gtggagtagt aacccattca cgttcggctc ggggacaaag     300
ttggaaataa aacgggctga tgctgcacca actgtat                              337

<210> SEQ ID NO 10
<211> LENGTH: 112
<212> TYPE: PRT
<213> ORGANISM: Mus musculus

<400> SEQUENCE: 10

Val Met Thr Gln Ser Pro Ala Ile Leu Ser Val Tyr Pro Gly Glu Lys
1               5                   10                  15

Val Thr Met Thr Cys Arg Ala Ser Leu Ser Val Ser Tyr Met His Trp
            20                  25                  30

Cys Gln Gln Lys Pro Gly Ser Ser Pro Lys Ser Trp Ile Tyr Ala Thr
        35                  40                  45

Ser Asn Leu Ala Ser Gly Val Pro Ala Arg Phe Ser Gly Ser Gly Ser
    50                  55                  60

Gly Thr Ser Tyr Ser Leu Thr Ile Ser Arg Val Glu Ala Glu Asp Ala
65                  70                  75                  80

Ala Thr Tyr Tyr Cys Gln Gln Trp Ser Ser Asn Pro Phe Thr Phe Gly
                85                  90                  95

Ser Gly Thr Lys Leu Glu Ile Lys Arg Ala Asp Ala Ala Pro Thr Val
            100                 105                 110

<210> SEQ ID NO 11
<211> LENGTH: 32
<212> TYPE: DNA
<213> ORGANISM: artificial
<220> FEATURE:
<223> OTHER INFORMATION: nucleotide sequence of a primer for cloning a
      sequence encoding a mouse immunoglobulin light chain

<400> SEQUENCE: 11
gggagctcga yattgtgmts acmcarwctm ca                                    32

<210> SEQ ID NO 12
<211> LENGTH: 30
<212> TYPE: DNA
<213> ORGANISM: artificial
<220> FEATURE:
<223> OTHER INFORMATION: nucleotide sequence of a primer for cloning a
      sequence encoding a mouse immunoglobulin light chain

<400> SEQUENCE: 12
ggtgcatgcg gatacagttg gtgcagcatc                                       30

<210> SEQ ID NO 13
<211> LENGTH: 34
<212> TYPE: DNA

<213> ORGANISM: artificial
<220> FEATURE:
<223> OTHER INFORMATION: nucleotide sequence of a primer for cloning a
      sequence encoding a mouse immunoglobulin heavy chain

<400> SEQUENCE: 13
cttccggaat tccaggttac tctgaaagwg tstg                        34

<210> SEQ ID NO 14
<211> LENGTH: 32
<212> TYPE: DNA
<213> ORGANISM: artificial
<220> FEATURE:
<223> OTHER INFORMATION: nucleotide sequence of a primer for cloning a
      sequence encoding a mouse immunoglobulin heavy chain

<400> SEQUENCE: 14
cttccggaat tcgaggtcca rctgcaacar tc                          32

<210> SEQ ID NO 15
<211> LENGTH: 32
<212> TYPE: DNA
<213> ORGANISM: artificial
<220> FEATURE:
<223> OTHER INFORMATION: nucleotide sequence of a primer for cloning a
      sequence encoding a mouse immunoglobulin heavy chain

<400> SEQUENCE: 15
cttccggaat tccaggtcca actvcagcar cc                          32

<210> SEQ ID NO 16
<211> LENGTH: 32
<212> TYPE: DNA
<213> ORGANISM: artificial
<220> FEATURE:
<223> OTHER INFORMATION: nucleotide sequence of a primer for cloning a
      sequence encoding a mouse immunoglobulin heavy chain

<400> SEQUENCE: 16
cttccggaat tcgaggtgaa sstggtggaa tc                          32

<210> SEQ ID NO 17
<211> LENGTH: 32
<212> TYPE: DNA
<213> ORGANISM: artificial
<220> FEATURE:
<223> OTHER INFORMATION: nucleotide sequence of a primer for cloning a
      sequence encoding a mouse immunoglobulin heavy chain

<400> SEQUENCE: 17
cttccggaat tcgatgtgaa cttggaagtg tc                          32

<210> SEQ ID NO 18
<211> LENGTH: 36
<212> TYPE: DNA
<213> ORGANISM: artificial
<220> FEATURE:
<223> OTHER INFORMATION: nucleotide sequence of a primer for cloning a
      sequence encoding a mouse immunoglobulin heavy chain

<400> SEQUENCE: 18
ggaagatcta tagacagatg ggggtgtcgt tttggc                      36

<210> SEQ ID NO 19
<211> LENGTH: 17
<212> TYPE: DNA
<213> ORGANISM: artificial

```
<220> FEATURE:
<223> OTHER INFORMATION: nucleotide sequence of a primer for amplifying
      a region of FoxP3

<400> SEQUENCE: 19
atggcccagc ggatgag                                                          17

<210> SEQ ID NO 20
<211> LENGTH: 21
<212> TYPE: DNA
<213> ORGANISM: artificial
<220> FEATURE:
<223> OTHER INFORMATION: nucleotide sequence of a primer for amplifying
      a region of FoxP3

<400> SEQUENCE: 20
gaaacagcac attcccagag t                                                     21

<210> SEQ ID NO 21
<211> LENGTH: 21
<212> TYPE: DNA
<213> ORGANISM: artificial
<220> FEATURE:
<223> OTHER INFORMATION: nucleotide sequence of a primer for amplifying
      a region of PI16

<400> SEQUENCE: 21
gagaatctgt tcgccatcac a                                                     21

<210> SEQ ID NO 22
<211> LENGTH: 23
<212> TYPE: DNA
<213> ORGANISM: artificial
<220> FEATURE:
<223> OTHER INFORMATION: nucleotide sequence of a primer for amplifying
      a region of PI16

<400> SEQUENCE: 22
gaaacagcac attcccagag ttc                                                   23

<210> SEQ ID NO 23
<211> LENGTH: 20
<212> TYPE: DNA
<213> ORGANISM: artificial
<220> FEATURE:
<223> OTHER INFORMATION: nucleotide sequence of a primer for amplifying
      a region of RPL13a

<400> SEQUENCE: 23
cgaggttggc tggaagtacc                                                       20

<210> SEQ ID NO 24
<211> LENGTH: 21
<212> TYPE: DNA
<213> ORGANISM: artificial
<220> FEATURE:
<223> OTHER INFORMATION: nucleotide sequence of a primer for amplifying
      a region of RPL13a

<400> SEQUENCE: 24
cttctcggcc tgtttccgta g                                                     21

<210> SEQ ID NO 25
<211> LENGTH: 35
<212> TYPE: DNA
<213> ORGANISM: artificial
<220> FEATURE:
```

```
<223> OTHER INFORMATION: nucleotide sequence of a primer for amplifying
      a nucleic acid encoding amino acids 28-443 of PI16

<400> SEQUENCE: 25
ttgatatcac tcacagatga ggagaaacgt ttgat                                  35

<210> SEQ ID NO 26
<211> LENGTH: 54
<212> TYPE: DNA
<213> ORGANISM: artificial
<220> FEATURE:
<223> OTHER INFORMATION: nucleotide sequence of a primer for amplifying
      a nucleic acid encoding amino acids 28-443 of PI16

<400> SEQUENCE: 26
aaagatctac cctgaaaata caggttttca tgaccagggc ccgagttcag ccct             54

<210> SEQ ID NO 27
<211> LENGTH: 25
<212> TYPE: PRT
<213> ORGANISM: artificial
<220> FEATURE:
<223> OTHER INFORMATION: amino acid sequence of a peptide fragment of
      PI16

<400> SEQUENCE: 27

Gly Glu Asn Leu Phe Ala Ile Thr Asp Glu Gly Met Asp Val Pro Leu
1               5                   10                  15

Ala Met Glu Glu Trp His His Glu Arg
            20                  25

<210> SEQ ID NO 28
<211> LENGTH: 20
<212> TYPE: DNA
<213> ORGANISM: artificial
<220> FEATURE:
<223> OTHER INFORMATION: primer for amplifying TSDR

<400> SEQUENCE: 28
tgtttggggg tagaggattt                                                   20

<210> SEQ ID NO 29
<211> LENGTH: 20
<212> TYPE: DNA
<213> ORGANISM: artificial
<220> FEATURE:
<223> OTHER INFORMATION: primer for amplifying TSDR

<400> SEQUENCE: 29
tatcacccca cctaaaccaa                                                   20

<210> SEQ ID NO 30
<211> LENGTH: 16
<212> TYPE: DNA
<213> ORGANISM: artificial
<220> FEATURE:
<223> OTHER INFORMATION: M13 universal forward primer

<400> SEQUENCE: 30
gtaaaacgac ggccag                                                       16

<210> SEQ ID NO 31
<211> LENGTH: 17
<212> TYPE: DNA
<213> ORGANISM: artificial
<220> FEATURE:
```

<223> OTHER INFORMATION: M13 universal reverse primer

<400> SEQUENCE: 31
gttttcccag tcacgac                                                   17

<210> SEQ ID NO 32
<211> LENGTH: 10
<212> TYPE: PRT
<213> ORGANISM: Homo sapiens

<400> SEQUENCE: 32

Trp Asp Glu Glu Leu Ala Ala Phe Ala Lys
1               5                   10

<210> SEQ ID NO 33
<211> LENGTH: 31
<212> TYPE: PRT
<213> ORGANISM: Homo sapiens

<400> SEQUENCE: 33

Leu His Met Arg Trp Asp Glu Glu Leu Ala Ala Phe Ala Lys Ala Tyr
1               5                   10                  15

Ala Arg Gln Cys Val Trp Gly His Asn Lys Glu Arg Gly Arg Arg
            20                  25                  30

<210> SEQ ID NO 34
<211> LENGTH: 19
<212> TYPE: PRT
<213> ORGANISM: Homo sapiens

<400> SEQUENCE: 34

Leu His Met Arg Trp Asp Glu Glu Leu Ala Ala Phe Ala Lys Ala Tyr
1               5                   10                  15

Ala Arg Gln

<210> SEQ ID NO 35
<211> LENGTH: 68
<212> TYPE: PRT
<213> ORGANISM: Homo sapiens

<400> SEQUENCE: 35

Arg Trp Asp Glu Glu Leu Ala Ala Phe Ala Lys Ala Tyr Ala Arg Gln
1               5                   10                  15

Cys Val Trp Gly His Asn Lys Glu Arg Gly Arg Arg Gly Glu Asn Leu
            20                  25                  30

Phe Ala Ile Thr Asp Glu Gly Met Asp Val Pro Leu Ala Met Glu Glu
        35                  40                  45

Trp His His Glu Arg Glu His Tyr Asn Leu Ser Ala Ala Thr Cys Ser
    50                  55                  60

Pro Gly Gln Met
65

<210> SEQ ID NO 36
<211> LENGTH: 28
<212> TYPE: PRT
<213> ORGANISM: Homo sapiens

<400> SEQUENCE: 36

Leu His Met Arg Trp Asp Glu Glu Leu Ala Ala Phe Ala Lys Ala Tyr
1               5                   10                  15

Ala Arg Gln Cys Val Trp Gly His Asn Lys Glu Arg

```
                20                  25

<210> SEQ ID NO 37
<211> LENGTH: 38
<212> TYPE: PRT
<213> ORGANISM: Homo sapiens

<400> SEQUENCE: 37

Leu His Met Arg Trp Asp Glu Glu Leu Ala Ala Phe Ala Lys Ala Tyr
1               5                   10                  15

Ala Arg Gln Cys Val Trp Gly His Asn Lys Glu Arg Gly Arg Gly
            20                  25                  30

Glu Asn Leu Phe Ala Ile
        35

<210> SEQ ID NO 38
<211> LENGTH: 16
<212> TYPE: PRT
<213> ORGANISM: Homo sapiens

<400> SEQUENCE: 38

Arg Trp Asp Glu Glu Leu Ala Ala Phe Ala Lys Ala Tyr Ala Arg Gln
1               5                   10                  15

<210> SEQ ID NO 39
<211> LENGTH: 29
<212> TYPE: PRT
<213> ORGANISM: Homo sapiens

<400> SEQUENCE: 39

Leu His Met Arg Trp Asp Glu Glu Leu Ala Ala Phe Phe Ala Lys Ala
1               5                   10                  15

Tyr Ala Arg Gln Cys Val Trp Gly His Asn Lys Glu Arg
            20                  25

<210> SEQ ID NO 40
<211> LENGTH: 416
<212> TYPE: PRT
<213> ORGANISM: Homo sapiens

<400> SEQUENCE: 40

Leu Thr Asp Glu Glu Lys Arg Leu Met Val Glu Leu His Asn Leu Tyr
1               5                   10                  15

Arg Ala Gln Val Ser Pro Pro Ala Ser Asp Met Leu His Met Arg Trp
            20                  25                  30

Asp Glu Glu Leu Ala Ala Phe Ala Lys Ala Tyr Ala Arg Gln Cys Val
        35                  40                  45

Trp Gly His Asn Lys Glu Arg Gly Arg Arg Gly Glu Asn Leu Phe Ala
    50                  55                  60

Ile Thr Asp Glu Gly Met Asp Val Pro Leu Ala Met Glu Glu Trp His
65                  70                  75                  80

His Glu Arg Glu His Tyr Asn Leu Ser Ala Ala Thr Cys Ser Pro Gly
                85                  90                  95

Gln Met Cys Gly His Tyr Thr Gln Val Val Trp Ala Lys Thr Glu Arg
            100                 105                 110

Ile Gly Cys Gly Ser His Phe Cys Glu Lys Leu Gln Gly Val Glu Glu
        115                 120                 125

Thr Asn Ile Glu Leu Leu Val Cys Asn Tyr Glu Pro Pro Gly Asn Val
    130                 135                 140
```

-continued

```
Lys Gly Lys Arg Pro Tyr Gln Glu Gly Thr Pro Cys Ser Gln Cys Pro
145                 150                 155                 160

Ser Gly Tyr His Cys Lys Asn Ser Leu Cys Glu Pro Ile Gly Ser Pro
                165                 170                 175

Glu Asp Ala Gln Asp Leu Pro Tyr Leu Val Thr Glu Ala Pro Ser Phe
            180                 185                 190

Arg Ala Thr Glu Ala Ser Asp Ser Arg Lys Met Gly Thr Pro Ser Ser
            195                 200                 205

Leu Ala Thr Gly Ile Pro Ala Phe Leu Val Thr Glu Val Ser Gly Ser
            210                 215                 220

Leu Ala Thr Lys Ala Leu Pro Ala Val Glu Thr Gln Ala Pro Thr Ser
225                 230                 235                 240

Leu Ala Thr Lys Asp Pro Pro Ser Met Ala Thr Glu Ala Pro Pro Cys
                245                 250                 255

Val Thr Thr Glu Val Pro Ser Ile Leu Ala Ala His Ser Leu Pro Ser
                260                 265                 270

Leu Asp Glu Glu Pro Val Thr Phe Pro Lys Ser Thr His Val Pro Ile
            275                 280                 285

Pro Lys Ser Ala Asp Lys Val Thr Asp Lys Thr Lys Val Pro Ser Arg
        290                 295                 300

Ser Pro Glu Asn Ser Leu Asp Pro Lys Met Ser Leu Thr Gly Ala Arg
305                 310                 315                 320

Glu Leu Leu Pro His Ala Gln Glu Glu Ala Glu Ala Glu Leu
                325                 330                 335

Pro Pro Ser Ser Glu Val Leu Ala Ser Val Phe Pro Ala Gln Asp Lys
            340                 345                 350

Pro Gly Glu Leu Gln Ala Thr Leu Asp His Thr Gly His Thr Ser Ser
            355                 360                 365

Lys Ser Leu Pro Asn Phe Pro Asn Thr Ser Ala Thr Ala Asn Ala Thr
        370                 375                 380

Gly Gly Arg Ala Leu Ala Leu Gln Ser Ser Leu Pro Gly Ala Glu Gly
385                 390                 395                 400

Pro Asp Lys Pro Ser Val Val Ser Gly Leu Asn Ser Gly Pro Gly His
                405                 410                 415
```